United States Patent
Sherman et al.

(10) Patent No.: US 11,524,990 B2
(45) Date of Patent: *Dec. 13, 2022

(54) METHODS FOR TREATING VASCULAR EYE DISORDERS WITH ACTRII ANTAGONISTS

(71) Applicant: Acceleron Pharma Inc., Cambridge, MA (US)

(72) Inventors: Matthew L. Sherman, Newton, MA (US); Kenneth M. Attie, Boston, MA (US)

(73) Assignee: ACCELERON PHARMA INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/380,196

(22) Filed: Apr. 10, 2019

(65) Prior Publication Data

US 2020/0071383 A1  Mar. 5, 2020

Related U.S. Application Data

(63) Continuation of application No. 15/360,588, filed on Nov. 23, 2016, now Pat. No. 10,550,170.

(60) Provisional application No. 62/258,934, filed on Nov. 23, 2015.

(51) Int. Cl.
| | |
|---|---|
| *A61P 27/02* | (2006.01) |
| *A61K 38/17* | (2006.01) |
| *C07K 14/71* | (2006.01) |
| *A61K 38/18* | (2006.01) |
| *C07K 16/22* | (2006.01) |
| *A61K 38/00* | (2006.01) |
| *A61K 39/00* | (2006.01) |
| *G01N 33/50* | (2006.01) |
| *G01N 33/80* | (2006.01) |

(52) U.S. Cl.
CPC ............ *C07K 14/71* (2013.01); *A61K 38/179* (2013.01); *A61P 27/02* (2018.01); *A61K 38/00* (2013.01); *A61K 38/17* (2013.01); *A61K 38/1796* (2013.01); *A61K 38/1841* (2013.01); *A61K 39/00* (2013.01); *C07K 16/22* (2013.01); *C07K 2319/30* (2013.01); *C07K 2319/31* (2013.01); *G01N 33/5088* (2013.01); *G01N 33/80* (2013.01); *G01N 2500/04* (2013.01)

(58) Field of Classification Search
CPC ........ A61P 27/02; A61K 38/179; C07K 14/71
See application file for complete search history.

(56) References Cited

U.S. PATENT DOCUMENTS

| | | | |
|---|---|---|---|
| 5,078,486 A | 1/1992 | Evans | |
| 7,988,973 B2 | 8/2011 | Sherman | |
| 8,058,229 B2 | 11/2011 | Seehra et al. | |
| 8,216,997 B2 | 7/2012 | Seehra et al. | |
| 8,343,933 B2 | 1/2013 | Knopf et al. | |
| 8,361,957 B2 | 1/2013 | Seehra et al. | |
| 9,505,813 B2 | 11/2016 | Seehra et al. | |
| 10,550,170 B2* | 2/2020 | Sherman | G01N 33/5088 |
| 2010/0008918 A1 | 1/2010 | Sherman et al. | |
| 2010/0028332 A1 | 2/2010 | Sherman et al. | |
| 2012/0003218 A1 | 1/2012 | Sherman et al. | |
| 2013/0243743 A1 | 9/2013 | Seehra et al. | |
| 2015/0361163 A1 | 12/2015 | Kumar et al. | |
| 2016/0039922 A1 | 2/2016 | Attie | |
| 2016/0046690 A1 | 2/2016 | Kumar et al. | |
| 2016/0279197 A1 | 9/2016 | Sherman et al. | |
| 2016/0289286 A1 | 10/2016 | Attie et al. | |
| 2017/0204382 A1 | 7/2017 | Seehra et al. | |
| 2017/0274077 A1 | 9/2017 | Kumar et al. | |
| 2017/0360887 A1 | 12/2017 | Attie et al. | |
| 2018/0050085 A1 | 2/2018 | Kumar et al. | |

FOREIGN PATENT DOCUMENTS

| | | |
|---|---|---|
| WO | WO-2004/064770 A2 | 8/2004 |
| WO | WO-2008/076437 A2 | 6/2008 |
| WO | WO-2009/146408 A1 | 12/2009 |
| WO | WO-2009/158015 A2 | 12/2009 |
| WO | WO-2010/121162 A1 | 10/2010 |
| WO | WO-2010/125416 A1 | 11/2010 |
| WO | WO-2011/020045 A1 | 2/2011 |
| WO | WO-2013/059347 A1 | 4/2013 |
| WO | WO-2015/143403 A1 | 9/2015 |
| WO | WO-2015/161220 A1 | 10/2015 |
| WO | WO-2015/192111 A1 | 12/2015 |
| WO | WO-2016/183280 A1 | 11/2016 |
| WO | WO-2017/079591 A2 | 5/2017 |
| WO | WO-2017/091706 A1 | 6/2017 |

OTHER PUBLICATIONS

Atkins et al (2010. Surv. Opthalmol. 55(1): 47-63).*
Cazzola et al, 2008. Hematology Am Soc Hematol Educ Program. 1: 166-175.*
Abu El-Asrar, et al., "Expression of Apoptosis Markers in the Retinas of Human Subjects with Diabetes," Investigative Ophthalmology & Visual Science, vol. 45(8): 2760-2766 (2004).
Aksoy, et al., "Retinal Fiber Layer Thickness in Children with Thalessemia Major and Iron Deficiency Anemia," Seminars in Ophthalmology, vol. 29(1): 22-26 (2014).
Ali, et al., "The course of retinal vasculitis," The British Journal of Ophthalmology, vol. 98: 785-789 (2014).
Ames III, A., "Energy requirements of CNS cells as related to their function and to their vulnerability to ischemia: a commentary based on studies on retina," The Canadian Journal of Physiology and Pharmacology, vol. 70: S158-S164 (1992).
Anderson, et al., "Retinal Oxygen Utilization Measured by Hyperbaric Blackout," Archives of Ophthalmology, vol. 72: 792-795 (1964).

(Continued)

*Primary Examiner* — Zachary C Howard
(74) *Attorney, Agent, or Firm* — White & Case LLP

(57) ABSTRACT

Disclosed herein are compositions and methods for increasing visual acuity in patients in need thereof and for treating vascular disorders of the eye.

43 Claims, 23 Drawing Sheets
(15 of 23 Drawing Sheet(s) Filed in Color)
Specification includes a Sequence Listing.

(56) References Cited

OTHER PUBLICATIONS

Antcliff, et al., "The Pathogenesis of Edema in Diabetic Maculopathy," Seminars in Ophthalmology, vol. 14(4): 223-232 (1999).
Arden, et al., "Hypoxia and Oxidative Stress in the Causation of Diabetic Retinopathy," Current Diabetes Reviews, vol. 7: 291-304 (2011).
Ashton, et al., "Ocular Pathology in Macroglobulinaemia," The Journal of Pathology and Bacteriology, vol. 86: 453-461 (1963).
Attie, et al., "A phase 1 study of ACE-536, a regulator of erythroid differentiation, in healthy volunteers," American Journal of Hematology, vol. 89(7): 766-770 (2014).
Ballas, et al., "Red Blood Cell Changes During the Evolution of the Sickle Cell Painful Crisis," Blood, vol. 79(8): 2154-2163 (1992).
Bejar, et al., "Recent developments in myelodysplastic syndromes," Blood, vol. 124(18): 2793-2803 (2014).
Benson, et al., "Complications of Vitrectomy for Non-clearing Vitreous Hemorrhage in Diabetic Patients," Ophthalmic Surgery, vol. 19(12): 862-864 (1988).
Biankin, et al., "Pancreatic Cancer Genomes Reveal Aberrations in Axon Guidance Pathway Genes," Nature, vol. 491: 399-405 (2012).
Block, et al., "Effects of Antioxidants on Ischemic Retinal Dysfunction," Experimental Eye Research, vol. 64: 559-564 (1997).
Bottomley, et al., "Sideroblastic Anemia Diagnosis and Management," Hematology/Oncology Clinics of North America, vol. 28: 653-670 (2014).
Bressler, et al., "Chapter 66 Neovasular (Exudative) Age-Related Macular Degeneration," In: Retina, Third Edition, vol. 2: 1100-1135 (2001).
Brouzas, et al., "Nonarteritic anterior ischemic optic neuropathy associated with chronic anemia: a case series of myelodysplastic syndrome patients," Clinical Ophthalmology, vol. 3: 133-137 (2009).
Brown, "Chapter 91 Ocular ischemic syndrome," In: Retina, Second Edition, vol. 2: 1515-1527 (1994).
Brown, et al., "The ocular ischemic syndrome," International Ophthalmology, vol. 11: 239-251 (1988).
Buckley, et al., "Purtscher's retinopathy," Postgraduate Medical Journal, vol. 72: 409-412 (1996).
Cazzola, et al., "The Genetic Basis of Myelodysplasia and Its Clinical Relevance," Blood, vol. 122(25): 4021-4034 (2013).
Chen, et al., "Ocular Ischemic Syndrome: Review of Clinical Presentations, Etiology, Investigation, and Management," Comprehensive Ophthalmology Update, vol. 8(1): 17-28 (2007).
Chen, et al., "Oxygen Tension Regulates Survival and Fate of Mouse Central Nervous System Precursors at Multiple Levels," Stem Cells, vol. 25: 2291-2301 (2007).
Chesnais, et al., "Spliceosome Mutations in Myelodysplastic Syndromes and Chronic Myelomonocytic Leukemia," Oncotarget, vol. 3(11): 1284-1293 (2012).
Cheson, et al., "Clinical Application and Proposal for Modification of the International Working Group (IWG) Response Criteria in Myelodysplasia," Blood, vol. 108(2): 419-425 (2006).
Cheson, et al., "Report of an international working group to standardize response criteria for myelodysplastic syndromes," Blood, vol. 96(12): 3671-3674 (2000).
Chew, et al., "Long-Term Effects of Vitamins C, E, Beta-Carotene and Zinc on Age-Related Macular Degeneration. AREDS Report No. 35;" Ophthalmology, vol. 120(8): 1604-1611 (2013).
Chew, et al., "Lutein/Zeaxanthin for the Treatment of Age-Related Cataract AREDS2 Randomized Trial Report No. 4," JAMA Ophthalmology, vol. 131(7): 843-850 (2013).
Christen, et al., "Folic Acid, Vitamin B6, and Vitamin B12 in Combination and Age-related Macular Degeneration in a Randomized Trial of Women," Archives of Internal Medicine, vol. 169(4): 335-341 (2009).
Chung, et al., "Vasular Aspects in the Pathophysiology of Glaucomatous Optic Neuropathy," Survey of Ophthalmology, vol. 43(Suppl. 1): S43-S50 (1999).
Cohen, et al., "Relationships between Visual Function and Metabolism," Biochemistry of the Retina, 1st International Symposium on the Biochemistry of the Retina: 36-50 (1965).
De Jong, P., "Age-Related Macular Degeneration," The New England Journal of Medicine, vol. 355(14): 1474-1485 (2006).
De Melo, M., "An Eye on Sickle Cell Retinopathy," Brazilian Journal of Hematology and Hemotherapy, vol. 36(5): 319-321 (2014).
Del Re, et al., "Reconstitution and Analysis of Soluble Inhibin and Activin Receptor Complexes in a Cell-free System," The Journal of Biological Chemistry, 279(51): 53126-53135 (2004).
Dennler, et al., "Direct binding of Smad3 and Smad4 to critical TGFβ-inducible elements in the promoter of human plasminogen activator inhibitor-type 1 gene," The EMBO Journal, vol. 17(11): 3091-3100 (1998).
Dolatshad, et al., "Disruption of SF3B1 Results in Deregulated Expression and Splicing of Key Genes and Pathways in Myelodysplastic Syndrome Hematopoietic Stem and Progenitor Cells," Leukemia, vol. 29: 1092-1103 (2015).
Dryja et al., "ABCR Gene and Age-Related Macular Degeneration," Science, vol. 279: 1107a (4 pages)(1998).
Eaton, et al., "Sickle Cell Hemoglobin Polymerization," Advances in Protein Chemisty, vol. 40: 63-279 (1990).
Eshaq, et al., "Oxygen delivery, consumption, and conversion to reactive oxygen species in experimental models of diabetic retinopathy," Redox Biology, vol. 2: 661-666 (2014).
Falavarjani, et al., "Adverse events and complications with intravitreal injection of anti-VEGF agents: a review of literature," Eye, vol. 27: 787-794 (2013).
Flammer, J., "The Vascular Concept of Glaucoma," Survey of Ophthalmology, vol. 38, S3-S6 (1994).
Furney, et al., "SF3B1 Mutations Are Associated with Alternative Splicing in Uveal Melanoma," Cancer Discovery, vol. 3(10): 1122-1129 (2013).
Guex-Crosier, Y., "The pathogenesis and clinical presentation of macular edema in inflammatory diseases," Documenta Ophthalmologica, vol. 97: 297-309 (1999).
Guerra, Amaliris et al.; "Lack of GDF11 Does Not Ameliorate Erythropoiesis in β-Thalassemia and Does Not Prevent the Activity of the Trap-Ligand RAP-536", Blood, 2018, 132:165 (6 pages).
Hamann, et al., "Water homeostasis in the ischaemic retina: is aquaporin-4 involved?," Acta Ophthalmologica Scandinavica, vol. 83: 523-525 (2005).
Harris, A., "Hypoxia—A Key Regulatory Factor in Tumour Growth," Nature Reviews Cancer, vol. 2: 38-47 (2002).
Hayreh, et al., "Non-arteritic anterior ischemic optic neuropathy: role of systemic corticosteroid therapy," Graefe's Archive for Clinical and Experimental Ophthalmology, vol. 246(7): 1029-1046 (2008).
International Search Report dated Feb. 13, 2017 in corresponding International Application No. PCT/US2016/063557 (11 pages).
Iyer, et al., "Cellular and developmental control of O2 homeostasis by hypoxia-inducible factor 1α," Genes & Development, vol. 12: 149-162 (1998).
Janáky, et al., "Hypobaric hypoxia reduces the amplitude of oscillatory potentials in the human ERG," Documenta Ophthalmologica, vol. 114: 45-51 (2007).
Je, et al., "Mutational Analysis of Splicing Machinery Genes SF3B1, U2AF1 and SRSF2 in Myelodysplasia and Other Common Tumors," International Journal of Cancer, vol. 133: 260-266 (2013).
Kassim, et al., "Sickle Cell Disease, Vasculopathy, and Therapeutics," Annual Reviews in Medicine, vol. 64: 451-466 (2013).
Kaur, et al., "Blood-retinal barrier disruption and ultrastructural changes in the hypoxic retina in adult rats: the beneficial effect of melatonin administration," Journal of Pathology, vol. 212: 429-439 (2007).
Kaur, et al., "Early Response of Neurons and Glial Cells to Hypoxia in the Retina," Investigative Ophthalmology & Visual Science, vol. 47(3): 1126-1141 (2006).
Kaur, et al., "Hypoxia-ischemia and retinal ganglion cell damage," Clinical Ophthalmology, vol. 2(4): 879-889 (2008).
Kergoat, et al., "RGC Sensitivity to Mild Systemic Hypoxia," Investigative Ophthalmology & Visual Science, vol. 47(12): 5423-5427 (2006).

(56) References Cited

OTHER PUBLICATIONS

Kiel, J., "Chapter 2 Anatomy," In: The Ocular Circulation, Morgan & Claypool Life Sciences: 3-9 (2011).
Kitagawa, et al., "'Ischemic Tolerance' phenomenon found in the brain," Brain Research, vol. 528: 21-24 (1990).
Klein, et al., "The Epidemiology of Retinal Vein Occlusion: The Beaver Dam Eye Study," Transactions of the American Ophthalmological Society, vol. 98: 133-143 (2000).
Kuroiwa, et al., "The Biphasic Opening of the Blood-Brain Barrier to Proteins Following Temporary Middle Cerebral Artery Occlusion," Acta Neuropathologica, vol. 68: 122-129 (1985).
Lee, et al., "Abiotrophia defectiva Bleb-associated Endophthalmitis Confirmed with 16S Ribosomal RNA Sequencing," Journal of Glaucoma, vol. 24(1): 87-88 (2015).
Lin, et al., "NUP98-HOXD13 transgenic mice develop a highly penetrant, severe myelodysplastic syndrome that progresses to acute leukemia," Blood, vol. 106(1): 287-295 (2005).
Linsenmeier, et al., "Retinal Hypoxia in Long-Term Diabetic Cats," Investigative Ophthalmology & Visual Science, vol. 39(9): 1647-1657 (1998).
Malcovati, et al., "Clinical significance of SF3B1 mutations in myelodysplastic syndromes and myelodysplastic/myeloproliferative neoplasms," Blood, vol. 118(24): 6239-6246 (2011).
Marmor, M., "Mechanisms of fluid accumulation in retinal edema," Documenta Ophthalmologica, vol. 97: 239-249 (1999).
Marumo, et al., "Significance of Nitric Oxide and Peroxynitrite in Permeability Changes of the Retinal Microvascular Endothelial Cell Monolayer Induced by Vascular Endothelial Growth Factor," Journal of Vascular Research, vol. 36: 510-515 (1999).
Miyake, et al., "Prostaglandins and Cystoid Macular Edema," Survey of Ophthalmology, vol. 47(Suppl. 1): S203-S218 (2002).
Mizener, et al., "Ocular Ischemic Syndrome," Ophthalmology, vol. 104(5): 859-864 (1997).
Muller, et al., "Free Radicals in Rabbit Retina Under Ocular Hyperpressure and Functional Consequences," Experimental Eye Research, vol. 64: 637-643 (1997).
Osborne, et al., "Retinal ischemia: mechanisms of damage and potential therapeutic strategies," Progress in Retinal and Eye Research, vol. 23: 91-147 (2004).
Papaemmanuil, et al., "Somatic SF3B1 Mutation in Myelodysplasia with Ring Sideroblasts," The New England Journal of Medicine, vol. 365(15): 1384-1395 (2011).
Phelps, D., "Retinopathy of Prematurity: History, Classification, and Pathophysiology," NeoReviews, vol. 2(7): e153-e166 (2001).
Poulaki, et al., "Activin A in the Regulation of Corneal Neovascularization and Vascular Endothelial Growth Factor Expression," American Journal of Pathology, vol. 164(4): 1293-1302 (2004).
Prass, et al., "Hypoxia-Induced Stroke Tolerance in the Mouse Is Mediated by Erythropoietin," Stroke, vol. 34: 1981-1986 (2003).
Reichenbach, et al., "Müller cells as players in retinal degeneration and edema," Graefe's Archive for Clinical and Experimental Ophthalmology, vol. 245: 627-636 (2007).
Ristori, et al., "Role of the Adrenergic System in a Mouse Model of Oxygen-Induced Retinopathy: Antiangiogenic Effects of β-Adrenoreceptor Bloackade," Investigative Ophthalmology & Visual Science, vol. 52(1): 155-170 (2011).
Rund, et al., "Medical Progress β-Thalassemia," The New England Journal of Medicine, vol. 353(11): 1135-1146 (2005).
Sapitro, et al., "Suppression of transforming growth factor-β effects in rabbit subconjunctival fibroblasts by activin receptor-like kinase 5 inhibitor," Molecular Vision, vol. 16: 1880-1892 (2010).
Semeraro, et al., "Diabetic Retinopathy: Vascular and Inflammatory Disease," Journal of Diabetes Research, vol. 2015: 1-16 (2015).
Setty, et al., "Role of erythrocyte phosphatidylserine in sickle red cell-endothelial adhesion," Blood, vol. 99(5): 1564-1571 (2002).
Shelhamer, et al., "Takayasu's Arteritis and Its Therapy," Annals of Internal Medicine, vol. 103: 121-126 (1985).
Shin, et al., "Diabetes and Retinal Vascular Dysfunction," Journal of Ophthalmic and Vision Research, vol. 9(3): 362-373 (2014).
Steinberg, M., "Management of Sickle Cell Disease," The New England Journal of Medicine, vol. 340(13): 1021-1030 (1999).
Sucher, et al., "Molecular Basis of Glutamate Toxicity in Retinal Ganglion Cells," Vision Research, vol. 37(24): 3483-3493 (1997).
Suk-Yee, et al., "Hypoxia-Induced Oxidative Stress in Ischemic Retinopathy," Oxidative Medicine and Cellular Longevity, vol. 2012: 1-10 (2012).
Suragani, et al., "Transforming growth factor-β superfamily ligand trap ACE-536 corrects anemia by promoting late-stage erythropoiesis," Nature Medicine, vol. 20(4): 408-414 (2014).
Szabo, et al., "Direct Measurement of Free Radicals in Ischemic/Reperfused Diabetic Rat Retina," Clinical Neuroscience, vol. 4: 240-245 (1997).
Tezel, et al., "The immune system and glaucoma," Current Opinion in Ophthalmology, vol. 15: 80-84 (2004).
The Cancer Genome Atlas Network, "Comprehensive molecular portraits of human breast tumours," Nature, vol. 490: 61-70 (2012).
Tinjust, et al., "Neuroretinal Function During Mild Systemic Hypoxia," Aviation, Space, and Environmental Medicine, vol. 73(12): 1189-1194 (2002).
Tothova, et al., "New Strategies in Myelodysplastic Syndromes: Application of molecular diagnostics to clinical practice," Clinical Cancer Research, vol. 19(7): 1637-1643 (2013).
Tso, M., "Pathology of Cystoid Macular Edema," Ophthalmology, vol. 89(8): 902-915 (1982).
Van Dam, P., "Oxidative stress and diabetic neuropathy: pathophysiological mechanisms and treatment perspectives," Diabetes/Metabolism Research and Reviews, vol. 18: 176-184 (2002).
Vichinsky, E., "Changing Patterns of Thalassemia Worldwide," Annals of the New York Academy of Sciences, vol. 1054: 18-24 (2005).
Walton, et al., "Retinal vasculitis," Current Opinion in Ophthalmology, vol. 14: 413-419 (2003).
Wang, et al., "SF3B1 and Other Novel Cancer Genes in Chronic Lymphocytic Leukemia," The New England Journal of Medicine, vol. 365(26): 2497-2506 (2011).
Wax, et al., "Neurobiology of Glaucomatous Optic Neuropathy," Molecular Neurobiology, vol. 26: 45-55 (2002).
Webb, et al., "The Development and Application of Small Molecule Modulators of SF3b as Therapeutic Agents for Cancer," Drug Discovery Today, vol. 18(1-2): 43-49 (2013).
Yanoff, et al., "Pathology of Human Cystoid Macular Edema," Survey of Ophthalmology, vol. 28: 505-511 (1984).
Zhou, et al., "Inhibition of the TGF-β receptor I kinase promotes hematopoiesis in MDS," Blood, vol. 112(8): 3434-3443 (2008).

\* cited by examiner

```
ActRIIa    ILGRSETQEC  LFFNANWEKD  RTNQTGVEPC  YGDKDKRRHC  FATWKNISGS
ActRIIb    GRGEAETREC  IYYNANWELE  RTNQSGLERC  EGEQDKRLHC  YASWRNSSGT

IEIVKQGCWL  DDINCYDRTD  CVEKKDSPEV  YFCCCEGNMC  NEKFSYFPEM
           IELVKKGCWL  DDFNCYDRQE  CVATEENPQV  YFCCCEGNFC  NERFTHLPEA

EVTQPTSNPV  TPKPPT
           GGPEVTYEPP  PTAPT
```

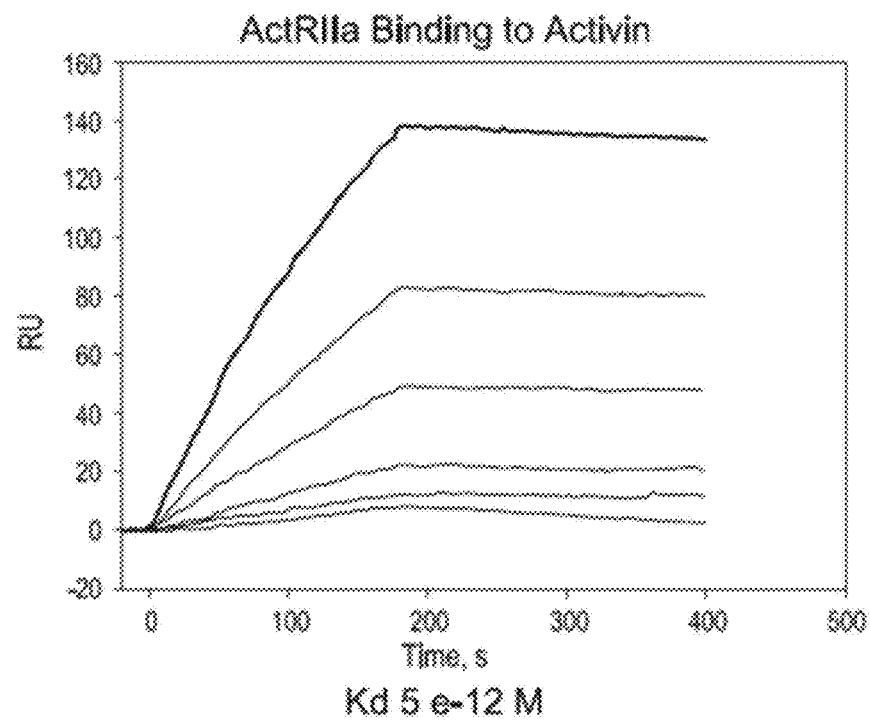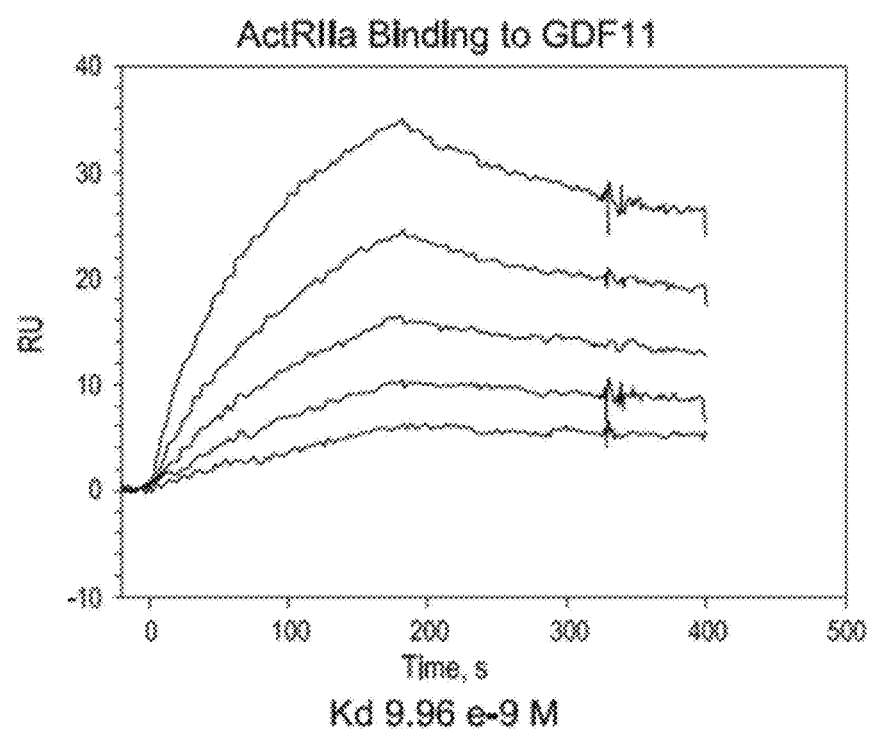
FIGURE 4

1    MDAMKRGLCC VLLLCGAVFV SPGASCRGEA ETRECIYYNA NWELERTNQS

51   GLERCEGEQD KRLHCYASWR NSSGTIELVK KGCWLDDFNC YDRQECVATE

101  ENPQVYFCCC EGNFCNERFT HLPEAGGPEV TYEPPPTAPT GGGTHTCPPC

151  PAPELLGGPS VFLFPPKPKD TLMISRTPEV TCVVVDVSHE DPEVKFNWYV

201  DGVEVHNAKT KPREEQYNST YRVVSVLTVL HQDWLNGKEY KCKVSNKALP

251  APIEKTISKA KGQPREPQVY TLPPSREEMT KNQVSLTCLV KGFYPSDIAV

301  EWESNGQPEN NYKTTPPVLD SDGSFFLYSK LTVDKSRWQQ GNVFSCSVMH

351  EALHNHYTQK SLSLSPGK (SEQ ID NO:46)

FIGURE 5

```
  1  ATGGATGCAA TGAAGAGAGG GCTCTGCTGT GTGCTGCTGC TGTGTGGAGC
     TACCTACGTT ACTTCTCTCC CGAGACGACA CACGACGACG ACACACCTCG

51  AGTCTTCGTT TCGCCCGGCG CCTCTGGGCG TGGGGAGGCT GAGACACGGG
     TCAGAAGCAA AGCGGGCCGC GGAGACCCGC ACCCCTCCGA CTCTGTGCCC

101  AGTGCATCTA CTACAACGCC AACTGGAGC TGGAGCGCAC CAACCAGAGC
     TCACGTAGAT GATGTTGCGG TTGACCCTCG ACCTCGCGTG GTTGGTCTCG

151  GGCCTGGAGC GCTGCGAAGG CGAGCAGGAC AAGCGGCTGC ACTGCTACGC
     CCGGACCTCG CGACGCTTCC GCTCGTCCTG TTCGCCGACG TGACGATGCG

201  CTCCTGGCGC AACAGCTCTG GCACCATCGA GCTCGTGAAG AAGGGCTGCT
     GAGGACCGCG TTGTCGAGAC CGTGGTAGCT CGAGCACTTC TTCCCGACGA

251  GGGATGATGA CTTCAACTGC TACGATAGGC AGGAGTGTGT GGCCACTGAG
     CCCTACTACT GAAGTTGACG ATGCTATCCG TCCTCACACA CCGGTGACTC

301  GAGAACCCCC AGGTGTACTT CTGCTGCTGT GAAGGCAACT TCTGCAACGA
     CTCTTGGGGG TCCACATGAA GACGACGACA CTTCCGTTGA AGACGTTGCT

351  GCGCTTCACT CATTTGCCAG AGGCTGGGGG CCCGGAAGTC ACGTACGAGC
     CGCGAAGTGA GTAAACGGTC TCCGACCCCC GGGCCTTCAG TGCATGCTCG

401  CACCCCCGAC AGCCCCCACC GGTGGTGGAA CTCACACATG CCCACCGTGC
     GTGGGGGCTG TCGGGGGTGG CCACCACCTT GAGTGTGTAC GGGTGGCACG

451  CCAGCACCTG AACTCCTGGG GGGACCGTCA GTCTTCCTCT TCCCCCCAAA
     GGTCGTGGAC TTGAGGACCC CCCTGGCAGT CAGAAGGAGA AGGGGGGTTT

501  ACCCAAGGAC ACCCTCATGA TCTCCCGGAC CCCTGAGGTC ACATGCGTGG
     TGGGTTCCTG TGGGAGTACT AGAGGGCCTG GGGACTCCAG TGTACGCACC

551  TGGTGGACGT GAGCCACGAA GACCCTGAGG TCAAGTTCAA CTGGTACGTG
     ACCACCTGCA CTCGGTGCTT CTGGGACTCC AGTTCAAGTT GACCATGCAC

601  GACGGCGTGG AGGTGCATAA TGCCAAGACA AAGCCGCGGG AGGAGCAGTA
     CTGCCGCACC TCCACGTATT ACGGTTCTGT TTCGGCGCCC TCCTCGTCAT

651  CAACAGCACG TACCGTGTGG TCAGCGTCCT CACCGTCCTG CACCAGGACT
     GTTGTCGTGC ATGGCACACC AGTCGCAGGA GTGGCAGGAC GTGGTCCTGA

701  GGCTGAATGG CAAGGAGTAC AAGTGCAAGG TCTCCAACAA AGCCCTCCCA
     CCGACTTACC GTTCCTCATG TTCACGTTCC AGAGGTTGTT TCGGGAGGGT

751  GCCCCCATCG AGAAAACCAT CTCCAAAGCC AAAGGGCAGC CCCGAGAACC
     CGGGGGTAGC TCTTTTGGTA GAGGTTTCGG TTTCCCGTCG GGGCTCTTGG
```

FIGURE 6A

```
 801   ACAGGTGTAC ACCCTGCCCC CATCCCGGGA GGAGATGACC AAGAACCAGG
       TGTCCACATG TGGGACGGGG GTAGGGCCCT CCTCTACTGG TTCTTGGTCC

851   TCAGCCTGAC CTGCCTGGTC AAAGGCTTCT ATCCCAGCGA CATCGCCGTG
       AGTCGGACTG GACGGACCAG TTTCCGAAGA TAGGGTCGCT GTAGCGGCAC

901   GAGTGGGAGA GCAATGGGCA GCCGGAGAAC AACTACAAGA CCACGCCTCC
       CTCACCCTCT CGTTACCCGT CGGCCTCTTG TTGATGTTCT GGTGCGGAGG

951   CGTGCTGGAC TCCGACGGCT CCTTCTTCCT CTATAGCAAG CTCACCGTGG
       GCACGACCTG AGGCTGCCGA GGAAGAAGGA GATATCGTTC GAGTGGCACC

1001   ACAAGAGCAG GTGGCAGCAG GGGAACGTCT TCTCATGCTC CGTGATGCAT
       TGTTCTCGTC CACCGTCGTC CCCTTGCAGA AGAGTACGAG GCACTACGTA

1051   GAGGCTCTGC ACAACCACTA CACGCAGAAG AGCCTCTCCC TGTCCCCGGG
       CTCCGAGACG TGTTGGTGAT GTGCGTCTTC TCGGAGAGGG ACAGGGGCCC

1101   TAAATGA (SEQ ID NO:86)
       ATTTACT (SEQ ID NO:60)
```

FIGURE 6B

```
  1  MDAMKRGLCC VLLLCGAVFV SPGAA TREC IYYNANWELE RTNQSGLERC
 51  EGEQDKRLHC YASWRNSSGT IELVKKGCW  DDFNCYDRQE CVATEENPQV
101  YFCCCEGNFC NERFTHLPEA GGPEVTYEPP PTGGGTHTCP PCPAPELLGG
151  PSVFLFPPKP KDTLMISRTP EVTCVVVDVS HEDPEVKFNW YVDGVEVHNA
201  KTKPREEQYN STYRVVSVLT VLHQDWLNGK EYKCKVSNKA LPAPIEKTIS
251  KAKGQPREPQ VYTLPPSREE MTKNQVSLTC LVKGFYPSDI AVEWESNGQP
301  ENNYKTTPPV LDSDGSFFLY SKLTVDKSRW QQGNVFSCSV MHEALHNHYT
351  QKSLSLSPGK (SEQ ID NO: 61)
```

FIGURE 7

```
                                                      E   T   R   E   I   Y   Y
  1  ATGGATGCAA TGAAGAGAGG GCTCTGCTGT GTGCTGCTGC TGTGTGGAGC
     TACCTACGTT ACTTCTCTCC CGAGACGACA CACGACGACG ACACACCTCG

E   T   R   E   C   I   Y   Y
 51  AGTCTTCGTT TCGCCCGGCG CCGCTGAGAC ACGGGAGTGC ATCTACTACA
     TCAGAAGCAA AGCGGGCCGC GGCGACTCTG TGCCCTCACG TAGATGATGT

N   A   N   W   E   L   E   R   T   N   Q   S   G   L   E   R   C
101  ACGCCAACTG GGAGCTGGAG CGCACCAACC AGAGCGGCCT GGAGCGCTGC
     TGCGGTTGAC CCTCGACCTC GCGTGGTTGG TCTCGCCGGA CCTCGCGACG

E   G   E   Q   D   K   R   L   H   C   Y   A   S   W   R   N   S
151  GAAGGCGAGC AGGACAAGCG GCTGCACTGC TACGCCTCCT GGCGCAACAG
     CTTCCGCTCG TCCTGTTCGC CGACGTGACG ATGCGGAGGA CCGCGTTGTC

S   G   T   I   E   L   V   K   G   C   W   D   D   D   F
201  CTCTGGCACC ATCGAGCTCG TGAAGAAGGG CTGCTGGGAC GATGACTTCA
     GAGACCGTGG TAGCTCGAGC ACTTCTTCCC GACGACCCTG CTACTGAAGT

N   C   Y   D   R   Q   E   C   V   A   T   E   E   N   P   Q   V
251  ACTGCTACGA TAGGCAGGAG TGTGTGGCCA CTGAGGAGAA CCCCCAGGTG
     TGACGATGCT ATCCGTCCTC ACACACCGGT GACTCCTCTT GGGGGTCCAC

Y   F   C   C   E   G   N   F   C   N   E   R   F   T   H   L
301  TACTTCTGCT GCTGTGAAGG CAACTTCTGC AACGAGCGCT TCACTCATTT
     ATGAAGACGA CGACACTTCC GTTGAAGACG TTGCTCGCGA AGTGAGTAAA

P   E   A   G   G   P   E   V   T   Y   E   P   P   T
351  GCCAGAGGCT GGGGGCCCGG AAGTCACGTA CGAGCCACCC CCGACAGGTG
     CGGTCTCCGA CCCCCGGGCC TTCAGTGCAT GCTCGGTGGG GGCTGTCCAC

401  GTGGAACTCA CACATGCCCA CCGTGCCCAG CACCTGAACT CCTGGGGGGA
     CACCTTGAGT GTGTACGGGT GGCACGGGTC GTGGACTTGA GGACCCCCCT

451  CCGTCAGTCT TCCTCTTCCC CCCAAAACCC AAGGACACCC TCATGATCTC
     GGCAGTCAGA AGGAGAAGGG GGGTTTTGGG TTCCTGTGGG AGTACTAGAG

501  CCGGACCCCT GAGGTCACAT GCGTGGTGGT GGACGTGAGC CACGAAGACC
     GGCCTGGGGA CTCCAGTGTA CGCACCACCA CCTGCACTCG GTGCTTCTGG

551  CTGAGGTCAA GTTCAACTGG TACGTGGACG GCGTGGAGGT GCATAATGCC
     GACTCCAGTT CAAGTTGACC ATGCACCTGC CGCACCTCCA CGTATTACGG
```

FIGURE 8A

```
 601   AAGACAAAGC CGCGGGAGGA GCAGTACAAC AGCACGTACC GTGTGGTCAG
       TTCTGTTTCG GCGCCCTCCT CGTCATGTTG TCGTGCATGG CACACCAGTC

651   CGTCCTCACC GTCCTGCACC AGGACTGGCT GAATGGCAAG GAGTACAAGT
       GCAGGAGTGG CAGGACGTGG TCCTGACCGA CTTACCGTTC CTCATGTTCA

701   GCAAGGTCTC CAACAAAGCC CTCCCAGCCC CCATCGAGAA AACCATCTCC
       CGTTCCAGAG GTTGTTTCGG GAGGGTCGGG GGTAGCTCTT TTGGTAGAGG

751   AAAGCCAAAG GGCAGCCCCG AGAACCACAG GTGTACACCC TGCCCCCATC
       TTTCGGTTTC CCGTCGGGGC TCTTGGTGTC CACATGTGGG ACGGGGGTAG

801   CCGGGAGGAG ATGACCAAGA ACCAGGTCAG CCTGACCTGC CTGGTCAAAG
       GGCCCTCCTC TACTGGTTCT TGGTCCAGTC GGACTGGACG GACCAGTTTC

851   GCTTCTATCC CAGCGACATC GCCGTGGAGT GGGAGAGCAA TGGGCAGCCG
       CGAAGATAGG GTCGCTGTAG CGGCACCTCA CCCTCTCGTT ACCCGTCGGC

901   GAGAACAACT ACAAGACCAC GCCTCCCGTG CTGGACTCCG ACGGCTCCTT
       CTCTTGTTGA TGTTCTGGTG CGGAGGGCAC GACCTGAGGC TGCCGAGGAA

951   CTTCCTCTAT AGCAAGCTCA CCGTGGACAA GAGCAGGTGG CAGCAGGGGA
       GAAGGAGATA TCGTTCGAGT GGCACCTGTT CTCGTCCACC GTCGTCCCCT

1001   ACGTCTTCTC ATGCTCCGTG ATGCATGAGG CTCTGCACAA CCACTACACG
       TGCAGAAGAG TACGAGGCAC TACGTACTCC GAGACGTGTT GGTGATGTGC

1051   CAGAAGAGCC TCTCCCTGTC CCCGGGTAAA TGA  (SEQ ID NO: 62)
       GTCTTCTCGG AGAGGGACAG GGGCCCATTT ACT  (SEQ ID NO: 63)
```

FIGURE 8B

```
  1    XTRECIYYNA NWELERTNQS GLERCEGEQD KRLHCYASWR NSSGTIELVK

51    KGCWXDDFNC YDRQECVATE ENPQVYFCCC EGNFCNERFT HLPEAGGPEV

101    TYEPPPTGGG THTCPPCPAP ELLGGPSVFL FPPKPKDTLM ISRTPEVTCV

151    VVDVSHEDPE VKFNWYVDGV EVHNAKTKPR EEQYNSTYRV VSVLTVLHQD

201    WLNGKEYKCK VSNKALPAPI EKTISKAKGQ PREPQVYTLP PSREEMTKNQ

251    VSLTCLVKGF YPSDIAVEWE SNGQPENNYK TTPPVLDSDG SFFLYSKLTV

301    DKSRWQQGNV FSCSVMHEAL HNHYTQKSLS LSPGK (SEQ ID NO: 64)
```

FIGURE 9

1    $TRECIYYNA NWELERTNQS GLERCEGEQD KRLHCYASWR NSSGTIELVK

51   KGCW$DDFNC YDRQECVATE ENPQVYFCCC EGNFCNERFT HLPEAGGPEV

101  TYEPPPT  (SEQ ID NO: 65)

FIGURE 10

```
  1   ATGGATGCAA TGAAGAGAGG GCTCTGCTGT GTGCTGCTGC TGTGTGGAGC
      TACCTACGTT ACTTCTCTCC CGAGACGACA CACGACGACG ACACACCTCG

E   T   R   E   C   I   Y   Y
 51   AGTCTTCGTT TCGCCCGGCG CCGCCGAAAC CCGCGAATGC ATCTACTACA
      TCAGAAGCAA AGCGGGCCGC GGCGGCTTTG GGCGCTTACA TAGATGATGT

N   A   N   W   E   L   E   R   T   N   Q   S   G   L   E   R   C
101   ATGCTAATTG GGAACTCGAA CGCACAAACC AATCCGGCCT CGAACGCTGC
      TACGATTAAC CCTTGAGCTT GCCTGCTTGG TTAGGCCGGA GCTTGCCACA

E   G   E   Q   D   K   R   L   H   C   Y   A   S   W   R   N   S
151   GAGGGCGAAC AGGACAAACG CCTCCACTGC TACGCCTCCT GGAGGAACTC
      CTCCCGCTTG TCCTGTTTGC GGAGGTGACG ATGCGGAGGA CCTCCTTGAG

S   G   T   I   E   L   V   K   G   C   W   D   D   D   F
201   CTCGGGCACG ATCGAACTCG TCAAGAAGGG CTGCTGGGAC GACGACTTCA
      GAGCCCGTGC TAGCTTGAGC AGTTCTTCCC GACGACCCTG CTGCTGAAGT

N   C   Y   D   R   Q   E   C   V   A   T   E   N   P   Q   V
251   ATTGCTACGA CCGGCAGGAG TGTGTCGCCA CCGAGGAGAA TCCCCAGGTC
      TAACGATGCT GGCCGTCCTC ACACAGCGGT GGCTCCTCTT AGGGGTCCAG

Y   F   C   C   E   G   N   F   C   N   E   R   F   T   H   L
301   TACTTCTGCT GCGAGGAGGG GAATTTCTGC AACGAGCGCT TCACCCACCT
      ATGAAGACGA CGCTCCTCCC CTTAAAGACG TTGCTCGCGA AGTGGGTGGA

P   E   A   G   G   P   E   V   T   Y   E   P   P   P   T
351   CCCCGAAGCG GGCGGGCCCG AGGTGACGTA CGAGCCCCCG CCGACGGGTG
      GGGGCTTCGC CCGCCCGGGC TCCACTGCAT GCTCGGGGGC GGCTGCCCAC

401   GTGGAACTCA CACATGCCCA CCGTGCCCAG CACCTGAACT CCTGGGGGGA
      CACCTTGAGT GTGTACGGGT GGCACGGGTC GTGGACTTGA GGACCCCCCT

451   CCGTCAGTCT TCCTCTTCCC CCCAAAACCC AAGGACACCC TCATGATCTC
      GGCAGTCAGA AGGAGAAGGG GGGTTTTGGG TTCCTGTGGG AGTACTAGAG

501   CCGGACCCCT GAGGTCACAT GCGTGGTGGT GGACGTGAGC CACGAAGACC
      GGCCTGGGGA CTCCAGTGTA CGCACCACCA CCTGCACTCG GTGCTTCTGG

551   CTGAGGTCAA GTTCAACTGG TACGTGGACG GCGTGGAGGT GCATAATGCC
      GACTCCAGTT CAAGTTGACC ATGCACCTGC CGCACCTCCA CGTATTACGG

601   AAGACAAAGC CGCGGGAGGA GCAGTACAAC AGCACGTACC GTGTGGTCAG
      TTCTGTTTCG GCGCCCTCCT CGTCATGTTG TCGTGCATGG CACACCAGTC

651   CGTCCTCACC GTCCTGCACC AGGACTGGCT GAATGGCAAG GAGTACAAGT
      GCAGGAGTGG CAGGACGTGG TCCTGACCGA CTTACCGTTC CTCATGTTCA
```

FIGURE 11A

```
 701   GCAAGGTCTC CAACAAAGCC CTCCCAGCCC CCATCGAGAA AACCATCTCC
       CGTTCCAGAG GTTGTTTCGG GAGGGTCGGG GGTAGCTCTT TTGGTAGAGG

751   AAAGCCAAAG GGCAGCCCCG AGAACCACAG GTGTACACCC TGCCCCCATC
       TTTCGGTTTC CCGTCGGGGC TCTTGGTGTC CACATGTGGG ACGGGGGTAG

801   CCGGGAGGAG ATGACCAAGA ACCAGGTCAG CCTGACCTGC CTGGTCAAAG
       GGCCCTCCTC TACTGGTTCT TGGTCCAGTC GGACTGGACG GACCAGTTTC

851   GCTTCTATCC CAGCGACATC GCCGTGGAGT GGGAGAGCAA TGGGCAGCCG
       CGAAGATAGG GTCGCTGTAG CGGCACCTCA CCCTCTCGTT ACCCGTCGGC

901   GAGAACAACT ACAAGACCAC GCCTCCCGTG CTGGACTCCG ACGGCTCCTT
       CTCTTGTTGA TGTTCTGGTG CGGAGGGCAC GACCTGAGGC TGCCGAGGAA

951   CTTCCTCTAT AGCAAGCTCA CCGTGGACAA GAGCAGGTGG CAGCAGGGGA
       GAAGGAGATA TCGTTCGAGT GGCACCTGTT CTCGTCCACC GTCGTCCCCT

1001   ACGTCTTCTC ATGCTCCGTG ATGCATGAGG CTCTGCACAA CCACTACACG
       TGCAGAAGAG TACGAGGCAC TACGTACTCC GAGACGTGTT GGTGATGTGC

1051   CAGAAGAGCC TCTCCCTGTC CCCGGGTAAA TGA (SEQ ID NO: 66)
       GTCTTCTCGG AGAGGACAG GGGCCCATTT ACT (SEQ ID NO: 67)
```

FIGURE 11B

```
GAAAC CCGCGAATGT ATTTATTACA ATGCTAATTG GGAACTTGAA CGGACGAACC
AATCCGGCCT CGAACGGTGT GACGGCGAAC AGGATAAACG CCTCCATTGC TAGCCTCCT
GGAGGAACTC CTCCGGCACT ATTGAACTGG TCAAGAAGGG CTGCTGGGAC GACGATTCA
ATTGTTATGA CCGCCAGGAT TGTGTCGCCA CCGATGAGAA TCCCCAGGTC TATTTCTGTT
GTTGCGAGGG GAATTTCTGT AATGAACGGT TTACCCACCT CCCGGAAGCC GGCGGCCCCG
ACGTCACCTA TGAACCCCCC CCCACC    (SEQ ID NO: 68)
```

```
IgG1    --------THTCPPCPAPELLGGPSVFLFPPKPKDTLMISRTPEVTCVVVDVSHEDPEVKF  53
IgG4    ---ESKYGPPCPSCPAPEFLGGPSVFLFPPKPKDTLMISRTPEVTCVVVDVSQEDPEVQF  57
IgG2    --------VECPPCPAPPVAG-PSVFLFPPKPKDTLMISRTPEVTCVVVDVSHEDPEVQF  51
IgG3    EPKSCDTPPPCPRCPAPELLGGPSVFLFPPKPKDTLMISRTPEVTCVVVDVSHEDPEVQF  60
                  ** ****   *  ********************************:*****:*

IgG1    NWYVDGVEVHNAKTKPREEQYNSTYRVVSVLTVLHQDWLNGKEYKCKVSNKALPAPIEKT  113
IgG4    NWYVDGVEVHNAKTKPREEQFNSTYRVVSVLTVLHQDWLNGKEYKCKVSNKGLPSSIEKT  117
IgG2    NWYVDGVEVHNAKTKPREEQFNSTFRVVSVLTVVHQDWLNGKEYKCKVSNKGLPAPIEKT  111
IgG3    KWYVDGVEVHNAKTKPREEQYNSTFRVVSVLTVLHQDWLNGKEYKCKVSNKALPAPIEKT  120
        :******************:***:***********************.**:.****

IgG1    ISKAKGQPREPQVYTLPPSREEMTKNQVSLTCLVKGFYPSDIAVEWESNGQPENNYKTTP  173
IgG4    ISKAKGQPREPQVYTLPPSQEEMTKNQVSLTCLVKGFYPSDIAVEWESNGQPENNYKTTP  177
IgG2    ISKTKGQPREPQVYTLPPSREEMTKNQVSLTCLVKGFYPSDIAVEWESNGQPENNYKTTP  171
IgG3    ISKTKGQPREPQVYTLPPSREEMTKNQVSLTCLVKGFYPSDIAVEWESSGQPENNYNTTP  180
        ***:**************:*****************************.*******:***

IgG1    PVLDSDGSFFLYSKLTVDKSRWQQGNVFSCSVMHEALHNHYTQKSLSLSPGK  225
IgG4    PVLDSDGSFFLYSRLTVDKSRWQEGNVFSCSVMHEALHNHYTQKSLSLSLGK  229
IgG2    PMLDSDGSFFLYSKLTVDKSRWQQGNVFSCSVMHEALHNHYTQKSLSLSPGK  223
IgG3    PMLDSDGSFFLYSKLTVDKSRWQQGNIFSCSVMHEALHNRFTQKSLSLSPGK  232
        *:***********:*********:**:***********::******* **
```

FIGURE 15

```
  1  MDAMKRGLCC VLLLCGAVFV SPGAA▓TREC IYYNANWELE RTNQSGLERC
 51  EGEQDKRLHC YASWRNSSGT IELVKKGCWL DDFNCYDRQE CVATEENPQV
101  YFCCCEGNFC NERFTHLPEA GGPEVTYEPP PTGGGTHTCP PCPAPELLGG
151  PSVFLFPPKP KDTLMISRTP EVTCVVVDVS HEDPEVKFNW YVDGVEVHNA
201  KTKPREEQYN STYRVVSVLT VLHQDWLNGK EYKCKVSNKA LPAPIEKTIS
251  KAKGQPREPQ VYTLPPSREE MTKNQVSLTC LVKGFYPSDI AVEWESNGQP
301  ENNYKTTPPV LDSDGSFFLY SKLTVDKSRW QQGNVFSCSV MHEALHNHYT
351  QKSLSLSPGK (SEQ ID NO: 79)
```

FIGURE 16

```
                                    A  E  T  R  E  C  I  Y  Y
  1    ATGGATGCAA TGAAGAGAGG GCTCTGCTGT GTGCTGCTGC TGTGTGGAGC
       TACCTACGTT ACTTCTCTCC CGAGACGACA CACGACGACG ACACACCTCG

A  E  T  R  E  C  I  Y  Y
 51    AGTCTTCGTT TCGCCCGGCG CCGCTGAGAC ACGGGAGTGC ATCTACTACA
       TCAGAAGCAA AGCGGGCCGC GGCGACTCTG TGCCCTCACG TAGATGATGT

N  A  N  W  E  L  E  R  T  N  Q  S  G  L  E  R  C
101    ACGCCAACTG GGAGCTGGAG CGCACCAACC AGAGCGGCCT GGAGCGCTGC
       TGCGGTTGAC CCTCGACCTC GCGTGGTTGG TCTCGCCGGA CCTCGCGACG

E  G  E  Q  D  K  R  L  C  Y  A  S  W  R  N  S
151    GAAGGCGAGC AGGACAAGCG GCTGCACTGC TACGCCTCCT GGCGCAACAG
       CTTCCGCTCG TCCTGTTCGC CGACGTGACG ATGCGGAGGA CCGCGTTGTC

S  G  T  I  E  L  V  K  K  G  C  W  L  D  D  F
201    CTCTGGCACC ATCGAGCTCG TGAAGAAGGG CTGCTGGCTA GATGACTTCA
       GAGACCGTGG TAGCTCGAGC ACTTCTTCCC GACGACCGAT CTACTGAAGT

N  C  Y  D  R  Q  E  C  V  A  T  E  E  N  P  Q  V
251    ACTGCTACGA TAGGCAGGAG TGTGTGGCCA CTGAGGAGAA CCCCCAGGTG
       TGACGATGCT ATCCGTCCTC ACACACCGGT GACTCCTCTT GGGGGTCCAC

Y  F  C  C  C  E  G  N  F  C  N  E  R  F  T  H  L
301    TACTTCTGCT GCTGTGAAGG CAACTTCTGC AACGAGCGCT TCACTCATTT
       ATGAAGACGA CGACACTTCC GTTGAAGACG TTGCTCGCGA AGTGAGTAAA

P  E  A  G  G  P  E  V  T  Y  E  P  P  P  T
351    GCCAGAGGCT GGGGGCCCGG AAGTCACGTA CGAGCCACCC CCGACAGGTG
       CGGTCTCCGA CCCCCGGGCC TTCAGTGCAT GCTCGGTGGG GGCTGTCCAC

401    GTGGAACTCA CACATGCCCA CCGTGCCCAG CACCTGAACT CCTGGGGGGA
       CACCTTGAGT GTGTACGGGT GGCACGGGTC GTGGACTTGA GGACCCCCCT

451    CCGTCAGTCT TCCTCTTCCC CCCAAAACCC AAGGACACCC TCATGATCTC
       GGCAGTCAGA AGGAGAAGGG GGGTTTTGGG TTCCTGTGGG AGTACTAGAG

501    CCGGACCCCT GAGGTCACAT GCGTGGTGGT GGACGTGAGC CACGAAGACC
       GGCCTGGGGA CTCCAGTGTA CGCACCACCA CCTGCACTCG GTGCTTCTGG

551    CTGAGGTCAA GTTCAACTGG TACGTGGACG GCGTGGAGGT GCATAATGCC
       GACTCCAGTT CAAGTTGACC ATGCACCTGC CGCACCTCCA CGTATTACGG

601    AAGACAAAGC CGCGGGAGGA GCAGTACAAC AGCACGTACC GTGTGGTCAG
       TTCTGTTTCG GCGCCCTCCT CGTCATGTTG TCGTGCATGG CACACCAGTC

651    CGTCCTCACC GTCCTGCACC AGGACTGGCT GAATGGCAAG GAGTACAAGT
       GCAGGAGTGG CAGGACGTGG TCCTGACCGA CTTACCGTTC CTCATGTTCA

701    GCAAGGTCTC CAACAAAGCC CTCCCAGCCC CCATCGAGAA AACCATCTCC
       CGTTCCAGAG GTTGTTTCGG GAGGGTCGGG GGTAGCTCTT TTGGTAGAGG

751    AAAGCCAAAG GGCAGCCCCG AGAACCACAG GTGTACACCC TGCCCCCATC
       TTTCGGTTTC CCGTCGGGGC TCTTGGTGTC CACATGTGGG ACGGGGGTAG
```

FIGURE 17A

```
 801    CCGGGAGGAG ATGACCAAGA ACCAGGTCAG CCTGACCTGC CTGGTCAAAG
        GGCCCTCCTC TACTGGTTCT TGGTCCAGTC GGACTGGACG GACCAGTTTC

851    GCTTCTATCC CAGCGACATC GCCGTGGAGT GGGAGAGCAA TGGGCAGCCG
        CGAAGATAGG GTCGCTGTAG CGGCACCTCA CCCTCTCGTT ACCCGTCGGC

901    GAGAACAACT ACAAGACCAC GCCTCCCGTG CTGGACTCCG ACGGCTCCTT
        CTCTTGTTGA TGTTCTGGTG CGGAGGGCAC GACCTGAGGC TGCCGAGGAA

951    CTTCCTCTAT AGCAAGCTCA CCGTGGACAA GAGCAGGTGG CAGCAGGGGA
        GAAGGAGATA TCGTTCGAGT GGCACCTGTT CTCGTCCACC GTCGTCCCCT

1001    ACGTCTTCTC ATGCTCCGTG ATGCATGAGG CTCTGCACAA CCACTACACG
        TGCAGAAGAG TACGAGGCAC TACGTACTCC GAGACGTGTT GGTGATGTGC

1051    CAGAAGAGCC TCTCCCTGTC CCCGGGTAAA TGA (SEQ ID NO: 80)
        GTCTTCTCGG AGAGGGACAG GGGCCCATTT ACT (SEQ ID NO: 81)
```

FIGURE 17B

```
                                    A   E   T   R   E   C   I   Y   Y
  1  ATGGATGCAA TGAAGAGAGG GCTCTGCTGT GTGCTGCTGC TGTGTGGAGC
     TACCTACGTT ACTTCTCTCC CGAGACGACA CACGACGACG ACACACCTCG

A   E   T   R   E   C   I   Y   Y
 51  AGTCTTCGTT TCGCCCGGCG CCGCGGAAAC CCGGGAATGT ATTTATTACA
     TCAGAAGCAA AGCGGGCCGC GGCGGCTTTG GGCGCTTACA TAAATAATGT

N   A   N   W   E   L   E   R   T   N   Q   S   G   L   E   R   C
101  AATGCTAATTG GGAACTCGAA CGGACGAACC AATCCGGGCT CGAACGCTGT
     TACGATTAAC CCTTGAGCTT GCCTGCTTGG TTAGGCCCGA GCTTGCCACA

E   G   E   Q   D   K   R   L   H   C   Y   A   S   W   R   N   S
151  GAAGGCGAAC AGGATAAACG GCTTCATTGC TATGCCTCTT GGAGGAACTC
     CTCCCCCTTG TCCTATTTGC GGAGGTAACG ATACGGAGCA CCTCCTTGAG

S   G   T   I   E   L   V   K   G   C   W   L   D   D   F
201  CTCCGGGACC ATTGAACTCG TAAAGAAAGG GTGCTGGCTC GACGATTTCA
     GAGGCCCTGC TAACTTGAGC ATTTCTTTCC CACGACCGAG CTGCTAAAGT

N   C   Y   D   R   Q   E   C   V   A   T   E   N   P   Q   V
251  AATGTTATGA TCGCCAGGAA TGTGTCGCCA CCGAAGAGAA TCCTCAGGTT
     TAACAATACT GGCGGTCCTT ACACAGCGGT GGCTTCTCTT AGGAGTCCAA

Y   F   C   C   E   G   N   F   C   N   E   R   F   T   H   L
301  TATTTCTGTT GTTGCGAAGG GAATTTCTGT AATGAACGTT TTACCCATCT
     ATAAAGACAA CAACGCTTCC CTTAAAGACA TTACTTGCAA AATGGGTAGA

P   E   A   G   G   P   E   V   T   Y   E   P   P   P   T
351  CCCCGAAGCC GGCGGACCCG AGGTTACCTA TGAACCTCCT CCCACCGGTG
     GGGGCTTCGG CCGCCTGGGC TCCAATGGAT ACTTGGAGGA GGGTGGCCAC

401  GTGGAACTCA CACATGCCCA CCGTGCCCAG CACCTGAACT CCTGGGGGGA
     CACCTTGAGT GTGTACGGGT GGCACGGGTC GTGGACTTGA GGACCCCCCT

451  CCGTCAGTCT TCCTCTTCCC CCCAAAACCC AAGGACACCC TCATGATCTC
     GGCAGTCAGA AGGAGAAGGG GGGTTTTGGG TTCCTGTGGG AGTACTAGAG

501  CCGGACCCCT GAGGTCACAT GCGTGGTGGT GGACGTGAGC CACGAAGACC
     GGCCTGGGGA CTCCAGTGTA CGCACCACCA CCTGCACTCG GTGCTTCTGG

551  CTGAGGTCAA GTTCAACTGG TACGTGGACG GCGTGGAGGT GCATAATGCC
     GACTCCAGTT CAAGTTGACC ATGCACCTGC CGCACCTCCA CGTATTACGG

601  AAGACAAAGC CGCGGGAGGA GCAGTACAAC AGCACGTACC GTGTGGTCAG
     TTCTGTTTCG GCGCCCTCCT CGTCATGTTG TCGTGCATGG CACACCAGTC

651  CGTCCTCACC GTCCTGCACC AGGACTGGCT GAATGGCAAG GAGTACAAGT
     GCAGGAGTGG CAGGACGTGG TCCTGACCGA CTTACCGTTC CTCATGTTCA

701  GCAAGGTCTC CAACAAAGCC CTCCCAGCCC CCATCGAGAA AACCATCTCC
     CGTTCCAGAG GTTGTTTCGG GAGGGTCGGG GGTAGCTCTT TTGGTAGAGG

751  AAAGCCAAAG GGCAGCCCCG AGAACCACAG GTGTACACCC TGCCCCCATC
     TTTCGGTTTC CCGTCGGGGC TCTTGGTGTC CACATGTGGG ACGGGGGTAG
```

FIGURE 18A

```
801   CCGGGAGGAG ATGACCAAGA ACCAGGTCAG CCTGACCTGC CTGGTCAAAG
      GGCCCTCCTC TACTGGTTCT TGGTCCAGTC GGACTGGACG GACCAGTTTC

851   GCTTCTATCC CAGCGACATC GCCGTGGAGT GGGAGAGCAA TGGGCAGCCG
      CGAAGATAGG GTCGCTGTAG CGGCACCTCA CCCTCTCGTT ACCCGTCGGC

901   GAGAACAACT ACAAGACCAC GCCTCCCGTG CTGGACTCCG ACGGCTCCTT
      CTCTTGTTGA TGTTCTGGTG CGGAGGGCAC GACCTGAGGC TGCCGAGGAA

951   CTTCCTCTAT AGCAAGCTCA CCGTGGACAA GAGCAGGTGG CAGCAGGGGA
      GAAGGAGATA TCGTTCGAGT GGCACCTGTT CTCGTCCACC GTCGTCCCCT

1001  ACGTCTTCTC ATGCTCCGTG ATGCATGAGG CTCTGCACAA CCACTACACG
      TGCAGAAGAG TACGAGGCAC TACGTACTCC GAGACGTGTT GGTGATGTGC

1051  CAGAAGAGCC TCTCCCTGTC CCCGGGTAAA TGA (SEQ ID NO: 82)
      GTCTTCTCGG AGAGGGACAG GGGCCCATTT ACT (SEQ ID NO: 83)
```

FIGURE 18B

METHODS FOR TREATING VASCULAR EYE DISORDERS WITH ACTRII ANTAGONISTS

CROSS-REFERENCE TO RELATED APPLICATIONS

This application is a continuation of U.S. application Ser. No. 15/360,588, filed Nov. 23, 2016 (now allowed), which claims the benefit of priority from U.S. Provisional Application No. 62/258,934, filed Nov. 23, 2015. The specifications of each of the foregoing applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Apr. 9, 2019, is named 1848179-0002-092-102_SL.txt and is 138,291 bytes in size.

BACKGROUND OF THE INVENTION

As one of the most metabolically active tissues, the structural and functional integrity of the eye depends on a regular oxygen supply and nutrients from the blood [Suk-Yee et al. (2012) *Oxidative Medicine and Cellular Longevity* 2012:1-10]. In order to meet this high metabolic demand, the eye contains several structurally and functionally distinct vascular beds, which supply oxygen and nutrients to ocular components critical for the maintenance of vision [Kiel J. W. (2010) *The Ocular Circulation*. San Rafael (Calif.) Morgan & Claypool Life Sciences, Chapter 2, Anatomy]. These include the retinal and choroidal vasculatures, which supply the inner and outer portions of the retina, respectively, and the limbal vasculature located at the periphery of the cornea. Injuries and diseases that impair the normal structure and/or function of blood vessels in the eye, particularly those associated with ischemia and vascular complications such as neovascularization, blood vessel leakage, and blood vessel occlusion, are among the leading causes of visual impairment and blindness [Kaur et al. (2008) Clinical Ophthalmology 2(4):879-999]. Such injuries and disease often result in hypoxia and/or increased oxidative stress (e.g., increased levels of reactive oxygen species) within the eye, which can be particularly damaging to the retina and ocular nerve. Accordingly, in many ischemic and microvascular insufficiency disorders, vision loss is due to one or more of retinal damage, optic nerve damage, and vitreous hemorrhage (extravasation, or leakage, of blood and fluid into the areas in and around the vitreous humor of the eye).

For example, diabetic retinopathy is one of the most common diseases affecting the retinal vasculature, which can manifest in both type 1 diabetes or type 2 diabetes patients [Shin et al. (2014) *J Opthalmic Vis Res.* 9(3):362-373]. At first, diabetic retinopathy is generally asymptomatic or only results in mild vision problems. However, left untreated, diabetic retinopathy eventually can result in blindness. In the early stage of the disease, classified as non-proliferative retinopathy, microaneurysms develop in the retina's blood vessels. As the disease progresses, more blood vessels become damaged or blocked resulting in ischemia, which promotes growth of new blood vessels (neovascularization) in attempt to compensate for reduced oxygen and nutrient circulation. This stage of the disease is called proliferative retinopathy. New blood vessels form along the retina and the surface of the clear vitreous gel that fills the inside of the eye. These new blood vessels have thin, fragile walls which are prone to fluid leakage (whole blood and/or some constituents thereof) and rupture. Such leakage leads to blood and/or fluid pooling within the layers of the retina and in the vitreous humor, clouding vision. Also, blood and/or fluid can leak into the macula of the retina, the part of the eye responsible for sharp, straight-ahead vision. As the macula swells, the patient's central vision becomes distorted. This condition is referred to as macular edema and, left untreated, can result in macular degeneration in diabetic patients.

Ischemia and microvascular pathology are also associated with many other ocular disorders including, for example, macular degeneration (e.g., age-related macular degeneration, juvenile macular degeneration, wet macular degeneration, Stargardt's disease, and Best's disease), retinal vein occlusion (e.g., central retinal vein occlusion, hemi-retinal vein occlusion, branch retinal vein occlusion, and ischemic retinal vein occlusion), retinal artery occlusion (e.g., central retinal artery occlusion, hemi-retinal artery occlusion, branch retinal artery occlusion, and ischemic retinal artery occlusion), ischemic optic neuropathy [e.g., anterior ischemic optic neuropathy (arteritic and non-arteritic) and posterior ischemic optic neuropathy], macular telangiectasia (type I or type II), retinal ischemia (e.g., acute retinal ischemia or chronic retinal ischemia), ocular ischemic syndrome, retinal vasculitis, and retinopathy of prematurity.

Most available treatments for vascular disorders of the eye are directed at ameliorating vascular and nerve damage and include, for example, laser photocoagulation therapy, low dose radiation, and surgery (e.g., removal of neovascular membranes and vitrectomy). Unfortunately, many of these therapies have limited or short lasting effects. For example, neovascular membranes, which initially respond to laser therapy, have high recurrent rates and there also is risk of vision loss due to damage during laser treatment. Similarly, there is a high rate of recurrence of neovacuolization in patients receiving low dose radiation therapy. Surgical removal of neovascular membranes and vitrectomy can result in retinal detachment and are frequently associated with cataract development following treatment [Benson et al. (1988) *Ophthalmic Surgery* 19(20):826-824]. Recently, various VEGF antagonists have been approved for use in age-related macular degeneration and trials are ongoing for other ocular indications. However, VEGF antagonist therapy also has been associated with various adverse complications [Falavarjani et al. (2013) *Eye* 27:787-794].

Thus, there is high unmet need for effective therapies for treating ocular disorders, particularly those associated with ischemia and/or microvascular insufficiency. Accordingly, it is an object of the present disclosure to provide methods for improving vision in patients in need thereof and treating vascular disorders of the eye.

SUMMARY OF THE INVENTION

As described herein, it has been discovered that an ActRII antagonist (inhibitor) may be used to treat eye (ocular) disorders. In particular, it was observed that treatment with an ActRII polypeptide improves vision in a patient having a disease associated with vascular eye damage. Accordingly, in certain aspects, the present disclosure relates to methods for treating or preventing eye disorders, particular vascular disorders of the eye, by administering to a patient in need thereof one or more ActRII antagonists including, for example, ActRII polypeptides (ActRIIA and ActRIIB polypeptides as well as variants thereof such as GDF traps).

ActRII polypeptides described herein, as well as variants thereof, bind various ligands of the TGF-β super family [e.g., GDF11, GDF8, activin (activin A, activin B, activin AB, activin C, activin E) BMP6, GDF3, BMP10, and/or BMP9]. Accordingly, ActRII polypeptides, particularly soluble polypeptides, may be used to inhibit ActRII-ligand interactions (e.g., naturally occurring ligand-receptor interactions occurring at cellular membranes) and thus may be used to inhibit ActRII-mediated Smad (e.g., Smads 1, 2, 3, Sand 8) signaling. Therefore, while not wishing to be bound to a particular mechanism of action, it is expected that other ActRII inhibitors, or combinations of ActRII inhibitors, that mimic the antagonistic properties of ActRII polypeptides described herein will have similar biological effects in vivo including, for example, the ability to improve vision in a patient having an eye disorder, particularly a vascular disorder of the eye. Such antagonistic mimetics (e.g., one or more variant ActRII polypeptides that inhibit at least one ActRII ligand and/or ActRII receptor, one or more antibodies that inhibit at least one ActRII ligand and/or ActRII receptor, one or more nucleic acids that inhibit at least one ActRII ligand and/or ActRII receptor, one or more small molecules that inhibit at least one ActRII ligand and/or ActRII receptor, as well as combinations thereof) are collectively referred to herein as "ActRII antagonists" or "ActRII inhibitors".

Therefore, in certain aspects, the disclosure provides methods for treating or preventing an eye disorder (e.g., a vascular disorder of the eye), particularly treating or preventing one or more complications of the disorder, comprising administering an effective amount of an ActRII antagonist (inhibitor), or combination of ActRII antagonists, to a subject (patient) in need thereof. For example, the disclosure provides methods for improving vision in a patient that has an eye disorder, particularly a vascular disorder of the eye, comprising administering an effective amount of an ActRII antagonist, or combination of ActRII antagonists. In some embodiments, such methods increase the visual acuity in the patient. In other embodiments, such methods increase visual field in the patient. In still other embodiments, such methods increase visual acuity and visual field in the patient. In some embodiments, an ActRII antagonist, or combination of ActRII antagonists, can be used to treat or prevent an eye disorder, particularly a vascular disorder of the eye, that is associated with ischemia. In some embodiments, an ActRII antagonist, or combination of ActRII antagonists, can be used to treat or prevent an eye disorder, particularly a vascular disorder of the eye, that is associated with microvascular insufficiency. In some embodiments, an ActRII antagonist, or combination of ActRII antagonists, can be used to treat or prevent an eye disorder, particularly a vascular disorder of the eye, that is associated with retinopathy. In some embodiments, an ActRII antagonist, or combination of ActRII antagonists, can be used to treat or prevent an eye disorder, particularly a vascular disorder of the eye, that is associated with optic neuropathy. Therefore, in certain aspects, an ActRII antagonist, or combination of ActRII antagonists, can be used to treat or prevent one or more an eye disorders, particularly a vascular disorders of the eye, selected from the group consisting of: macular degeneration (e.g., age-related macular degeneration, juvenile macular degeneration, wet macular degeneration, dry macular degeneration, Stargardt's disease, and Best's disease), retinal vein occlusion (e.g, central retinal vein occlusion, hemi-retinal vein occlusion, branch retinal vein occlusion, and ischemic retinal vein occlusion), retinal artery occlusion (e.g, central retinal artery occlusion, hemi-retinal artery occlusion, branch retinal artery occlusion, macular edema following retinal vein occlusion, and ischemic retinal artery occlusion), diabetic retinopathy, diabetic macular edema, ischemic optic neuropathy [e.g., anterior ischemic optic neuropathy (arteritic and non-arteritic) and posterior ischemic optic neuropathy], macular telangiectasia (type I or type II), retinal ischemia (e.g., acute retinal ischemia or chronic retinal ischemia), ocular ischemic syndrome, retinal vasculitis, and retinopathy of prematurity. In some embodiments, a patient in need of treatment or prevention of an eye disorder, particularly a vascular disorder of the eye, has anemia. For example, a patient in need of treatment or prevention of an eye disorder, particularly a vascular disorder of the eye, may have sideroblastic anemia. In some embodiments, a patient in need of treatment or prevention of an eye disorder, particularly a vascular disorder of the eye, has myelodysplastic syndrome. In some embodiments, a patient in need of treatment or prevention of an eye disorder, particularly a vascular disorder of the eye, has a hemoglobinopathy. For example, a patient in need of treatment or prevention of an eye disorder, particularly a vascular disorder of the eye, may have a thalassemia disorder including, but not limited to, β-thalassemia or thalassemia intermedia. In some embodiments, a patient in need of treatment or prevention of an eye disorder, particularly a vascular disorder of the eye, does not have sickle-cell disease. In some embodiments, a patient in need of treatment or prevention of an eye disorder, particularly a vascular disorder of the eye, does not have peripheral retinal ischemia as a complication of sickle-cell disease. In some embodiments, a patient in need of treatment or prevention of an eye disorder, particularly a vascular disorder of the eye, does not have proliferative sickle retinopathy as a complication of sickle-cell disease. In some embodiments, a patient in need of treatment or prevention of an eye disorder, particularly a vascular disorder of the eye, does not have vitreous hemorrhage as a complication of sickle-cell disease. Similarly, the disclosure provides compositions and medicaments comprising ActRII antagonist (inhibitors), or combinations of ActRII antagonists, for use in treating or preventing a vascular disorder of the eye as described herein.

In certain aspects, the disclosure relates to methods of treating an eye disorder in a patient comprising administering to a patient in need thereof an effective amount of an ActRII antagonist. In some embodiments, the disclosure relates to methods of preventing an eye disorder in a patient comprising administering to a patient in need thereof an effective amount of an ActRII antagonist. In some embodiments, the disclosure relates to methods of reducing the severity of an eye disorder in a patient comprising administering to a patient in need thereof an effective amount of an ActRII antagonist. In some embodiments, the eye disorder is a vascular eye disorder. In some embodiments, the eye disorder is selected from the group consisting of: macular degeneration (e.g., age-related macular degeneration, juvenile macular degeneration, wet macular degeneration, dry macular degeneration, Stargardt's disease, neovascular age-related macular degeneration, and Best's disease), retinal vein occlusion (e.g, central retinal vein occlusion, hemi-retinal vein occlusion, branch retinal vein occlusion, and ischemic retinal vein occlusion), retinal artery occlusion (e.g, central retinal artery occlusion, hemi-retinal artery occlusion, branch retinal artery occlusion, and ischemic retinal artery occlusion), macular edema (e.g., macular edema following retinal vein occlusion and diabetic macular edema) diabetic retinopathy (e.g., diabetic retinopathy and diabetic retinopathy in patients with diabetic macular edema), ischemic optic neuropathy [e.g., anterior ischemic optic neuropathy (arteritic and non-arteritic) and posterior ischemic optic neuropathy], macular telangiectasia (type I or type II), retinal ischemia (e.g., acute retinal ischemia or chronic retinal ischemia), ocular ischemic syndrome, retinal vasculitis, and retinopathy of prematurity. In some embodiments, the method maintains visual acuity. In some embodiments, the method maintains visual acuity compared to baseline (visual acuity in the patient prior to start of treatment). In some embodiments, the method maintains visual acuity as compared to baseline for at least 30, 45, 60, 90, 100, 120, 140, 160, 180, 200, 250, 300, or 360 or more days. In some embodiments, the method maintains visual acuity as compared to baseline for at least 160 days. In some embodiments, the method maintains visual acuity as compared to baseline for at least 360 days. In some embodiments, the patient loses less than 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 letter of visual acuity. In some embodiments, the patient loses less than 15 letter of visual acuity. In some embodiments, the patient loses less than 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 letter of visual acuity compared to baseline (visual acuity in the patient prior to start of treatment). In some embodiments, the patient loses less than 15 letters of visual acuity compared to baseline (visual acuity in the patient prior to start of treatment). In some embodiments, the method improves visual acuity. In some embodiments, the method improves visual acuity as compared to baseline for at least 30, 45, 60, 90, 100, 120, 140, 160, 180, 200, 250, 300, or 360 or more days. In some embodiments, the method improves visual acuity as compared to baseline for at least 160 days. In some embodiments, the method improves visual acuity as compared to baseline for at least 360 days. In some embodiments, the method improves visual acuity wherein the patient gains at least 50, 40, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 letters of visual acuity. In some embodiments, the method improves visual acuity wherein the patient gains at least 50, 40, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 letters of visual acuity compared to baseline (visual acuity in the patient prior to start of treatment). In some embodiments, the method improves visual acuity wherein the patient gains at least 15 letters of visual acuity. In some embodiments, the method improves visual acuity wherein the patient gains at least 15 letters of visual acuity compared to baseline (visual acuity in the patient prior to start of treatment). In some embodiments, the method reduces retinal thickness. In some embodiments, the patient has previously been treated with a VEGF inhibitor. In some embodiments, the patient is refractory to or intolerant of treatment with a VEGF inhibitor. In some embodiments, the VEGF inhibitor is aflibercept. In some embodiments, the VEGF inhibitor is ranibizumab. In some embodiments, the VEGF inhibitor is bevacizumab. In some embodiments, the patient has been previously treated with pegaptanib. In some embodiments, the patient is refractory to or intolerant of treatment with pegaptanib. In some embodiments, the patient has been previously treated with fluocinolone acetonide. In some embodiments, the patient is refractory to or intolerant of treatment with fluocinolone acetonide. In some embodiments, the patient does not have an ocular or periocular infection. In some embodiments, the patient does not have glaucoma. In some embodiments, the patient does not have active intraocular inflammation. In some embodiments, the patient does not have sickle-cell disease. In some embodiments, the patient does not have peripheral retinal ischemia as a complication of sickle-cell disease. In some embodiments, the patient does not have proliferative sickle retinopathy as a complication of sickle-cell disease. In some embodiments, the patient does not have vitreous hemorrhage as a complication of sickle-cell disease. In some embodiments, the method further comprises administering the ActRII antagonist in combination with one or more additional active agents or supportive therapy for treating preventing, or reducing the severity of an eye disorder. In some embodiments, the one or more supportive therapies is selected from the group consisting of: surgery, laser therapy (e.g., photocoagulation), anti-angiogenic therapy [e.g., VEGF inhibitors such as bevacizumab (Avastin®), ranibizumab (Lucentis®), and Aflibercept (Eylea®)], $Ca^{2+}$ inhibitors (e.g., flunarizine and nifedipine), cryotherapy, hyperbaric oxygenation, $Na^+$ channel blockers (e.g., topiramate), iGluR antagonists (e.g., MK-801, dextromethorphan, eliprodil, and flupirtine), antioxidants (e.g., dimethylthiourea, vitamin E, alph-lipoic acid, superoxide dismutase, catalase, desferrioxamine, mannitol, allopurinol, calcium dobesilate, flupirtine, trimetazidine, and EGB-761), anti-inflammatory agents, cyclodiathermy, cyclocryotherapy, ocular filtering procedures, implantation of drainage valves, antiplatelet therapy (e.g., aspirin, ticlopidine, and clopidogrel), anticoagulant therapy (e.g., warfarin and heparin), steroids, systemic or local corticosteroids (e.g., prednisone triamcinolone (Triesence®) and fluocinolone acetonide (Iluvien)), and dexamethasone (Ozurdex®), steroid-sparing immunosuppressants (e.g., cyclosporine, azathioprine, cyclophosphamide, mycophenolate, mofetil, infliximab and etanercept), dietary supplements (e.g., vitamin C, vitamin E, lutein, zeaxanthin, zinc, folic acid, vitamins B6, vitamin B12, and zeaxanthin), vitrectomy, scleral buckle surgery, and pneumatic retinopexy. In some embodiments, the one or more additional active agents is a vascular endothelial growth factor (VEGF) inhibitor. In some embodiments, the VEGF inhibitor is a VEGF-A inhibitor. In some embodiments, the one or more additional active agents is a placental growth factor (PLGF) inhibitor. In some embodiments, the one or more additional active agents inhibits VEGF and PLGF. In some embodiments, the one or more additional active agents is aflibercept. In some embodiments, the one or more additional active agents is ranibizumab. In some embodiments, the one or more additional active agents is bevacizumab. In some embodiments, the ActRII antagonist is administered by parenteral administration. In some embodiments, the ActRII antagonist is administered by subcutaneous administration. In some embodiments, the ActRII antagonist is administered by ocular administration. In some embodiments, the ActRII antagonist is administered by intravitreal administration.

In certain aspects, the disclosure relates to methods of treating macular degeneration in a patient comprising administering to a patient in need thereof an effective amount of an ActRII antagonist. In some embodiments, the disclosure relates to methods of preventing macular degeneration in a patient comprising administering to a patient in need thereof an effective amount of an ActRII antagonist. In some embodiments, the disclosure relates to methods of reducing the severity of macular degeneration in a patient comprising administering to a patient in need thereof an effective amount of an ActRII antagonist. In some embodiments, the macular degeneration is age-related macular degeneration (AMD). In some embodiments, the patient has category 2 AMD based on the Age-Related Eye Disease Study (AREDS). In some embodiments, the patient has category 3 AMD based on the Age-Related Eye Disease Study (AREDS). In some embodiments, the patient has category 4 AMD based on the Age-Related Eye Disease Study (AREDS). In some embodiments, the AMD is neovascular (wet) AMD. In some embodiments, the AMD is non-neovascular (dry) AMD. In some embodiments, the method results in at least a 1 step improvement in AMD based on AREDS (e.g., improves AMD from category 4 to category 3 based on AREDS, improves AMD from category 3 to category 2 based on AREDS, or improves AMD from category 2 to category 1 based on AREDS). In some embodiments, the method results in at least a 2 step improvement in AMD based on AREDS (e.g., improves AMD from category 4 to category 2 based on AREDS or improves AMD from category 3 to category 1 based on AREDS). In some embodiments, the patient has at least early AMD based on the Beckman Initiative for Macular Research Classification Committee (BIMRCC) classification. See, e.g., Frederick L. Ferris III et al. (2013) American Academy of Ophthalmology. 120(4): 844-851. In some embodiments, the patient has intermediate AMD based on the BIMRCC classification. In some embodiments, the patient has late AMD based on the BIMRCC classification. In some embodiments, the method results in at least a 1 step improvement in AMD based on (BIMRCC) classification (e.g., improves from late to intermediate AMD based on BIMRCC or improves from intermediate to early AMD based on BIMRCC). In some embodiments, the method results in at least a 2 step improvement in AMD based on (BIMRCC) classification (e.g., improves from late to early AMD based on BIMRCC). In some embodiments, the method maintains visual acuity. In some embodiments, the method maintains visual acuity compared to baseline (visual acuity in the patient prior to start of treatment). In some embodiments, the method maintains visual acuity as compared to baseline for at least 30, 45, 60, 90, 100, 120, 140, 160, 180, 200, 250, 300, or 360 or more days. In some embodiments, the method maintains visual acuity as compared to baseline for at least 160 days. In some embodiments, the method maintains visual acuity as compared to baseline for at least 360 days. In some embodiments, the patient loses less than 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 letter of visual acuity. In some embodiments, the patient loses less than 15 letter of visual acuity. In some embodiments, the patient loses less than 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 letter of visual acuity compared to baseline (visual acuity in the patient prior to start of treatment). In some embodiments, the patient loses less than 15 letters of visual acuity compared to baseline (visual acuity in the patient prior to start of treatment). In some embodiments, the method improves visual acuity. In some embodiments, the method improves visual acuity as compared to baseline for at least 30, 45, 60, 90, 100, 120, 140, 160, 180, 200, 250, 300, or 360 or more days. In some embodiments, the method improves visual acuity as compared to baseline for at least 160 days. In some embodiments, the method improves visual acuity as compared to baseline for at least 360 days. In some embodiments, the method improves visual acuity wherein the patient gains at least 50, 40, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 letters of visual acuity. In some embodiments, the method improves visual acuity wherein the patient gains at least 50, 40, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 letters of visual acuity compared to baseline (visual acuity in the patient prior to start of treatment). In some embodiments, the method improves visual acuity wherein the patient gains at least 15 letters of visual acuity. In some embodiments, the method improves visual acuity wherein the patient gains at least 15 letters of visual acuity compared to baseline (visual acuity in the patient prior to start of treatment). In some embodiments, the method reduces retinal thickness. In some embodiments, the patient has previously been treated with a VEGF inhibitor. In some embodiments, the patient is refractory to or intolerant of treatment with a VEGF inhibitor. In some embodiments, the VEGF inhibitor is aflibercept. In some embodiments, the VEGF inhibitor is ranibizumab. In some embodiments, the VEGF inhibitor is bevacizumab. In some embodiments, the patient has been previously treated with pegaptanib. In some embodiments, the patient is refractory to or intolerant of treatment with pegaptanib. In some embodiments, the patient has been previously treated with fluocinolone acetonide. In some embodiments, the patient is refractory to or intolerant of treatment with fluocinolone acetonide. In some embodiments, the patient does not have an ocular or periocular infection. In some embodiments, the patient does not have glaucoma. In some embodiments, the patient does not have active intraocular inflammation. In some embodiments, the patient does not have sickle-cell disease. In some embodiments, the patient does not have peripheral retinal ischemia as a complication of sickle-cell disease. In some embodiments, the patient does not have proliferative sickle retinopathy as a complication of sickle-cell disease. In some embodiments, the patient does not have vitreous hemorrhage as a complication of sickle-cell disease. In some embodiments, the method further comprises administering the ActRII antagonist in combination with one or more additional active agents or supportive therapy for treating preventing, or reducing the severity of an eye disorder. In some embodiments, the one or more supportive therapies is selected from the group consisting of: surgery, laser therapy (e.g., photocoagulation), anti-angiogenic therapy [e.g., VEGF inhibitors such as bevacizumab (Avastin®), ranibizumab (Lucentis®), and Aflibercept (Eylea®)], $Ca^{2+}$ inhibitors (e.g., flunarizine and nifedipine), cryotherapy, hyperbaric oxygenation, $Na^+$ channel blockers (e.g., topiramate), iGluR antagonists (e.g., MK-801, dextromethorphan, eliprodil, and flupirtine), antioxidants (e.g., dimethylthiourea, vitamin E, alph-lipoic acid, superoxide dismutase, catalase, desferrioxamine, mannitol, allopurinol, calcium dobesilate, flupirtine, trimetazidine, and EGB-761), anti-inflammatory agents, cyclodiathermy, cyclocryotherapy, ocular filtering procedures, implantation of drainage valves, antiplatelet therapy (e.g., aspirin, ticlopidine, and clopidogrel), anticoagulant therapy (e.g., warfarin and heparin), steroids, systemic or local corticosteroids (e.g., prednisone triamcinolone (Triesence®) and fluocinolone acetonide (Iluvien)), and dexamethasone (Ozurdex®), steroid-sparing immunosuppressants (e.g., cyclosporine, azathioprine, cyclophosphamide, mycophenolate, mofetil, infliximab and etanercept), dietary supplements (e.g., vitamin C, vitamin E, lutein, zeaxanthin, zinc, folic acid, vitamins B6, vitamin B12, and zeaxanthin), vitrectomy, scleral buckle surgery, and pneumatic retinopexy. In some embodiments, the one or more additional active agents is a vascular endothelial growth factor (VEGF) inhibitor. In some embodiments, the VEGF inhibitor is a VEGF-A inhibitor. In some embodiments, the one or more additional active agents is a placental growth factor (PLGF) inhibitor. In some embodiments, the one or more additional active agents inhibits VEGF and PLGF. In some embodiments, the one or more additional active agents is aflibercept. In some embodiments, the one or more additional active agents is ranibizumab. In some embodiments, the one or more additional active agents is bevacizumab. In some embodiments, the ActRII antagonist is administered by parenteral administration. In some embodiments, the ActRII antagonist is administered by subcutaneous administration. In some embodiments, the ActRII antagonist is administered by ocular administration. In some embodiments, the ActRII antagonist is administered by intravitreal administration.

In certain aspects, the disclosure relates to methods of treating macular edema in a patient comprising administering to a patient in need thereof an effective amount of an ActRII antagonist. In some embodiments, the disclosure relates to methods of preventing macular edema in a patient comprising administering to a patient in need thereof an effective amount of an ActRII antagonist. In some embodiments, the disclosure relates to methods of reducing the severity of macular edema in a patient comprising administering to a patient in need thereof an effective amount of an ActRII antagonist. In some embodiments, the patient has macular edema following retinal vein occlusion (RVO). In some embodiments, the RVO is branched RVO. In some embodiments, the RVO is central RVO. In some embodiments, the patient has both branched and central RVO. In some embodiments, the RVO is hemi-central RVO. In some embodiments, the macular edema is diabetic macular edema. In some embodiments, the method maintains visual acuity. In some embodiments, the method maintains visual acuity compared to baseline (visual acuity in the patient prior to start of treatment). In some embodiments, the method maintains visual acuity as compared to baseline for at least 30, 45, 60, 90, 100, 120, 140, 160, 180, 200, 250, 300, or 360 or more days. In some embodiments, the method maintains visual acuity as compared to baseline for at least 160 days. In some embodiments, the method maintains visual acuity as compared to baseline for at least 360 days. In some embodiments, the patient loses less than 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 letter of visual acuity. In some embodiments, the patient loses less than 15 letter of visual acuity. In some embodiments, the patient loses less than 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 letter of visual acuity compared to baseline (visual acuity in the patient prior to start of treatment). In some embodiments, the patient loses less than 15 letters of visual acuity compared to baseline (visual acuity in the patient prior to start of treatment). In some embodiments, the method improves visual acuity. In some embodiments, the method improves visual acuity as compared to baseline for at least 30, 45, 60, 90, 100, 120, 140, 160, 180, 200, 250, 300, or 360 or more days. In some embodiments, the method improves visual acuity as compared to baseline for at least 160 days. In some embodiments, the method improves visual acuity as compared to baseline for at least 360 days. In some embodiments, the method improves visual acuity wherein the patient gains at least 50, 40, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 letters of visual acuity. In some embodiments, the method improves visual acuity wherein the patient gains at least 50, 40, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 letters of visual acuity compared to baseline (visual acuity in the patient prior to start of treatment). In some embodiments, the method improves visual acuity wherein the patient gains at least 15 letters of visual acuity. In some embodiments, the method improves visual acuity wherein the patient gains at least 15 letters of visual acuity compared to baseline (visual acuity in the patient prior to start of treatment). In some embodiments, the method reduces retinal thickness. In some embodiments, the patient has previously been treated with a VEGF inhibitor. In some embodiments, the patient is refractory to or intolerant of treatment with a VEGF inhibitor. In some embodiments, the VEGF inhibitor is aflibercept. In some embodiments, the VEGF inhibitor is ranibizumab. In some embodiments, the VEGF inhibitor is bevacizumab. In some embodiments, the patient has been previously treated with pegaptanib. In some embodiments, the patient is refractory to or intolerant of treatment with pegaptanib. In some embodiments, the patient has been previously treated with fluocinolone acetonide. In some embodiments, the patient is refractory to or intolerant of treatment with fluocinolone acetonide. In some embodiments, the patient does not have an ocular or periocular infection. In some embodiments, the patient does not have glaucoma. In some embodiments, the patient does not have active intraocular inflammation. In some embodiments, the patient does not have sickle-cell disease. In some embodiments, the patient does not have peripheral retinal ischemia as a complication of sickle-cell disease. In some embodiments, the patient does not have proliferative sickle retinopathy as a complication of sickle-cell disease. In some embodiments, the patient does not have vitreous hemorrhage as a complication of sickle-cell disease. In some embodiments, the method further comprises administering the ActRII antagonist in combination with one or more additional active agents or supportive therapy for treating preventing, or reducing the severity of an eye disorder. In some embodiments, the one or more supportive therapies is selected from the group consisting of: surgery, laser therapy (e.g., photocoagulation), anti-angiogenic therapy [e.g., VEGF inhibitors such as bevacizumab (Avastin®), ranibizumab (Lucentis®), and Aflibercept (Eylea®)], $Ca^{2+}$ inhibitors (e.g., flunarizine and nifedipine), cryotherapy, hyperbaric oxygenation, $Na^+$ channel blockers (e.g., topiramate), iGluR antagonists (e.g., MK-801, dextromethorphan, eliprodil, and flupirtine), antioxidants (e.g., dimethylthiourea, vitamin E, alph-lipoic acid, superoxide dismutase, catalase, desferrioxamine, mannitol, allopurinol, calcium dobesilate, flupirtine, trimetazidine, and EGB-761), anti-inflammatory agents, cyclodiathermy, cyclocryotherapy, ocular filtering procedures, implantation of drainage valves, antiplatelet therapy (e.g., aspirin, ticlopidine, and clopidogrel), anticoagulant therapy (e.g., warfarin and heparin), steroids, systemic or local corticosteroids (e.g., prednisone triamcinolone (Triesence®) and fluocinolone acetonide (Iluvien)), and dexamethasone (Ozurdex®), steroid-sparing immunosuppressants (e.g., cyclosporine, azathioprine, cyclophosphamide, mycophenolate, mofetil, infliximab and etanercept), dietary supplements (e.g., vitamin C, vitamin E, lutein, zeaxanthin, zinc, folic acid, vitamins B6, vitamin B12, and zeaxanthin), vitrectomy, scleral buckle surgery, and pneumatic retinopexy. In some embodiments, the one or more additional active agents is a vascular endothelial growth factor (VEGF) inhibitor. In some embodiments, the VEGF inhibitor is a VEGF-A inhibitor. In some embodiments, the one or more additional active agents is a placental growth factor (PLGF) inhibitor. In some embodiments, the one or more additional active agents inhibits VEGF and PLGF. In some embodiments, the one or more additional active agents is aflibercept. In some embodiments, the one or more additional active agents is ranibizumab. In some embodiments, the one or more additional active agents is bevacizumab. In some embodiments, the ActRII antagonist is administered by parenteral administration. In some embodiments, the ActRII antagonist is administered by subcutaneous administration. In some embodiments, the ActRII antagonist is administered by ocular administration. In some embodiments, the ActRII antagonist is administered by intravitreal administration.

In certain aspects, the disclosure relates to methods of treating RVO in a patient comprising administering to a patient in need thereof an effective amount of an ActRII antagonist. In some embodiments, the disclosure relates to methods of preventing RVO in a patient comprising administering to a patient in need thereof an effective amount of an ActRII antagonist. In some embodiments, the disclosure relates to methods of reducing the severity of RVO in a patient comprising administering to a patient in need thereof an effective amount of an ActRII antagonist. In some embodiments, the RVO is branched RVO. In some embodiments, the RVO is central RVO. In some embodiments, the patient has both branched and central RVO. In some embodiments, the patient has hemi-central RVO. In some embodiments, the patient has macular edema following retinal vein occlusion (RVO). In some embodiments, the method maintains visual acuity. In some embodiments, the method maintains visual acuity compared to baseline (visual acuity in the patient prior to start of treatment). In some embodiments, the method maintains visual acuity as compared to baseline for at least 30, 45, 60, 90, 100, 120, 140, 160, 180, 200, 250, 300, or 360 or more days. In some embodiments, the method maintains visual acuity as compared to baseline for at least 160 days. In some embodiments, the method maintains visual acuity as compared to baseline for at least 360 days. In some embodiments, the patient loses less than 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 letter of visual acuity. In some embodiments, the patient loses less than 15 letter of visual acuity. In some embodiments, the patient loses less than 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 letter of visual acuity compared to baseline (visual acuity in the patient prior to start of treatment). In some embodiments, the patient loses less than 15 letters of visual acuity compared to baseline (visual acuity in the patient prior to start of treatment). In some embodiments, the method improves visual acuity. In some embodiments, the method improves visual acuity as compared to baseline for at least 30, 45, 60, 90, 100, 120, 140, 160, 180, 200, 250, 300, or 360 or more days. In some embodiments, the method improves visual acuity as compared to baseline for at least 160 days. In some embodiments, the method improves visual acuity as compared to baseline for at least 360 days. In some embodiments, the method improves visual acuity wherein the patient gains at least 50, 40, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 letters of visual acuity. In some embodiments, the method improves visual acuity wherein the patient gains at least 50, 40, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 letters of visual acuity compared to baseline (visual acuity in the patient prior to start of treatment). In some embodiments, the method improves visual acuity wherein the patient gains at least 15 letters of visual acuity. In some embodiments, the method improves visual acuity wherein the patient gains at least 15 letters of visual acuity compared to baseline (visual acuity in the patient prior to start of treatment). In some embodiments, the method reduces retinal thickness. In some embodiments, the patient has previously been treated with a VEGF inhibitor. In some embodiments, the patient is refractory to or intolerant of treatment with a VEGF inhibitor. In some embodiments, the VEGF inhibitor is aflibercept. In some embodiments, the VEGF inhibitor is ranibizumab. In some embodiments, the VEGF inhibitor is bevacizumab. In some embodiments, the patient has been previously treated with pegaptanib. In some embodiments, the patient is refractory to or intolerant of treatment with pegaptanib. In some embodiments, the patient has been previously treated with fluocinolone acetonide. In some embodiments, the patient is refractory to or intolerant of treatment with fluocinolone acetonide. In some embodiments, the patient does not have an ocular or periocular infection. In some embodiments, the patient does not have glaucoma. In some embodiments, the patient does not have active intraocular inflammation. In some embodiments, the patient does not have sickle-cell disease. In some embodiments, the patient does not have peripheral retinal ischemia as a complication of sickle-cell disease. In some embodiments, the patient does not have proliferative sickle retinopathy as a complication of sickle-cell disease. In some embodiments, the patient does not have vitreous hemorrhage as a complication of sickle-cell disease. In some embodiments, the method further comprises administering the ActRII antagonist in combination with one or more additional active agents or supportive therapy for treating preventing, or reducing the severity of an eye disorder. In some embodiments, the one or more supportive therapies is selected from the group consisting of: surgery, laser therapy (e.g., photocoagulation), anti-angiogenic therapy [e.g., VEGF inhibitors such as bevacizumab (Avastin®), ranibizumab (Lucentis®), and Aflibercept (Eylea®)], $Ca^{2+}$ inhibitors (e.g., flunarizine and nifedipine), cryotherapy, hyperbaric oxygenation, $Na^+$ channel blockers (e.g., topiramate), iGluR antagonists (e.g., MK-801, dextromethorphan, eliprodil, and flupirtine), antioxidants (e.g., dimethylthiourea, vitamin E, alph-lipoic acid, superoxide dismutase, catalase, desferrioxamine, mannitol, allopurinol, calcium dobesilate, flupirtine, trimetazidine, and EGB-761), anti-inflammatory agents, cyclodiathermy, cyclocryotherapy, ocular filtering procedures, implantation of drainage valves, antiplatelet therapy (e.g., aspirin, ticlopidine, and clopidogrel), anticoagulant therapy (e.g., warfarin and heparin), steroids, systemic or local corticosteroids (e.g., prednisone triamcinolone (Triesence®) and fluocinolone acetonide (Iluvien)), and dexamethasone (Ozurdex®), steroid-sparing immunosuppressants (e.g., cyclosporine, azathioprine, cyclophosphamide, mycophenolate, mofetil, infliximab and etanercept), dietary supplements (e.g., vitamin C, vitamin E, lutein, zeaxanthin, zinc, folic acid, vitamins B6, vitamin B12, and zeaxanthin), vitrectomy, scleral buckle surgery, and pneumatic retinopexy. In some embodiments, the one or more additional active agents is a vascular endothelial growth factor (VEGF) inhibitor. In some embodiments, the VEGF inhibitor is a VEGF-A inhibitor. In some embodiments, the one or more additional active agents is a placental growth factor (PLGF) inhibitor. In some embodiments, the one or more additional active agents inhibits VEGF and PLGF. In some embodiments, the one or more additional active agents is aflibercept. In some embodiments, the one or more additional active agents is ranibizumab. In some embodiments, the one or more additional active agents is bevacizumab. In some embodiments, the ActRII antagonist is administered by parenteral administration. In some embodiments, the ActRII antagonist is administered by subcutaneous administration. In some embodiments, the ActRII antagonist is administered by ocular administration. In some embodiments, the ActRII antagonist is administered by intravitreal administration.

In certain aspects, the disclosure relates to methods of treating retinopathy in a patient comprising administering to a patient in need thereof an effective amount of an ActRII antagonist. In some embodiments, the disclosure relates to methods of preventing retinopathy in a patient comprising administering to a patient in need thereof an effective amount of an ActRII antagonist. In some embodiments, the disclosure relates to methods of reducing the severity of retinopathy in a patient comprising administering to a patient in need thereof an effective amount of an ActRII antagonist. In some embodiments, the retinopathy is diabetic retinopathy. In some embodiments, the patient has diabetic macular edema. In some embodiments, the patient has at least mild non-proliferative diabetic retinopathy (NPDR) based on the Early Treatment Diabetic Retinopathy Study (ETDRS) classification. In some embodiments, the patient has moderate NPDR based on the ETDRS classification. In some embodiments, the patient has severe NPDR based on the ETDRS classification. In some embodiments, the patient has very severe NPDR based on the ETDRS classification. In some embodiments, the patient has early proliferative diabetic retinopathy (PDR) based on the ETDRS classification. In some embodiments, the patient has high risk PDR based on the ETDRS classification. In some embodiments, the patient has advanced PDR based on the ETDRS classification. In some embodiments, the patient has advanced PDR with clinically significant macular degeneration based on the ETDRS classification. In some embodiments, the method results in at least a 1 step improvement in diabetic retinopathy based on ETDRS classification (e.g., improvement from advanced PDR with clinically significant macular degeneration to advanced PDR without significant macular degeneration, improvement from advanced PDR to high risk PDR, improvement from high risk PDR to early PDR, improvement from early PDR to very severe NPDR, improvement from very severe NPDR to severe NPDR, improvement from severe NPDR to moderate NPDR, or improvement from moderate NPDR to mild NPDR). In some embodiments, the method results in at least a 2 step improvement in diabetic retinopathy based on ETDRS classification (e.g., improvement from advanced PDR with clinically significant macular degeneration to high risk PDR, improvement from advanced PDR to early PDR, improvement from high risk PDR to very severe NPDR, improvement from early PDR to severe NPDR, improvement from very severe NPDR to moderate NPDR, improvement from severe NPDR to mild NPDR, or improvement from moderate NPDR to no apparent retinopathy). In some embodiments, the patient has at least mild NPDR based on the ETDRS Diabetic Retinopathy Severity Scale (ETDRS-DRSS) classification. In some embodiments, the patient has moderate NPDR based on the ETDRS-DRSS classification. In some embodiments, the patient has severe NPDR based on the ETDRS-DRSS classification. In some embodiments, the patient has PDR based on the ETDRS-DRSS classification. In some embodiments, the patient has PDR with diabetic macular edema absent based on the ETDRS-DRSS classification. In some embodiments, the patient has PDR with diabetic macular edema present based on the ETDRS-DRSS classification. In some embodiments, the method results in at least a 1 step improvement in diabetic retinopathy based on ETDRS-DRSS classification (e.g., improvement from PDR with diabetic macular edema present to PDR with diabetic macular edema absent, improvement from PDR with diabetic macular edema absent to PDR, improvement from PDR to severe NPDR, improvement from severe NPDR to moderate NPDR, improvement from moderate NPDR to mild NPDR, or improvement from mild NPDR to no apparent retinopathy). In some embodiments, the method results in at least a 2 step improvement in diabetic retinopathy based on ETDRS-DRSS classification (e.g., improvement from PDR with diabetic macular edema present to PDR, improvement from PDR with diabetic macular edema absent to severe NPDR, improvement from PDR to moderate NPDR, improvement from severe NPDR to mild NPDR, improvement from moderate NPDR to no apparent, or improvement from mild NPDR to no apparent retinopathy). In some embodiments, the method maintains visual acuity. In some embodiments, the method maintains visual acuity compared to baseline (visual acuity in the patient prior to start of treatment). In some embodiments, the method maintains visual acuity as compared to baseline for at least 30, 45, 60, 90, 100, 120, 140, 160, 180, 200, 250, 300, or 360 or more days. In some embodiments, the method maintains visual acuity as compared to baseline for at least 160 days. In some embodiments, the method maintains visual acuity as compared to baseline for at least 360 days. In some embodiments, the patient loses less than 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 letter of visual acuity. In some embodiments, the patient loses less than 15 letter of visual acuity. In some embodiments, the patient loses less than 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 letter of visual acuity compared to baseline (visual acuity in the patient prior to start of treatment). In some embodiments, the patient loses less than 15 letters of visual acuity compared to baseline (visual acuity in the patient prior to start of treatment). In some embodiments, the method improves visual acuity. In some embodiments, the method improves visual acuity as compared to baseline for at least 30, 45, 60, 90, 100, 120, 140, 160, 180, 200, 250, 300, or 360 or more days. In some embodiments, the method improves visual acuity as compared to baseline for at least 160 days. In some embodiments, the method improves visual acuity as compared to baseline for at least 360 days. In some embodiments, the method improves visual acuity wherein the patient gains at least 50, 40, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 letters of visual acuity. In some embodiments, the method improves visual acuity wherein the patient gains at least 50, 40, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 letters of visual acuity compared to baseline (visual acuity in the patient prior to start of treatment). In some embodiments, the method improves visual acuity wherein the patient gains at least 15 letters of visual acuity. In some embodiments, the method improves visual acuity wherein the patient gains at least 15 letters of visual acuity compared to baseline (visual acuity in the patient prior to start of treatment). In some embodiments, the method reduces retinal thickness. In some embodiments, the patient has previously been treated with a VEGF inhibitor. In some embodiments, the patient is refractory to or intolerant of treatment with a VEGF inhibitor. In some embodiments, the VEGF inhibitor is aflibercept. In some embodiments, the VEGF inhibitor is ranibizumab. In some embodiments, the VEGF inhibitor is bevacizumab. In some embodiments, the patient has been previously treated with pegaptanib. In some embodiments, the patient is refractory to or intolerant of treatment with pegaptanib. In some embodiments, the patient has been previously treated with fluocinolone acetonide. In some embodiments, the patient is refractory to or intolerant of treatment with fluocinolone acetonide. In some embodiments, the patient does not have an ocular or periocular infection. In some embodiments, the patient does not have glaucoma. In some embodiments, the patient does not have active intraocular inflammation. In some embodiments, the patient does not have sickle-cell disease. In some embodiments, the patient does not have peripheral retinal ischemia as a complication of sickle-cell disease. In some embodiments, the patient does not have proliferative sickle retinopathy as a complication of sickle-cell disease. In some embodiments, the patient does not have vitreous hemorrhage as a complication of sickle-cell disease. In some embodiments, the method further comprises administering the ActRII antagonist in combination with one or more additional active agents or supportive therapy for treating preventing, or reducing the severity of an eye disorder. In some embodiments, the one or more supportive therapies is selected from the group consisting of: surgery, laser therapy (e.g., photocoagulation), anti-angiogenic therapy [e.g., VEGF inhibitors such as bevacizumab (Avastin®), ranibizumab (Lucentis®), and Aflibercept (Eylea®)], $Ca^{2+}$ inhibitors (e.g., flunarizine and nifedipine), cryotherapy, hyperbaric oxygenation, $Na^+$ channel blockers (e.g., topiramate), iGluR antagonists (e.g., MK-801, dextromethorphan, eliprodil, and flupirtine), antioxidants (e.g., dimethylthiourea, vitamin E, alph-lipoic acid, superoxide dismutase, catalase, desferrioxamine, mannitol, allopurinol, calcium dobesilate, flupirtine, trimetazidine, and EGB-761), anti-inflammatory agents, cyclodiathermy, cyclocryotherapy, ocular filtering procedures, implantation of drainage valves, antiplatelet therapy (e.g., aspirin, ticlopidine, and clopidogrel), anticoagulant therapy (e.g., warfarin and heparin), steroids, systemic or local corticosteroids (e.g., prednisone triamcinolone (Triesence®) and fluocinolone acetonide (Iluvien)), and dexamethasone (Ozurdex®), steroid-sparing immunosuppressants (e.g., cyclosporine, azathioprine, cyclophosphamide, mycophenolate, mofetil, infliximab and etanercept), dietary supplements (e.g., vitamin C, vitamin E, lutein, zeaxanthin, zinc, folic acid, vitamins B6, vitamin B12, and zeaxanthin), vitrectomy, scleral buckle surgery, and pneumatic retinopexy. In some embodiments, the one or more additional active agents is a vascular endothelial growth factor (VEGF) inhibitor. In some embodiments, the VEGF inhibitor is a VEGF-A inhibitor. In some embodiments, the one or more additional active agents is a placental growth factor (PLGF) inhibitor. In some embodiments, the one or more additional active agents inhibits VEGF and PLGF. In some embodiments, the one or more additional active agents is aflibercept. In some embodiments, the one or more additional active agents is ranibizumab. In some embodiments, the one or more additional active agents is bevacizumab. In some embodiments, the ActRII antagonist is administered by parenteral administration. In some embodiments, the ActRII antagonist is administered by subcutaneous administration. In some embodiments, the ActRII antagonist is administered by ocular administration. In some embodiments, the ActRII antagonist is administered by intravitreal administration.

ActRII antagonists of the disclosure include, for example, agents that can inhibit an ActRII receptor (e.g., an ActRIIA and/or ActRIIB receptor) signal transduction pathway (e.g., activation of signal transduction via intracellular mediators such as Smads 1, 2, 3, 5, and/or 8); agents that can inhibit one or more ActRII ligands [e.g., GDF11, GDF8, activin (activin A, activin B, activin AB, activin C, activin E) BMP6, GDF3, BMP10, and/or BMP9], from, e.g., binding to and/or activating an ActRII receptor; agents that inhibit expression (e.g., transcription, translation, cellular secretion, or combinations thereof) of an ActRII ligand and/or an ActRII receptor; and agents that can inhibit one or more intracellular mediators of the ActRII signaling pathway (e.g., Smads 1, 2, 3, 5, and/or 8). Such agents include, for example, an ActRII (ActRIIA or ActRIIB) polypeptide, or combination of ActRII polypeptides as well as variants thereof (e.g., a GDF trap polypeptide); an antibody, or combination of antibodies, that binds to one or more ActRII ligand and/or ActRII receptor; an RNA, or combination of RNAs, that inhibits expression of one or more ActRII ligand and/or ActRII receptor; a small molecule, or combination of small molecules, that inhibits expression of one or more ActRII ligand and/or ActRII receptor, as well as combinations thereof.

In certain aspects, a preferred ActRII antagonist, or combination of antagonists, to be used in accordance with methods and uses described herein is an agent that inhibits at least GDF11-mediated signaling transduction (e.g., Smad 2/3 signaling transduction). Effects on ligand-mediated signaling transduction may be determined, for example, using a cell-based assay including, for example, those described herein. Therefore, an ActRII inhibitor, or combination of inhibitors, of the disclosure may bind to at least GDF11. Ligand binding activity may be determined, for example, using a binding affinity assay including, for example, those described herein. In some embodiments, an ActRII inhibitor, or combination of inhibitors, of the disclosure binds to at least GDF11 with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M).

In other aspects, a preferred ActRII antagonist, or combination of antagonists, to be used in accordance with methods and uses described herein is an agent that inhibits at least GDF8-mediated signaling transduction (e.g., Smad 2/3 signaling transduction). Therefore, an ActRII inhibitor, or combination of inhibitors, of the disclosure may bind to at least GDF8. In some embodiments, an ActRII inhibitor, or combination of inhibitors, of the disclosure binds to at least GDF8 with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M).

In still other aspects, a preferred ActRII antagonist, or combination of antagonists, to be used in accordance with methods and uses described herein is an agent that inhibits at least activin-mediated signaling transduction (e.g., Smad 2/3 signaling transduction). Therefore, an ActRII inhibitor, or combination of inhibitors, of the disclosure may bind to at least activin (e.g., activin A, activin B, activin AB, activin C, and/or activin E). In some embodiments, an ActRII inhibitor, or combination of inhibitors, of the disclosure binds to at least activin A, activin B, activin AB, activin C, and/or activin E with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M). In some embodiments, an ActRII inhibitor, or combination of inhibitors, of the disclosure binds to at least activin B with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M). In some embodiments, an ActRII inhibitor, or combination of inhibitors, of the disclosure does not substantially bind to activin A (e.g., binds to activin A with a $K_D$ higher than $1\times10^{-7}$ M or has relatively modest binding, e.g., about $1\times10^{-8}$ M or about $1\times10^{-9}$ M) and/or inhibit activin A activity. In some embodiments, an ActRII inhibitor, or combination of inhibitors, of the disclosure binds to at least activin B (e.g., binds with a $K_D$ of at least $1\times10^{-7}$ M, at least $1\times10^{-8}$ M, at least $1\times10^{-9}$ M, at least $1\times10^{-10}$ M, at least $1\times10^{-11}$ M, or at least $1\times10^{-12}$ M), but does not substantially bind to activin A (e.g., binds to activin A with a $K_D$ higher than $1\times10^{-7}$ M or has relatively modest binding, e.g., about $1\times10^{-8}$ M or about $1\times10^{-9}$ M) and/or inhibit activin A activity.

In even other aspects, a preferred ActRII antagonist, or combination of antagonists, to be used in accordance with methods and uses described herein is an agent that inhibits at least BMP6-mediated signaling transduction (e.g., Smad 2/3 signaling transduction). Therefore, an ActRII inhibitor, or combination of inhibitors, of the disclosure may bind to at least BMP6. In some embodiments, an ActRII inhibitor, or combination of inhibitors, of the disclosure binds to at least BMP6 with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M). Alternatively, in other aspects, an ActRII inhibitor, or combination of inhibitors, of the disclosure does not substantially bind to BMP6 (e.g., binds to BMP6 with a $K_D$ higher than $1\times10^{-7}$ M or has relatively modest binding, e.g., about $1\times10^{-8}$ M or about $1\times10^{-9}$ M) and/or inhibit BMP6 activity.

In even other aspects, a preferred ActRII antagonist, or combination of antagonists, to be used in accordance with methods and uses described herein is an agent that inhibits at least GDF3-mediated signaling transduction (e.g., Smad 2/3 signaling transduction). Therefore, an ActRII inhibitor, or combination of inhibitors, of the disclosure may bind to at least GDF3. In some embodiments, an ActRII inhibitor, or combination of inhibitors, of the disclosure binds to at least GDF3 with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M). Alternatively, in other aspects, an ActRII inhibitor, or combination of inhibitors, of the disclosure does not substantially bind to GDF3 (e.g., binds to GDF3 with a $K_D$ higher than $1\times10^{-7}$ M or has relatively modest binding, e.g., about $1\times10^{-8}$M or about $1\times10^{-9}$M) and/or inhibit GDF3 activity.

In still even other aspects, a preferred ActRII antagonist, or combination of antagonists, to be used in accordance with methods and uses described herein is an agent that inhibits at least BMP9-mediated signaling transduction (e.g., Smad 2/3 signaling transduction). Therefore, an ActRII inhibitor, or combination of inhibitors, of the disclosure may bind to at least BMP9. In some embodiments, an ActRII inhibitor, or combination of inhibitors, of the disclosure binds to at least BMP9 with a $K_D$ of at least $1\times10^{-7}$ M (e.g., at least $1\times10^{-8}$M, at least $1\times10^{-9}$M, at least $1\times10^{-10}$ M, at least $1\times10^{-11}$ M, or at least $1\times10^{-12}$ M). Alternatively, in other aspects, an ActRII inhibitor, or combination of inhibitors, of the disclosure does not substantially bind to BMP9 (e.g., binds to BMP9 with a $K_D$ higher than $1\times10^{-7}$ M or has relatively modest binding, e.g., about $1\times10^{-8}$M or about $1\times10^{-9}$M) and/or inhibit BMP9 activity.

In even other aspects, a preferred ActRII antagonist, or combination of antagonists, to be used in accordance with methods and uses described herein is an agent that inhibits at least BMP10-mediated signaling transduction (e.g., Smad 2/3 signaling transduction). Therefore, an ActRII inhibitor, or combination of inhibitors, of the disclosure may bind to at least BMP10. In some embodiments, an ActRII inhibitor, or combination of inhibitors, of the disclosure binds to at least BMP10 with a $K_D$ of at least $1\times10^{-7}$ M (e.g., at least $1\times10^{-8}$M, at least $1\times10^{-9}$M, at least $1\times10^{-10}$ M, at least $1\times10^{-11}$ M, or at least $1\times10^{-12}$ M). Alternatively, in other aspects, an ActRII inhibitor, or combination of inhibitors, of the disclosure does not substantially bind to BMP10 (e.g., binds to BMP10 with a $K_D$ higher than $1\times10^{-7}$ M or has relatively modest binding, e.g., about $1\times10^{-8}$M or about $1\times10^{-9}$M) and/or inhibit BMP10 activity.

In further aspects, a preferred ActRII antagonist, or combination of antagonists, to be used in accordance with methods and uses described herein is an agent that inhibits at least GDF11- and GDF8-mediated signaling transduction (e.g., Smad 2/3 signaling transduction). Therefore, an ActRII inhibitor, or combination of inhibitors, of the disclosure may bind to at least GDF11 and GDF8. In some embodiments, ActRII inhibitors of the disclosure binds to at least GDF11 with a $K_D$ of at least $1\times10^{-7}$ M (e.g., at least $1\times10^{-8}$M, at least $1\times10^{-9}$M, at least $1\times10^{-10}$ M, at least $1\times10^{-11}$M, or at least $1\times10^{-12}$ M) and GDF8 with a $K_D$ of at least $1\times10^{-7}$ M (e.g., at least $1\times10^{-8}$M, at least $1\times10^{-9}$M, at least $1\times10^{-10}$ M, at least $1\times10^{-11}$ M, or at least $1\times10^{-12}$ M). In some embodiments, an ActRII inhibitor, or combination of inhibitors, of the disclosure that binds to GDF11 and GDF8 does not substantially bind to activin A (e.g., binds to activin A with a $K_D$ higher than $1\times10^{-7}$ M or has relatively modest binding, e.g., about $1\times10^{-8}$ M or about $1\times10^{-9}$M). In some embodiments, an ActRII inhibitor, or combination of inhibitors, of the disclosure that binds to GDF11 and GDF8 does not substantially bind to BMP9 (e.g., binds to BMP9 with a $K_D$ higher than $1\times10^{-7}$ M or has relatively modest binding, e.g., about $1\times10^{-8}$M or about $1\times10^{-9}$M). In some embodiments, an ActRII inhibitor, or combination of inhibitors, of the disclosure that binds to GDF11 and GDF8 does not substantially bind to BMP10 (e.g., binds to BMP10 with a $K_D$ higher than $1\times10^{-7}$ M or has relatively modest binding, e.g., about $1\times10^{-8}$M or about $1\times10^{-9}$M). In some embodiments, an ActRII inhibitor, or combination of inhibitors, of the disclosure that binds to GDF11 and GDF8 does not substantially bind to BMP9 or BMP10 (e.g., binds to BMP9 and BMP10 with a $K_D$ higher than $1\times10^{-7}$ M or has relatively modest binding, e.g., about $1\times10^{-8}$M or about $1\times10^{-9}$M In some embodiments, an ActRII inhibitor, or combination of inhibitors, of the disclosure that binds to GDF11 and GDF8 does not substantially bind to activin A, BMP9, or BMP10 (e.g., binds to activin A, BMP9 and BMP10 with a $K_D$ higher than $1\times10^{-7}$ M or has relatively modest binding, e.g., about $1\times10^{-8}$M or about $1\times10^{-9}$ M).

In other further aspects, an antagonist, or combination of antagonists, to that inhibits at GDF11- and/or GDF8-mediated signaling transduction (e.g., Smad 2/3 signaling transduction) may further inhibit activin-mediated signaling transduction. Therefore, an ActRII inhibitor, or combination of inhibitors, of the disclosure that binds to GDF11 and/or GDF8 may further bind to at least activin (e.g., activin A, activin B, activin AB, activin C, and/or activin E). In some embodiments, an ActRII inhibitor, or combination of inhibitors, of the disclosure that binds to GDF11 and/or GDF8 may further bind to at least activin (e.g., activin A, activin B, activin AB, activin C, and/or activin E) with a $K_D$ of at least $1\times10^{-7}$ M (e.g., at least $1\times10^{-8}$M, at least $1\times10^{-9}$M, at least $1\times10^{-10}$ M, at least $1\times10^{-11}$ M, or at least $1\times10^{-12}$ M). In some embodiments, an ActRII inhibitor, or combination of inhibitors, of the disclosure that binds to GDF11 and/or GDF8 may further bind to at least activin B (e.g., binds with a $K_D$ of at least $1\times10^{-7}$ M, at least $1\times10^{-8}$M, at least $1\times10^{-9}$M, at least $1\times10^{-10}$ M, at least $1\times10^{-11}$ M, or at least $1\times10^{-12}$ M). In some embodiments, an ActRII inhibitor, or combination of inhibitors, of the disclosure that binds to GDF11 and/or GDF8 does not substantially bind to activin A (e.g., binds to activin A with a $K_D$ higher than $1\times10^{-7}$ M or has relatively modest binding, e.g., about $1\times10^{-8}$M or about $1\times10^{-9}$M). In some embodiments, an ActRII inhibitor, or combination of inhibitors, of the disclosure that binds to GDF11 and/or GDF8 may further bind to at least activin B (e.g., binds with a $K_D$ of at least $1\times10^{-7}$ M, at least $1\times10^{-8}$M, at least $1\times10^{-9}$M, at least $1\times10^{-10}$ M, at least $1\times10^{-11}$ M, or at least $1\times10^{-12}$ M), but does not substantially bind to activin A (e.g., binds to activin A with a $K_D$ higher than $1\times10^{-7}$ M or has relatively modest binding, e.g., about $1\times10^{-8}$ M or about $1\times10^{-9}$M). In some embodiments, an ActRII inhibitor, or combination of inhibitors, of the disclosure that binds to GDF11 and/or GDF8 does not substantially bind to BMP9 (e.g., binds to BMP9 with a $K_D$ higher than $1\times10^{-7}$ M or has relatively modest binding, e.g., about $1\times10^{-8}$M or about $1\times10^{-9}$M). In some embodiments, an ActRII inhibitor, or combination of inhibitors, of the disclosure that binds to GDF11 and/or GDF8 does not substantially bind to BMP10 (e.g., binds to BMP10 with a $K_D$ higher than $1\times10^{-7}$ M or has relatively modest binding, e.g., about $1\times10^{-8}$M or about $1\times10^{-9}$M). In some embodiments, an ActRII inhibitor, or combination of inhibitors, of the disclosure that binds to GDF11 and/or GDF8 does not substantially bind to BMP9 or BMP10 (e.g., binds to BMP9 and BMP10 with a $K_D$ higher than $1\times10^{-7}$ M or has relatively modest binding, e.g., about $1\times10^{-8}$M or about $1\times10^{-9}$M). In some embodiments, an ActRII inhibitor, or combination of inhibitors, of the disclosure that binds to GDF11 and/or GDF8 does not substantially bind to activin A, BMP9, or BMP10 (e.g., binds to activin A, BMP9 and BMP10 with a $K_D$ higher than $1\times10^{-7}$ M or has relatively modest binding, e.g., about $1\times10^{-8}$M or about $1\times10^{-9}$M).

In other further aspects, an antagonist, or combination of antagonists, to that inhibits at GDF11-, GDF8-, and/or activin (e.g., activin A, activin B, activin AB, activin C, and/or activin E) mediated signaling transduction (e.g., Smad 2/3 signaling transduction) may further inhibit BMP6-mediated signaling transduction. Therefore, an ActRII inhibitor, or combination of inhibitors, of the disclosure that binds to GDF11, GDF8, and/or activin may further bind to at least BMP6. In some embodiments, an ActRII inhibitor, or combination of inhibitors, of the disclosure that binds to GDF11, GDF8, and/or activin may further bind to at least BMP6 with a $K_D$ of at least $1\times10^{-7}$ M (e.g., at least $1\times10^{-8}$M, at least $1\times10^{-9}$M, at least $1\times10^{-10}$ M, at least $1\times10^{-11}$M, or at least $1\times10^{-12}$ M). In some embodiments, an ActRII inhibitor, or combination of inhibitors, of the disclosure that binds to GDF11, GDF8, activin B, and/or BMP6 does not substantially bind to activin A (e.g., binds to activin A with a $K_D$ higher than $1\times10^{-7}$ M or has relatively modest binding, e.g., about $1\times10^{-8}$M or about $1\times10^{-9}$M). In some embodiments, an ActRII inhibitor, or combination of inhibitors, of the disclosure that binds to GDF11, GDF8, activin, and/or BMP6 does not substantially bind to BMP9 (e.g., binds to BMP9 with a $K_D$ higher than $1\times10^{-7}$ M or has relatively modest binding, e.g., about $1\times10^{-8}$M or about $1\times10^{-9}$M). In some embodiments, an ActRII inhibitor, or combination of inhibitors, of the disclosure that binds to GDF11, GDF8, activin, and/or BMP6 does not substantially bind to BMP10 (e.g., binds to BMP10 with a $K_D$ higher than $1\times10^{-7}$ M or has relatively modest binding, e.g., about $1\times10^{-8}$M or about $1\times10^{-9}$M). In some embodiments, an ActRII inhibitor, or combination of inhibitors, of the disclosure that binds to GDF11, GDF8, activin, and/or BMP6 does not substantially bind to BMP9 or BMP10 (e.g., binds to BMP9 and BMP10 with a $K_D$ higher than $1\times10^{-7}$ M or has relatively modest binding, e.g., about $1\times10^{-8}$M or about $1\times10^{-9}$M). In some embodiments, an ActRII inhibitor, or combination of inhibitors, of the disclosure that binds to GDF11, GDF8, activin B, and/or BMP6 does not substantially bind to activin A, BMP9, or BMP10 (e.g., binds to activin A, BMP9, and BMP10 with a $K_D$ higher than $1\times10^{-7}$ M or has relatively modest binding, e.g., about $1\times10^{-8}$M or about $1\times10^{-9}$M).

In still further aspects, an antagonist, or combination of antagonists, to that inhibits at GDF11-, GDF8-, activin (e.g., activin A, activin B, activin AB, activin C, and/or activin E) and/or BMP6-mediated signaling transduction (e.g., Smad 2/3 signaling transduction) may further inhibit GDF3-mediated signaling transduction. Therefore, an ActRII inhibitor, or combination of inhibitors, of the disclosure that binds to GDF11, GDF8, activin and/or BMP6 may further bind to at least GDF3. In some embodiments, an ActRII inhibitor, or combination of inhibitors, of the disclosure that binds to GDF11, GDF8, activin, and/or BMP6 may further bind to at least GDF3 with a $K_D$ of at least $1\times10^{-7}$ M (e.g., at least $1\times10^{-8}$M, at least $1\times10^{-9}$ M, at least $1\times10^{-10}$ M, at least $1\times10^{-11}$M, or at least $1\times10^{-12}$ M). In some embodiments, an ActRII inhibitor, or combination of inhibitors, of the disclosure that binds to GDF11, GDF8, activin B, and/or BMP6 does not substantially bind to activin A (e.g., binding to activin A with a $K_D$ higher than $1\times10^{-7}$ M or has relatively modest binding, e.g., about $1\times10^{-8}$M or about $1\times10^{-9}$ M). In some embodiments, an ActRII inhibitor, or combination of inhibitors, of the disclosure that binds to GDF11, GDF8, activin, and/or BMP6 does not substantially bind to BMP9 (e.g., binding to BMP9 with a $K_D$ higher than $1\times10^{-7}$ M or has relatively modest binding, e.g., about $1\times10^{-8}$M or about $1\times10^{-9}$ M). In some embodiments, an ActRII inhibitor, or combination of inhibitors, of the disclosure that binds to GDF11, GDF8, activin, and/or BMP6 does not substantially bind to BMP10 (e.g., binding to BMP9 with a $K_D$ higher than $1\times10^{-7}$ M or has relatively modest binding, e.g., about $1\times10^{-8}$M or about $1\times10^{-9}$M). In some embodiments, an ActRII inhibitor, or combination of inhibitors, of the disclosure that binds to GDF11, GDF8, activin, and/or BMP6 does not substantially bind to BMP9 or BMP10 (e.g., binding to BMP9 and BMP10 with a $K_D$ higher than $1\times10^{-7}$M or has relatively modest binding, e.g., about $1\times10^{-8}$ M or about $1\times10^{-9}$M). In some embodiments, an ActRII inhibitor, or combination of inhibitors, of the disclosure that binds to GDF11, GDF8, activin B, and/or BMP6 does not substantially bind to activin A, BMP9, or BMP10 (e.g., binding to activin A, BMP9, and BMP10 with a $K_D$ higher than $1\times10^{-7}$M or has relatively modest binding, e.g., about $1\times10^{-8}$M or about $1\times10^{-9}$ M).

In even further aspects, an antagonist, or combination of antagonists, to that inhibits at GDF11-, GDF8-, activin (e.g., activin A, activin B, activin AB, activin C, and/or activin E), BMP6, and/or GDF3-mediated signaling transduction (e.g., Smad 2/3 signaling transduction) may further inhibit BMP10-mediated signaling transduction. Therefore, an ActRII inhibitor, or combination of inhibitors, of the disclosure that binds to GDF11, GDF8, activin, BMP6, and/or GDF3 may further bind to at least BMP10. In some embodiments, an ActRII inhibitor, or combination of inhibitors, of the disclosure that binds to GDF11, GDF8, activin, BMP6, and/or GDF3 may further bind to at least BMP10 with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$M, or at least $1\times10^{-12}$ M). In some embodiments, an ActRII inhibitor, or combination of inhibitors, of the disclosure that binds to GDF11, GDF8, activin B, BMP6, GDF3 and/or BMP10 does not substantially bind to activin A (e.g., binding to activin A with a $K_D$ higher than $1\times10^{-7}$ M or has relatively modest binding, e.g., about $1\times10^{-8}$M or about $1\times10^{-9}$M). In some embodiments, an ActRII inhibitor, or combination of inhibitors, of the disclosure that binds to GDF11, GDF8, activin B, BMP6, GDF3 and/or BMP10 does not substantially bind to BMP9 (e.g., binding to BMP9 with a $K_D$ higher than $1\times10^{-7}$ M or has relatively modest binding, e.g., about $1\times10^{-8}$M or about $1\times10^{-9}$M). In some embodiments, an ActRII inhibitor, or combination of inhibitors, of the disclosure that binds to GDF11, GDF8, activin B, BMP6, GDF3 and/or BMP10 does not substantially bind to activin A or BMP9 (e.g., binding to activin A and BMP9 with a $K_D$ higher than $1\times10^{-7}$ M or has relatively modest binding, e.g., about $1\times10^{-8}$M or about $1\times10^{-9}$M).

In other aspects, an antagonist, or combination of antagonists, to that inhibits at GDF11-, GDF8-, activin (e.g., activin A, activin B, activin AB, activin C, and/or activin E), BMP6, GDF3 and/or BMP10-mediated signaling transduction (e.g., Smad 2/3 signaling transduction) may further inhibit BMP9-mediated signaling transduction. Therefore, an ActRII inhibitor, or combination of inhibitors, of the disclosure that binds to GDF11, GDF8, activin, BMP6, GDF3 and/or BMP10 may further bind to at least BMP9. In some embodiments, an ActRII inhibitor, or combination of inhibitors, of the disclosure that binds to GDF11, GDF8, activin, BMP6, GDF3 and/or BMP10 may further bind to at least BMP9 with a $K_D$ of at least $1\times10^{-7}$ M (e.g., at least $1\times10^{-8}$M, at least $1\times10^{-9}$M, at least $1\times10^{-10}$ M, at least $1\times10^{-11}$M, or at least $1\times10^{-12}$ M). In some embodiments, an ActRII inhibitor, or combination of inhibitors, of the disclosure that binds to GDF11, GDF8, activin, BMP6, GDF3, BMP10, and/or BMP9 does not substantially bind to activin A (e.g., binding to activin A with a $K_D$ higher than $1\times10^{-7}$ M or has relatively modest binding, e.g., about $1\times10^{-8}$M or about $1\times10^{-9}$M).

In certain aspects, the present disclosure relates to methods and compositions for treating or preventing a vascular disorder of the eye comprising administering to a patient in need thereof an effective amount of an ActRII polypeptide. The term "ActRII polypeptide" collectively refers to naturally occurring ActRIIA and ActRIIB polypeptides as well as truncations and variants thereof such as those described herein (e.g., GDF trap polypeptides). Preferably ActRII polypeptides comprise, consist essentially of, or consist of a ligand-binding domain of an ActRII polypeptide or modified (variant) form thereof. For example, in some embodiments, an ActRIIA polypeptide comprises, consists essentially of, or consists of an ActRIIA ligand-binding domain of an ActRIIA polypeptide, for example, a portion of the ActRIIA extracellular domain. Similarly, an ActRIIB polypeptide may comprise, consist essentially of, or consist of an ActRIIB ligand-binding domain of an ActRIIB polypeptide, for example, a portion of the ActRIIB extracellular domain. Preferably, ActRII polypeptides to be used in accordance with the methods and uses described herein are soluble polypeptides.

In certain aspects, the present disclosure relates to methods and compositions for treating or preventing a vascular disorder of the eye comprising administering to a patient in need thereof an effective amount of an ActRIIA polypeptide. For example, in some embodiments, an ActRIIA polypeptide of the disclosure comprises, consists essentially of, or consists of an amino acid sequence that is at least 70%, 75%, 80%, 85%, 90%, 91%, 92%, 93%, 94%, 95%, 96%, 97%, 98%, 99%, or 100% identical to the sequence of amino acids 30-110 of SEQ ID NO: 9. In other embodiments, an ActRIIA polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 9. In other embodiments, an ActRIIA polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 10. In even other embodiments, an ActRIIA polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 11. In still other embodiments, an ActRIIA polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 32. In still even other embodiments, an ActRIIA polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 36. In still even other embodiments, an ActRIIA polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 39.

In other aspects, the present disclosure relates to methods and compositions for treating or preventing a vascular disorder of the eye comprising administering to a patient in need thereof an effective amount of an ActRIIB polypeptide. For example, in some embodiments, an ActRIIB polypeptide of the disclosure comprises, consists essentially of, or consists of an amino acid sequence that is at least 70%, 75%, 80%, 85%, 90%, 91%, 92%, 93%, 94%, 95%, 96%, 97%, 98%, 99%, or 100% identical to the sequence of amino acids 29-109 of SEQ ID NO: 1. In some embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the sequence of amino acids 29-109 of SEQ ID NO: 1, wherein the ActRIIB polypeptide comprises an acidic amino acid [naturally occurring (E or D) or artificial acidic amino acid] at position 79 with respect to SEQ ID NO: 1. In other embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the sequence of amino acids 25-131 of SEQ ID NO: 1. In some embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the sequence of amino acids 25-131 of SEQ ID NO: 1, wherein the ActRIIB polypeptide comprises an acidic amino acid at position 79 with respect to SEQ ID NO: 1. In other embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 1. In some embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 1, wherein the ActRIIB polypeptide comprises an acidic amino acid at position 79 with respect to SEQ ID NO: 1. In even other embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 2. In other embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 2, wherein the ActRIIB polypeptide comprises an acidic amino acid at position 79 with respect to SEQ ID NO: 1. In still other embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 3. In other, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 3, wherein the ActRIIB polypeptide comprises an acidic amino acid at position 79 with respect to SEQ ID NO: 1. In other embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 4. In some embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 4, wherein the ActRIIB polypeptide comprises an acidic amino acid at position 79 with respect to SEQ ID NO: 4. In other embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 5. In some embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 5, wherein the ActRIIB polypeptide comprises an acidic amino acid at position 79 with respect to SEQ ID NO: 4. In other embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 6. In some embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 6, wherein the ActRIIB polypeptide comprises an acidic amino acid at position 79 with respect to SEQ ID NO: 4. In still even other embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 44. In some embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 44, wherein the ActRIIB polypeptide comprises an acidic amino acid at position 79 with respect to SEQ ID NO: 1. In still even other embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 45. In some embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 45, wherein the ActRIIB polypeptide comprises an acidic amino acid at position 79 with respect to SEQ ID NO: 1. In still even other embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 46. In some embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 46, wherein the ActRIIB polypeptide comprises an acidic amino acid at position 79 with respect to SEQ ID NO: 1. In still even other embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 48. In some embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 48, wherein the ActRIIB polypeptide comprises an acidic amino acid at position 79 with respect to SEQ ID NO: 1. In other, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 49. In some embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 49, wherein the ActRIIB polypeptide comprises an acidic amino acid at position 79 with respect to SEQ ID NO: 1. In still even other embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 50. In some embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 50, wherein the ActRIIB polypeptide comprises an acidic amino acid at position 79 with respect to SEQ ID NO: 1. In still even other embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 79. In other, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 79, wherein the ActRIIB polypeptide comprises an acidic amino acid at position 79 with respect to SEQ ID NO: 1. In still even other embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 61. In other, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 61, wherein the ActRIIB polypeptide comprises an acidic amino acid at position 79 with respect to SEQ ID NO: 1. In still even other embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 64. In other, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 64, wherein the ActRIIB polypeptide comprises an acidic amino acid at position 79 with respect to SEQ ID NO: 1. In still even other embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 65. In other, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 65, wherein the ActRIIB polypeptide comprises an acidic amino acid at position 79 with respect to SEQ ID NO: 1. In still even other embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 40. In some embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 40, wherein the ActRIIB polypeptide comprises an acidic amino acid at position 79 with respect to SEQ ID NO: 1. In still even other embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 41. In some embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 41, wherein the ActRIIB polypeptide comprises an acidic amino acid at position 79 with respect to SEQ ID NO: 1. In still even other embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 78. In some embodiments, an ActRIIB polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 78, wherein the ActRIIB polypeptide comprises an acidic amino acid at position 79 with respect to SEQ ID NO: 1. In certain embodiments, ActRIIB polypeptides to be used in accordance with the methods and uses described herein do not comprise an acidic amino acid at the position corresponding to L79 of SEQ ID NO: 1.

In other aspects, the present disclosure relates to methods and compositions for treating or preventing a vascular disorder of the eye comprising administering to a patient in need thereof an effective amount of a GDF trap polypeptide (GDF trap). In some embodiments, a GDF trap comprises, consists essentially of, or consists of an altered ActRII ligand-binding domain has a ratio of $K_d$ for activin A binding to $K_d$ for GDF11 and/or GDF8 binding that is at least 2-, 5-, 10-, 20, 50-, 100-, or even 1000-fold greater relative to the ratio for the wild-type ligand-binding domain. Optionally, the GDF trap comprising an altered ligand-binding domain has a ratio of $IC_{50}$ for inhibiting activin A to $IC_{50}$ for inhibiting GDF11 and/or GDF8 that is at least 2-, 5-, 10-, 20-, 25-, 50-, 100-, or even 1000-fold greater relative to the wild-type ActRII ligand-binding domain. Optionally, the GDF trap comprising an altered ligand-binding domain inhibits GDF11 and/or GDF8 with an $IC_{50}$ at least 2, 5, 10, 20, 50, or even 100 times less than the $IC_{50}$ for inhibiting activin A. These GDF traps can be fusion proteins that include an immunoglobulin Fc domain (either wild-type or mutant). In certain cases, the subject soluble GDF traps are antagonists (inhibitors) of GDF8 and/or GDF11-mediated intracellular signaling (e.g., Smad 2/3 signaling).

In some embodiments, the disclosure provides GDF traps which are soluble ActRIIB polypeptides comprising an altered ligand-binding (e.g., GDF11-binding) domain. GDF traps with altered ligand-binding domains may comprise, for example, one or more mutations at amino acid residues such as E37, E39, R40, K55, R56, Y60, A64, K74, W78, L79, D80, F82 and F101 of human ActRIIB (numbering is relative to SEQ ID NO: 1). Optionally, the altered ligand-binding domain can have increased selectivity for a ligand such as GDF8/GDF11 relative to a wild-type ligand-binding domain of an ActRIIB receptor. To illustrate, these mutations are demonstrated herein to increase the selectivity of the altered ligand-binding domain for GDF11 (and therefore, presumably, GDF8) over activin: K74Y, K74F, K74I, L79D, L79E, and D80I. The following mutations have the reverse effect, increasing the ratio of activin binding over GDF11: D54A, K55A, L79A and F82A. The overall (GDF11 and activin) binding activity can be increased by inclusion of the "tail" region or, presumably, an unstructured linker region, and also by use of a K74A mutation. Other mutations that caused an overall decrease in ligand binding affinity, include: R40A, E37A, R56A, W78A, D80K, D80R, D80A, D80G, D80F, D80M and D80N. Mutations may be combined to achieve desired effects. For example, many of the mutations that affect the ratio of GDF11:activin binding have an overall negative effect on ligand binding, and therefore, these may be combined with mutations that generally increase ligand binding to produce an improved binding protein with ligand selectivity. In an exemplary embodiment, a GDF trap is an ActRIIB polypeptide comprising an L79D or L79E mutation, optionally in combination with additional amino acid substitutions, additions, or deletions.

As described herein, ActRII polypeptides and variants thereof (GDF traps) may be homomultimers, for example, homodimer, homotrimers, homotetramers, homopentamers, and higher order homomultimer complexes. In certain preferred embodiments, ActRII polypeptides and variants thereof are homodimers. In certain embodiments, ActRII polypeptide dimers described herein comprise an first ActRII polypeptide covalently, or non-covalently, associated with an second ActRII polypeptide wherein the first polypeptide comprises an ActRII domain and an amino acid sequence of a first member (or second member) of an interaction pair (e.g., a constant domain of an immunoglobulin) and the second polypeptide comprises an ActRII polypeptide and an amino acid sequence of a second member (or first member) of the interaction pair.

In certain aspects, ActRII polypeptides, including variants thereof (e.g., GDF traps), may be fusion proteins. For example, in some embodiments, an ActRII polypeptide may be a fusion protein comprising an ActRII polypeptide domain and one or more heterologous (non-ActRII) polypeptide domains. In some embodiments, an ActRII polypeptide may be a fusion protein that has, as one domain, an amino acid sequence derived from an ActRII polypeptide (e.g., a ligand-binding domain of an ActRII receptor or a variant thereof) and one or more heterologous domains that provide a desirable property, such as improved pharmacokinetics, easier purification, targeting to particular tissues, etc. For example, a domain of a fusion protein may enhance one or more of in vivo stability, in vivo half-life, uptake/administration, tissue localization or distribution, formation of protein complexes, multimerization of the fusion protein, and/or purification. Optionally, an ActRII polypeptide domain of a fusion protein is connected directly (fused) to one or more heterologous polypeptide domains, or an intervening sequence, such as a linker, may be positioned between the amino acid sequence of the ActRII polypeptide and the amino acid sequence of the one or more heterologous domains. In certain embodiments, an ActRII fusion protein comprises a relatively unstructured linker positioned between the heterologous domain and the ActRII domain. This unstructured linker may correspond to the roughly 15 amino acid unstructured region at the C-terminal end of the extracellular domain of ActRIIA or ActRIIB (the "tail"), or it may be an artificial sequence of between 3 and 15, 20, 30, 50 or more amino acids that are relatively free of secondary structure. A linker may be rich in glycine and proline residues and may, for example, contain repeating sequences of threonine/serine and glycines. Examples of linkers include, but are not limited to, the sequences TGGG (SEQ ID NO: 23), SGGG (SEQ ID NO: 24), TGGGG (SEQ ID NO: 21), SGGGG (SEQ ID NO: 22), GGGGS (SEQ ID NO: 25), GGGG (SEQ ID NO: 20), and GGG (SEQ ID NO: 19). In some embodiments, ActRII fusion proteins may comprise a constant domain of an immunoglobulin, including, for example, the Fc portion of an immunoglobulin. For example, an amino acid sequence that is derived from an Fc domain of an IgG (IgG1, IgG2, IgG3, or IgG4), IgA (IgA1 or IgA2), IgE, or IgM immunoglobulin. For example, am Fc portion of an immunoglobulin domain may comprise, consist essentially of, or consist of an amino acid sequence that is at least 70%, 75%, 80%, 85%, 90%, 91%, 92%, 93%, 94%, 95%, 96%, 97%, 98%, 99% or 100% identical to any one of SEQ ID NOs: 14-18. Such immunoglobulin domains may comprise one or more amino acid modifications (e.g., deletions, additions, and/or substitutions) that confer an altered Fc activity, e.g., decrease of one or more Fc effector functions. In some embodiment, an ActRII fusion protein comprises an amino acid sequence as set forth in the formula A-B-C. For example, the B portion is an N- and C-terminally truncated ActRII polypeptide as described herein. The A and C portions may be independently zero, one, or more than one amino acids, and both A and C portions are heterologous to B. The A and/or C portions may be attached to the B portion via a linker sequence. In certain embodiments, an ActRII fusion protein comprises a leader sequence. The leader sequence may be a native ActRII leader sequence (e.g., a native ActRIIA or ActRIIB leader sequence) or a heterologous leader sequence. In certain embodiments, the leader sequence is a tissue plasminogen activator (TPA) leader sequence.

An ActRII polypeptide, including variants thereof (e.g., GDF traps), may comprise a purification subsequence, such as an epitope tag, a FLAG tag, a polyhistidine sequence, and a GST fusion. Optionally, an ActRII polypeptide includes one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent. ActRII polypeptides may comprise at least one N-linked sugar, and may include two, three or more N-linked sugars. Such polypeptides may also comprise O-linked sugars. In general, it is preferable that ActRII antagonist polypeptides be expressed in a mammalian cell line that mediates suitably natural glycosylation of the polypeptide so as to diminish the likelihood of an unfavorable immune response in a patient. ActRII polypeptides may be produced in a variety of cell lines that glycosylate the protein in a manner that is suitable for patient use, including engineered insect or yeast cells, and mammalian cells such as COS cells, CHO cells, HEK cells and NSO cells. In some embodiments, an ActRII polypeptide is glycosylated and has a glycosylation pattern obtainable from a Chinese hamster ovary cell line. In some embodiments, ActRII polypeptides of the disclosure exhibit a serum half-life of at least 4, 6, 12, 24, 36, 48, or 72 hours in a mammal (e.g., a mouse or a human). Optionally, ActRII polypeptides may exhibit a serum half-life of at least 6, 8, 10, 12, 14, 20, 25, or 30 days in a mammal (e.g., a mouse or a human).

In certain aspects, the disclosure provides pharmaceutical preparations comprising one or more ActRII antagonist of the present disclosure and a pharmaceutically acceptable carrier. A pharmaceutical preparation may also comprise one or more additional active agents such as a compound that is used to treat a vascular disorder of the eye such as those described herein. Preferably, a pharmaceutical preparation of the disclosure is substantially pyrogen-free. In certain embodiments, the disclosure provides packaged pharmaceuticals comprising a pharmaceutical preparation described herein and labeled for use in one or more of increasing treating or preventing one or more vascular disorders of the eye [e.g., age-related macular degeneration, juvenile macular degeneration, wet macular degeneration, dry macular degeneration, Stargardt's disease, and Best's disease), retinal vein occlusion (e.g., central retinal vein occlusion, hemi-retinal vein occlusion, branch retinal vein occlusion, and ischemic retinal vein occlusion), retinal artery occlusion (e.g., central retinal artery occlusion, hemi-retinal artery occlusion, branch retinal artery occlusion, and ischemic retinal artery occlusion), diabetic retinopathy, ischemic optic neuropathy [e.g., anterior ischemic optic neuropathy (arteritic and non-arteritic) and posterior ischemic optic neuropathy], macular telangiectasia (type I or type II), retinal ischemia (e.g., acute retinal ischemia or chronic retinal ischemia)].

In certain aspects, the present disclosure relates to treating or preventing a vascular disorder of the eye in a patient comprising administering to a patient in need thereof at least one ActRII antagonists and at least one additional therapy for treating the disorder including, for example, surgery, laser therapy (e.g., photocoagulation), anti-angiogenic therapy [e.g., VEGF inhibitors such as bevacizumab (Avastin®), ranibizumab (Lucentis®), and Aflibercept (Eylea®)], $Ca^{2+}$ inhibitors (e.g., flunarizine and nifedipine), cryotherapy, hyperbaric oxygenation, $Na^+$ channel blockers (e.g., topiramate), iGluR antagonists (e.g., MK-801, dextromethorphan, eliprodil, and flupirtine), antioxidants (e.g., dimethylthiourea, vitamin E, alph-lipoic acid, superoxide dismutase, catalase, desferrioxamine, mannitol, allopurinol, calcium dobesilate, flupirtine, trimetazidine, and EGB-761), anti-inflammatory agents, cyclodiathermy, cyclocryotherapy, ocular filtering procedures, implantation of drainage valves, antiplatelet therapy (e.g., aspirin, ticlopidine, and clopidogrel), anticoagulant therapy (e.g., warfarin and heparin), steroids, systemic or local corticosteroids (e.g., prednisone triamcinolone (Triesence®), and dexamethasone (Ozurdex®), steroid-sparing immunosuppressants (e.g., cyclosporine, azathioprine, cyclophosphamide, mycophenolate, mofetil, infliximab and etanercept), dietary supplements (e.g., vitamin C, vitamin E, lutein, zeaxanthin, zinc, folic acid, vitamins B6, vitamin B12, and zeaxanthin), vitrectomy, scleral buckle surgery, and pneumatic retinopexy.

In certain aspects, the present disclosure relates to an antibody, or combination of antibodies, that antagonize ActRII activity (e.g., inhibition of ActRIIA and/or ActRIIB signaling transduction, e.g., Smad 1, 2, 3, 5, and 8 signaling). In particular, the disclosure provides methods for treating or preventing a vascular disorder of the eye comprising administering an effective amount of an antibody ActRII antagonist, or combination of antibody ActRII antagonists (e.g., ActRII ligand-binding antibodies, ActRII antibodies, etc.) to a subject in need thereof. For example, in certain embodiments, a preferred ActRII antagonist of the disclosure is an antibody, or combination of antibodies, that binds to at least GDF11. In other embodiments, a preferred ActRII antagonist of the disclosure is an antibody, or combination of antibodies, that binds to at least GDF8. In other embodiments, a preferred ActRII antagonist of the disclosure is an antibody, or combination of antibodies, that binds to at least activin (e.g., activin A, activin B, activin AB, activin C, and/or activin E). In further embodiments, a preferred ActRII antagonist of the disclosure is an antibody, or combination of antibodies, that binds to at least activin A and activin B. In further embodiments, a preferred ActRII antagonist of the disclosure is an antibody, or combination of antibodies, that binds to at least activin A, activin B, activin AB. In still other embodiments, a preferred ActRII antagonist of the disclosure is an antibody, or combination of antibodies, that binds to at least GDF11 and GDF8, particular in the context of a multispecific antibodies such as a bispecific antibody. Optionally, an antibody, or combination of antibodies, of the disclosure that binds to GDF11 and/or GDF8 further binds to one of more of activin (activin A, activin B, activin AB, activin C, activin E), BMP6, or BMP10. In some embodiments, an antibody, or combination of antibodies, of the disclosure that binds to GDF11 and/or GDF8 further binds to at least activin B. In some embodiments, an antibody, or combination of antibodies, of the disclosure does bind to, or does not substantially bind to, activin A (e.g., binds to activin A with a $K_D$ of greater than $1\times10^{-7}$ M or has relatively modest binding, e.g., about $1\times10^{-8}$M or about $1\times10^{-9}$M). In some embodiments, an antibody, or combination of antibodies, of the disclosure does not bind to, or does not substantially bind to, BMP10 (e.g., binds to BMP10 with a $K_D$ of greater than $1\times10^{-7}$ M or has relatively modest binding, e.g., about $1\times10^{-8}$ M or about $1\times10^{-9}$M).

In certain instances, when administering an ActRII antagonist, or combination of antagonists, of the disclosure to treat or prevent a vascular disorder of the eye, it may be desirable to monitor the effects on red blood cells during administration of the ActRII antagonist, or to determine or adjust the dosing of the ActRII antagonist, in order to reduce undesired effects on red blood cells. For example, increases in red blood cell levels, hemoglobin levels, or hematocrit levels may cause undesirable increases in blood pressure.

BRIEF DESCRIPTION OF THE DRAWINGS

The patent or patent application file contains at least one drawing executed in color. Copies of this patent or patent application publication with color drawing(s) will be provided by the Office upon request and payment of the necessary fee.

FIG. 1 shows an alignment of extracellular domains of human ActRIIA (SEQ ID NO: 51) and human ActRIIB (SEQ ID NO: 2) with the residues that are deduced herein, based on composite analysis of multiple ActRIIB and ActRIIA crystal structures, to directly contact ligand indicated with boxes.

FIG. 2 shows a multiple sequence alignment of various vertebrate ActRIIB proteins and human ActRIIA (SEQ ID NOs: 52-58) as well as a consensus ActRII sequence derived from the alignment (SEQ ID NO: 59).

FIG. 4 shows the binding of ActRIIA-hFc to activin (top panel) and GDF-11 (bottom panel), as measured by Biacore™ assay.

FIG. 5 shows the full amino acid sequence for the GDF trap ActRIIB(L79D 20-134)-hFc (SEQ ID NO: 46), including the TPA leader sequence (double underline), ActRIIB extracellular domain (residues 20-134 in SEQ ID NO: 1; single underline), and hFc domain. The aspartate substituted at position 79 in the native sequence is double underlined and highlighted, as is the glycine revealed by sequencing to be the N-terminal residue in the mature fusion protein.

FIGS. 6A and 6B show a nucleotide sequence encoding ActRIIB(L79D 20-134)-hFc. SEQ ID NO: 86 corresponds to the sense strand, and SEQ ID NO: 60 corresponds to the antisense strand. The TPA leader (nucleotides 1-66) is double underlined, and the ActRIIB extracellular domain (nucleotides 76-420) is single underlined.

FIG. 7 shows the full amino acid sequence for the truncated GDF trap ActRIIB(L79D 25-131)-hFc (SEQ ID NO: 61), including the TPA leader (double underline), truncated ActRIIB extracellular domain (residues 25-131 in SEQ ID NO:1; single underline), and hFc domain. The aspartate substituted at position 79 in the native sequence is double underlined and highlighted, as is the glutamate revealed by sequencing to be the N-terminal residue in the mature fusion protein.

FIGS. 8A and 8B show a nucleotide sequence encoding ActRIIB(L79D 25-131)-hFc. SEQ ID NO: 62 corresponds to the sense strand, and SEQ ID NO: 63 corresponds to the antisense strand. The TPA leader (nucleotides 1-66) is double underlined, and the truncated ActRIIB extracellular domain (nucleotides 76-396) is single underlined. The amino acid sequence for the ActRIIB extracellular domain (SEQ ID NO: 65) is also shown.

FIG. 9 shows the amino acid sequence for the truncated GDF trap ActRIIB(L79D 25-131)-hFc without a leader (SEQ ID NO: 64). The truncated ActRIIB extracellular domain (SEQ ID NO: 65) is underlined. The aspartate substituted at position 79 in the native sequence is double underlined and highlighted, as is the glutamate revealed by sequencing to be the N-terminal residue in the mature fusion protein.

FIG. 10 shows the amino acid sequence for the truncated GDF trap ActRIIB(L79D 25-131) without the leader, hFc domain, and linker (SEQ ID NO: 65). The aspartate substituted at position 79 in the native sequence is underlined and highlighted, as is the glutamate revealed by sequencing to be the N-terminal residue in the mature fusion protein.

FIGS. 11A and 11B show an alternative nucleotide sequence encoding ActRIIB(L79D 25-131)-hFc. SEQ ID NO: 66 corresponds to the sense strand, and SEQ ID NO: 67 corresponds to the antisense strand. The TPA leader (nucleotides 1-66) is double underlined, the truncated ActRIIB extracellular domain (nucleotides 76-396) is underlined, and substitutions in the wild-type nucleotide sequence of the extracellular domain are double underlined and highlighted (compare with SEQ ID NO: 62, FIG. 8). The amino acid sequence for the ActRIIB extracellular domain (SEQ ID NO: 65) is also shown.

FIG. 12 shows nucleotides 76-396 (SEQ ID NO: 68) of the alternative nucleotide sequence shown in FIG. 11 (SEQ ID NO: 66). The same nucleotide substitutions indicated in FIG. 11 are also underlined and highlighted here. SEQ ID NO: 68 encodes only the truncated ActRIIB extracellular domain (corresponding to residues 25-131 in SEQ ID NO: 1) with a L79D substitution, e.g., ActRIIB(L79D 25-131).

FIG. 13A RBC numbers and hemoglobin concentrations (top) and morphological enumeration of hematopoietic precursors in bone marrow (bottom) in wild-type (Wt) mice treated with vehicle (Tris-buffered saline, TBS, n=5), MDS mice treated with TBS (n=5), and MDS mice treated with ActRIIB(L79D 25-131)-mFc (10 mg/kg, n=6) twice weekly for 8 weeks ending at approximately 6 months of age (early stage). *P<0.05, **P<0.01, vs. TB S-treated MDS mice; ####P<0.001 vs. wild-type mice. FIG. 13B Same endpoints as in panel A in MDS mice treated with ActRIIB(L79D 25-131)-mFc (10 mg/kg, twice weekly, n=5) or TBS (n=4) for 7 weeks ending at approximately 12 months of age (late stage). *P<0.05 vs. TBS-treated MDS mice. Data are means±SEM.

Figure 14:
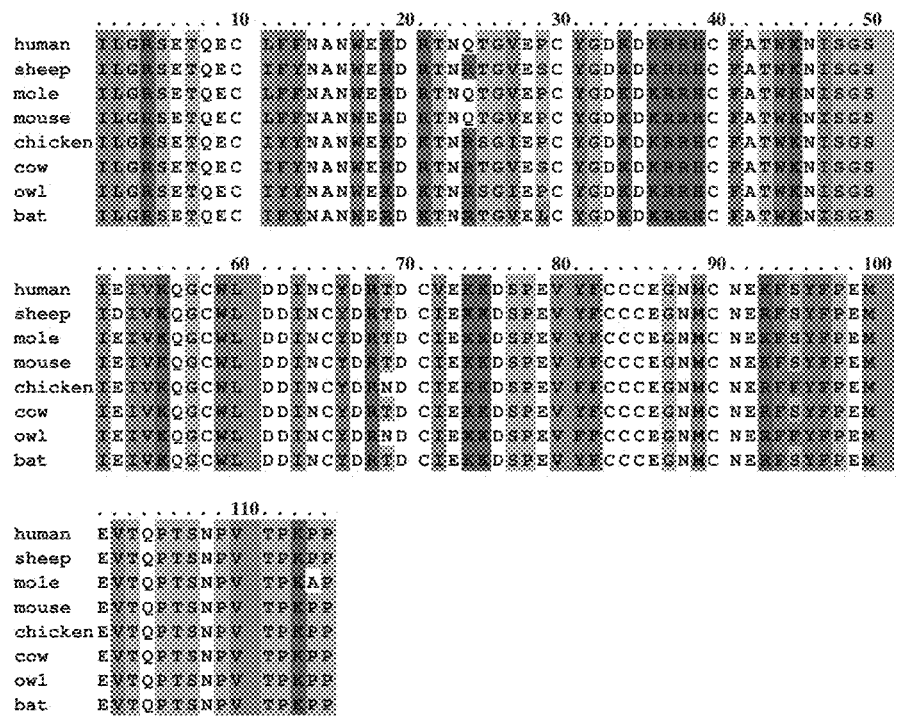

FIG. 14 shows a multiple sequence alignment of various vertebrate ActRIIA proteins and human ActRIIA (SEQ ID NOs: 69-76).

FIG. 15 shows multiple sequence alignment of Fc domains from human IgG isotypes using Clustal 2.1. Hinge regions are indicated by dotted underline. FIG. 15 discloses SEQ ID NOS 14, 18, 15 and 16, respectively, in order of appearance.

FIG. 16 shows the full, unprocessed amino acid sequence for ActRIIB(25-131)-hFc (SEQ ID NO: 79). The TPA leader (residues 1-22) and double-truncated ActRIIB extracellular domain (residues 24-131, using numbering based on the native sequence in SEQ ID NO: 1) are each underlined. Highlighted is the glutamate revealed by sequencing to be the N-terminal amino acid of the mature fusion protein, which is at position 25 relative to SEQ ID NO: 1.

FIGS. 17A and 17B show a nucleotide sequence encoding ActRIIB(25-131)-hFc (the coding strand is shown at top, SEQ ID NO: 80, and the complement shown at bottom 3'-5', SEQ ID NO: 81). Sequences encoding the TPA leader (nucleotides 1-66) and ActRIIB extracellular domain (nucleotides 73-396) are underlined. The corresponding amino acid sequence for ActRIIB(25-131) is also shown (SEQ ID NO: 85).

FIGS. 18A and 18B show an alternative nucleotide sequence encoding ActRIIB(25-131)-hFc (the coding strand is shown at top, SEQ ID NO: 82, and the complement shown at bottom 3'-5', SEQ ID NO: 83). This sequence confers a greater level of protein expression in initial transformants, making cell line development a more rapid process. Sequences encoding the TPA leader (nucleotides 1-66) and ActRIIB extracellular domain (nucleotides 73-396) are underlined, and substitutions in the wild type nucleotide sequence of the ECD (see FIGS. 17A and 17B) are highlighted. The corresponding amino acid sequence for ActRIIB(25-131) is also shown (SEQ ID NO: 85).

DETAIL DESCRIPTION OF THE INVENTION

1. Overview

Figure 3:
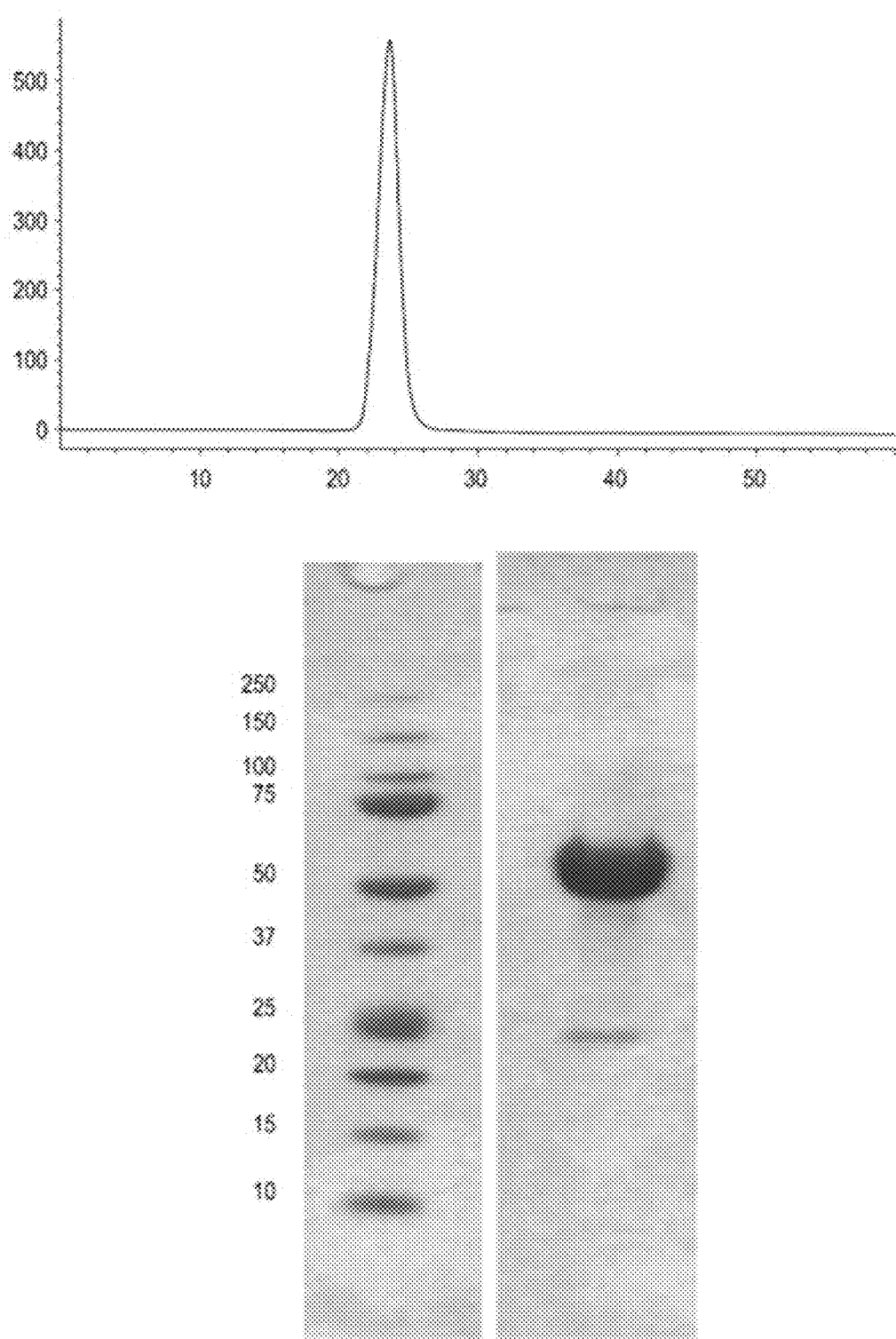
FIG. 3 shows the purification of ActRIIA-hFc expressed in CHO cells. The protein purifies as a single, well-defined peak as visualized by sizing column (top panel) and Coomassie stained SDS-PAGE (bottom panel) (left lane: molecular weight standards; right lane: ActRIIA-hFc).

The transforming growth factor-beta (TGF-beta) superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. By manipulating the activity of a member of the TGF-beta family, it is often possible to cause significant physiological changes in an organism. For example, the Piedmontese and Belgian Blue cattle breeds carry a loss-of-function mutation in the GDF8 (also called myostatin) gene that causes a marked increase in muscle mass [see, e.g., Grobet et al. (1997) Nat Genet. 17(1):71-4]. Furthermore, in humans, inactive alleles of GDF8 are associated with increased muscle mass and, reportedly, exceptional strength [see, e.g., Schuelke et al. (2004) N Engl J Med, 350:2682-8].

TGF-β signals are mediated by heteromeric complexes of type I and type II serine/threonine kinase receptors, which phosphorylate and activate downstream SMAD proteins (e.g., SMAD proteins 1, 2, 3, 5, and 8) upon ligand stimulation [see, e.g., Massagué (2000) Nat. Rev. Mol. Cell Biol. 1:169-178]. These type I and type II receptors are transmembrane proteins, composed of a ligand-binding extracellular domain with cysteine-rich region, a transmembrane domain, and a cytoplasmic domain with predicted serine/threonine specificity. Type I receptors are essential for signaling. Type II receptors are required for binding ligands and for activation of type I receptors. Type I and II activin receptors form a stable complex after ligand binding, resulting in phosphorylation of type I receptors by type II receptors.

Two related type II receptors (ActRII), ActRIIA and ActRIIB, have been identified as the type II receptors for activins [see, e.g., Mathews and Vale (1991) Cell 65:973-982; and Attisano et al. (1992) Cell 68: 97-108]. Besides activins, ActRIIA and ActRIIB can biochemically interact with several other TGF-β family proteins including, for example, BMP6, BMP7, Nodal, GDF8, and GDF11 [see, e.g., Yamashita et al. (1995) J. Cell Biol. 130:217-226; Lee and McPherron (2001) Proc. Natl. Acad. Sci. USA 98:9306-9311; Yeo and Whitman (2001) Mol. Cell 7: 949-957; and Oh et al. (2002) Genes Dev. 16:2749-54]. ALK4 is the primary type I receptor for activins, particularly for activin A, and ALK-7 may serve as a receptor for other activins as well, particularly for activin B. In certain embodiments, the present disclosure relates to antagonizing a ligand of an ActRII receptor (also referred to as an ActRII ligand) with one or more inhibitor agents disclosed herein, particularly inhibitor agents that can antagonize one or more of activin A, activin B, activin C, activin E, BMP9, BMP10, BMP6, GDF3, GDF11 and/or GDF8.

Activins are dimeric polypeptide growth factors that belong to the TGF-beta superfamily. There are three principal activin forms (A, B, and AB) that are homo/heterodimers of two closely related β subunits ($\beta_A\beta_A$, $\beta_B\beta_B$, and $\beta_A\beta_B$, respectively). The human genome also encodes an activin C and an activin E, which are primarily expressed in the liver, and heterodimeric forms containing $\beta_C$ or $\beta_E$ are also known.

In the TGF-beta superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos [DePaolo et al. (1991) Proc Soc Ep Biol Med. 198:500-512; Dyson et al. (1997) Curr Biol. 7:81-84; and Woodruff (1998) Biochem Pharmacol. 55:953-963]. Moreover, erythroid differentiation factor (EDF) isolated from the stimulated human monocytic leukemic cells was found to be identical to activin A [Murata et al. (1988) PNAS, 85:2434]. It has been suggested that activin A promotes erythropoiesis in the bone marrow. In several tissues, activin signaling is antagonized by its related heterodimer, inhibin. For example, during the release of follicle-stimulating hormone (FSH) from the pituitary, activin promotes FSH secretion and synthesis, while inhibin prevents FSH secretion and synthesis. Other proteins that may regulate activin bioactivity and/or bind to activin include follistatin (FS), follistatin-related protein (FSRP, also known as FLRG or FSTL3), and α-macroglobulin.

As described herein, agents that bind to "activin A" are agents that specifically bind to the $\beta_A$ subunit, whether in the context of an isolated $\beta_A$ subunit or as a dimeric complex (e.g., a $\beta_A\beta_A$ homodimer or a $\beta_A\beta_B$ heterodimer). In the case of a heterodimer complex (e.g., a $\beta_A\beta_B$ heterodimer), agents that bind to "activin A" are specific for epitopes present within the $\beta_A$ subunit, but do not bind to epitopes present within the non-$\beta_A$ subunit of the complex (e.g., the $\beta_B$ subunit of the complex). Similarly, agents disclosed herein that antagonize (inhibit) "activin A" are agents that inhibit one or more activities as mediated by a $\beta_A$ subunit, whether in the context of an isolated $\beta_A$ subunit or as a dimeric complex (e.g., a $\beta_A\beta_A$ homodimer or a $\beta_A\beta_B$ heterodimer). In the case of $\beta_A\beta_B$ heterodimers, agents that inhibit "activin A" are agents that specifically inhibit one or more activities of the $\beta_A$ subunit, but do not inhibit the activity of the non-$\beta_A$ subunit of the complex (e.g., the $\beta_B$ subunit of the complex). This principle applies also to agents that bind to and/or inhibit "activin B", "activin C", and "activin E". Agents disclosed herein that antagonize "activin AB" are agents that inhibit one or more activities as mediated by the $\beta_A$ subunit and one or more activities as mediated by the $\beta_B$ subunit.

Growth and differentiation factor-8 (GDF8) is also known as myostatin. GDF8 is a negative regulator of skeletal muscle mass. GDF8 is highly expressed in the developing and adult skeletal muscle. The GDF8 null mutation in transgenic mice is characterized by a marked hypertrophy and hyperplasia of the skeletal muscle [McPherron et al., Nature (1997) 387:83-90]. Similar increases in skeletal muscle mass are evident in naturally occurring mutations of GDF8 in cattle [see, e.g., Ashmore et al. (1974) Growth, 38:501-507; Swatland and Kieffer (1994) J. Anim. Sci. 38:752-757; McPherron and Lee (1997) Proc. Natl. Acad. Sci. USA 94:12457-12461; and Kambadur et al. (1997) Genome Res. 7:910-915] and, strikingly, in humans [see, e.g., Schuelke et al. (2004) N Engl J Med 350:2682-8]. Studies have also shown that muscle wasting associated with HIV-infection in humans is accompanied by increases in GDF8 protein expression [see, e.g., Gonzalez-Cadavid et al. (1998) PNAS 95:14938-43]. In addition, GDF8 can modulate the production of muscle-specific enzymes (e.g., creatine kinase) and modulate myoblast cell proliferation [see, e.g. international patent application publication no. WO 00/43781]. The GDF8 propeptide can noncovalently bind to the mature GDF8 domain dimer, inactivating its biological activity [see, e.g., Miyazono et al. (1988) J. Biol. Chem., 263: 6407-6415; Wakefield et al. (1988) J. Biol. Chem., 263: 7646-7654; and Brown et al. (1990) Growth Factors, 3: 35-43]. Other proteins which bind to GDF8 or structurally related proteins and inhibit their biological activity include follistatin, and potentially, follistatin-related proteins [see, e.g., Gamer et al. (1999) Dev. Biol., 208: 222-232].

Growth and differentiation factor-11 (GDF11), also known as BMP11, is a secreted protein [McPherron et al. (1999) Nat. Genet. 22: 260-264]. GDF11 is expressed in the tail bud, limb bud, maxillary and mandibular arches, and dorsal root ganglia during mouse development [see, e.g., Nakashima et al. (1999) Mech. Dev. 80: 185-189]. GDF11 plays a unique role in patterning both mesodermal and neural tissues [see, e.g., Gamer et al. (1999) Dev Biol., 208:222-32]. GDF11 was shown to be a negative regulator of chondrogenesis and myogenesis in developing chick limb [see, e.g., Gamer et al. (2001) Dev Biol. 229:407-20]. The expression of GDF11 in muscle also suggests its role in regulating muscle growth in a similar way to GDF8. In addition, the expression of GDF11 in brain suggests that GDF11 may also possess activities that relate to the function of the nervous system. Interestingly, GDF11 was found to inhibit neurogenesis in the olfactory epithelium [see, e.g., Wu et al. (2003) Neuron. 37:197-207].

It has been demonstrated that ActRII polypeptides (e.g., ActRIIA and ActRIIB polypeptides as well as variants thereof such as GDF traps) can be used to increase red blood cell levels in vivo (see, e.g., WO 2008/046437 and WO 2010/019261). In certain examples described herein, it is shown that a GDF trap polypeptide is characterized by unique biological properties in comparison to a corresponding sample of an unmodified ActRII polypeptide. This GDF trap is characterized, in part, by substantial loss of binding affinity for activin A, and therefore significantly diminished capacity to antagonize activin A activity, but retains near wild-type levels of binding and inhibition of GDF11. The GDF trap is more effective at increasing red blood cell levels compared to the corresponding unmodified ActRIIB polypeptide and has beneficial effects in a variety of models for anemia. The data therefore indicate that the observed biological activity of an ActRII polypeptide, with respect to red blood cell levels, is not dependent on activin A inhibition. However, it is to be noted that the unmodified ActRII polypeptide, which retains activin A binding, still demonstrates the capacity to increase red blood cells in vivo. Furthermore, an ActRII polypeptide that retains activin A inhibition may be more desirable in some applications, in comparison to a GDF trap having diminished binding affinity for activin A, where more modest gains in red blood cell levels are desirable and/or where some level of off-target activity is acceptable (or even desirable). It should be noted that hematopoiesis is a complex process, regulated by a variety of factors, including erythropoietin, G-CSF, and iron homeostasis. The terms "increase red blood cell levels" and "promote red blood cell formation" refer to clinically observable metrics, such as hematocrit, red blood cell counts, and hemoglobin measurements, and are intended to be neutral as to the mechanism by which such changes occur.

As described herein, it has been determined that an ActRII antagonist (inhibitor) can be used to increase hemoglobin levels and reduce blood transfusion burden in MDS patients. Accordingly, these data indicate that ActRII inhibitors, optionally in combination with one or more supportive therapies, can be used to treat myelodysplastic syndrome, treat sideroblastic anemia in a subject in need thereof, and to treat or prevent one or more complications of sideroblastic anemia or myelodysplastic syndrome (e.g., anemia, blood, transfusion requirement, iron overload, neutropenia, splenomegaly, and progression to acute myeloid leukemia), and, optionally, in a subgroup of patients with ring sideroblasts and/or one or more mutations in the SF3B1 gene in bone marrow cells.

Surprisingly, the ActRII antagonist also was observed to improve vision in an MDS patient. Therefore, in addition to positive effects on treating anemia, ActRII inhibitors may result in increased vision (e.g., increased visual acuity and/or visual field) in MDS patients. Moreover, in view of the reported mechanism for MDS-associated vision loss [Han et al. (2015) J Glaucoma (Epub ahead of print); Brouzas et al. (2009) Clinical Ophthalmology 3:133-137] the data suggest that ActRII inhibitors also may have positive effects on treating other types of ocular (eye) disorders, particularly those associated with ischemia and vascular insufficiency.

Accordingly, the methods of the present disclosure, in part, are directed to the use of one or more ActRII antagonists (inhibitors), optionally in combination with one or more supportive therapies, to treat or prevent a vascular disorder of the eye in a subject in need thereof, improve vision (e.g., increase visual acuity and/or visual field) in a patient that has a vascular disorder of the eye, and/or to treat or prevent one or more complications of a vascular disorder of the eye.

The terms used in this specification generally have their ordinary meanings in the art, within the context of this disclosure and in the specific context where each term is used. Certain terms are discussed below or elsewhere in the specification, to provide additional guidance to the practitioner in describing the compositions and methods of the disclosure and how to make and use them. The scope or meaning of any use of a term will be apparent from the specific context in which they are used.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions. The term "sequence similarity," in all its grammatical forms, refers to the degree of identity or correspondence between nucleic acid or amino acid sequences that may or may not share a common evolutionary origin. However, in common usage and in the instant application, the term "homologous," when modified with an adverb such as "highly," may refer to sequence similarity and may or may not relate to a common evolutionary origin.

"Percent (%) sequence identity" with respect to a reference polypeptide (or nucleotide) sequence is defined as the percentage of amino acid residues (or nucleic acids) in a candidate sequence that are identical to the amino acid residues (or nucleic acids) in the reference polypeptide (nucleotide) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid (nucleic acid) sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

"Agonize", in all its grammatical forms, refers to the process of activating a protein and/or gene (e.g., by activating or amplifying that protein's gene expression or by inducing an inactive protein to enter an active state) or increasing a protein's and/or gene's activity.

"Antagonize", in all its grammatical forms, refers to the process of inhibiting a protein and/or gene (e.g., by inhibiting or decreasing that protein's gene expression or by inducing an active protein to enter an inactive state) or decreasing a protein's and/or gene's activity.

As used herein, unless otherwise stated, "does not substantially bind to X" is intended to mean that an agent has a $K_D$ that is greater than about $10^{-7}$, $10^{-6}$, $10^{-5}$, $10^{-4}$, or greater (e.g., no detectable binding by the assay used to determine the $K_D$ for "X" or has relatively modest binding for "X", e.g., about $1\times10^{-8}$ M or about $1\times10^{-9}$M).

The terms "about" and "approximately" as used in connection with a numerical value throughout the specification and the claims denotes an interval of accuracy, familiar and acceptable to a person skilled in the art. In general, such interval of accuracy is ±10%. Alternatively, and particularly in biological systems, the terms "about" and "approximately" may mean values that are within an order of magnitude, preferably ≤5-fold and more preferably ≤2-fold of a given value.

Numeric ranges disclosed herein are inclusive of the numbers defining the ranges.

The terms "a" and "an" include plural referents unless the context in which the term is used clearly dictates otherwise. The terms "a" (or "an"), as well as the terms "one or more," and "at least one" can be used interchangeably herein. Furthermore, "and/or" where used herein is to be taken as specific disclosure of each of the two or more specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Throughout this specification, the word "comprise" or variations such as "comprises" or "comprising" will be understood to imply the inclusion of a stated integer or groups of integers but not the exclusion of any other integer or group of integers.

2. ActRII Antagonists

The data presented herein demonstrates that ActRII antagonists (inhibitors) (e.g., inhibitors of ActRII-mediated Smad 1, 2, 3, 5, and 8 signaling transduction) can be used to treat a vascular disorder of the eye. In particular, an ActRII antagonist was shown to be effective in increasing vision in an MDS patient. Vision loss in MDS patients has been associated with vascular distress mediated by ischemia and/or vascular insufficiency [Han et al. (2015) J Glaucoma (Epub ahead of print); Brouzas et al. (2009) Clinical Ophthalmology 3:133-137]. Accordingly, the present disclosure provides, in part, various ActRII antagonists that can be used, alone or in combination with one or more additional supportive therapies, to treat or prevent vascular disorders of the eye [e.g., macular degeneration (e.g., age-related macular degeneration, juvenile macular degeneration, wet macular degeneration, dry macular degeneration, Stargardt's disease, and Best's disease), retinal vein occlusion (e.g, central retinal vein occlusion, hemi-retinal vein occlusion, branch retinal vein occlusion, macular edema following retinal vein occlusion, and ischemic retinal vein occlusion), retinal artery occlusion (e.g, central retinal artery occlusion, hemi-retinal artery occlusion, branch retinal artery occlusion, and ischemic retinal artery occlusion), diabetic retinopathy, diabetic macular edema, ischemic optic neuropathy [e.g., anterior ischemic optic neuropathy (arteritic and non-arteritic) and posterior ischemic optic neuropathy], macular telangiectasia (type I or type II), retinal ischemia (e.g., acute retinal ischemia or chronic retinal ischemia), ocular ischemic syndrome, retinal vasculitis, and retinopathy of prematurity] in a patient in need thereof; increase vision (e.g., visual acuity and/or visual field) in patient in need thereof that has a vascular disorder of the eye; and/or treat or prevent one or more complications of a vascular disorder of the eye.

In certain aspects, ActRII antagonists to be used in accordance with the methods disclosed herein are ActRII polypeptides (ActRIIA or ActRIIB polypeptides) including truncations and variants thereof. In some embodiments, preferred ActRII antagonists to be used in accordance with the methods disclosed herein are variant ActRII polypeptides that retain strong to intermediate binding affinity to GDF11 and/or GDF8 but have reduced binding to one or more ActRII ligands (e.g., activin A) compared to a corresponding, non-variant ActRII polypeptide. Such variant ActRII polypeptides are generally referred to herein as "GDF traps" or "GDF trap polypeptides".

Although soluble ActRII polypeptides and variants thereof (e.g., GDF traps) may affect vision or other complication of vascular disorders of the eye through a mechanism other than inhibition of ActRII ligands [e.g., inhibition of one or more of GDF11, GDF8, activin, BMP6, GDF3, BMP10, and/or BMP9 may be an indicator of the tendency of an agent to inhibit the activities of a spectrum of additional agents, including, perhaps, other members of the TGF-beta superfamily and such collective inhibition may lead to the desired effect on, for example, vision], other types of ActRII ligand and receptor inhibitors, or combination of inhibitors, are expected to be useful in accordance with the methods of disclosure including, for example, anti-GDF11 antibodies; anti-GDF8 antibodies; anti-ActRIIA antibodies; anti-ActRIIB antibodies; anti-ActRIIA/IIB antibodies; anti-activin antibodies; anti-BMP6 antibodies; anti-GDF3 antibodies; andti-BMP10 antibodies; anti-BMP9 antibodies; nucleic acids that inhibit the expression (e.g., transcription, translation, secretion from a cell, or combinations thereof) of one or more of GDF11, GDF8, ActRIIA, ActRIIB, activin, BMP6, GDF3, BMP10, and BMP9; as well as small molecule inhibitors of one or more of GDF11, GDF8, ActRIIA, ActRIIB, activin, BMP6, GDF3, BMP10, and BMP9.

A. ActRII Polypeptides

In certain aspects, the present disclosure relates to ActRII polypeptides. In particular, the disclosure provides methods of using ActRII polypeptides, alone or in combination with one or more additional active agents or supportive therapies, to treat or prevent an eye disorder, particularly a vascular disorder of the eye [e.g., macular degeneration (e.g., age-related macular degeneration, juvenile macular degeneration, wet macular degeneration, dry macular degeneration, Stargardt's disease, and Best's disease), retinal vein occlusion (e.g., central retinal vein occlusion, hemi-retinal vein occlusion, branch retinal vein occlusion, macular edema following retinal vein occlusion, and ischemic retinal vein occlusion), retinal artery occlusion (e.g., central retinal artery occlusion, hemi-retinal artery occlusion, branch retinal artery occlusion, and ischemic retinal artery occlusion), diabetic retinopathy, diabetic macular edema, ischemic optic neuropathy [e.g., anterior ischemic optic neuropathy (arteritic and non-arteritic) and posterior ischemic optic neuropathy], macular telangiectasia (type I or type II), retinal ischemia (e.g., acute retinal ischemia or chronic retinal ischemia), ocular ischemic syndrome, retinal vasculitis, and retinopathy of prematurity] in a patient in need thereof, improve (increase) vision (e.g., increase visual acuity and/or increase visual field) in patient in need thereof that has a vascular disorder of the eye, and/or treat or prevent one or more complications of a vascular disorder of the eye. As used herein the term "ActRII" refers to the family of type II activin receptors. This family includes the activin receptor type IIA (ActRIIA) and the activin receptor type IIB (ActRIIB).

As used herein, the term "ActRIIB" refers to a family of activin receptor type IIB (ActRIIB) proteins from any species and variants derived from such ActRIIB proteins by mutagenesis or other modification. Reference to ActRIIB herein is understood to be a reference to any one of the currently identified forms. Members of the ActRIIB family are generally transmembrane proteins, composed of a ligand-binding extracellular domain comprising a cysteine-rich region, a transmembrane domain, and a cytoplasmic domain with predicted serine/threonine kinase activity.

The term "ActRIIB polypeptide" includes polypeptides comprising any naturally occurring polypeptide of an ActRIIB family member as well as any variants thereof (including mutants, fragments, fusions, and peptidomimetic forms) that retain a useful activity. Examples of such variant ActRIIA polypeptides are provided throughout the present disclosure as well as in International Patent Application Publication No. WO 2006/012627, which is incorporated herein by reference in its entirety. Numbering of amino acids for all ActRIIB-related polypeptides described herein is based on the numbering of the human ActRIIB precursor protein sequence provided below (SEQ ID NO: 1), unless specifically designated otherwise.

The human ActRIIB precursor protein sequence is as follows:

(SEQ ID NO: 1)

```
  1 MTAPWVALAL LWGSLCAGSG RGEAETRECI YYNANWELER TNQSGLERCE

51 GEQDKRLHCY ASWRNSSGTI ELVKKGCWLD DFNCYDRQEC VATEENPQVY

101 FCCCEGNFCN ERFTHLPEAG GPEVTYEPPP TAPTLLTVLA YSLLPIGGLS

151 LIVLLAFWMY RHRKPPYGHV DIHEDPGPPP PSPLVGLKPL QLLEIKARGR

201 FGCVWKAQLM NDFVAVKIFP LQDKQSWQSE REIFSTPGMK HENLLQFIAA

251 EKRGSNLEVE LWLITAFHDK GSLTDYLKGN IITWNELCHV AETMSRGLSY

301 LHEDVPWCRG EGHKPSIAHR DFKSKNVLLK SDLTAVLADF GLAVRFEPGK

351 PPGDTHGQVG TRRYMAPEVL EGAINFQRDA FLRIDMYAMG LVLWELVSRC

401 KAADGPVDEY MLPFEEEIGQ HPSLEELQEV VVHKKMRPTI KDHWLKHPGL

451 AQLCVTIEEC WDHDAEARLS AGCVEERVSL IRRSVNGTTS DCLVSLVTSV

501 TNVDLPPKES SI
```

The signal peptide is indicated with a single underline; the extracellular domain is indicated in bold font; and the potential, endogenous N-linked glycosylation sites are indicated with a double underline.

A processed extracellular ActRIIB polypeptide sequence is as follows: GRGEAETRECIYYNANWELERTNQSGLERCEGEQDKRLHCYASWRNSSGTIELVKKGCWLDDFN CYDRQECVATEENPQVYFCCCEGNFCNERFTHLPEAGGPEVTYEPPPTAPT (SEQ ID NO: 2).

In some embodiments, the protein may be produced with an "SGR . . . " sequence at the N-terminus. The C-terminal "tail" of the extracellular domain is indicated by a single underline. The sequence with the "tail" deleted (a Δ15 sequence) is as follows: GRGEAETRECIYYNANWELERTNQSGLERCEGEQDKRLHCYASWRNSSGTIELVKKGCWLDDFN CYDRQECVATEENPQVYFCCCEGNFCNERFTHLPEA (SEQ ID NO: 3).

A form of ActRIIB with an alanine at position 64 of SEQ ID NO: 1 (A64) is also reported in the literature [Hilden et al. (1994) Blood, 83(8): 2163-2170]. Applicants have ascertained that an ActRIIB-Fc fusion protein comprising an extracellular domain of ActRIIB with the A64 substitution has a relatively low affinity for activin and GDF11. By contrast, the same ActRIIB-Fc fusion protein with an arginine at position 64 (R64) has an affinity for activin and GDF11 in the low nanomolar to high picomolar range. Therefore, sequences with an R64 are used as the "wild-type" reference sequence for human ActRIIB in this disclosure.

A form of ActRIIB with an alanine at position 64 is as follows:

(SEQ ID NO: 4)

```
  1 MTAPWVALAL LWGSLCAGSG RGEAETRECI YYNANWELER TNQSGLERCE

51 GEQDKRLHCY ASWANSSGTI ELVKKGCWLD DFNCYDRQEC VATEENPQVY

101 FCCCEGNFCN ERFTHLPEAG GPEVTYEPPP TAPTLLTVLA YSLLPIGGLS

151 LIVLLAFWMY RHRKPPYGHV DIHEDPGPPP PSPLVGLKPL QLLEIKARGR

201 FGCVWKAQLM NDFVAVKIFP LQDKQSWQSE REIFSTPGMK HENLLQFIAA

251 EKRGSNLEVE LWLITAFHDK GSLTDYLKGN IITWNELCHV AETMSRGLSY

301 LHEDVPWCRG EGHKPSIAHR DFKSKNVLLK SDLTAVLADF GLAVRFEPGK

351 PPGDTHGQVG TRRYMAPEVL EGAINFQRDA FLRIDMYAMG LVLWELVSRC

401 KAADGPVDEY MLPFEEEIGQ HPSLEELQEV VVHKKMRPTI KDHWLKHPGL

451 AQLCVTIEEC WDHDAEARLS AGCVEERVSL IRRSVNGTTS DCLVSLVTSV

501 TNVDLPPKES SI
```

The signal peptide is indicated by a single underline and the extracellular domain is indicated by bold font.

A processed extracellular ActRIIB polypeptide sequence of the alternative A64 form is as follows:

(SEQ ID NO: 5)
GRGEAETRECIYYNANWELERTNQSGLERCEGEQDKRLHCYASWANSSGT

IELVKKGCWLDDFNCYDRQECVATEENPQVYFCCCEGNFCNERFTHLPEA

<u>GGPEVTYEPPPTAPT</u>

In some embodiments, the protein may be produced with an "SGR . . . " sequence at the N-terminus. The C-terminal "tail" of the extracellular domain is indicated by single underline. The sequence with the "tail" deleted (a 415 sequence) is as follows:

(SEQ ID NO: 6)
GRGEAETRECIYYNANWELERTNQSGLERCEGEQDKRLHCYASWANSSGT

IELVKKGCWLDDFNCYDRQECVATEENPQVYFCCCEGNFCNERFTHLPEA

A nucleic acid sequence encoding human ActRIIB precursor protein is shown below (SEQ ID NO: 7), consisting of nucleotides 25-1560 of Genbank Reference Sequence NM_001106.3, which encode amino acids 1-513 of the ActRIIB precursor. The sequence as shown provides an arginine at position 64 and may be modified to provide an alanine instead. The signal sequence is underlined.

(SEQ ID NO: 7)
```
   1 ATGACGGCGC CCTGGGTGGC CCTCGCCCTC CTCTGGGGAT CGCTGTGCGC
  51 CGGCTCTGGG CGTGGGGAGG CTGAGACACG GGAGTGCATC TACTACAACG
 101 CCAACTGGGA GCTGGAGCGC ACCAACCAGA GCGGCCTGGA GCGCTGCGAA
 151 GGCGAGCAGG ACAAGCGGCT GCACTGCTAC GCCTCCTGGC GCAACAGCTC
 201 TGGCACCATC GAGCTCGTGA AGAAGGGCTG CTGGCTAGAT GACTTCAACT
 251 GCTACGATAG GCAGGAGTGT GTGGCCACTG AGGAGAACCC CCAGGTGTAC
 301 TTCTGCTGCT GTGAAGGCAA CTTCTGCAAC GAACGCTTCA CTCATTTGCC
 351 AGAGGCTGGG GGCCCGGAAG TCACGTACGA GCCACCCCCG ACAGCCCCCA
 401 CCCTGCTCAC GGTGCTGGCC TACTCACTGC TGCCCATCGG GGGCCTTTCC
 451 CTCATCGTCC TGCTGGCCTT TTGGATGTAC CGGCATCGCA AGCCCCCCTA
 501 CGGTCATGTG GACATCCATG AGGACCCTGG GCCTCCACCA CCATCCCCTC
 551 TGGTGGGCCT GAAGCCACTG CAGCTGCTGG AGATCAAGGC TCGGGGGCGC
 601 TTTGGCTGTG TCTGGAAGGC CCAGCTCATG AATGACTTTG TAGCTGTCAA
 651 GATCTTCCCA CTCCAGGACA AGCAGTCGTG GCAGAGTGAA CGGGAGATCT
 701 TCAGCACACC TGGCATGAAG CACGAGAACC TGCTACAGTT CATTGCTGCC
 751 GAGAAGCGAG GCTCCAACCT CGAAGTAGAG CTGTGGCTCA TCACGGCCTT
 801 CCATGACAAG GGCTCCCTCA CGGATTACCT CAAGGGGAAC ATCATCACAT
 851 GGAACGAACT GTGTCATGTA GCAGAGACGA TGTCACGAGG CCTCTCATAC
 901 CTGCATGAGG ATGTGCCCTG GTGCCGTGGC GAGGGCCACA AGCCGTCTAT
 951 TGCCCACAGG GACTTTAAAA GTAAGAATGT ATTGCTGAAG AGCGACCTCA
1001 CAGCCGTGCT GGCTGACTTT GGCTTGGCTG TTCGATTTGA GCCAGGGAAA
1051 CCTCCAGGGG ACACCCACGG ACAGGTAGGC ACGAGACGGT ACATGGCTCC
1101 TGAGGTGCTC GAGGGAGCCA TCAACTTCCA GAGAGATGCC TTCCTGCGCA
1151 TTGACATGTA TGCCATGGGG TTGGTGCTGT GGGAGCTTGT GTCTCGCTGC
1201 AAGGCTGCAG ACGGACCCGT GGATGAGTAC ATGCTGCCCT TTGAGGAAGA
1251 GATTGGCCAG CACCCTTCGT TGGAGGAGCT GCAGGAGGTG GTGGTGCACA
1301 AGAAGATGAG GCCCACCATT AAAGATCACT GGTTGAAACA CCCGGGCCTG
1351 GCCCAGCTTT GTGTGACCAT CGAGGAGTGC TGGGACCATG ATGCAGAGGC
```

-continued

```
1401 TCGCTTGTCC GCGGGCTGTG TGGAGGAGCG GGTGTCCCTG ATTCGGAGGT

1451 CGGTCAACGG CACTACCTCG GACTGTCTCG TTTCCCTGGT GACCTCTGTC

1501 ACCAATGTGG ACCTGCCCCC TAAAGAGTCA AGCATC
```

A nucleic acid sequence encoding the processed extracellular human ActRIIB polypeptide is as follows (SEQ ID NO: 8):

```
                                                  (SEQ ID NO: 8)
  1 GGGCGTGGGG AGGCTGAGAC ACGGGAGTGC ATCTACTACA ACGCCAACTG

51 GGAGCTGGAG CGCACCAACC AGAGCGGCCT GGAGCGCTGC GAAGGCGAGC

101 AGGACAAGCG GCTGCACTGC TACGCCTCCT GGCGCAACAG CTCTGGCACC

151 ATCGAGCTCG TGAAGAAGGG CTGCTGGCTA GATGACTTCA ACTGCTACGA

201 TAGGCAGGAG TGTGTGGCCA CTGAGGAGAA CCCCCAGGTG TACTTCTGCT

251 GCTGTGAAGG CAACTTCTGC AACGAACGCT TCACTCATTT GCCAGAGGCT

301 GGGGGCCCGG AAGTCACGTA CGAGCCACCC CCGACAGCCC CACC
```

The sequence as shown provides an arginine at position 64, and may be modified to provide an alanine instead.

An alignment of the amino acid sequences of human ActRIIB extracellular domain and human ActRIIA extracellular domain are illustrated in FIG. 1. This alignment indicates amino acid residues within both receptors that are believed to directly contact ActRII ligands. For example, the composite ActRII structures indicated that the ActRIIB-ligand binding pocket is defined, in part, by residues Y31, N33, N35, L38 through T41, E47, E50, Q53 through K55, L57, H58, Y60, S62, K74, W78 through N83, Y85, R87, A92, and E94 through F101. At these positions, it is expected that conservative mutations will be tolerated.

Figure 2:
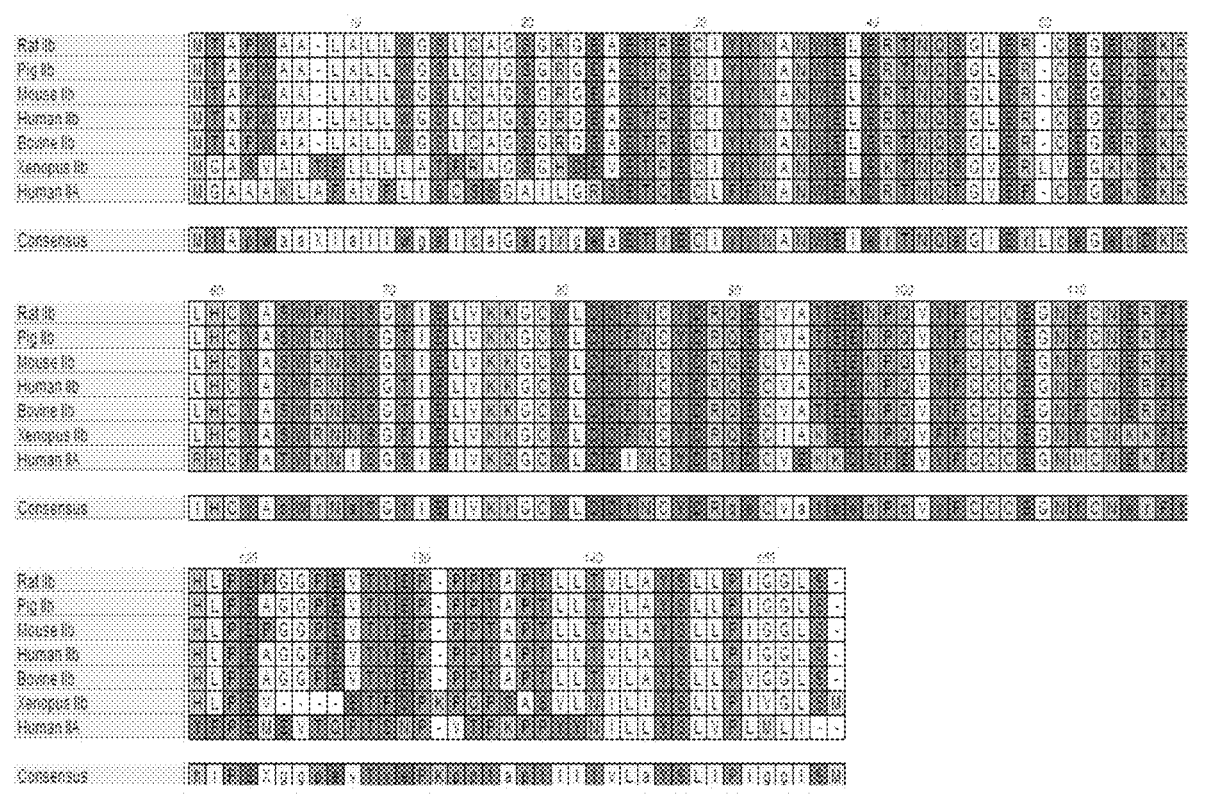

In addition, ActRIIB is generally well-conserved among vertebrates, with large stretches of the extracellular domain completely conserved. For example, FIG. 2 depicts a multi-sequence alignment of a human ActRIIB extracellular domain compared to various ActRIIB orthologs. Many of the ligands that bind to ActRIIB are also highly conserved. Accordingly, from these alignments, it is possible to predict key amino acid positions within the ligand-binding domain that are important for normal ActRIIB-ligand binding activities as well as to predict amino acid positions that are likely to be tolerant to substitution without significantly altering normal ActRIIB-ligand binding activities. Therefore, an active, human ActRIIB variant polypeptide useful in accordance with the presently disclosed methods may include one or more amino acids at corresponding positions from the sequence of another vertebrate ActRIIB, or may include a residue that is similar to that in the human or other vertebrate sequences.

Without meaning to be limiting, the following examples illustrate this approach to defining an active ActRIIB variant. L46 in the human extracellular domain (SEQ ID NO: 2) is a valine in *Xenopus* ActRIIB (SEQ ID NO: 57), and so this position may be altered, and optionally may be altered to another hydrophobic residue, such as V, I or F, or a non-polar residue such as A. E52 in the human extracellular domain is a K in *Xenopus*, indicating that this site may be tolerant of a wide variety of changes, including polar residues, such as E, D, K, R, H, S, T, P, G, Y and probably A. T93 in the human extracellular domain is a K in *Xenopus*, indicating that a wide structural variation is tolerated at this position, with polar residues favored, such as S, K, R, E, D, H, G, P, G and Y. F108 in the human extracellular domain is a Y in *Xenopus*, and therefore Y or other hydrophobic group, such as I, V or L should be tolerated. E111 in the human extracellular domain is K in *Xenopus*, indicating that charged residues will be tolerated at this position, including D, R, K and H, as well as Q and N. R112 in the human extracellular domain is K in *Xenopus*, indicating that basic residues are tolerated at this position, including R and H. A at position 119 in the human extracellular domain is relatively poorly conserved, and appears as P in rodents (SEQ ID NOs: 52 and 54) and V in *Xenopus*, thus essentially any amino acid should be tolerated at this position.

Moreover, ActRII proteins have been characterized in the art in terms of structural/functional characteristics, particularly with respect to ligand binding [Attisano et al. (1992) Cell 68(1):97-108; Greenwald et al. (1999) Nature Structural Biology 6(1): 18-22; Allendorph et al. (2006) PNAS 103(20: 7643-7648; Thompson et al. (2003) The EMBO Journal 22(7): 1555-1566; as well as U.S. Pat. Nos. 7,709, 605, 7,612,041, and 7,842,663]. In addition to the teachings herein, these references provide amply guidance for how to generate ActRII variants that retain one or more desired activities (e.g., ligand-binding activity).

For example, a defining structural motif known as a three-finger toxin fold is important for ligand binding by type I and type II receptors and is formed by conserved cysteine residues located at varying positions within the extracellular domain of each monomeric receptor [Greenwald et al. (1999) Nat Struct Biol 6:18-22; and Hinck (2012) FEBS Lett 586:1860-1870]. Accordingly, the core ligand-binding domains of human ActRIIB, as demarcated by the outermost of these conserved cysteines, corresponds to positions 29-109 of SEQ ID NO: 1 (ActRIIB precursor). The structurally less-ordered amino acids flanking these cysteine-demarcated core sequences can be truncated by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37 residues without necessarily altering ligand binding. Exemplary ActRIIB extracellular domains for N-terminal and/or C-terminal truncation include SEQ ID NOs: 2, 3, 5, and 6.

Attisano et al. showed that a deletion of the proline knot at the C-terminus of the extracellular domain of ActRIIB reduced the affinity of the receptor for activin. An ActRIIB-Fc fusion protein containing amino acids 20-119 of present SEQ ID NO: 1, "ActRIIB(20-119)-Fc", has reduced binding to GDF11 and activin relative to an ActRIIB(20-134)-Fc, which includes the proline knot region and the complete juxtamembrane domain (see, e.g., U.S. Pat. No. 7,842,663). However, an ActRIIB(20-129)-Fc protein retains similar, but somewhat reduced activity, relative to the wild-type, even though the proline knot region is disrupted. Thus, ActRIIB extracellular domains that stop at amino acid 134, 133, 132, 131, 130 and 129 (with respect to SEQ ID NO: 1) are all expected to be active, but constructs stopping at 134 or 133 may be most active. Similarly, mutations at any of residues 129-134 (with respect to SEQ ID NO: 1) are not expected to alter ligand-binding affinity by large margins. In support of this, it is known in the art that mutations of P129 and P130 (with respect to SEQ ID NO: 1) do not substantially decrease ligand binding. Therefore, an ActRIIB polypeptide of the present disclosure may end as early as amino acid 109 (the final cysteine), however, forms ending at or between 109 and 119 (e.g., 109, 110, 111, 112, 113, 114, 115, 116, 117, 118, or 119) are expected to have reduced ligand binding. Amino acid 119 (with respect to present SEQ ID NO: 1) is poorly conserved and so is readily altered or truncated. ActRIIB polypeptides ending at 128 (with respect to SEQ ID NO: 1) or later should retain ligand-binding activity. ActRIIB polypeptides ending at or between 119 and 127 (e.g., 119, 120, 121, 122, 123, 124, 125, 126, or 127), with respect to SEQ ID NO: 1, will have an intermediate binding ability. Any of these forms may be desirable to use, depending on the clinical or experimental setting.

At the N-terminus of ActRIIB, it is expected that a protein beginning at amino acid 29 or before (with respect to SEQ ID NO: 1) will retain ligand-binding activity. Amino acid 29 represents the initial cysteine. An alanine-to-asparagine mutation at position 24 (with respect to SEQ ID NO: 1) introduces an N-linked glycosylation sequence without substantially affecting ligand binding [U.S. Pat. No. 7,842,663]. This confirms that mutations in the region between the signal cleavage peptide and the cysteine cross-linked region, corresponding to amino acids 20-29, are well tolerated. In particular, ActRIIB polypeptides beginning at position 20, 21, 22, 23, and 24 (with respect to SEQ ID NO: 1) should retain general ligand-biding activity, and ActRIIB polypeptides beginning at positions 25, 26, 27, 28, and 29 (with respect to SEQ ID NO: 1) are also expected to retain ligand-biding activity. It has been demonstrated, e.g., U.S. Pat. No. 7,842,663, that, surprisingly, an ActRIIB construct beginning at 22, 23, 24, or 25 will have the most activity.

Taken together, a general formula for an active portion (e.g., ligand-binding portion) of ActRIIB comprises amino acids 29-109 of SEQ ID NO: 1. Therefore ActRIIB polypeptides may, for example, comprise, consists essentially of, or consists of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRIIB beginning at a residue corresponding to any one of amino acids 20-29 (e.g., beginning at any one of amino acids 20, 21, 22, 23, 24, 25, 26, 27, 28, or 29) of SEQ ID NO: 1 and ending at a position corresponding to any one amino acids 109-134 (e.g., ending at any one of amino acids 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 1. Other examples include polypeptides that begin at a position from 20-29 (e.g., any one of positions 20, 21, 22, 23, 24, 25, 26, 27, 28, or 29) or 21-29 (e.g., any one of positions 21, 22, 23, 24, 25, 26, 27, 28, or 29) and end at a position from 119-134 (e.g., any one of positions 119, 120, 121, 122, 123, 124, 125, 126, 127, 128, 129, 130, 131, 132, 133, or 134), 119-133 (e.g., any one of positions 119, 120, 121, 122, 123, 124, 125, 126, 127, 128, 129, 130, 131, 132, or 133), 129-134 (e.g., any one of positions 129, 130, 131, 132, 133, or 134), or 129-133 (e.g., any one of positions 129, 130, 131, 132, or 133) of SEQ ID NO: 1. Other examples include constructs that begin at a position from 20-24 (e.g., any one of positions 20, 21, 22, 23, or 24), 21-24 (e.g., any one of positions 21, 22, 23, or 24), or 22-25 (e.g., any one of positions 22, 22, 23, or 25) and end at a position from 109-134 (e.g., any one of positions 109, 110, 111, 112, 113, 114, 115, 116, 117, 118, 119, 120, 121, 122, 123, 124, 125, 126, 127, 128, 129, 130, 131, 132, 133, or 134), 119-134 (e.g., any one of positions 119, 120, 121, 122, 123, 124, 125, 126, 127, 128, 129, 130, 131, 132, 133, or 134) or 129-134 (e.g., any one of positions 129, 130, 131, 132, 133, or 134) of SEQ ID NO: 1. Variants within these ranges are also contemplated, particularly those having at least 70%, 75%, 80%, 85%, 86%, 87%, 88%, 89%, 90%, 91%, 92%, 93%, 94%, 95%, 96%, 97%, 98%, 99%, or 100% identity to the corresponding portion of SEQ ID NO: 1.

The variations described herein may be combined in various ways. In some embodiments, ActRIIB variants comprise no more than 1, 2, 5, 6, 7, 8, 9, 10 or 15 conservative amino acid changes in the ligand-binding pocket, and zero, one or more non-conservative alterations at positions 40, 53, 55, 74, 79 and/or 82 in the ligand-binding pocket. Sites outside the binding pocket, at which variability may be particularly well tolerated, include the amino and carboxy termini of the extracellular domain (as noted above), and positions 42-46 and 65-73 (with respect to SEQ ID NO: 1). An asparagine-to-alanine alteration at position 65 (N65A) actually improves ligand binding in the A64 background, and is thus expected to have no detrimental effect on ligand binding in the R64 background [U.S. Pat. No. 7,842,663]. This change probably eliminates glycosylation at N65 in the A64 background, thus demonstrating that a significant change in this region is likely to be tolerated. While an R64A change is poorly tolerated, R64K is well-tolerated, and thus another basic residue, such as H may be tolerated at position 64 [U.S. Pat. No. 7,842,663]. Additionally, the results of the mutagenesis program described in the art indicate that there are amino acid positions in ActRIIB that are often beneficial to conserve. With respect to SEQ ID NO: 1, these include position 80 (acidic or hydrophobic amino acid), position 78 (hydrophobic, and particularly tryptophan), position 37 (acidic, and particularly aspartic or glutamic acid), position 56 (basic amino acid), position 60 (hydrophobic amino acid, particularly phenylalanine or tyrosine). Thus, the disclosure provides a framework of amino acids that may be conserved in ActRIIB polypeptides. Other positions that may be desirable to conserve are as follows: position 52 (acidic amino acid), position 55 (basic amino acid), position 81 (acidic), 98 (polar or charged, particularly E, D, R or K), all with respect to SEQ ID NO: 1.

It has been previously demonstrated that the addition of a further N-linked glycosylation site (N-X-S/T) into the ActRIIB extracellular domain is well-tolerated (see, e.g., U.S. Pat. No. 7,842,663). Therefore, N-X-S/T sequences may be generally introduced at positions outside the ligand binding pocket defined in FIG. 1 in ActRIIB polypeptide of the present disclosure. Particularly suitable sites for the introduction of non-endogenous N-X-S/T sequences include amino acids 20-29, 20-24, 22-25, 109-134, 120-134 or 129-134 (with respect to SEQ ID NO: 1). N-X-S/T sequences may also be introduced into the linker between the ActRIIB sequence and an Fc domain or other fusion component. Such a site may be introduced with minimal effort by introducing an N in the correct position with respect to a pre-existing S or T, or by introducing an S or T at a position corresponding to a pre-existing N. Thus, desirable alterations that would create an N-linked glycosylation site are: A24N, R64N, S67N (possibly combined with an N65A alteration), E105N, R112N, G120N, E123N, P129N, A132N, R112S and R112T (with respect to SEQ ID NO: 1). Any S that is predicted to be glycosylated may be altered to a T without creating an immunogenic site, because of the protection afforded by the glycosylation. Likewise, any T that is predicted to be glycosylated may be altered to an S. Thus the alterations S67T and S44T (with respect to SEQ ID NO: 1) are contemplated. Likewise, in an A24N variant, an S26T alteration may be used. Accordingly, an ActRIIB polypeptide of the present disclosure may be a variant having one or more additional, non-endogenous N-linked glycosylation consensus sequences as described above.

In certain embodiments, the disclosure relates to ActRII inhibitors that comprise at least one ActRIIB polypeptide, which includes fragments, functional variants, and modified forms thereof. Preferably, ActRIIB polypeptides for use in accordance with the disclosure are soluble (e.g., an extracellular domain of ActRIIB) In some embodiments, ActRIIB polypeptides for use in accordance with the disclosure inhibit (antagonize) activity (e.g., induction of Smad 1, 2, 3, 5, or 8 signaling) of one or more TGF-beta superfamily ligands [e.g., GDF11, GDF8, activin (activin A, activin B, activin AB, activin C, activin E) BMP6, GDF3, BMP10, and/or BMP9]. In some embodiments, ActRIIB polypeptides for use in accordance with the disclosure bind to one or more TGF-beta superfamily ligands [e.g., GDF11, GDF8, activin (activin A, activin B, activin AB, activin C, activin E) BMP6, GDF3, BMP10, and/or BMP9]. In some embodiments, ActRIIB polypeptide of the disclosure comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRIIB beginning at a residue corresponding to amino acids 20-29 (e.g., beginning at any one of amino acids 20, 21, 22, 23, 24, 25, 26, 27, 28, or 29) of SEQ ID NO: 1 and ending at a position corresponding to amino acids 109-134 (e.g., ending at any one of amino acids 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 1. In some embodiments, ActRIIB polypeptides of the disclosure comprise, consist, or consist essentially of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 29-109 of SEQ ID NO: 1. In some embodiments, ActRIIB polypeptides of the disclosure comprise, consist, or consist essentially of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 29-109 of SEQ ID NO: 1, wherein the position corresponding to L79 of SEQ ID NO: 1 is an acidic amino acid (naturally occurring acidic amino acids D and E or an artificial acidic amino acid). In certain preferred embodiments, ActRIIB polypeptides of the disclosure comprise, consist, or consist essentially of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 25-131 of SEQ ID NO: 1. In certain preferred embodiments, ActRIIB polypeptides of the disclosure comprise, consist, or consist essentially of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 25-131 of SEQ ID NO: 1, wherein the position corresponding to L79 of SEQ ID NO: 1 is an acidic amino acid. In some embodiments, ActRIIB polypeptide of disclosure comprise, consist, or consist essentially of an amino acid sequence that is at least 70%, 75%, 80%, 85%, 86%, 87%, 88%, 89%, 90%, 91%, 92%, 93%, 94%, 95%, 97%, 98%, 99%, or 100% identical to the amino acid sequence of any one of SEQ ID NOs: 1, 2, 3, 4, 5, 6, 40, 41, 44, 45, 46, 48, 49, 50, 61, 64, 65, 78, and 79. In some embodiments, ActRIIB polypeptide of disclosure comprise, consist, or consist essentially of an amino acid sequence that is at least 70%, 75%, 80%, 85%, 86%, 87%, 88%, 89%, 90%, 91%, 92%, 93%, 94%, 95%, 97%, 98%, 99%, or 100% identical to the amino acid sequence of any one of SEQ ID NOs: 1, 2, 3, 4, 5, 6, 40, 41, 44, 45, 46, 48, 49, 50, 61, 64, 65, 78, and 79, wherein the position corresponding to L79 of SEQ ID NO: 1 is an acidic amino acid. In some embodiments, ActRIIB polypeptides of the disclosure consist, or consist essentially of, at least one ActRIIB polypeptide wherein the position corresponding to L79 of SEQ ID NO: 1 is not an acidic amino acid (i.e., is not a naturally occurring acid amino acids D or E or an artificial acidic amino acid residue).

In certain embodiments, the present disclosure relates to ActRIIA polypeptides. As used herein, the term "ActRIIA" refers to a family of activin receptor type IIA (ActRIIA) proteins from any species and variants derived from such ActRIIA proteins by mutagenesis or other modification. Reference to ActRIIA herein is understood to be a reference to any one of the currently identified forms. Members of the ActRIIA family are generally transmembrane proteins, composed of a ligand-binding extracellular domain comprising a cysteine-rich region, a transmembrane domain, and a cytoplasmic domain with predicted serine/threonine kinase activity.

The term "ActRIIA polypeptide" includes polypeptides comprising any naturally occurring polypeptide of an ActRIIA family member as well as any variants thereof (including mutants, fragments, fusions, and peptidomimetic forms) that retain a useful activity. Examples of such variant ActRIIA polypeptides are provided throughout the present disclosure as well as in International Patent Application Publication No. WO 2006/012627, which is incorporated herein by reference in its entirety. Numbering of amino acids for all ActRIIA-related polypeptides described herein is based on the numbering of the human ActRIIA precursor protein sequence provided below (SEQ ID NO: 9), unless specifically designated otherwise.

The canonical human ActRIIA precursor protein sequence is as follows:

```
                                                              (SEQ ID NO: 9)
  1 MGAAAKLAFA VFLISCSSGA ILGRSETQEC LFFNANWEKD RTNQTGVEPC

51 YGDKDKRRHC FATWKNISGS IEIVKQGCWL DDINCYDRTD CVEKKDSPEV

101 YFCCCEGNMC NEKFSYFPEM EVTQPTSNPV TPKPPYYNIL LYSLVPLMLI
```

```
151 AGIVICAFWV YRHHKMAYPP VLVPTQDPGP PPPSPLLGLK PLQLLEVKAR

201 GRFGCVWKAQ LLNEYVAVKI FPIQDKQSWQ NEYEVYSLPG MKHENILQFI

251 GAEKRGTSVD VDLWLITAFH EKGSLSDFLK ANVVSWNELC HIAETMARGL

301 AYLHEDIPGL KDGHKPAISH RDIKSKNVLL KNNLTACIAD FGLALKFEAG

351 KSAGDTHGQV GTRRYMAPEV LEGAINFQRD AFLRIDMYAM GLVLWELASR

401 CTAADGPVDE YMLPFEEEIG QHPSLEDMQE VVVHKKKRPV LRDYWQKHAG

451 MAMLCETIEE CWDHDAEARL SAGCVGERIT QMQRLTNIIT TEDIVTVVTM

501 VTNVDFPPKE SSL
```

The signal peptide is indicated by a single underline; the extracellular domain is indicated in bold font; and the potential, endogenous N-linked glycosylation sites are indicated by a double underline.

A processed extracellular human ActRIIA polypeptide sequence is as follows:

```
                                          (SEQ ID NO: 10)
ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM

EVTQPTSNPVTPKPP
```

The C-terminal "tail" of the extracellular domain is indicated by single underline. The sequence with the "tail" deleted (a 415 sequence) is as follows:

```
                                          (SEQ ID NO: 11)
ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM
```

The nucleic acid sequence encoding human ActRIIA precursor protein is shown below (SEQ ID NO: 12), as follows nucleotides 159-1700 of Genbank Reference Sequence NM_001616.4. The signal sequence is underlined.

```
                                          (SEQ ID NO: 12)
   1 ATGGGAGCTG CTGCAAAGTT GGCGTTTGCC GTCTTTCTTA TCTCCTGTTC

51 TTCAGGTGCT ATACTTGGTA GATCAGAAAC TCAGGAGTGT CTTTTCTTTA

101 ATGCTAATTG GGAAAAAGAC AGAACCAATC AAACTGGTGT TGAACCGTGT

151 TATGGTGACA AAGATAAACG GCGGCATTGT TTTGCTACCT GGAAGAATAT

201 TTCTGGTTCC ATTGAAATAG TGAAACAAGG TTGTTGGCTG GATGATATCA

251 ACTGCTATGA CAGGACTGAT TGTGTAGAAA AAAAGACAG CCCTGAAGTA

301 TATTTTTGTT GCTGTGAGGG CAATATGTGT AATGAAAAGT TTTCTTATTT

351 TCCGGAGATG GAAGTCACAC AGCCCACTTC AAATCCAGTT ACACCTAAGC

401 CACCCTATTA CAACATCCTG CTCTATTCCT TGGTGCCACT TATGTTAATT

451 GCGGGGATTG TCATTTGTGC ATTTTGGGTG TACAGGCATC ACAAGATGGC

501 CTACCCTCCT GTACTTGTTC CAACTCAAGA CCCAGGACCA CCCCCACCTT

551 CTCCATTACT AGGTTTGAAA CCACTGCAGT TATTAGAAGT GAAAGCAAGG

601 GGAAGATTTG GTTGTGTCTG GAAAGCCCAG TTGCTTAACG AATATGTGGC

651 TGTCAAAATA TTTCCAATAC AGGACAAACA GTCATGGCAA AATGAATACG

701 AAGTCTACAG TTTGCCTGGA ATGAAGCATG AGAACATATT ACAGTTCATT

751 GGTGCAGAAA AACGAGGCAC CAGTGTTGAT GTGGATCTTT GGCTGATCAC

801 AGCATTTCAT GAAAAGGGTT CACTATCAGA CTTTCTTAAG GCTAATGTGG

851 TCTCTTGGAA TGAACTGTGT CATATTGCAG AAACCATGGC TAGAGGATTG

901 GCATATTTAC ATGAGGATAT ACCTGGCCTA AAAGATGGCC ACAAACCTGC

951 CATATCTCAC AGGGACATCA AAGTAAAAA TGTGCTGTTG AAAACAACC

1001 TGACAGCTTG CATTGCTGAC TTTGGGTTGG CCTTAAAATT TGAGGCTGGC

1051 AAGTCTGCAG GCGATACCCA TGGACAGGTT GGTACCCGGA GGTACATGGC
```

```
-continued
1101 TCCAGAGGTA TTAGAGGGTG CTATAAACTT CCAAAGGGAT GCATTTTTGA

1151 GGATAGATAT GTATGCCATG GGATTAGTCC TATGGGAACT GGCTTCTCGC

1201 TGTACTGCTG CAGATGGACC TGTAGATGAA TACATGTTGC CATTTGAGGA

1251 GGAAATTGGC CAGCATCCAT CTCTTGAAGA CATGCAGGAA GTTGTTGTGC

1301 ATAAAAAAAA GAGGCCTGTT TTAAGAGATT ATTGGCAGAA ACATGCTGGA

1351 ATGGCAATGC TCTGTGAAAC CATTGAAGAA TGTTGGGATC ACGACGCAGA

1401 AGCCAGGTTA TCAGCTGGAT GTGTAGGTGA AAGAATTACC CAGATGCAGA

1451 GACTAACAAA TATTATTACC ACAGAGGACA TTGTAACAGT GGTCACAATG

1501 GTGACAAATG TTGACTTTCC TCCCAAAGAA TCTAGTCTA
```

The nucleic acid sequence encoding processed soluble (extracellular) human ActRIIA polypeptide is as follows:

```
                                                   (SEQ ID NO: 13)
  1 ATACTTGGTA GATCAGAAAC TCAGGAGTGT CTTTTCTTTA ATGCTAATTG

51 GGAAAAAGAC AGAACCAATC AAACTGGTGT TGAACCGTGT TATGGTGACA

101 AAGATAAACG GCGGCATTGT TTTGCTACCT GGAAGAATAT TTCTGGTTCC

151 ATTGAAATAG TGAAACAAGG TTGTTGGCTG GATGATATCA ACTGCTATGA

201 CAGGACTGAT TGTGTAGAAA AAAAAGACAG CCCTGAAGTA TATTTTTGTT

251 GCTGTGAGGG CAATATGTGT AATGAAAAGT TTTCTTATTT TCCGGAGATG

301 GAAGTCACAC AGCCCACTTC AAATCCAGTT ACACCTAAGC CACCC
```

ActRIIA is well-conserved among vertebrates, with large stretches of the extracellular domain completely conserved. For example, FIG. 14 depicts a multi-sequence alignment of a human ActRIIA extracellular domain compared to various ActRIIA orthologs. Many of the ligands that bind to ActRIIA are also highly conserved. Accordingly, from these alignments, it is possible to predict key amino acid positions within the ligand-binding domain that are important for normal ActRIIA-ligand binding activities as well as to predict amino acid positions that are likely to be tolerant to substitution without significantly altering normal ActRIIA-ligand binding activities. Therefore, an active, human ActRIIA variant polypeptide useful in accordance with the presently disclosed methods may include one or more amino acids at corresponding positions from the sequence of another vertebrate ActRIIA, or may include a residue that is similar to that in the human or other vertebrate sequences.

Without meaning to be limiting, the following examples illustrate this approach to defining an active ActRIIA variant. F13 in the human extracellular domain is Y in *Ovis aries* (SEQ ID NO: 70), *Gallus gallus* (SEQ ID NO: 73), *Bos Taurus* (SEQ ID NO: 74), *Tyto alba* (SEQ ID NO: 75), and *Myotis davidii* (SEQ ID NO: 76) ActRIIA, indicating that aromatic residues are tolerated at this position, including F, W, and Y. Q24 in the human extracellular domain is R in *Bos Taurus* ActRIIA, indicating that charged residues will be tolerated at this position, including D, R, K, H, and E. S95 in the human extracellular domain is F in *Gallus gallus* and *Tyto alba* ActRIIA, indicating that this site may be tolerant of a wide variety of changes, including polar residues, such as E, D, K, R, H, S, T, P, G, Y, and probably hydrophobic residue such as L, I, or F. E52 in the human extracellular domain is D in *Ovis aries* ActRIIA, indicating that acidic residues are tolerated at this position, including D and E. P29 in the human extracellular domain is relatively poorly conserved, appearing as S in *Ovis aries* ActRIIA and L in *Myotis davidii* ActRIIA, thus essentially any amino acid should be tolerated at this position.

Moreover, as discussed above, ActRII proteins have been characterized in the art in terms of structural/functional characteristics, particularly with respect to ligand binding [Attisano et al. (1992) Cell 68(1):97-108; Greenwald et al. (1999) Nature Structural Biology 6(1): 18-22; Allendorph et al. (2006) PNAS 103(20: 7643-7648; Thompson et al. (2003) The EMBO Journal 22(7): 1555-1566; as well as U.S. Pat. Nos. 7,709,605, 7,612,041, and 7,842,663]. In addition to the teachings herein, these references provide amply guidance for how to generate ActRII variants that retain one or more desired activities (e.g., ligand-binding activity).

For example, a defining structural motif known as a three-finger toxin fold is important for ligand binding by type I and type II receptors and is formed by conserved cysteine residues located at varying positions within the extracellular domain of each monomeric receptor [Greenwald et al. (1999) Nat Struct Biol 6:18-22; and Hinck (2012) FEBS Lett 586:1860-1870]. Accordingly, the core ligand-binding domains of human ActRIIA, as demarcated by the outermost of these conserved cysteines, corresponds to positions 30-110 of SEQ ID NO: 9 (ActRIIA precursor). Therefore, the structurally less-ordered amino acids flanking these cysteine-demarcated core sequences can be truncated by about 1, 2, 3, 4, 5, 6, 7, 8, 9, 10, 11, 12, 13, 14, 15, 16, 17, 18, 19, 20, 21, 22, 23, 24, 25, 26, 27, 28, or 29 residues at the N-terminus and by about 1, 2, 3, 4, 5, 6, 7, 8, 9, 10, 11, 12, 13, 14, 15, 16, 17, 18, 19, 20, 21, 22, 23, 24, or 25 residues at the C-terminus without necessarily altering ligand binding. Exemplary ActRIIA extracellular domains truncations include SEQ ID NOs: 10 and 11.

Accordingly, a general formula for an active portion (e.g., ligand binding) of ActRIIA is a polypeptide that comprises, consists essentially of, or consists of amino acids 30-110 of SEQ ID NO: 9. Therefore ActRIIA polypeptides may, for example, comprise, consists essentially of, or consists of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRIIA beginning at a residue corresponding to any one of amino acids 21-30 (e.g., beginning at any one of amino acids 21, 22, 23, 24, 25, 26, 27, 28, 29, or 30) of SEQ ID NO: 9 and ending at a position corresponding to any one amino acids 110-135 (e.g., ending at any one of amino acids 110, 111, 112, 113, 114, 115, 116, 117, 118, 119, 120, 121, 122, 123, 124, 125, 126, 127, 128, 129, 130, 131, 132, 133, or 135) of SEQ ID NO: 9. Other examples include constructs that begin at a position selected from 21-30 (e.g., beginning at any one of amino acids 21, 22, 23, 24, 25, 26, 27, 28, 29, or 30), 22-30 (e.g., beginning at any one of amino acids 22, 23, 24, 25, 26, 27, 28, 29, or 30), 23-30 (e.g., beginning at any one of amino acids 23, 24, 25, 26, 27, 28, 29, or 30), 24-30 (e.g., beginning at any one of amino acids 24, 25, 26, 27, 28, 29, or 30) of SEQ ID NO: 9, and end at a position selected from 111-135 (e.g., ending at any one of amino acids 111, 112, 113, 114, 115, 116, 117, 118, 119, 120, 121, 122, 123, 124, 125, 126, 127, 128, 129, 130, 131, 132, 133, 134 or 135), 112-135 (e.g., ending at any one of amino acids 112, 113, 114, 115, 116, 117, 118, 119, 120, 121, 122, 123, 124, 125, 126, 127, 128, 129, 130, 131, 132, 133, 134 or 135), 113-135 (e.g., ending at any one of amino acids 113, 114, 115, 116, 117, 118, 119, 120, 121, 122, 123, 124, 125, 126, 127, 128, 129, 130, 131, 132, 133, 134 or 135), 120-135 (e.g., ending at any one of amino acids 120, 121, 122, 123, 124, 125, 126, 127, 128, 129, 130, 131, 132, 133, 134 or 135), 130-135 (e.g., ending at any one of amino acids 130, 131, 132, 133, 134 or 135), 111-134 (e.g., ending at any one of amino acids 110, 111, 112, 113, 114, 115, 116, 117, 118, 119, 120, 121, 122, 123, 124, 125, 126, 127, 128, 129, 130, 131, 132, 133, or 134), 111-133 (e.g., ending at any one of amino acids 110, 111, 112, 113, 114, 115, 116, 117, 118, 119, 120, 121, 122, 123, 124, 125, 126, 127, 128, 129, 130, 131, 132, or 133), 111-132 (e.g., ending at any one of amino acids 110, 111, 112, 113, 114, 115, 116, 117, 118, 119, 120, 121, 122, 123, 124, 125, 126, 127, 128, 129, 130, 131, or 132), or 111-131 (e.g., ending at any one of amino acids 110, 111, 112, 113, 114, 115, 116, 117, 118, 119, 120, 121, 122, 123, 124, 125, 126, 127, 128, 129, 130, or 131) of SEQ ID NO: 9. Thus, ActRIIA of the present disclosure may comprise, consists essentially of, or consist of a polypeptide that is at least 70%, 75%, 80%, 85%, 86%, 87%, 88%, 89%, 90%, 91%, 92%, 93%, 94%, 95%, 96%, 97%, 98%, 99%, or 100% identical to amino acids 30-110 of SEQ ID NO: 9. Optionally, ActRIIA polypeptides of the present disclosure comprise a polypeptide that is at least 70%, 75%, 80%, 85%, 86%, 87%, 88%, 89%, 90%, 91%, 92%, 93%, 94%, 95%, 96%, 97%, 98%, 99%, or 100% identical to amino acids 30-110 of SEQ ID NO: 9, and comprising no more than 1, 2, 5, 10 or 15 conservative amino acid changes in the ligand binding pocket, and zero, one or more non-conservative alterations at positions 40, 53, 55, 74, 79 and/or 82 in the ligand-binding pocket with respect to SEQ ID NO: 9.

In certain embodiments, the disclosure relates to ActRII inhibitors that comprise at least one ActRIIA polypeptide, which includes fragments, functional variants, and modified forms thereof. Preferably, ActRIIA polypeptides for use in accordance with the disclosure are soluble (e.g., an extracellular domain of ActRIIA). In some embodiments, ActRIIA polypeptides for use in accordance with the disclosure inhibit (antagonize) activity (e.g., induction of Smad 1, 2, 3, 5, or 8 signaling) of one or more TGF-beta superfamily ligands [e.g., GDF11, GDF8, activin (activin A, activin B, activin AB, activin C, activin E) BMP6, GDF3, BMP10, and/or BMP9]. In some embodiments, ActRIIA polypeptides for use in accordance with the disclosure bind to one or more TGF-beta superfamily ligands [e.g., GDF11, GDF8, activin (activin A, activin B, activin AB, activin C, activin E) BMP6, GDF3, BMP10, and/or BMP9]. In some embodiments, ActRIIA polypeptide of the disclosure comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRIIA beginning at a residue corresponding to amino acids 21-30 (e.g., beginning at any one of amino acids 21, 22, 23, 24, 25, 26, 27, 28, 29, or 30) of SEQ ID NO: 9 and ending at a position corresponding to any one amino acids 110-135 (e.g., ending at any one of amino acids 110, 111, 112, 113, 114, 115, 116, 117, 118, 119, 120, 121, 122, 123, 124, 125, 126, 127, 128, 129, 130, 131, 132, 133, or 135) of SEQ ID NO: 9. In some embodiments, ActRIIA polypeptides of the disclosure comprise, consist, or consist essentially of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 30-110 of SEQ ID NO: 9. In certain embodiments, ActRIIA polypeptides of the disclosure comprise, consist, or consist essentially of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 21-135 of SEQ ID NO: 9. In some embodiments, ActRIIA polypeptide of disclosure comprise, consist, or consist essentially of an amino acid sequence that is at least 70%, 75%, 80%, 85%, 86%, 87%, 88%, 89%, 90%, 91%, 92%, 93%, 94%, 95%, 97%, 98%, 99%, or 100% identical to the amino acid sequence of any one of SEQ ID NOs: 9, 10, 11, 32, 36, and 39.

In certain aspects, the present disclosure relates to GDF trap polypeptides (also referred to as "GDF traps"). In some embodiments, GDF traps of the present disclosure are variant ActRII polypeptides (e.g., ActRIIA and ActRIIB polypeptides) that comprise one or more mutations (e.g., amino acid additions, deletions, substitutions, and combinations thereof) in the extracellular domain (also referred to as the ligand-binding domain) of an ActRII polypeptide (e.g., a "wild-type" or unmodified ActRII polypeptide) such that the variant ActRII polypeptide has one or more altered ligand-binding activities than the corresponding wild-type ActRII polypeptide. In preferred embodiments, GDF trap polypeptides of the present disclosure retain at least one similar activity as a corresponding wild-type ActRII polypeptide. For example, preferable GDF traps bind to and inhibit (e.g. antagonize) the function of GDF11 and/or GDF8. In some embodiments, GDF traps of the present disclosure further bind to and inhibit one or more of ligand of the TGF-beta superfamily. Accordingly, the present disclosure provides GDF trap polypeptides that have an altered binding specificity for one or more ActRII ligands.

To illustrate, one or more mutations may be selected that increase the selectivity of the altered ligand-binding domain for GDF11 and/or GDF8 over one or more ActRII-binding ligands such as activins (activin A, activin B, activin AB, activin C, and/or activin E), particularly activin A. Optionally, the altered ligand-binding domain has a ratio of $K_d$ for activin binding to $K_d$ for GDF11 and/or GDF8 binding that is at least 2-, 5-, 10-, 20-, 50-, 100- or even 1000-fold greater relative to the ratio for the wild-type ligand-binding domain. Optionally, the altered ligand-binding domain has a ratio of $IC_{50}$ for inhibiting activin to $IC_{50}$ for inhibiting GDF11 and/or GDF8 that is at least 2-, 5-, 10-, 20-, 50-, 100- or even 1000-fold greater relative to the wild-type ligand-binding domain. Optionally, the altered ligand-binding domain inhibits GDF11 and/or GDF8 with an $IC_{50}$ at least 2-, 5-, 10-, 20-, 50-, 100- or even 1000-times less than the $IC_{50}$ for inhibiting activin.

In certain preferred embodiments, GDF traps of the present disclosure are designed to preferentially bind to GDF11 and/or GDF8 (also known as myostatin). Optionally, GDF11 and/or GDF8-binding traps may further bind to activin B. Optionally, GDF11 and/or GDF8-binding traps may further bind to BMP6. Optionally, GDF11 and/or GDF8-binding traps may further bind to BMP10. Optionally, GDF11 and/or GDF8-binding traps may further bind to activin B and BMP6. In certain embodiments, GDF traps of the present disclosure have diminished binding affinity for activins (e.g., activin A, activin A/B, activin B, activin C, activin E), e.g., in comparison to a wild-type ActRII polypeptide. In certain preferred embodiments, a GDF trap polypeptide of the present disclosure has diminished binding affinity for activin A.

Amino acid residues of the ActRIIB proteins (e.g., E39, K55, Y60, K74, W78, L79, D80, and F101) are in the ActRIIB ligand-binding pocket and help mediated binding to its ligands including, for example, activin A, GDF11, and GDF8. Thus the present disclosure provides GDF trap polypeptides comprising an altered-ligand binding domain (e.g., a GDF8/GDF11-binding domain) of an ActRIIB receptor which comprises one or more mutations at those amino acid residues.

As a specific example, the positively-charged amino acid residue Asp (D80) of the ligand-binding domain of ActRIIB can be mutated to a different amino acid residue to produce a GDF trap polypeptide that preferentially binds to GDF8, but not activin. Preferably, the D80 residue with respect to SEQ ID NO: 1 is changed to an amino acid residue selected from the group consisting of: an uncharged amino acid residue, a negative amino acid residue, and a hydrophobic amino acid residue. As a further specific example, the hydrophobic residue L79 of SEQ ID NO: 1 can be altered to confer altered activin-GDF11/GDF8 binding properties. For example, an L79P substitution reduces GDF11 binding to a greater extent than activin binding. In contrast, replacement of L79 with an acidic amino acid [an aspartic acid or glutamic acid; an L79D or an L79E substitution] greatly reduces activin A binding affinity while retaining GDF11 binding affinity. In exemplary embodiments, the methods described herein utilize a GDF trap polypeptide which is a variant ActRIIB polypeptide comprising an acidic amino acid (e.g., D or E) at the position corresponding to position 79 of SEQ ID NO: 1, optionally in combination with one or more additional amino acid substitutions, additions, or deletions.

In some embodiments, the present disclosure contemplates making functional variants by modifying the structure of an ActRII polypeptide for such purposes as enhancing therapeutic efficacy or stability (e.g., shelf-life and resistance to proteolytic degradation in vivo). Variants can be produced by amino acid substitution, deletion, addition, or combinations thereof. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a polypeptide of the disclosure results in a functional homolog can be readily determined by assessing the ability of the variant polypeptide to produce a response in cells in a fashion similar to the wild-type polypeptide, or to bind to one or more TGF-beta ligands including, for example, BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, nodal, glial cell-derived neurotrophic factor (GDNF), neurturin, artemin, persephin, MIS, and Lefty.

In certain embodiments, the present disclosure contemplates specific mutations of an ActRII polypeptide so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine or asparagine-X-serine (where "X" is any amino acid) which is specifically recognized by appropriate cellular glycosylation enzymes. The alteration may also be made by the addition of, or substitution by, one or more serine or threonine residues to the sequence of the polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a polypeptide is by chemical or enzymatic coupling of glycosides to the polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. Removal of one or more carbohydrate moieties present on a polypeptide may be accomplished chemically and/or enzymatically. Chemical deglycosylation may involve, for example, exposure of a polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Enzymatic cleavage of carbohydrate moieties on polypeptides can be achieved by the use of a variety of endo- and exo-glycosidases as described by Thotakura et al. [Meth. Enzymol. (1987) 138:350]. The sequence of a polypeptide may be adjusted, as appropriate, depending on the type of expression system used, as mammalian, yeast, insect, and plant cells may all introduce differing glycosylation patterns that can be affected by the amino acid sequence of the peptide. In general, polypeptides of the present disclosure for use in humans may be expressed in a mammalian cell line that provides proper glycosylation, such as HEK293 or CHO cell lines, although other mammalian expression cell lines are expected to be useful as well.

The present disclosure further contemplates a method of generating mutants, particularly sets of combinatorial mutants of an ActRII polypeptide as well as truncation mutants. Pools of combinatorial mutants are especially useful for identifying functionally active (e.g., TGF-beta superfamily ligand binding) ActRII sequences. The purpose of screening such combinatorial libraries may be to generate, for example, polypeptides variants which have altered properties, such as altered pharmacokinetic or altered ligand binding. A variety of screening assays are provided below, and such assays may be used to evaluate variants. For example, ActRII variants may be screened for ability to bind to one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-$\beta$1, TGF-$\beta$2, TGF-$\beta$3, activin A, activin B, activin AB, activin AC, nodal, glial cell-derived neurotrophic factor (GDNF), neurturin, artemin, persephin, MIS, and Lefty), to prevent binding of a TGF-beta superfamily ligand to a TGF-beta superfamily receptor, and/or to interfere with signaling caused by an TGF-beta superfamily ligand.

The activity of an ActRII polypeptides may also be tested in a cell-based or in vivo assay. For example, the effect of an ActRII polypeptide on the expression of genes involved in visual acuity may be assessed. This may, as needed, be performed in the presence of one or more recombinant ActRII ligand proteins (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-$\beta$1, TGF-$\beta$2, TGF-$\beta$3, activin A, activin B, activin C, activin E, activin AB, activin AC, nodal, glial cell-derived neurotrophic factor (GDNF), neurturin, artemin, persephin, MIS, and Lefty), and cells may be transfected so as to produce an ActRII polypeptide, and optionally, an ActRII ligand. Likewise, an ActRII polypeptide may be administered to a mouse or other animal and visual acuity may be assessed using art-recognized methods. Similarly, the activity of an ActRII polypeptide or variant thereof may be tested in blood cell precursor cells for any effect on growth of these cells, for example, by the assays as described herein and those of common knowledge in the art. A SMAD-responsive reporter gene may be used in such cell lines to monitor effects on downstream signaling.

Combinatorial-derived variants can be generated which have increased selectivity or generally increased potency relative to a reference ActRII polypeptide. Such variants, when expressed from recombinant DNA constructs, can be used in gene therapy protocols. Likewise, mutagenesis can give rise to variants which have intracellular half-lives dramatically different than the corresponding unmodified ActRII polypeptide. For example, the altered protein can be rendered either more stable or less stable to proteolytic degradation or other cellular processes which result in destruction, or otherwise inactivation, of an unmodified polypeptide. Such variants, and the genes which encode them, can be utilized to alter polypeptide complex levels by modulating the half-life of the polypeptide. For instance, a short half-life can give rise to more transient biological effects and, when part of an inducible expression system, can allow tighter control of recombinant polypeptide complex levels within the cell. In an Fc fusion protein, mutations may be made in the linker (if any) and/or the Fc portion to alter the half-life of the ActRII polypeptide.

A combinatorial library may be produced by way of a degenerate library of genes encoding a library of polypeptides which each include at least a portion of potential ActRII sequences. For instance, a mixture of synthetic oligonucleotides can be enzymatically ligated into gene sequences such that the degenerate set of potential ActRII encoding nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes can then be ligated into an appropriate vector for expression. The synthesis of degenerate oligonucleotides is well known in the art [Narang, S A (1983) Tetrahedron 39:3; Itakura et al. (1981) Recombinant DNA, Proc. 3rd Cleveland Sympos. Macromolecules, ed. AG Walton, Amsterdam: Elsevier pp 273-289; Itakura et al. (1984) Annu. Rev. Biochem. 53:323; Itakura et al. (1984) Science 198:1056; and Ike et al. (1983) Nucleic Acid Res. 11:477]. Such techniques have been employed in the directed evolution of other proteins [Scott et al., (1990) Science 249:386-390; Roberts et al. (1992) PNAS USA 89:2429-2433; Devlin et al. (1990) Science 249: 404-406; Cwirla et al., (1990) PNAS USA 87: 6378-6382; as well as U.S. Pat. Nos. 5,223,409, 5,198,346, and 5,096,815].

Alternatively, other forms of mutagenesis can be utilized to generate a combinatorial library. For example, ActRII polypeptides of the disclosure can be generated and isolated from a library by screening using, for example, alanine scanning mutagenesis [Ruf et al. (1994) Biochemistry 33:1565-1572; Wang et al. (1994) J. Biol. Chem. 269:3095-3099; Balint et al. (1993) Gene 137:109-118; Grodberg et al. (1993) Eur. J. Biochem. 218:597-601; Nagashima et al. (1993) J. Biol. Chem. 268:2888-2892; Lowman et al. (1991) Biochemistry 30:10832-10838; and Cunningham et al. (1989) Science 244:1081-1085], by linker scanning mutagenesis [Gustin et al. (1993) Virology 193:653-660; and Brown et al. (1992) Mol. Cell Biol. 12:2644-2652; McKnight et al. (1982) Science 232:316], by saturation mutagenesis [Meyers et al., (1986) Science 232:613]; by PCR mutagenesis [Leung et al. (1989) Method Cell Mol Biol 1:11-19]; or by random mutagenesis, including chemical mutagenesis [Miller et al. (1992) A Short Course in Bacterial Genetics, CSHL Press, Cold Spring Harbor, N.Y.; and Greener et al. (1994) Strategies in Mol Biol 7:32-34]. Linker scanning mutagenesis, particularly in a combinatorial setting, is an attractive method for identifying truncated (bioactive) forms of ActRII polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of ActRII polypeptides. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include TGF-beta ligand (e.g., BMP2, BMP2/7, BMP3, BMP4, BMP4/7, BMP5, BMP6, BMP7, BMP8a, BMP8b, BMP9, BMP10, GDF3, GDF5, GDF6/

BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, nodal, glial cell-derived neurotrophic factor (GDNF), neurturin, artemin, persephin, MIS, and Lefty) binding assays and/or TGF-beta ligand-mediated cell signaling assays.

As will be recognized by one of skill in the art, most of the described mutations, variants or modifications described herein may be made at the nucleic acid level or, in some cases, by post-translational modification or chemical synthesis. Such techniques are well known in the art and some of which are described herein. In part, the present disclosure identifies functionally active portions (fragments) and variants of ActRII polypeptides that can be used as guidance for generating and using other variant ActRII polypeptides within the scope of the inventions described herein.

In certain embodiments, functionally active fragments of ActRII polypeptides of the present disclosure can be obtained by screening polypeptides recombinantly produced from the corresponding fragment of the nucleic acid encoding an ActRII polypeptide (e.g., SEQ ID NOs: 7, 8, 12, 13, 37, 42, 47, 60, 62, 63, 66, 67, 68, 80, 81, 82, and 83). In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function as antagonists (inhibitors) of ActRII receptors and/or one or more ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, nodal, glial cell-derived neurotrophic factor (GDNF), neurturin, artemin, persephin, MIS, and Lefty).

In certain embodiments, ActRII polypeptides of the present disclosure may further comprise post-translational modifications in addition to any that are naturally present in the ActRII (e.g. an ActRIIA or ActRIIB polypeptide). Such modifications include, but are not limited to, acetylation, carboxylation, glycosylation, phosphorylation, lipidation, and acylation. As a result, the ActRII polypeptide may contain non-amino acid elements, such as polyethylene glycols, lipids, polysaccharide or monosaccharide, and phosphates. Effects of such non-amino acid elements on the functionality of a ligand trap polypeptide may be tested as described herein for other ActRII variants. When a polypeptide of the disclosure is produced in cells by cleaving a nascent form of the polypeptide, post-translational processing may also be important for correct folding and/or function of the protein. Different cells (e.g., CHO, HeLa, MDCK, 293, WI38, NIH-3T3 or HEK293) have specific cellular machinery and characteristic mechanisms for such post-translational activities and may be chosen to ensure the correct modification and processing of the ActRII polypeptides.

In certain aspects, ActRII polypeptides of the present disclosure include fusion proteins having at least a portion (domain) of an ActRII polypeptide (e.g., an ActRIIA or ActRIIB polypeptide) and one or more heterologous portions (domains). Well-known examples of such fusion domains include, but are not limited to, polyhistidine, Glu-Glu, glutathione S-transferase (GST), thioredoxin, protein A, protein G, an immunoglobulin heavy-chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress' system (Qiagen) useful with (HIS$_6$(SEQ ID NO: 84)) fusion partners. As another example, a fusion domain may be selected so as to facilitate detection of the ActRII polypeptide. Examples of such detection domains include the various fluorescent proteins (e.g., GFP) as well as "epitope tags," which are usually short peptide sequences for which a specific antibody is available. Well-known epitope tags for which specific monoclonal antibodies are readily available include FLAG, influenza virus haemagglutinin (HA), and c-myc tags. In some cases, the fusion domains have a protease cleavage site, such as for Factor Xa or thrombin, which allows the relevant protease to partially digest the fusion proteins and thereby liberate the recombinant proteins therefrom. The liberated proteins can then be isolated from the fusion domain by subsequent chromatographic separation. Other types of fusion domains that may be selected include multimerizing (e.g., dimerizing, tetramerizing) domains and functional domains (that confer an additional biological function) including, for example constant domains from immunoglobulins (e.g., Fc domains).

In certain aspects, ActRII polypeptides of the present disclosure contain one or more modifications that are capable of "stabilizing" the polypeptides. By "stabilizing" is meant anything that increases the in vitro half-life, serum half-life, regardless of whether this is because of decreased destruction, decreased clearance by the kidney, or other pharmacokinetic effect of the agent. For example, such modifications enhance the shelf-life of the polypeptides, enhance circulatory half-life of the polypeptides, and/or reduce proteolytic degradation of the polypeptides. Such stabilizing modifications include, but are not limited to, fusion proteins (including, for example, fusion proteins comprising an ActRII polypeptide domain and a stabilizer domain), modifications of a glycosylation site (including, for example, addition of a glycosylation site to a polypeptide of the disclosure), and modifications of carbohydrate moiety (including, for example, removal of carbohydrate moieties from a polypeptide of the disclosure). As used herein, the term "stabilizer domain" not only refers to a fusion domain (e.g., an immunoglobulin Fc domain) as in the case of fusion proteins, but also includes nonproteinaceous modifications such as a carbohydrate moiety, or nonproteinaceous moiety, such as polyethylene glycol. In certain preferred embodiments, an ActRII polypeptide is fused with a heterologous domain that stabilizes the polypeptide (a "stabilizer" domain), preferably a heterologous domain that increases stability of the polypeptide in vivo. Fusions with a constant domain of an immunoglobulin (e.g., a Fc domain) are known to confer desirable pharmacokinetic properties on a wide range of proteins. Likewise, fusions to human serum albumin can confer desirable properties.

An example of a native amino acid sequence that may be used for the Fc portion of human IgG1 (G1Fc) is shown below (SEQ ID NO: 14). Dotted underline indicates the hinge region, and solid underline indicates positions with naturally occurring variants. In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NO: 14. Naturally occurring variants in G1Fc would include E134D and M136L according to the numbering system used in SEQ ID NO: 14 (see Uniprot P01857).

```
                                                               (SEQ ID NO: 14)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYK TTPPVLDSDG SFFLYSKLTV DKSRWQQGNV

201 FSCSVMHEAL HNHYTQKSLS LSPGK
```

Optionally, the IgG1 Fc domain has one or more mutations at residues such as Asp-265, lysine 322, and Asn-434. In certain cases, the mutant IgG1 Fc domain having one or more of these mutations (e.g., Asp-265 mutation) has reduced ability of binding to the Fcγ receptor relative to a wild-type Fc domain. In other cases, the mutant Fc domain having one or more of these mutations (e.g., Asn-434 mutation) has increased ability of binding to the MEW class I-related Fc-receptor (FcRN) relative to a wild-type IgG1 Fc domain.

An example of a native amino acid sequence that may be used for the Fc portion of human IgG2 (G2Fc) is shown below (SEQ ID NO: 15). Dotted underline indicates the hinge region and double underline indicates positions where there are data base conflicts in the sequence (according to UniProt P01859). In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NO: 15.

```
                                                               (SEQ ID NO: 15)
  1 VECPPCPAPP VAGPSVFLFP PKPKDTLMIS RTPEVTCVVV DVSHEDPEVQ

51 FNWYVDGVEV HNAKTKPREE QFNSTFRVVS VLTVVHQDWL NGKEYKCKVS

101 NKGLPAPIEK TISKTKGQPR EPQVYTLPPS REEMTKNQVS LTCLVKGFYP

151 SDIAVEWESN GQPENNYKTT PPMLDSDGSF FLYSKLTVDK SRWQQGNVFS

201 CSVMHEALHN HYTQKSLSLS PGK
```

Two examples of amino acid sequences that may be used for the Fc portion of human IgG3 (G3Fc) are shown below. The hinge region in G3Fc can be up to four times as long as in other Fc chains and contains three identical 15-residue segments preceded by a similar 17-residue segment. The first G3Fc sequence shown below (SEQ ID NO: 16) contains a short hinge region consisting of a single 15-residue segment, whereas the second G3Fc sequence (SEQ ID NO: 17) contains a full-length hinge region. In each case, dotted underline indicates the hinge region, and solid underline indicates positions with naturally occurring variants according to UniProt P01859. In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NOs: 16 and 17.

```
                                                               (SEQ ID NO: 16)
  1 EPKSCDTPPP CPRCPAPELL GGPSVFLFPP KPKDTLMISR TPEVTCVVVD

51 VSHEDPEVQF KWYVDGVEVH NAKTKPREEQ YNSTFRVVSV LTVLHQDWLN

101 GKEYKCKVSN KALPAPIEKT ISKTKGQPRE PQVYTLPPSR EEMTKNQVSL

151 TCLVKGFYPS DIAVEWESSG QPENNYNTTP PMLDSDGSFF LYSKLTVDKS

201 RWQQGNIFSC SVMHEALHNR FTQKSLSLSP GK
```

```
                                                               (SEQ ID NO: 17)
  1 ELKTPLGDTT HTCPRCPEPK SCDTPPPCPR CPEPKSCDTP PPCPRCPEPK

51 SCDTPPPCPR CPAPELLGGP SVFLFPPKPK DTLMISRTPE VTCVVVDVSH
```

```
-continued
101 EDPEVQFKWY VDGVEVHNAK TKPREEQYNS TFRVVSVLTV LHQDWLNGKE

151 YKCKVSNKAL PAPIEKTISK TKGQPREPQV YTLPPSREEM TKNQVSLTCL

201 VKGFYPSDIA VEWESSGQPE NNYNTTPPML DSDGSFFLYS KLTVDKSRWQ

251 QGNIFSCSVM HEALHNRFTQ KSLSLSPGK
```

Naturally occurring variants in G3Fc (for example, see Uniprot P01860) include E68Q, P76L, E79Q, Y81F, D97N, N100D, T124A, S169N, S169del, F221Y when converted to the numbering system used in SEQ ID NO: 16, and the present disclosure provides fusion proteins comprising G3Fc domains containing one or more of these variations. In addition, the human immunoglobulin IgG3 gene (IGHG3) shows a structural polymorphism characterized by different hinge lengths [see Uniprot P01859]. Specifically, variant WIS is lacking most of the V region and all of the CH1 region. It has an extra interchain disulfide bond at position 7 in addition to the 11 normally present in the hinge region. Variant ZUC lacks most of the V region, all of the CH1 region, and part of the hinge. Variant OMM may represent an allelic form or another gamma chain subclass. The present disclosure provides additional fusion proteins comprising G3Fc domains containing one or more of these variants.

An example of a native amino acid sequence that may be used for the Fc portion of human IgG4 (G4Fc) is shown below (SEQ ID NO: 18). Dotted underline indicates the hinge region. In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NO: 18.

```
                                                       (SEQ ID NO: 18)
  1 ESKYGPPCPS CPAPEFLGGP SVFLFPPKPK DTLMISRTPE VTCVVVDVSQ

51 EDPEVQFNWY VDGVEVHNAK TKPREEQFNS TYRVVSVLTV LHQDWLNGKE

101 YKCKVSNKGL PSSIEKTISK AKGQPREPQV YTLPPSQEEM TKNQVSLTCL

151 VKGFYPSDIA VEWESNGQPE NNYKTTPPVL DSDGSFFLYS RLTVDKSRWQ

201 EGNVFSCSVM HEALHNHYTQ KSLSLSLGK
```

A variety of engineered mutations in the Fc domain are presented herein with respect to the G1Fc sequence (SEQ ID NO: 14), and analogous mutations in G2Fc, G3Fc, and G4Fc can be derived from their alignment with G1Fc in FIG. 15. Due to unequal hinge lengths, analogous Fc positions based on isotype alignment (FIG. 15) possess different amino acid numbers in SEQ ID NOs: 14, 15, 16, 17, and 18. It can also be appreciated that a given amino acid position in an immunoglobulin sequence consisting of hinge, CH2, and CH3 regions (e.g., SEQ ID NOs: 14, 15, 16, 17, and 18) will be identified by a different number than the same position when numbering encompasses the entire IgG1 heavy-chain constant domain (consisting of the CH1, hinge, CH2, and CH3 regions) as in the Uniprot database. For example, correspondence between selected CH3 positions in a human G1Fc sequence (SEQ ID NO: 14), the human IgG1 heavy chain constant domain (Uniprot P01857), and the human IgG1 heavy chain is as follows.

| Correspondence of $C_H3$ Positions in Different Numbering Systems | | |
|---|---|---|
| G1Fc (Numbering begins at first threonine in hinge region) | IgG1 heavy chain constant domain (Numbering begins at $C_H1$) | IgG1 heavy chain (EU numbering scheme of Kabat et al., 1991*) |
| Y127 | Y232 | Y349 |
| S132 | S237 | S354 |
| E134 | E239 | E356 |
| T144 | T249 | T366 |
| L146 | L251 | L368 |
| K170 | K275 | K392 |
| D177 | D282 | D399 |
| Y185 | Y290 | Y407 |
| K187 | K292 | K409 |

*Kabat et al. (eds) 1991; pp. 688-696 in Sequences of Proteins of Immunological Interest, 5th ed., Vol. 1, NIH, Bethesda, MD.

It is understood that different elements of the fusion proteins (e.g., immunoglobulin Fc fusion proteins) may be arranged in any manner that is consistent with desired functionality. For example, an ActRII polypeptide domain may be placed C-terminal to a heterologous domain, or alternatively, a heterologous domain may be placed C-terminal to an ActRII polypeptide domain. The ActRII polypeptide domain and the heterologous domain need not be adjacent in a fusion protein, and additional domains or amino acid sequences may be included C- or N-terminal to either domain or between the domains.

For example, an ActRII receptor fusion protein may comprise an amino acid sequence as set forth in the formula A-B-C. The B portion corresponds to an ActRII polypeptide domain. The A and C portions may be independently zero, one, or more than one amino acid, and both the A and C portions when present are heterologous to B. The A and/or C portions may be attached to the B portion via a linker sequence. A linker may be rich in glycine (e.g., 2-10, 2-5, 2-4, 2-3 glycine residues) or glycine and proline residues and may, for example, contain a single sequence of threonine/serine and glycines or repeating sequences of threonine/serine and/or glycines, e.g., GGG (SEQ ID NO: 19), GGGG (SEQ ID NO: 20), TGGGG (SEQ ID NO: 21), SGGGG (SEQ ID NO: 22), TGGG (SEQ ID NO: 23), SGGG (SEQ ID NO: 24), or GGGGS (SEQ ID NO: 25) singlets, or repeats. In certain embodiments, an ActRII fusion protein comprises an amino acid sequence as set forth in the formula A-B-C, wherein A is a leader (signal) sequence, B consists of an ActRII polypeptide domain, and C is a polypeptide portion that enhances one or more of in vivo stability, in vivo half-life, uptake/administration, tissue localization or distribution, formation of protein complexes, and/or purification. In certain embodiments, an ActRII fusion protein comprises an amino acid sequence as set forth in the formula A-B-C, wherein A is a TPA leader sequence, B consists of an ActRII receptor polypeptide domain, and C is an immunoglobulin Fc domain. Preferred fusion proteins comprise the amino acid sequence set forth in any one of SEQ ID NOs: 32, 36, 39, 40, 41, 44, 46, 50, 61, 64, 78, and 79.

In preferred embodiments, ActRII polypeptides to be used in accordance with the methods described herein are isolated polypeptides. As used herein, an isolated protein or polypeptide is one which has been separated from a component of its natural environment. In some embodiments, a polypeptide of the disclosure is purified to greater than 95%, 96%, 97%, 98%, or 99% purity as determined by, for example, electrophoretic (e.g., SDS-PAGE, isoelectric focusing (IEF), capillary electrophoresis) or chromatographic (e.g., ion exchange or reverse phase HPLC). Methods for assessment of antibody purity are well known in the art [see, e.g., Flatman et al., (2007) J. Chromatogr. B 848:79-87]. In some embodiments, ActRII polypeptides to be used in accordance with the methods described herein are recombinant polypeptides.

ActRII polypeptides of the disclosure can be produced by a variety of art-known techniques. For example, polypeptides of the disclosure can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). Alternatively, the polypeptides of the disclosure, including fragments or variants thereof, may be recombinantly produced using various expression systems [e.g., E. coli, Chinese Hamster Ovary (CHO) cells, COS cells, baculovirus] as is well known in the art. In a further embodiment, the modified or unmodified polypeptides of the disclosure may be produced by digestion of recombinantly produced full-length ActRII polypeptides by using, for example, a protease, e.g., trypsin, thermolysin, chymotrypsin, pepsin, or paired basic amino acid converting enzyme (PACE). Computer analysis (using commercially available software, e.g., MacVector, Omega, PCGene, Molecular Simulation, Inc.) can be used to identify proteolytic cleavage sites. Alternatively, such polypeptides may be produced from recombinantly generated full-length ActRII polypeptides using chemical cleavage (e.g., cyanogen bromide, hydroxylamine, etc.).

Any of the ActRII polypeptides described herein (e.g., ActRIIA or ActRIIB polypeptides as well as variants thereof such as GDF traps) can be combined with one or more additional ActRII antagonists to achieve the desired effect (e.g., treat or prevent a vascular disorder of the eye in a patient in need thereof, increase vision in patient in need thereof that has a vascular disorder of the eye, and/or treat or prevent one or more complications of a vascular disorder of the eye). For example, an ActRII polypeptide can be used in combination with: i) one or more additional ActRII polypeptides, ii) one or more ActRII antagonist antibodies; iii) one or more small molecule ActRII antagonists; iv) one or more polynucleotide ActRII antagonists; v) one or more follistatin polypeptides; and/or vi) one or more FLRG polypeptides.

B. Nucleic Acids Encoding ActRII Polypeptides

In certain embodiments, the present disclosure provides isolated and/or recombinant nucleic acids encoding the ActRII polypeptides (including fragments, functional variants (e.g., GDF traps), and fusion proteins thereof). For example, SEQ ID NO: 12 encodes the naturally occurring human ActRIIA precursor polypeptide, while SEQ ID NO: 13 encodes the processed extracellular domain of ActRIIA. In addition, SEQ ID NO: 7 encodes a naturally occurring human ActRIIB precursor polypeptide (the R64 variant described above), while SEQ ID NO: 8 encodes the processed extracellular domain of ActRIIB (the R64 variant described above). The subject nucleic acids may be single-stranded or double stranded. Such nucleic acids may be DNA or RNA molecules. These nucleic acids may be used, for example, in methods for making ActRII-based ligand trap polypeptides as described herein.

As used herein, isolated nucleic acid(s) refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

In certain embodiments, nucleic acids encoding ActRII polypeptides of the disclosure are understood to include nucleic acids that are variants of any one of SEQ ID NOs: 7, 8, 12, 13, 37, 42, 47, 60, 62, 63, 66, 67, 68, 80, 81, 82, and 83. Variant nucleotide sequences include sequences that differ by one or more nucleotide substitutions, additions, or deletions including allelic variants, and therefore, will include coding sequence that differ from the nucleotide sequence designated in any one of SEQ ID NOs: 7, 8, 12, 13, 37, 42, 47, 60, 62, 63, 66, 67, 68, 80, 81, 82, and 83.

In certain embodiments, ActRII polypeptides of the disclosure are encoded by isolated and/or recombinant nucleic acid sequences that are at least 70%, 75%, 80%, 85%, 90%, 91%, 92%, 93%, 94% 95%, 96%, 97%, 98%, 99%, or 100% identical to any one of SEQ ID NOs: 7, 8, 12, 13, 37, 42, 47, 60, 62, 63, 66, 67, 68, 80, 81, 82, and 83. One of ordinary skill in the art will appreciate that nucleic acid sequences that are at least 70%, 75%, 80%, 85%, 90%, 91%, 92%, 93%, 94% 95%, 96%, 97%, 98%, 99%, or 100% identical to the sequences complementary to SEQ ID NOs: 7, 8, 12, 13, 37, 42, 47, 60, 62, 63, 66, 67, 68, 80, 81, 82, and 83, and variants thereof, are also within the scope of the present disclosure. In further embodiments, the nucleic acid sequences of the disclosure can be isolated, recombinant, and/or fused with a heterologous nucleotide sequence, or in a DNA library.

In other embodiments, nucleic acids of the present disclosure also include nucleotide sequences that hybridize under highly stringent conditions to the nucleotide sequence designated in SEQ ID NOs: 7, 8, 12, 13, 37, 42, 47, 60, 62, 63, 66, 67, 68, 80, 81, 82, and 83, complement sequences of SEQ ID NOs: 7, 8, 12, 13, 37, 42, 47, 60, 62, 63, 66, 67, 68, 80, 81, 82, and 83, or fragments thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by a wash at 2×SSC at room temperature.

Isolated nucleic acids which differ from the nucleic acids as set forth in SEQ ID NOs: 7, 8, 12, 13, 37, 42, 47, 60, 62, 63, 66, 67, 68, 80, 81, 82, and 83 to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

In certain embodiments, the recombinant nucleic acids of the present disclosure may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art and can be used in a variety of host cells. Typically, one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In some embodiments, the expression vector contains a selectable marker gene to allow the selection of transformed host cells. Selectable marker genes are well known in the art and can vary with the host cell used.

In certain aspects, the subject nucleic acid disclosed herein is provided in an expression vector comprising a nucleotide sequence encoding an ActRII polypeptide and operably linked to at least one regulatory sequence. Regulatory sequences are art-recognized and are selected to direct expression of the ActRII polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding an ActRII polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the present disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant ActRII polypeptide include plasmids and other vectors. For instance, suitable vectors include plasmids of the following types: pBR322-derived plasmids, pEMBL-derived plasmids, pEX-derived plasmids, pBTac-derived plasmids and pUC-derived plasmids for expression in prokaryotic cells, such as *E. coli*.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells.

Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, e.g., Molecular Cloning A Laboratory Manual, 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of the subject ActRII polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject ActRII polypeptides in cells propagated in culture, e.g., to produce proteins, including fusion proteins or variant proteins, for purification.

This disclosure also pertains to a host cell transfected with a recombinant gene including a coding sequence for one or more of the subject ActRII polypeptides. The host cell may be any prokaryotic or eukaryotic cell. For example, an ActRII polypeptide of the disclosure may be expressed in bacterial cells such as *E. coli*, insect cells (e.g., using a baculovirus expression system), yeast, or mammalian cells [e.g. a Chinese hamster ovary (CHO) cell line]. Other suitable host cells are known to those skilled in the art.

Accordingly, the present disclosure further pertains to methods of producing the subject ActRII polypeptides. For example, a host cell transfected with an expression vector encoding an ActRII polypeptide can be cultured under appropriate conditions to allow expression of the ActRII polypeptide to occur. The polypeptide may be secreted and isolated from a mixture of cells and medium containing the polypeptide. Alternatively, the ActRII polypeptide may be retained cytoplasmically or in a membrane fraction and the cells harvested, lysed and the protein isolated. A cell culture includes host cells, media and other byproducts. Suitable media for cell culture are well known in the art. The subject polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the ActRII polypeptides, and affinity purification with an agent that binds to a domain fused to the ActRII polypeptide (e.g., a protein A column may be used to purify an ActRII-Fc fusion protein). In some embodiments, the ActRII polypeptide is a fusion protein containing a domain which facilitates its purification.

In some embodiments, purification is achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. An ActRII protein may be purified to a purity of >90%, >95%, >96%, >98%, or >99% as determined by size exclusion chromatography and >90%, >95%, >96%, >98%, or >99% as determined by SDS PAGE. The target level of purity should be one that is sufficient to achieve desirable results in mammalian systems, particularly non-human primates, rodents (mice), and humans.

In another embodiment, a fusion gene coding for a purification leader sequence, such as a poly-(His)/enterokinase cleavage site sequence at the N-terminus of the desired portion of the recombinant ActRII polypeptide, can allow purification of the expressed fusion protein by affinity chromatography using a $Ni^{2+}$ metal resin. The purification leader sequence can then be subsequently removed by treatment with enterokinase to provide the purified ActRII polypeptide. See, e.g., Hochuli et al. (1987) *J. Chromatography* 411:177; and Janknecht et al. (1991) *PNAS USA* 88:8972.

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence. See, e.g., Current Protocols in Molecular Biology, eds. Ausubel et al., John Wiley & Sons: 1992.

C. Antibody Antagonists

In other aspects, the present disclosure relates to an antibody, or combination of antibodies, that antagonize ActRII activity (e.g., inhibition of ActRII signaling transduction via Smads 1, 2, 3, 5, and 8). Such antibodies may bind to one or more TGF-β ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, nodal, glial cell-derived neurotrophic factor (GDNF), neurturin, artemin, persephin, MIS, and Lefty) or one or more type I and/or type II receptors (e.g., ActRIIA, ActRIIB, ALK4, ALK5). In particular, the disclosure provides methods of using an antibody ActRII antagonist, or combination of antibody ActRII antagonists, alone or in combination with one or more additional supportive therapies, to treat or prevent a vascular disorder of the eye [e.g., macular degeneration (e.g., age-related macular degeneration, juvenile macular degeneration, wet macular degeneration, dry macular degeneration, Stargardt's disease, and Best's disease), retinal vein occlusion (e.g, central retinal vein occlusion, hemi-retinal vein occlusion, branch retinal vein occlusion, macular edema following retinal vein occlusion, and ischemic retinal vein occlusion), retinal artery occlusion (e.g, central retinal artery occlusion, hemi-retinal artery occlusion, branch retinal artery occlusion, and ischemic retinal artery occlusion), diabetic retinopathy, diabetic macular edema, ischemic optic neuropathy [e.g., anterior ischemic optic neuropathy (arteritic and non-arteritic) and posterior ischemic optic neuropathy], macular telangiectasia (type I or type II), retinal ischemia (e.g., acute retinal ischemia or chronic retinal ischemia), ocular ischemic syndrome, retinal vasculitis, and retinopathy of prematurity] in a patient in need thereof; increase vision (increase visual acuity and/or visual field) in patient in need thereof that has a vascular disorder of the eye; and/or treat or prevent one or more complications of a vascular disorder of the eye.

In certain aspects, a preferred antibody ActRII antagonist of the disclosure is an antibody, or combination of antibodies, that binds to and/or inhibits activity of at least GDF11. In other aspects, a preferred antibody ActRII antagonist of the disclosure is an antibody, or combination of antibodies, that binds to and/or inhibits activity of at least GDF8. In other aspects, a preferred antibody ActRII antagonist of the disclosure is an antibody, or combination of antibodies, that binds to and/or inhibits activity of at least GDF3. In even other aspects, a preferred antibody ActRII antagonist of the disclosure is an antibody, or combination of antibodies, that binds to and/or inhibits activity of at least BMP6. In still other aspects, a preferred antibody ActRII antagonist of the disclosure is an antibody, or combination of antibodies, that binds to and/or inhibits activity of at least BMP9. In alternative aspects, a preferred antibody ActRII antagonist of the disclosure is an antibody, or combination of antibodies, that does not bind to and/or inhibits activity of BMP9. In still even other aspects, a preferred antibody ActRII antagonist of the disclosure is an antibody, or combination of antibodies, that binds to and/or inhibits activity of at least BMP10. In alternative aspects, a preferred antibody ActRII antagonist of the disclosure is an antibody, or combination of antibodies, that does not bind to and/or inhibits activity of BMP10. In further aspects, a preferred antibody ActRII antagonist of the disclosure is an antibody, or combination of antibodies, that binds to and/or inhibits activity of at least activin (e.g., activin A, activin B, activin AB, activin C, and activin D). In some embodiments, a preferred antibody ActRII antagonist of the disclosure is an antibody, or combination of antibodies, that binds to and/or inhibits activity of at least activin B. In some embodiments, a preferred antibody ActRII antagonist of the disclosure is an antibody, or combination of antibodies, that binds to and/or inhibits activity of at least activin A and activin B. Alternatively, in some embodiments, a preferred antibody ActRII antagonist of the disclosure is an antibody, or combination of antibodies, that binds to and/or inhibits activity of at least activin B, but does not bind to and/or inhibit activin A. In even further aspects, a preferred antibody ActRII antagonist of the disclosure is an antibody, or combination of antibodies, that does not bind to and/or inhibits activity one or more of BMP9, BMP10, and activin A.

In some embodiments, a preferred antibody ActRII antagonist of the disclosure is an antibody, or combination of antibodies, that binds to and/or inhibits activity of at least GDF11 and GDF8, particularly in the case of a multispecific antibody that has binding affinity for both GDF11 and GDF8 or in the context of a combination of one or more anti-GDF11 antibodies and one or more anti-GDF8 antibodies. In some embodiments, an antibody, or combination of antibodies, of the disclosure that binds to and/or inhibits the activity of GDF11 and/or GDF8 further binds to and/or inhibits activity of activin (e.g., activin A, activin B, activin AB, activin C, and/or activin E). In some embodiments, an antibody, or combination of antibodies, of the disclosure that binds to and/or inhibits the activity of GDF11 and/or GDF8 further binds to and/or inhibits activity of activin B. In some embodiments, an antibody, or combination of antibodies, of the disclosure that binds to and/or inhibits the activity of GDF11 and/or GDF8 does not bind to and/or inhibit, or does not substantially bind to and/or inhibit, activity of activin A (e.g., an antibody that has a $K_D$ of greater than $1 \times 10^{-7}$ for activin A). In some embodiments, an antibody, or combination of antibodies, of the disclosure that binds to and/or inhibits the activity of GDF11, GDF8, and/or activin further binds to and/or inhibits activity of BMP6. In some embodiments, an antibody, or combination of antibodies, of the disclosure that binds to and/or inhibits the activity of GDF11, GDF8, activin, and/or BMP6 further binds to and/or inhibits activity of GDF3. In some embodiments, an antibody, or combination of antibodies, of the disclosure that binds to and/or inhibits the activity of GDF11, GDF8, activin, BMP6, and/or GDF3 further binds to and/or inhibits activity of BMP10. In some embodiments, an antibody, or combination of antibodies, of the disclosure that binds to and/or inhibits the activity of GDF11, GDF8, activin, BMP6, GDF3, and/or BMP10 further binds to and/or inhibits activity of BMP9. In some embodiments, an antibody, or combination of antibodies, of the disclosure that binds to and/or inhibits the activity of GDF11, GDF8, activin, BMP6, and/or GDF3 does not bind to and/or inhibit BMP9 (e.g., an antibody that has a $K_D$ of greater than $1 \times 10^{-7}$ for BMP9). In some embodiments, an antibody, or combination of antibodies, of the disclosure that binds to and/or inhibits the activity of GDF11, GDF8, activin, BMP6, and/or GDF3 does not bind to and/or inhibit BMP10 (e.g., an antibody that has a $K_D$ of greater than $1 \times 10^{-7}$ for BMP10). In some embodiments, an antibody, or combination of antibodies, of the disclosure that binds to and/or inhibits the activity of GDF11, GDF8, activin, BMP6, and/or GDF3 does not bind to and/or inhibit BMP9 or BMP10 (e.g., an antibody that has a $K_D$ of greater than $1 \times 10^{-7}$ for BMP9 and BMP10). In some embodiments, an antibody, or combination of antibodies, of the disclosure that binds to and/or inhibits the activity of GDF11, GDF8, activin B, BMP6, and/or GDF3 does not bind to and/or inhibit BMP9 (e.g., an antibody that has a $K_D$ of greater than $1 \times 10^{-7}$ for BMP9). In some embodiments, an antibody, or combination of antibodies, of the disclosure that binds to and/or inhibits the activity of GDF11, GDF8, activin B, BMP6, and/or GDF3 does not bind to and/or inhibit BMP10 (e.g., an antibody that has a $K_D$ of greater than $1 \times 10^{-7}$ for BMP10). In some embodiments, an antibody, or combination of antibodies, of the disclosure that binds to and/or inhibits the activity of GDF11, GDF8, activin B, BMP6, and/or GDF3 does not bind to and/or inhibit BMP9 or BMP10 (e.g., an antibody that has a $K_D$ of greater than $1 \times 10^{-7}$ for BMP9 and BMP10). In some embodiments, an antibody, or combination of antibodies, of the disclosure that binds to and/or inhibits the activity of GDF11, GDF8, activin B, BMP6, and/or GDF3 does not bind to and/or inhibit activin A (e.g., an antibody that has a $K_D$ of greater than $1 \times 10^{-7}$ for activin A). In some embodiments, an antibody, or combination of antibodies, of the disclosure that binds to and/or inhibits the activity of GDF11, GDF8, activin B, BMP6, and/or GDF3 does not bind to and/or inhibit activin A or BMP10 (e.g., an antibody that has a $K_D$ of greater than $1 \times 10^{-7}$ for activin A and BMP10). In some embodiments, an antibody, or combination of antibodies, of the disclosure that binds to and/or inhibits the activity of GDF11, GDF8, activin B, BMP6, and/or GDF3 does not bind to and/or inhibit activin A or BMP9 (e.g., an antibody that has a $K_D$ of greater than $1 \times 10^{-7}$ for activin A and BMP9). In some embodiments, an antibody, or combination of antibodies, of the disclosure that binds to and/or inhibits the activity of GDF11, GDF8, activin B, BMP6, and/or GDF3 does not bind to and/or inhibit activin A, BMP9, or BMP10 (e.g., an antibody that has a $K_D$ of greater than $1\times10^{-7}$ for activin A, BMP9, and BMP10).

In another aspect, an ActRII antagonist of the present disclosure is an antibody, or combination of antibodies, that binds to and/or inhibits activity of an ActRII receptor (e.g. an ActRIIA and/or ActRIIB receptor). In some embodiments, an anti-ActRII receptor antibody, or combination of antibodies, of the disclosure binds to an ActRII receptor and prevents binding and/or activation of the ActRII receptor by at least GDF11. In some embodiments, an anti-ActRII receptor antibody, or combination of antibodies, of the disclosure binds to an ActRII receptor and prevents binding and/or activation of the ActRII receptor by at least GDF8. In some embodiments, an anti-ActRII receptor antibody, or combination of antibodies, of the disclosure binds to an ActRII receptor and prevents binding and/or activation of the ActRII receptor by at least GDF3. In some embodiments, an anti-ActRII receptor antibody, or combination of antibodies, of the disclosure binds to an ActRII receptor and prevents binding and/or activation of the ActRII receptor by at least BMP6. In some embodiments, an anti-ActRII receptor antibody, or combination of antibodies, of the disclosure binds to an ActRII receptor and prevents binding and/or activation of the ActRII receptor by at least BMP10. In alternative embodiments, an anti-ActRII receptor antibody, or combination of antibodies, of the disclosure does not prevent binding and/or activation of the ActRII receptor by BMP10. In some embodiments, an anti-ActRII receptor antibody, or combination of antibodies, of the disclosure binds to an ActRII receptor and prevents binding and/or activation of the ActRII receptor by at least BMP9. In alternative embodiments, an anti-ActRII receptor antibody, or combination of antibodies, of the disclosure does not prevent binding and/or activation of the ActRII receptor by BMP9. In some embodiments, an anti-ActRII receptor antibody, or combination of antibodies, of the disclosure binds to an ActRII receptor and prevents binding and/or activation of the ActRII receptor by at least activin (e.g., activin A, activin B, activin AB, activin C, and activin E). In some embodiments, an anti-ActRII receptor antibody, or combination of antibodies, of the disclosure binds to an ActRII receptor and prevents binding and/or activation of the ActRII receptor by at least activin B. In some embodiments, an anti-ActRII receptor antibody, or combination of antibodies, of the disclosure does not prevent binding and/or activation of the ActRII receptor by activin A. In some embodiments, an anti-ActRII receptor antibody, or combination of antibodies, of the disclosure binds to an ActRII receptor and prevents binding and/or activation of the ActRII receptor by at least activin B, but does not prevent binding and/or activation of the ActRII receptor by activin A.

The term antibody is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. An antibody fragment refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments. See, e.g., Hudson et al. (2003) Nat. Med. 9:129-134; Plückthun, in The Pharmacology of Monoclonal Antibodies, vol. 113, Rosenburg and Moore eds., (Springer-Verlag, New York), pp. 269-315 (1994); WO 93/16185; and U.S. Pat. Nos. 5,571,894, 5,587,458, and 5,869,046. Antibodies disclosed herein may be polyclonal antibodies or monoclonal antibodies. In certain embodiments, the antibodies of the present disclosure comprise a label attached thereto and able to be detected (e.g., the label can be a radioisotope, fluorescent compound, enzyme, or enzyme co-factor). In preferred embodiments, the antibodies of the present disclosure are isolated antibodies.

Diabodies are antibody fragments with two antigen-binding sites that may be bivalent or bispecific. See, e.g., EP 404,097; WO 1993/01161; Hudson et al. (2003) Nat. Med. 9:129-134 (2003); and Hollinger et al. (1993) Proc. Natl. Acad. Sci. USA 90: 6444-6448. Triabodies and tetrabodies are also described in Hudson et al. (2003) Nat. Med. 9:129-134.

Single-domain antibodies are antibody fragments comprising all or a portion of the heavy-chain variable domain or all or a portion of the light-chain variable domain of an antibody. In certain embodiments, a single-domain antibody is a human single-domain antibody. See, e.g., U.S. Pat. No. 6,248,516.

Antibody fragments can be made by various techniques, including but not limited to proteolytic digestion of an intact antibody as well as production by recombinant host cells (e.g., *E. coli* or phage), as described herein.

The antibodies herein may be of any class. The class of an antibody refers to the type of constant domain or constant region possessed by its heavy chain. There are five major classes of antibodies: IgA, IgD, IgE, IgG, and IgM, and several of these may be further divided into subclasses (isotypes), for example, IgG$_1$, IgG$_2$, IgG$_3$, IgG$_4$, IgA$_1$, and IgA$_2$. The heavy-chain constant domains that correspond to the different classes of immunoglobulins are called alpha, delta, epsilon, gamma, and mu.

In general, an antibody for use in the methods disclosed herein specifically binds to its target antigen, preferably with high binding affinity. Affinity may be expressed as a $K_D$ value and reflects the intrinsic binding affinity (e.g., with minimized avidity effects). Typically, binding affinity is measured in vitro, whether in a cell-free or cell-associated setting. Any of a number of assays known in the art, including those disclosed herein, can be used to obtain binding affinity measurements including, for example, surface plasmon resonance (Biacore™ assay), radiolabeled antigen binding assay (RIA), and ELISA. In some embodiments, antibodies of the present disclosure bind to their target antigens (e.g. GDF11, GDF8, ActRIIA, ActRIIB, etc.) with at least a $K_D$ of $1\times10^{-7}$ or stronger, $1\times10^{-8}$ or stronger, $1\times10^{-9}$ or stronger, $1\times10^{-10}$ or stronger, $1\times10^{-11}$ or stronger, $1\times10^{-12}$ or stronger, $1\times10^{-13}$ or stronger, or $1\times10^{-14}$ or stronger.

In certain embodiments, $K_D$ is measured by RIA performed with the Fab version of an antibody of interest and its target antigen as described by the following assay. Solution binding affinity of Fabs for the antigen is measured by equilibrating Fab with a minimal concentration of radiolabeled antigen (e.g., $^{125}$I-labeled) in the presence of a titration series of unlabeled antigen, then capturing bound antigen with an anti-Fab antibody-coated plate [see, e.g., Chen et al. (1999) J. Mol. Biol. 293:865-881]. To establish conditions for the assay, multi-well plates (e.g., MICROTITER® from Thermo Scientific) are coated (e.g., overnight) with a capturing anti-Fab antibody (e.g., from Cappel Labs) and subsequently blocked with bovine serum albumin, preferably at room temperature (e.g., approximately 23° C.). In a non-adsorbent plate, radiolabeled antigen are mixed with serial dilutions of a Fab of interest [e.g., consistent with assessment of the anti-VEGF antibody, Fab-12, in Presta et al., (1997) Cancer Res. 57:4593-4599]. The Fab of interest is then incubated, preferably overnight but the incubation may continue for a longer period (e.g., about 65 hours) to ensure that equilibrium is reached. Thereafter, the mixtures are transferred to the capture plate for incubation, preferably at room temperature for about one hour. The solution is then removed and the plate is washed times several times, preferably with polysorbate 20 and PBS mixture. When the plates have dried, scintillant (e.g., MICROSCINT® from Packard) is added, and the plates are counted on a gamma counter (e.g., TOPCOUNT® from Packard).

According to another embodiment, $K_D$ is measured using surface plasmon resonance assays using, for example a BIACORE® 2000 or a BIACORE® 3000 (Biacore, Inc., Piscataway, N.J.) with immobilized antigen CM5 chips at about 10 response units (RU). Briefly, carboxymethylated dextran biosensor chips (CM5, Biacore, Inc.) are activated with N-ethyl-N'-(3-dimethylaminopropyl)-carbodiimide hydrochloride (EDC) and N-hydroxysuccinimide (NETS) according to the supplier's instructions. For example, an antigen can be diluted with 10 mM sodium acetate, pH 4.8, to 5 µg/ml (about 0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20®) surfactant (PB ST) at at a flow rate of approximately 25 µl/min. Association rates ($k_{on}$) and dissociation rates ($k_{off}$) are calculated using, for example, a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$ [see, e.g., Chen et al., (1999) J. Mol. Biol. 293:865-881]. If the on-rate exceeds, for example, $10^6$ $M^{-1}$ $s^{-1}$ by the surface plasmon resonance assay above, then the on-rate can be determined by using a fluorescent quenching technique that measures the increase or decrease in fluorescence emission intensity (e.g., excitation=295 nm; emission=340 nm, 16 nm band-pass) of a 20 nM anti-antigen antibody (Fab form) in PBS in the presence of increasing concentrations of antigen as measured in a spectrometer, such as a stop-flow equipped spectrophotometer (Aviv Instruments) or a 8000-series SLM-AMINCO® spectrophotometer (ThermoSpectronic) with a stirred cuvette.

As used herein, anti-GDF11 antibody generally refers to an antibody that is capable of binding to GDF11 with sufficient affinity such that the antibody is useful as a diagnostic and/or therapeutic agent in targeting GDF11. In certain embodiments, the extent of binding of an anti-GDF11 antibody to an unrelated, non-GDF11 protein is less than about 10%, 9%, 8%, 7%, 6%, 5%, 4%, 3%, 2%, or less than 1% of the binding of the antibody to GDF11 as measured, for example, by a radioimmunoassay (RIA). In certain embodiments, an anti-GDF11 antibody binds to an epitope of GDF11 that is conserved among GDF11 from different species. In certain preferred embodiments, an anti-GDF11 antibody of the present disclosure is an antagonist antibody that can inhibit GDF11 activity. For example, an anti-GDF11 antibody of the disclosure may inhibit GDF11 from binding to a cognate receptor (e.g., ActRIIA or ActRIIB receptor) and/or inhibit GDF11-mediated signal transduction (activation) of a cognate receptor, such as Smad signaling by an ActRII receptor. In some embodiments, anti-GDF11 antibodies of the present disclosure, particularly in the case of multispecific antibodies, do not substantially bind to and/or inhibit activity of activin A (e.g., bind to activin A with a $K_D$ of greater than $1 \times 10^{-7}$ M or has relatively modest binding, e.g., about $1 \times 10^{-8}$ M or about $1 \times 10^{-9}$ M It should be noted that GDF11 has high sequence homology to GDF8 and therefore antibodies that bind and/or to GDF11, in some cases, may also bind to and/or inhibit GDF8.

As used herein, anti-GDF8 antibody generally refers to an antibody that is capable of binding to GDF8 with sufficient affinity such that the antibody is useful as a diagnostic and/or therapeutic agent in targeting GDF8. In certain embodiments, the extent of binding of an anti-GDF8 antibody to an unrelated, non-GDF8 protein is less than about 10%, 9%, 8%, 7%, 6%, 5%, 4%, 3%, 2%, or less than 1% of the binding of the antibody to GDF8 as measured, for example, by a radioimmunoassay (RIA). In certain embodiments, an anti-GDF8 antibody binds to an epitope of GDF8 that is conserved among GDF8 from different species. In certain preferred embodiments, an anti-GDF8 antibody of the present disclosure is an antagonist antibody that can inhibit GDF8 activity. For example, an anti-GDF8 antibody of the disclosure may inhibit GDF8 from binding to a cognate receptor (e.g., ActRIIA or ActRIIB receptor) and/or inhibit GDF8-mediated signal transduction (activation) of a cognate receptor, such as Smad signaling by an ActRII receptor. In some embodiments, anti-GDF8 antibodies of the present disclosure, particularly in the case of multispecific antibodies, do not substantially bind to and/or inhibit activity of activin A (e.g., bind to activin A with a $K_D$ of greater than $1 \times 10^{-7}$ M or has relatively modest binding, e.g., about $1 \times 10^{-8}$ M or about $1 \times 10^{-9}$ M). It should be noted that GDF8 has high sequence homology to GDF11 and therefore antibodies that bind and/or to GDF8, in some cases, may also bind to and/or inhibit GDF11.

As used herein, anti-activin antibody generally refers to an antibody that is capable of binding to activin (e.g., one or more of activin A, activin B, activin C, activin AB, and/or activin E) with sufficient affinity such that the antibody is useful as a diagnostic and/or therapeutic agent in targeting activin. In certain embodiments, the extent of binding of an anti-activin antibody to an unrelated, non-activin protein is less than about 10%, 9%, 8%, 7%, 6%, 5%, 4%, 3%, 2%, or less than 1% of the binding of the antibody to activin as measured, for example, by a radioimmunoassay (RIA). In certain embodiments, an anti-activin antibody binds to an epitope of activin that is conserved among activin from different species. In certain preferred embodiments, an anti-activin antibody of the present disclosure is an antagonist antibody that can inhibit activin activity. For example, an anti-activin antibody of the disclosure may inhibit activin from binding to a cognate receptor (e.g., ActRIIA or ActRIIB receptor) and/or inhibit activin-mediated signal transduction (activation) of a cognate receptor, such as Smad signaling by an ActRII receptor. In some embodiments, anti-activin antibodies of the present disclosure bind to and/or inhibit activity of activin B. In some embodiments, anti-activin antibodies of the present disclosure bind to and/or inhibit activity of activin A and activin B. In some embodiments, anti-activin antibodies of the present disclosure, particularly in the case of multispecific antibodies, do not substantially bind to and/or inhibit activity of activin A (e.g., bind to activin A with a $K_D$ of greater than $1 \times 10^{-7}$ M or has relatively modest binding, e.g., about $1 \times 10^{-8}$ M or about $1 \times 10^{-9}$ M).

As used herein, anti-BMP6 antibody generally refers to an antibody that is capable of binding to BMP6 with sufficient affinity such that the antibody is useful as a diagnostic and/or therapeutic agent in targeting BMP6. In certain embodiments, the extent of binding of an anti-BMP6 antibody to an unrelated, non-BMP6 protein is less than about 10%, 9%, 8%, 7%, 6%, 5%, 4%, 3%, 2%, or less than 1% of the binding of the antibody to BMP6 as measured, for example, by a radioimmunoassay (RIA). In certain embodiments, an anti-BMP6 antibody binds to an epitope of BMP6 that is conserved among BMP6 from different species. In certain preferred embodiments, an anti-BMP6 antibody of the present disclosure is an antagonist antibody that can inhibit BMP6 activity. For example, an anti-BMP6 antibody of the disclosure may inhibit BMP6 from binding to a cognate receptor (e.g., ActRIIA or ActRIIB receptor) and/or inhibit BMP6-mediated signal transduction (activation) of a cognate receptor, such as Smad signaling by an ActRII receptor. In some embodiments, anti-BMP6 antibodies of the present disclosure, particularly in the case of multispecific antibodies, do not substantially bind to and/or inhibit activity of activin A (e.g., bind to activin A with a $K_D$ of greater than $1\times10^{-7}$M or has relatively modest binding, e.g., about $1\times10^{-8}$ M or about $1\times10^{-9}$M).

As used herein, anti-GDF3 antibody generally refers to an antibody that is capable of binding to GDF3 with sufficient affinity such that the antibody is useful as a diagnostic and/or therapeutic agent in targeting GDF3. In certain embodiments, the extent of binding of an anti-GDF3 antibody to an unrelated, non-GDF3 protein is less than about 10%, 9%, 8%, 7%, 6%, 5%, 4%, 3%, 2%, or less than 1% of the binding of the antibody to GDF3 as measured, for example, by a radioimmunoassay (RIA). In certain embodiments, an anti-GDF3 antibody binds to an epitope of GDF3 that is conserved among GDF3 from different species. In certain preferred embodiments, an anti-GDF3 antibody of the present disclosure is an antagonist antibody that can inhibit GDF3 activity. For example, an anti-GDF3 antibody of the disclosure may inhibit GDF3 from binding to a cognate receptor (e.g., ActRIIA or ActRIIB receptor) and/or inhibit GDF3-mediated signal transduction (activation) of a cognate receptor, such as Smad signaling by an ActRII receptor. In some embodiments, anti-GDF3 antibodies of the present disclosure, particularly in the case of multispecific antibodies, do not substantially bind to and/or inhibit activity of activin A (e.g., bind to activin A with a $K_D$ of greater than $1\times10^{-7}$M or has relatively modest binding, e.g., about $1\times10^{-8}$ M or about $1\times10^{-9}$M).

As used herein, anti-BMP10 antibody generally refers to an antibody that is capable of binding to BMP10 with sufficient affinity such that the antibody is useful as a diagnostic and/or therapeutic agent in targeting BMP10. In certain embodiments, the extent of binding of an anti-BMP10 antibody to an unrelated, non-BMP10 protein is less than about 10%, 9%, 8%, 7%, 6%, 5%, 4%, 3%, 2%, or less than 1% of the binding of the antibody to BMP10 as measured, for example, by a radioimmunoassay (RIA). In certain embodiments, an anti-BMP10 antibody binds to an epitope of BMP10 that is conserved among BMP10 from different species. In certain preferred embodiments, an anti-BMP10 antibody of the present disclosure is an antagonist antibody that can inhibit BMP10 activity. For example, an anti-BMP10 antibody of the disclosure may inhibit BMP10 from binding to a cognate receptor (e.g., ActRIIA or ActRIIB receptor) and/or inhibit BMP10-mediated signal transduction (activation) of a cognate receptor, such as Smad signaling by an ActRII receptor. In some embodiments, anti-BMP10 antibodies of the present disclosure, particularly in the case of multispecific antibodies, do not substantially bind to and/or inhibit activity of activin A (e.g., bind to activin A with a $K_D$ of greater than $1\times10^{-7}$M or has relatively modest binding, e.g., about $1\times10^{-8}$ M or about $1\times10^{-9}$ M As used herein, anti-BMP9 antibody generally refers to an antibody that is capable of binding to BMP9 with sufficient affinity such that the antibody is useful as a diagnostic and/or therapeutic agent in targeting BMP9. In certain embodiments, the extent of binding of an anti-BMP9 antibody to an unrelated, non-BMP9 protein is less than about 10%, 9%, 8%, 7%, 6%, 5%, 4%, 3%, 2%, or less than 1% of the binding of the antibody to BMP9 as measured, for example, by a radioimmunoassay (RIA). In certain embodiments, an anti-BMP9 antibody binds to an epitope of BMP9 that is conserved among BMP9 from different species. In certain preferred embodiments, an anti-BMP9 antibody of the present disclosure is an antagonist antibody that can inhibit BMP9 activity. For example, an anti-BMP9 antibody of the disclosure may inhibit BMP9 from binding to a cognate receptor (e.g., ActRIIA or ActRIIB receptor) and/or inhibit BMP9-mediated signal transduction (activation) of a cognate receptor, such as Smad signaling by an ActRII receptor. In some embodiments, anti-BMP9 antibodies of the present disclosure, particularly in the case of multispecific antibodies, do not substantially bind to and/or inhibit activity of activin A (e.g., bind to activin A with a $K_D$ of greater than $1\times10^{-7}$ M or has relatively modest binding, e.g., about $1\times10^{-8}$M or about $1\times10^{-9}$M).

An anti-ActRII antibody refers to an antibody that is capable of binding to ActRII (ActRIIA and/or ActRIIB) with sufficient affinity such that the antibody is useful as a diagnostic and/or therapeutic agent in targeting ActRII. In certain embodiments, the extent of binding of an anti-ActRII antibody to an unrelated, non-ActRII protein is less than about 10%, 9%, 8%, 7%, 6%, 5%, 4%, 3%, 2%, or less than 1% of the binding of the antibody to ActRII as measured, for example, by a radioimmunoassay (RIA). In certain embodiments, an anti-ActRII antibody binds to an epitope of ActRII that is conserved among ActRII from different species. In preferred embodiments, an anti-ActRII antibody of the present disclosure is an antagonist antibody that can inhibit ActRII activity. For example, an anti-ActRII antibody of the present disclosure may inhibit one or more ActRII ligands selected from activin A, activin B, activin AB, activin C, activin E, GDF11, GDF8, activin A, BMP6, and BMP7 from binding to the ActRII receptor and/or inhibit one of these ligands from activating ActRII signaling (e.g., Smad 1, 2, 3, 5, and 8 signaling). In some embodiments, anti-ActRII antibodies of the present disclosure inhibit GDF11 from binding to the ActRII receptor and/or inhibit GDF11 from activating ActRII signaling. In some embodiments, anti-ActRII antibodies of the present disclosure inhibit GDF8 from binding to the ActRII receptor and/or inhibit GDF8 from activating ActRII signaling. In some embodiments, anti-ActRII antibodies of the present disclosure inhibit GDF8 and GDF11 from binding to the ActRII receptor and/or inhibit GDF8 and GDF11 from activating ActRII signaling. In some embodiments, an anti-ActRII antibody of the disclosure that inhibits GDF11 and/or GDF8 from binding to and/or activating an ActRII receptor further inhibits activin (e.g., activin A, activin B, activin AB, activin C, activin E) from binding to and/or activating the ActRII receptor. In some embodiments, an anti-ActRII antibody of the disclosure that inhibits GDF11 and/or GDF8 from binding to and/or activating an ActRII receptor further inhibits BMP6 from binding to and/or activating the ActRII receptor. In some embodiments, an anti-ActRII antibody of the disclosure that inhibits GDF11 and/or GDF8 from binding to and/or activating an ActRII receptor further inhibits BMP10 from binding to and/or activating the ActRII receptor. In some embodiments, an anti-ActRII antibody of the disclosure that inhibits GDF11 and/or GDF8 from binding to and/or activating an ActRII receptor further inhibits BMP6 and BMP10 from binding to and/or activating the ActRII receptor. In some embodiments, an anti-ActRII antibody of the disclosure that inhibits GDF11 and/or GDF8 from binding to and/or activating an ActRII receptor further inhibits activin (e.g., activin B) and BMP6 from binding to and/or activating the ActRII receptor. In some embodiments, an anti-ActRII antibody of the disclosure that inhibits GDF11 and/or GDF8 from binding to and/or activating an ActRII receptor further inhibits activin (e.g., activin B) and BMP10 from binding to and/or activating the ActRII receptor. In some embodiments, an anti-ActRII antibody of the disclosure that inhibits GDF11 and/or GDF8 from binding to and/or activating an ActRII receptor further inhibits activin (e.g., activin B), BMP6, and BMP10 from binding to and/or activating the ActRII receptor. In some embodiments, anti-ActRIIA antibodies of the present disclosure do not substantially inhibit activin A from binding to the ActRII receptor and/or do not substantially inhibit activin A-mediated activation of ActRII signaling.

The nucleic acid and amino acid sequences of human ActRII receptors and ligands (e.g., GDF11, GDF8, activin A, activin B, activin C, activin E, BMP6, BMP10, ActRIIB, and ActRIIA) are well known in the art and thus antibody antagonists for use in accordance with this disclosure may be routinely made by the skilled artisan based on the knowledge in the art and teachings provided herein.

In certain embodiments, an antibody provided herein is a chimeric antibody. A chimeric antibody refers to an antibody in which a portion of the heavy and/or light chain is derived from a particular source or species, while the remainder of the heavy and/or light chain is derived from a different source or species. Certain chimeric antibodies are described, for example, in U.S. Pat. No. 4,816,567; and Morrison et al., (1984) Proc. Natl. Acad. Sci. USA, 81:6851-6855. In some embodiments, a chimeric antibody comprises a non-human variable region (e.g., a variable region derived from a mouse, rat, hamster, rabbit, or non-human primate, such as a monkey) and a human constant region. In some embodiments, a chimeric antibody is a "class switched" antibody in which the class or subclass has been changed from that of the parent antibody. In general, chimeric antibodies include antigen-binding fragments thereof.

In certain embodiments, a chimeric antibody provided herein is a humanized antibody. A humanized antibody refers to a chimeric antibody comprising amino acid residues from non-human hypervariable regions (HVRs) and amino acid residues from human framework regions (FRs). In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

Humanized antibodies and methods of making them are reviewed, for example, in Almagro and Fransson (2008) Front. Biosci. 13:1619-1633 and are further described, for example, in Riechmann et al., (1988) Nature 332:323-329; Queen et al. (1989) Proc. Nat'l Acad. Sci. USA 86:10029-10033; U.S. Pat. Nos. 5,821,337, 7,527,791, 6,982,321, and 7,087,409; Kashmiri et al., (2005) Methods 36:25-34 [describing SDR (a-CDR) grafting]; Padlan, Mol. Immunol. (1991) 28:489-498 (describing "resurfacing"); Dall'Acqua et al. (2005) Methods 36:43-60 (describing "FR shuffling"); Osbourn et al. (2005) Methods 36:61-68; and Klimka et al. Br. J. Cancer (2000) 83:252-260 (describing the "guided selection" approach to FR shuffling).

Human framework regions that may be used for humanization include but are not limited to: framework regions selected using the "best-fit" method [see, e.g., Sims et al. (1993) J. Immunol. 151:2296]; framework regions derived from the consensus sequence of human antibodies of a particular subgroup of light-chain or heavy-chain variable regions [see, e.g., Carter et al. (1992) Proc. Natl. Acad. Sci. USA, 89:4285; and Presta et al. (1993) J. Immunol., 151: 2623]; human mature (somatically mutated) framework regions or human germline framework regions [see, e.g., Almagro and Fransson (2008) Front. Biosci. 13:1619-1633]; and framework regions derived from screening FR libraries [see, e.g., Baca et cd., (1997) J. Biol. Chem. 272:10678-10684; and Rosok et cd., (1996) J. Biol. Chem. 271:22611-22618].

In certain embodiments, an antibody provided herein is a human antibody. Human antibodies can be produced using various techniques known in the art. Human antibodies are described generally in van Dijk and van de Winkel (2001) Curr. Opin. Pharmacol. 5: 368-74 and Lonberg (2008) Curr. Opin. Immunol. 20:450-459.

Human antibodies may be prepared by administering an immunogen (e.g., a GDF11 polypeptide, GDF8 polypeptide, an ActRIIA polypeptide, or an ActRIIB polypeptide) to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. For a review of methods for obtaining human antibodies from transgenic animals, see, for example, Lonberg (2005) Nat. Biotechnol. 23:1117-1125; U.S. Pat. Nos. 6,075,181 and 6,150,584 (describing XENOMOUSE™ technology); U.S. Pat. No. 5,770,429 (describing HuMab® technology); U.S. Pat. No. 7,041,870 (describing K-M MOUSE® technology); and U.S. Patent Application Publication No. 2007/0061900 (describing VelociMouse® technology). Human variable regions from intact antibodies generated by such animals may be further modified, for example, by combining with a different human constant region.

Human antibodies provided herein can also be made by hybridoma-based methods. Human myeloma and mouse-human heteromyeloma cell lines for the production of human monoclonal antibodies have been described [see, e.g., Kozbor J. Immunol., (1984) 133: 3001; Brodeur et al. (1987) Monoclonal Antibody Production Techniques and Applications, pp. 51-63, Marcel Dekker, Inc., New York; and Boerner et al. (1991) J. Immunol., 147: 86]. Human antibodies generated via human B-cell hybridoma technology are also described in Li et al., (2006) Proc. Natl. Acad. Sci. USA, 103:3557-3562. Additional methods include those described, for example, in U.S. Pat. No. 7,189,826 (describing production of monoclonal human IgM antibodies from hybridoma cell lines) and Ni, Xiandai Mianyixue (2006) 26(4):265-268 (2006) (describing human-human hybridomas). Human hybridoma technology (Trioma technology) is also described in Vollmers and Brandlein (2005) Histol. Histopathol., 20(3):927-937 (2005) and Vollmers and Brandlein (2005) Methods Find Exp. Clin. Pharmacol., 27(3):185-91.

Human antibodies provided herein may also be generated by isolating Fv clone variable-domain sequences selected from human-derived phage display libraries. Such variable-domain sequences may then be combined with a desired human constant domain. Techniques for selecting human antibodies from antibody libraries are described herein.

For example, antibodies of the present disclosure may be isolated by screening combinatorial libraries for antibodies with the desired activity or activities. A variety of methods are known in the art for generating phage-display libraries and screening such libraries for antibodies possessing the desired binding characteristics. Such methods are reviewed, for example, in Hoogenboom et al. (2001) in Methods in Molecular Biology 178:1-37, O'Brien et al., ed., Human Press, Totowa, N.J. and further described, for example, in the McCafferty et al. (1991) Nature 348:552-554; Clackson et al., (1991) Nature 352: 624-628; Marks et al. (1992) J. Mol. Biol. 222:581-597; Marks and Bradbury (2003) in Methods in Molecular Biology 248:161-175, Lo, ed., Human Press, Totowa, N.J.; Sidhu et al. (2004) J. Mol. Biol. 338(2):299-310; Lee et al. (2004) J. Mol. Biol. 340(5):1073-1093; Fellouse (2004) Proc. Natl. Acad. Sci. USA 101(34): 12467-12472; and Lee et al. (2004) J. Immunol. Methods 284(1-2): 119-132.

In certain phage display methods, repertoires of VH and VL genes are separately cloned by polymerase chain reaction (PCR) and recombined randomly in phage libraries, which can then be screened for antigen-binding phage as described in Winter et al. (1994) Ann. Rev. Immunol., 12: 433-455. Phage typically display antibody fragments, either as single-chain Fv (scFv) fragments or as Fab fragments. Libraries from immunized sources provide high-affinity antibodies to the immunogen (e.g., GDF11, activin B, ActRIIA, or ActRIIB) without the requirement of constructing hybridomas. Alternatively, the naive repertoire can be cloned (e.g., from human) to provide a single source of antibodies directed against a wide range of non-self and also self-antigens without any immunization as described by Griffiths et al. (1993) EMBO J, 12: 725-734. Finally, naive libraries can also be made synthetically by cloning un-rearranged V-gene segments from stem cells and using PCR primers containing random sequence to encode the highly variable CDR3 regions and to accomplish rearrangement in vitro, as described by Hoogenboom and Winter (1992) J. Mol. Biol., 227: 381-388. Patent publications describing human antibody phage libraries include, for example: U.S. Pat. No. 5,750,373, and U.S. Patent Publication Nos. 2005/0079574, 2005/0119455, 2005/0266000, 2007/0117126, 2007/0160598, 2007/0237764, 2007/0292936, and 2009/0002360.

In certain embodiments, an antibody provided herein is a multispecific antibody, for example, a bispecific antibody. Multispecific antibodies (typically monoclonal antibodies) have binding specificities for at least two different epitopes (e.g., two, three, four, five, or six or more) on one or more (e.g., two, three, four, five, six or more) antigens.

In certain embodiments, a multispecific antibody of the present disclosure comprises two or more binding specificities, with at least one of the binding specificities being for a GDF11 epitope, and optionally one or more additional binding specificities being for an epitope on a different ActRII ligand (e.g., GDF8, activin, BMP6, and/or BMP10) and/or an ActRII receptor (e.g., an ActRIIA and/or ActRIIB receptor). In certain embodiments, multispecific antibodies may bind to two or more different epitopes of GDF11. Preferably a multispecific antibody of the disclosure that has binding affinity, in part, for a GDF11 epitope can be used to inhibit a GDF11 activity (e.g., the ability to bind to and/or activate an ActRII receptor), and optionally inhibit the activity of one or more different ActRII ligands (e.g., GDF8, activin, BMP6, and/or BMP10) and/or an ActRII receptor (e.g., an ActRIIA or ActRIIB receptor). In certain preferred embodiments, multispecific antibodies of the present disclosure that bind to and/or inhibit GDF11 further bind to and/or inhibit at least GDF8. Optionally, multispecific antibodies of the disclosure that bind to and/or inhibit GDF11 do not substantially bind to and/or substantially inhibit activin A.

In certain embodiments, a multispecific antibody of the present disclosure comprises two or more binding specificities, with at least one of the binding specificities being for a GDF8 epitope, and optionally one or more additional binding specificities being for an epitope on a different ActRII ligand (e.g., GDF11, activin, BMP6, BMP10, BMP9, and/or GDF3) and/or an ActRII receptor (e.g., an ActRIIA and/or ActRIIB receptor). In certain embodiments, multispecific antibodies may bind to two or more different epitopes of GDF8. Preferably a multispecific antibody of the disclosure that has binding affinity, in part, for an GDF8 epitope can be used to inhibit an GDF8 activity (e.g., the ability to bind to and/or activate an ActRII receptor), and optionally inhibit the activity of one or more different ActRII ligands (e.g., GDF11, activin, BMP6, BMP10, BMP9, and/or GDF3) and/or an ActRII receptor (e.g., an ActRIIA or ActRIIB receptor). In certain preferred embodiments, multispecific antibodies of the present disclosure that bind to and/or inhibit GDF8 further bind to and/or inhibit at least GDF11. Optionally, multispecific antibodies of the disclosure that bind to and/or inhibit GDF8 further bind to and/or inhibit at least activin (e.g., activin A, activin B, activin AB, activin C, and activin E). In some embodiments multispecific antibodies of the disclosure that bind to and/or inhibit GDF8 further bind to and/or inhibit at least activin B. In some embodiments, multispecific antibodies of the disclosure that bind to and/or inhibit GDF8 do not substantially bind to and/or substantially inhibit activin A. Optionally, multispecific antibodies of the disclosure that bind to and/or inhibit GDF8 further bind to and/or inhibit at least BMP6. Optionally, multispecific antibodies of the disclosure that bind to and/or inhibit GDF8 further bind to and/or inhibit at least BMP9. In some embodiments, multispecific antibodies of the disclosure that bind to and/or inhibit GDF8 do not substantially bind to and/or substantially inhibit BMP9. Optionally, multispecific antibodies of the disclosure that bind to and/or inhibit GDF8 further bind to and/or inhibit at least BMP10. In some embodiments, multispecific antibodies of the disclosure that bind to and/or inhibit GDF8 do not substantially bind to and/or substantially inhibit BMP10. Optionally, multispecific antibodies of the disclosure that bind to and/or inhibit GDF8 further bind to and/or inhibit at least GDF3.

In certain embodiments, a multispecific antibody of the present disclosure comprises two or more binding specificities, with at least one of the binding specificities being for a GDF11 epitope, and optionally one or more additional binding specificities being for an epitope on a different ActRII ligand (e.g., GDF8, activin, BMP6, BMP10, BMP9, and/or GDF3) and/or an ActRII receptor (e.g., an ActRIIA and/or ActRIIB receptor). In certain embodiments, multispecific antibodies may bind to two or more different epitopes of GDF11. Preferably a multispecific antibody of the disclosure that has binding affinity, in part, for an GDF11 epitope can be used to inhibit an GDF11 activity (e.g., the ability to bind to and/or activate an ActRII receptor), and optionally inhibit the activity of one or more different ActRII ligands (e.g., GDF8, activin, BMP6, BMP10, BMP9, and/or GDF3) and/or an ActRII receptor (e.g., an ActRIIA or ActRIIB receptor). In certain preferred embodiments, multispecific antibodies of the present disclosure that bind to and/or inhibit GDF11 further bind to and/or inhibit at least GDF8. Optionally, multispecific antibodies of the disclosure that bind to and/or inhibit GDF11 further bind to and/or inhibit at least activin (e.g., activin A, activin B, activin AB, activin C, and activin E). In some embodiments multispecific antibodies of the disclosure that bind to and/or inhibit GDF11 further bind to and/or inhibit at least activin B. In some embodiments, multispecific antibodies of the disclosure that bind to and/or inhibit GDF11 do not substantially bind to and/or substantially inhibit activin A. Optionally, multispecific antibodies of the disclosure that bind to and/or inhibit GDF11 further bind to and/or inhibit at least BMP6. Optionally, multispecific antibodies of the disclosure that bind to and/or inhibit GDF11 further bind to and/or inhibit at least BMP9. In some embodiments, multispecific antibodies of the disclosure that bind to and/or inhibit GDF11 do not substantially bind to and/or substantially inhibit BMP9. Optionally, multispecific antibodies of the disclosure that bind to and/or inhibit GDF11 further bind to and/or inhibit at least BMP10. In some embodiments, multispecific antibodies of the disclosure that bind to and/or inhibit GDF11 do not substantially bind to and/or substantially inhibit BMP10. Optionally, multispecific antibodies of the disclosure that bind to and/or inhibit GDF11 further bind to and/or inhibit at least GDF3.

In certain embodiments, a multispecific antibody of the present disclosure comprises two or more binding specificities, with at least one of the binding specificities being for activin, and optionally one or more additional binding specificities being for an epitope on a different ActRII ligand (e.g., GDF11, GDF8, BMP6, BMP10, BMP9, and/or GDF3) and/or an ActRII receptor (e.g., an ActRIIA and/or ActRIIB receptor). In certain embodiments, multispecific antibodies may bind to two or more different epitopes of activin or may bind to two or more different epitopes on different types of activin (e.g., binds an activin A epitope and binds an activin B epitope). Preferably a multispecific antibody of the disclosure that has binding affinity, in part, for an activin epitope can be used to inhibit an activin activity (e.g., the ability to bind to and/or activate an ActRII receptor), and optionally inhibit the activity of one or more different ActRII ligands (e.g., GDF11, GDF8, BMP6, BMP10, BMP9, and/or GDF3) and/or an ActRII receptor (e.g., an ActRIIA or ActRIIB receptor). In certain preferred embodiments, multispecific antibodies of the present disclosure that bind to and/or inhibit activin further bind to and/or inhibit at least GDF11. Optionally, multispecific antibodies of the disclosure that bind to and/or inhibit activin further bind to and/or inhibit at least GDF8. In some embodiments multispecific antibodies of the disclosure that bind to and/or inhibit activin B. In some embodiments, multispecific antibodies of the disclosure that bind to and/or inhibit activin B do not substantially bind to and/or substantially inhibit activin A. Optionally, multispecific antibodies of the disclosure that bind to and/or inhibit activin further bind to and/or inhibit at least BMP6. Optionally, multispecific antibodies of the disclosure that bind to and/or inhibit activin further bind to and/or inhibit at least BMP9. In some embodiments, multispecific antibodies of the disclosure that bind to and/or inhibit activin do not substantially bind to and/or substantially inhibit BMP9. Optionally, multispecific antibodies of the disclosure that bind to and/or inhibit activin further bind to and/or inhibit at least BMP10. In some embodiments, multispecific antibodies of the disclosure that bind to and/or inhibit activin do not substantially bind to and/or substantially inhibit BMP10. Optionally, multispecific antibodies of the disclosure that bind to and/or inhibit activin further bind to and/or inhibit at least GDF3.

Engineered antibodies with three or more functional antigen binding sites, including "octopus antibodies," are also included herein (see, e.g., US 2006/0025576A1).

In certain embodiments, the antibodies disclosed herein are monoclonal antibodies. Monoclonal antibody refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. Thus, the modifier "monoclonal" indicates the character of the antibody as being obtained from a substantially homogeneous population of antibodies and is not to be construed as requiring production of the antibody by any particular method. For example, the monoclonal antibodies to be used in accordance with the present methods may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

For example, by using immunogens derived from GDF11, anti-protein/anti-peptide antisera or monoclonal antibodies can be made by standard protocols [see, e.g., Antibodies: A Laboratory Manual (1988) ed. by Harlow and Lane, Cold Spring Harbor Press]. A mammal, such as a mouse, hamster, or rabbit can be immunized with an immunogenic form of the GDF11 polypeptide, an antigenic fragment which is capable of eliciting an antibody response, or a fusion protein. Techniques for conferring immunogenicity on a protein or peptide include conjugation to carriers or other techniques well known in the art. An immunogenic portion of a GDF11 polypeptide can be administered in the presence of adjuvant. The progress of immunization can be monitored by detection of antibody titers in plasma or serum. Standard ELISA or other immunoassays can be used with the immunogen as antigen to assess the levels of antibody production and/or level of binding affinity.

Following immunization of an animal with an antigenic preparation of GDF11, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique [see, e.g., Kohler and Milstein (1975) Nature, 256: 495-

497], the human B cell hybridoma technique [see, e.g., Kozbar et al. (1983) Immunology Today, 4:72], and the EBV-hybridoma technique to produce human monoclonal antibodies [Cole et al. (1985) Monoclonal Antibodies and Cancer Therapy, Alan R. Liss, Inc. pp. 77-96]. Hybridoma cells can be screened immunochemically for production of antibodies specifically reactive with a GDF11 polypeptide, and monoclonal antibodies isolated from a culture comprising such hybridoma cells.

In certain embodiments, one or more amino acid modifications may be introduced into the Fc region of an antibody provided herein thereby generating an Fc-region variant. The Fc-region variant may comprise a human Fc-region sequence (e.g., a human IgG1, IgG2, IgG3 or IgG4 Fc region) comprising an amino acid modification (e.g., a substitution, deletion, and/or addition) at one or more amino acid positions.

For example, the present disclosure contemplates an antibody variant that possesses some but not all effector functions, which make it a desirable candidate for applications in which the half-life of the antibody in vivo is important yet for which certain effector functions [e.g., complement-dependent cytotoxicity (CDC) and antibody-dependent cellular cytotoxicity (ADCC)] are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII FcR expression on hematopoietic cells is summarized in, for example, Ravetch and Kinet (1991) Annu. Rev. Immunol. 9:457-492. Non-limiting examples of in vitro assays to assess ADCC activity of a molecule of interest are described in U.S. Pat. No. 5,500,362; Hellstrom, I. et al. (1986) Proc. Nat'l Acad. Sci. USA 83:7059-7063; Hellstrom, I et al. (1985) Proc. Nat'l Acad. Sci. USA 82:1499-1502; U.S. Pat. No. 5,821,337; and Bruggemann, M. et al. (1987) J. Exp. Med. 166:1351-1361. Alternatively, non-radioactive assay methods may be employed (e.g., ACTI™, non-radioactive cytotoxicity assay for flow cytometry; CellTechnology, Inc. Mountain View, Calif.; and CytoTox 96® non-radioactive cytotoxicity assay, Promega, Madison, Wis.). Useful effector cells for such assays include peripheral blood mononuclear cells (PBMC) and natural killer (NK) cells. Alternatively, or additionally, ADCC activity of the molecule of interest may be assessed in vivo, for example, in an animal model such as that disclosed in Clynes et al. (1998) Proc. Nat'l Acad. Sci. USA 95:652-656. C1q binding assays may also be carried out to confirm that the antibody is unable to bind C1q and hence lacks CDC activity [see, e.g., C1q and C3c binding ELISA in WO 2006/029879 and WO 2005/100402]. To assess complement activation, a CDC assay may be performed [see, e.g., Gazzano-Santoro et al. (1996) J. Immunol. Methods 202:163; Cragg, M. S. et al. (2003) Blood 101:1045-1052; and Cragg, M. S, and M. J. Glennie (2004) Blood 103:2738-2743]. FcRn binding and in vivo clearance/half-life determinations can also be performed using methods known in the art [see, e.g., Petkova, S. B. et al. (2006) Int. Immunol. 18(12):1759-1769].

Antibodies of the present disclosure with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In certain embodiments, it may be desirable to create cysteine-engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy-chain Fc region. Cysteine engineered antibodies may be generated as described, for example, in U.S. Pat. No. 7,521,541.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interaction between antibodies and antigens to identify particularly desirable antibodies. Such techniques include ELISAs, surface plasmon resonance binding assays (e.g., the Biacore™ binding assay, Biacore AB, Uppsala, Sweden), sandwich assays (e.g., the paramagnetic bead system of IGEN International, Inc., Gaithersburg, Md.), western blots, immunoprecipitation assays, and immunohistochemistry.

In certain embodiments, amino acid sequence variants of the antibodies and/or the binding polypeptides provided herein are contemplated. For example, it may be desirable to improve the binding affinity and/or other biological properties of the antibody and/or binding polypeptide. Amino acid sequence variants of an antibody and/or binding polypeptides may be prepared by introducing appropriate modifications into the nucleotide sequence encoding the antibody and/or binding polypeptide, or by peptide synthesis. Such modifications include, for example, deletions from, and/or insertions into, and/or substitutions of residues within, the amino acid sequences of the antibody and/or binding polypeptide. Any combination of deletion, insertion, and substitution can be made to arrive at the final construct, provided that the final construct possesses the desired characteristics, e.g., target-binding (GDF11, GDF8, ActRIIA, and/or ActRIIB binding).

Alterations (e.g., substitutions) may be made in HVRs, for example, to improve antibody affinity. Such alterations may be made in HVR "hotspots," i.e., residues encoded by codons that undergo mutation at high frequency during the somatic maturation process (see, e.g., Chowdhury (2008) Methods Mol. Biol. 207:179-196 (2008)), and/or SDRs (a-CDRs), with the resulting variant VH or VL being tested for binding affinity. Affinity maturation by constructing and reselecting from secondary libraries has been described in the art [see, e.g., Hoogenboom et al., in Methods in Molecular Biology 178:1-37, O'Brien et al., ed., Human Press, Totowa, N.J., (2001)]. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind to the antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two, or three amino acid substitutions.

A useful method for identification of residues or regions of the antibody and/or the binding polypeptide that may be targeted for mutagenesis is called "alanine scanning mutagenesis", as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody or binding polypeptide with antigen is affected. Further substitutions may be introduced at the amino acid locations demonstrating functional sensitivity to the initial substitutions. Alternatively, or additionally, a crystal structure of an antigen-antibody complex can be used to identify contact points between the antibody and antigen. Such contact residues and neighboring residues may be targeted or eliminated as candidates for substitution. Variants may be screened to determine whether they contain the desired properties.

Amino-acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include fusion of the N- or C-terminus of the antibody to an enzyme (e.g., for ADEPT) or a polypeptide which increases the serum half-life of the antibody.

In certain embodiments, an antibody and/or binding polypeptide provided herein may be further modified to contain additional non-proteinaceous moieties that are known in the art and readily available. The moieties suitable for derivatization of the antibody and/or binding polypeptide include but are not limited to water-soluble polymers. Non-limiting examples of water-soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody and/or binding polypeptide may vary, and if more than one polymer are attached, they can be the same or different molecules. In general, the number and/or type of polymers used for derivatization can be determined based on considerations including, but not limited to, the particular properties or functions of the antibody and/or binding polypeptide to be improved, whether the antibody derivative and/or binding polypeptide derivative will be used in a therapy under defined conditions.

Any of the ActRII antagonist antibodies disclosed herein (e.g., an anti-activin A antibody, an anti-activin B antibody, an anti-activin C antibody, an anti-activin E antibody, an anti-GDF11 antibody, an anti-GDF8 antibody, an anti-BMP6 antibody, an anti-BMP10 antibody, an anti-ActRIIA antibody, an anti-GDF3 antibody, and/or or an anti-ActRIIB antibody) can be combined with one or more additional ActRII antagonist agents to achieve the desired effect [to treat or prevent a vascular disorder of the eye in a patient in need thereof; increase vision (e.g., increase visual acuity and/or visual field) in patient in need thereof that has a vascular disorder of the eye; and/or treat or prevent one or more complications of a vascular disorder of the eye]. For example, an ActRII antagonist antibody can be used in combination with i) one or more additional ActRII antagonist antibodies, ii) one or more ActRII polypeptides; iii) one or more small molecule ActRII antagonists; iv) one or more polynucleotide ActRII antagonists; v) one or more follistatin polypeptides; and/or vi) one or more FLRG polypeptides.

D. Small Molecule Antagonists

In another aspect, the present disclosure relates to a small molecule, or combination of small molecules, that antagonizes ActRII activity (e.g., inhibition of ActRII signaling transduction via Smads 1, 2, 3, 5, and 8). In particular, the disclosure provides methods of using a small molecule antagonist (inhibitors), or combination of small molecule antagonists, of ActRII, alone or in combination with one or more additional supportive therapies, to treat or prevent a vascular disorder of the eye [e.g., macular degeneration (e.g., age-related macular degeneration, juvenile macular degeneration, wet macular degeneration, dry macular degeneration, Stargardt's disease, and Best's disease), retinal vein occlusion (e.g, central retinal vein occlusion, hemi-retinal vein occlusion, branch retinal vein occlusion, macular edema following retinal vein occlusion, and ischemic retinal vein occlusion), retinal artery occlusion (e.g, central retinal artery occlusion, hemi-retinal artery occlusion, branch retinal artery occlusion, and ischemic retinal artery occlusion), diabetic retinopathy, diabetic macular edema, ischemic optic neuropathy [e.g., anterior ischemic optic neuropathy (arteritic and non-arteritic) and posterior ischemic optic neuropathy], macular telangiectasia (type I or type II), retinal ischemia (e.g., acute retinal ischemia or chronic retinal ischemia), ocular ischemic syndrome, retinal vasculitis, and retinopathy of prematurity] in a patient in need thereof; increase vision (e.g., increase visual acuity and/or increase visual field) in patient in need thereof that has a vascular disorder of the eye; and/or treat or prevent one or more complications of a vascular disorder of the eye.

In some embodiments, a preferred ActRII antagonist of the present disclosure is a small molecule antagonist, or combination of small molecule antagonists, that inhibits at least GDF11 activity. In some embodiments, a preferred ActRII antagonist of the present disclosure is a small molecule antagonist, or combination of small molecule antagonists, that inhibits at least GDF8 activity. In some embodiments, a preferred ActRII antagonist of the present disclosure is a small molecule antagonist, or combination of small molecule antagonists, that inhibits at least GDF3 activity. In some embodiments, a preferred ActRII antagonist of the present disclosure is a small molecule antagonist, or combination of small molecule antagonists, that inhibits at least BMP6 activity. In some embodiments, a preferred ActRII antagonist of the present disclosure is a small molecule antagonist, or combination of small molecule antagonists, that inhibits at least BMP9 activity. Alternatively, in other embodiments, a preferred small molecule ActRII antagonist of the present disclosure does not inhibit BMP9 activity. In some embodiments, a preferred ActRII antagonist of the present disclosure is a small molecule antagonist, or combination of small molecule antagonists, that inhibits at least BMP10 activity. Alternatively, in other embodiments, a preferred small molecule ActRII antagonist of the present disclosure does not inhibit BMP10 activity. In some embodiments, a preferred ActRII antagonist of the present disclosure is a small molecule antagonist, or combination of small molecule antagonists, that inhibits at least activin (e.g., activin A, activin B, activin AB, activin C, and activin E) activity. In some embodiments, a preferred ActRII antagonist of the present disclosure is a small molecule antagonist, or combination of small molecule antagonists, that inhibits at least activin (e.g., activin A, activin B, activin AB, activin C, and activin E) activity. In some embodiments, a preferred ActRII antagonist of the present disclosure is a small molecule antagonist, or combination of small molecule antagonists, that inhibits at least activin B activity. In some embodiments, a preferred small molecule ActRII antagonist of the present does not inhibit activin B activity.

In some embodiments, a preferred ActRII antagonist of the present disclosure is a small molecule antagonist, or combination of small molecule antagonists, that inhibits at least GDF11 and GDF8 activity. In some embodiments, a small molecule antagonist, or combination of small molecule antagonists, of the present disclosure that inhibits GDF11 and/or GDF8 activity further inhibits activin (e.g., activin A, activin B, activin AB, activin C, activin E). In some embodiments, a small molecule antagonist, or combination of small molecule antagonists, of the present disclosure that inhibits GDF11, GDF8, and/or activin activity further inhibits BMP6. In some embodiments, a small molecule antagonist, or combination of small molecule antagonists, of the present disclosure that inhibits GDF11, GDF8, activin, and/or BMP6 activity further inhibits GDF3. In some embodiments, a small molecule antagonist, or combination of small molecule antagonists, of the present disclosure that inhibits GDF11, GDF8, activin, BMP6, and/or GDF3 activity further inhibits BMP10. In some embodiments, a small molecule antagonist, or combination of small molecule antagonists, of the present disclosure that inhibits GDF11, GDF8, activin, BMP6, GDF3, and/or BMP10 activity further inhibits BMP9. In some embodiments, a small molecule antagonist, or combination of small molecule antagonists, of the present disclosure that inhibits GDF11, GDF8, activin, BMP6, GDF3, BMP9, and/or BMP10 activity do not inhibit activin A.

In some embodiments, a small molecule antagonist, or combination of small molecule antagonists, of the present disclosure inhibits an ActRII receptor (e.g. ActRII-mediated Smad 1, 2, 3, 5, and 8 signaling transduction). For example, in some embodiments, a small molecule antagonist, or combination of small molecule antagonists, of the disclosure inhibits GDF11 from binding to and/or activating an ActRII receptor (ActRIIA and/or ActRIIB) In some embodiments, a small molecule antagonist, or combination of small molecule antagonists, of the disclosure inhibits GDF8 from binding to and/or activating an ActRII receptor. In some embodiments, a small molecule antagonist, or combination of small molecule antagonists, of the disclosure inhibits GDF11 and GDF8 from binding to and/or activating an ActRII receptor. In some embodiments, a small molecule antagonist, or combination of small molecule antagonists, that inhibits GDF11 and/or GDF8 from binding to and/or activating an ActRII receptor further inhibits activin (e.g., activin A, activin B, activin AB, activin C, and/or activin E) from binding to and/or activation an ActRII receptor. In some embodiments, a small molecule antagonist, or combination of small molecule antagonists, that inhibits GDF11 and/or GDF8 from binding to and/or activating an ActRII receptor further inhibits BMP6 from binding to and/or activation an ActRII receptor. In some embodiments, a small molecule antagonist, or combination of small molecule antagonists, that inhibits GDF11 and/or GDF8 from binding to and/or activating an ActRII receptor further inhibits BMP10 from binding to and/or activation an ActRII receptor. In some embodiments, a small molecule antagonist, or combination of small molecule antagonists, that inhibits GDF11 and/or GDF8 from binding to and/or activating an ActRII receptor further inhibits BMP6 and BMP10 from binding to and/or activation an ActRII receptor. In some embodiments, a small molecule antagonist, or combination of small molecule antagonists, that inhibits GDF11 and/or GDF8 from binding to and/or activating an ActRII receptor further inhibits activin (e.g., activin B) and BMP6 from binding to and/or activation an ActRII receptor. In some embodiments, a small molecule antagonist, or combination of small molecule antagonists, that inhibits GDF11 and/or GDF8 from binding to and/or activating an ActRII receptor further inhibits activin (e.g., activin B) and BMP10 from binding to and/or activation an ActRII receptor. In some embodiments, a small molecule antagonist, or combination of small molecule antagonists, that inhibits GDF11 and/or GDF8 from binding to and/or activating an ActRII receptor further inhibits activin (e.g., activin B), BMP6, and BMP10 from binding to and/or activation an ActRII receptor. In some embodiments, a small molecule antagonist, or combination of small molecule antagonists, that inhibits GDF11 and/or GDF8 from binding to and/or activating an ActRII receptor does not inhibit activin A from binding to and/or activation an ActRII receptor.

Small molecule ActRII antagonists can be direct or indirect inhibitors. For example, an indirect small molecule ActRII antagonist, or combination of small molecule ActRII antagonists, may inhibit the expression (e.g., transcription, translation, cellular secretion, or combinations thereof) of at least one or more of GDF11, GDF8, activin (e.g., activin A, activin B, activin AB, activin C, activin E) BMP6, GDF3, BMP10, ActRIIA and/or ActRIIB Alternatively, a direct small molecule ActRII antagonist, or combination of small molecule ActRII antagonists, may directly bind to, for example, one or more ligand [e.g., GDF11, GDF8, GDF3, activin (e.g., activin A, activin B, activin AB, activin C, activin E) BMP6, and/or BMP10], receptor (ActRIIA and/or ActRIIB), or signaling component (e.g., one or more of Smad 1, 2, 3, 5, and 8) of an ActRII-ligand signaling pathway. Combinations of one or more indirect and one or more direct small molecule ActRII antagonists may be used in accordance with the methods disclosed herein.

Binding organic small molecule antagonists of the present disclosure may be identified and chemically synthesized using known methodology (see, e.g., PCT Publication Nos. WO 00/00823 and WO 00/39585). In general, small molecule antagonists of the disclosure are usually less than about 2000 daltons in size, alternatively less than about 1500, 750, 500, 250 or 200 daltons in size, wherein such organic small molecules that are capable of binding, preferably specifically, to a polypeptide as described herein (e.g., GDF11, GDF8, ActRIIA, and ActRIIB) Such small molecule antagonists may be identified without undue experimentation using well-known techniques. In this regard, it is noted that techniques for screening organic small molecule libraries for molecules that are capable of binding to a polypeptide target are well-known in the art (see, e.g., international patent publication Nos. WO00/00823 and WO00/39585).

Binding organic small molecules of the present disclosure may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, and acid chlorides.

Any of the small molecule ActRII antagonists disclosed herein (e.g., a small molecule antagonist of one or more of GDF11, GDF8, GDF3, activin A, activin B, activin AB, activin C, activin E, BMP6, BMP10, ActRIIA, and/or ActRIIB) can be combined with one or more additional ActRII antagonist agents to achieve the desired effect [e.g., to treat or prevent a vascular disorder of the eye in a patient in need thereof; increase vision (e.g., increase visual acuity and/or increase visual field) in patient in need thereof that has a vascular disorder of the eye; and/or treat or prevent one or more complications of a vascular disorder of the eye]. For example, a small molecule ActRII antagonist can be used in combination with i) one or more additional small molecule ActRII antagonists, ii) one or more ActRII antagonist antibodies disclosed herein; iii) one or more ActRII polypeptides; iv) one or more polynucleotide ActRII antagonists; v) one or more follistatin polypeptides; and/or vi) one or more FLRG polypeptides.

E. Antagonist Polynucleotides

In another aspect, the present disclosure relates to a polynucleotide, or combination of polynucleotides, that antagonizes ActRII activity (e.g., inhibition of ActRII signaling transduction via Smads 1, 2, 3, 5, and 8). In particular, the disclosure provides methods of using a polynucleotide ActRII antagonist, or combination of polynucleotide ActRII antagonists, alone or in combination with one or more additional supportive therapies, to treat or prevent a vascular disorder of the eye [e.g., macular degeneration (e.g., age-related macular degeneration, juvenile macular degeneration, wet macular degeneration, dry macular degeneration, Stargardt's disease, and Best's disease), retinal vein occlusion (e.g, central retinal vein occlusion, hemi-retinal vein occlusion, branch retinal vein occlusion, macular edema following retinal vein occlusion, and ischemic retinal vein occlusion), retinal artery occlusion (e.g, central retinal artery occlusion, hemi-retinal artery occlusion, branch retinal artery occlusion, and ischemic retinal artery occlusion), diabetic retinopathy, diabetic macular edema, ischemic optic neuropathy [e.g., anterior ischemic optic neuropathy (arteritic and non-arteritic) and posterior ischemic optic neuropathy], macular telangiectasia (type I or type II), retinal ischemia (e.g., acute retinal ischemia or chronic retinal ischemia), ocular ischemic syndrome, retinal vasculitis, and retinopathy of prematurity] in a patient in need thereof, increase vision (e.g., increase visual acuity and/or visual field) in patient in need thereof that has a vascular disorder of the eye, and/or treat or prevent one or more complications of a vascular disorder of the eye.

In some embodiments, a polynucleotide ActRII antagonist, or combination of polynucleotide ActRII antagonists, of the present disclosure can be used to inhibit the activity and/or expression (e.g., transcription, translation, secretion, or combinations thereof) of GDF11. In some embodiments, a polynucleotide ActRII antagonist, or combination of polynucleotide ActRII antagonists, of the present disclosure can be used to inhibit the activity and/or expression of GDF8. In some embodiments, a polynucleotide ActRII antagonist, or combination of polynucleotide ActRII antagonists, of the present disclosure can be used to inhibit the activity and/or expression of GDF3. In some embodiments, a polynucleotide ActRII antagonist, or combination of polynucleotide ActRII antagonists, of the present disclosure can be used to inhibit the activity and/or expression of BMP6. In some embodiments, a polynucleotide ActRII antagonist, or combination of polynucleotide ActRII antagonists, of the present disclosure can be used to inhibit the activity and/or expression of BMP9. Alternatively, in other embodiments, a polynucleotide ActRII antagonist, or combination of polynucleotide ActRII antagonists, of the present disclosure does not inhibit the activity and/or expression of BMP9. In some embodiments, a polynucleotide ActRII antagonist, or combination of polynucleotide ActRII antagonists, of the present disclosure can be used to inhibit the activity and/or expression of BMP10. Alternatively, in other embodiments, a polynucleotide ActRII antagonist, or combination of polynucleotide ActRII antagonists, of the present disclosure does not inhibit the activity and/or expression of BMP10. In some embodiments, a polynucleotide ActRII antagonist, or combination of polynucleotide ActRII antagonists, of the present disclosure can be used to inhibit the activity and/or expression of activin (e.g., activin A, activin B, activin AB, activin C, and activin E). In some embodiments, a polynucleotide ActRII antagonist, or combination of polynucleotide ActRII antagonists, of the present disclosure can be used to inhibit the activity and/or expression of activin B. In some embodiments, a polynucleotide ActRII antagonist, or combination of polynucleotide ActRII antagonists, of the present disclosure does not inhibit the activity and/or expression of activin A.). In some embodiments, a polynucleotide ActRII antagonist, or combination of polynucleotide ActRII antagonists, of the present disclosure can be used to inhibit the activity and/or expression of activin B, but does not inhibit the activity and/or expression of activin A.

In some embodiments, a polynucleotide ActRII antagonist, or combination of polynucleotide ActRII antagonists, of the present disclosure can be used to inhibit the activity and/or expression of GDF11 and GDF8. In some embodiments, a polynucleotide ActRII antagonist, or combination of polynucleotide ActRII antagonists, that inhibits the activity and/or expression of GDF11 and/or GDF8 further inhibits the activity and/or expression of activin (e.g., activin A, activin B, activin AB, activin C, and/or activin E). In some embodiments, a polynucleotide ActRII antagonist, or combination of polynucleotide ActRII antagonists, that inhibits the activity and/or expression of GDF11, GDF8, and/or activin further inhibits the activity and/or expression of BMP6. In some embodiments, a polynucleotide ActRII antagonist, or combination of polynucleotide ActRII antagonists, that inhibits the activity and/or expression of GDF11, GDF8, activin, and/or BMP6 further inhibits the activity and/or expression of GDF3. In some embodiments, a polynucleotide ActRII antagonist, or combination of polynucleotide ActRII antagonists, that inhibits the activity and/or expression of GDF11, GDF8, activin, BMP6, and/or GDF3 further inhibits the activity and/or expression of BMP10. In some embodiments, a polynucleotide ActRII antagonist, or combination of polynucleotide ActRII antagonists, that inhibits the activity and/or expression of GDF11, GDF8, activin, BMP6, GDF3, and/or BMP10 further inhibits the activity and/or expression of BMP9. In some embodiments, a polynucleotide ActRII antagonist, or combination of polynucleotide ActRII antagonists, that inhibits the activity and/or expression of GDF11, GDF8, activin B, BMP6, GDF3, BMP9, and/or BMP10 does not inhibit the activity and/or expression of activin A. In some embodiments, a polynucleotide ActRII antagonist, or combination of polynucleotide ActRII antagonists, that inhibits the activity and/or expression of GDF11, GDF8, activin B, BMP6, GDF3, and/or BMP10 does not inhibit the activity and/or expression of activin A or BMP9. In some embodiments, a polynucleotide ActRII antagonist, or combination of polynucleotide ActRII antagonists, that inhibits the activity and/or expression of GDF11, GDF8, activin B, BMP6, and/or GDF3 does not inhibit the activity and/or expression of activin A, BMP9, or BMP10.

In some embodiments, a polynucleotide antagonist, or combination of polynucleotide antagonists, of the disclosure inhibits the activity and/or expression (e.g., transcription, translation, secretion, or combinations thereof) of at ActRII (ActRIIA and/or ActRIIB) In some embodiments, a polynucleotide antagonist, or combination of polynucleotide antagonists, of the disclosure that inhibits the activity and/or expression of ActRII may further inhibit the activity and or expression of one or more of ligands (e.g., activin A, activin B, activin AB, activin C, activin E, BMP6, BMP9, GDF11, GDF8, and BMP10). In some embodiments, a polynucleotide antagonist, or combination of polynucleotide antagonists, of the disclosure that inhibits the activity and/or expression of ActRII does not inhibit the activity and or expression of activin A.

The polynucleotide antagonists of the present disclosure may be an antisense nucleic acid, an RNAi molecule [e.g., small interfering RNA (siRNA), small-hairpin RNA (shRNA), microRNA (miRNA)], an aptamer and/or a ribozyme. The nucleic acid and amino acid sequences of human GDF11, GDF8, activin A, activin B, activin C, activin E, BMP6, BMP10, ActRIIA, and ActRIIB are known in the art and thus polynucleotide antagonists for use in accordance with methods of the present disclosure may be routinely made by the skilled artisan based on the knowledge in the art and teachings provided herein.

For example, antisense technology can be used to control gene expression through antisense DNA or RNA, or through triple-helix formation. Antisense techniques are discussed, for example, in Okano (1991) J. Neurochem. 56:560; Oligodeoxynucleotides as Antisense Inhibitors of Gene Expression, CRC Press, Boca Raton, Fla. (1988). Triple helix formation is discussed in, for instance, Cooney et al. (1988) Science 241:456; and Dervan et al., (1991) Science 251: 1300. The methods are based on binding of a polynucleotide to a complementary DNA or RNA. In some embodiments, the antisense nucleic acids comprise a single-stranded RNA or DNA sequence that is complementary to at least a portion of an RNA transcript of a desired gene. However, absolute complementarity, although preferred, is not required.

A sequence "complementary to at least a portion of an RNA," referred to herein, means a sequence having sufficient complementarity to be able to hybridize with the RNA, forming a stable duplex; in the case of double-stranded antisense nucleic acids of a gene disclosed herein, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with an RNA it may contain and still form a stable duplex (or triplex as the case may be). One skilled in the art can ascertain a tolerable degree of mismatch by use of standard procedures to determine the melting point of the hybridized complex.

Polynucleotides that are complementary to the 5' end of the message, for example, the 5'-untranslated sequence up to and including the AUG initiation codon, should work most efficiently at inhibiting translation. However, sequences complementary to the 3'-untranslated sequences of mRNAs have been shown to be effective at inhibiting translation of mRNAs as well [see, e.g., Wagner, R., (1994) Nature 372:333-335]. Thus, oligonucleotides complementary to either the 5'- or 3'-untranslated, noncoding regions of a gene of the disclosure, could be used in an antisense approach to inhibit translation of an endogenous mRNA. Polynucleotides complementary to the 5'-untranslated region of the mRNA should include the complement of the AUG start codon. Antisense polynucleotides complementary to mRNA coding regions are less efficient inhibitors of translation but could be used in accordance with the methods of the present disclosure. Whether designed to hybridize to the 5'-untranslated, 3'-untranslated, or coding regions of an mRNA of the disclosure, antisense nucleic acids should be at least six nucleotides in length, and are preferably oligonucleotides ranging from 6 to about 50 nucleotides in length. In specific aspects, the oligonucleotide is at least 10 nucleotides, at least 17 nucleotides, at least 25 nucleotides, or at least 50 nucleotides.

In one embodiment, the antisense nucleic acid of the present disclosure is produced intracellularly by transcription from an exogenous sequence. For example, a vector or a portion thereof, is transcribed, producing an antisense nucleic acid (RNA) of a gene of the disclosure. Such a vector would contain a sequence encoding the desired antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding desired genes of the instant disclosure, or fragments thereof, can be by any promoter known in the art to act in vertebrate, preferably human cells. Such promoters can be inducible or constitutive. Such promoters include, but are not limited to, the SV40 early promoter region [see, e.g., Benoist and Chambon (1981) Nature 29:304-310], the promoter contained in the 3' long terminal repeat of Rous sarcoma virus [see, e.g., Yamamoto et al. (1980) Cell 22:787-797], the herpes thymidine promoter [see, e.g., Wagner et al. (1981) Proc. Natl. Acad. Sci. U.S.A. 78:1441-1445], and the regulatory sequences of the metallothionein gene [see, e.g., Brinster, et al. (1982) Nature 296:39-42].

In some embodiments, the polynucleotide antagonists are interfering RNA or RNAi molecules that target the expression of one or more genes. RNAi refers to the expression of an RNA which interferes with the expression of the targeted mRNA. Specifically, RNAi silences a targeted gene via interacting with the specific mRNA through a siRNA (small interfering RNA). The ds RNA complex is then targeted for degradation by the cell. An siRNA molecule is a double-stranded RNA duplex of 10 to 50 nucleotides in length, which interferes with the expression of a target gene which is sufficiently complementary (e.g. at least 80% identity to the gene). In some embodiments, the siRNA molecule comprises a nucleotide sequence that is at least 85, 90, 95, 96, 97, 98, 99, or 100% identical to the nucleotide sequence of the target gene.

Additional RNAi molecules include short-hairpin RNA (shRNA); also short-interfering hairpin and microRNA (miRNA). The shRNA molecule contains sense and antisense sequences from a target gene connected by a loop. The shRNA is transported from the nucleus into the cytoplasm, and it is degraded along with the mRNA. Pol III or U6 promoters can be used to express RNAs for RNAi. Paddison et al. [Genes & Dev. (2002) 16:948-958, 2002] have used small RNA molecules folded into hairpins as a means to effect RNAi. Accordingly, such short hairpin RNA (shRNA) molecules are also advantageously used in the methods described herein. The length of the stem and loop of functional shRNAs varies; stem lengths can range anywhere from about 25 to about 30 nt, and loop size can range between 4 to about 25 nt without affecting silencing activity. While not wishing to be bound by any particular theory, it is believed that these shRNAs resemble the double-stranded RNA (dsRNA) products of the DICER RNase and, in any event, have the same capacity for inhibiting expression of a specific gene. The shRNA can be expressed from a lentiviral vector. An miRNA is a single-stranded RNA of about 10 to 70 nucleotides in length that are initially transcribed as pre-miRNA characterized by a "stem-loop" structure and which are subsequently processed into mature miRNA after further processing through the RISC.

Molecules that mediate RNAi, including without limitation siRNA, can be produced in vitro by chemical synthesis (Hohjoh, FEBS Lett 521:195-199, 2002), hydrolysis of dsRNA (Yang et al., Proc Natl Acad Sci USA 99:9942-9947, 2002), by in vitro transcription with T7 RNA polymerase (Donzeet et al., Nucleic Acids Res 30:e46, 2002; Yu et al., Proc Natl Acad Sci USA 99:6047-6052, 2002), and by hydrolysis of double-stranded RNA using a nuclease such as E. coli RNase III (Yang et al., Proc Natl Acad Sci USA 99:9942-9947, 2002).

According to another aspect, the disclosure provides polynucleotide antagonists including but not limited to, a decoy DNA, a double-stranded DNA, a single-stranded DNA, a complexed DNA, an encapsulated DNA, a viral DNA, a plasmid DNA, a naked RNA, an encapsulated RNA, a viral RNA, a double-stranded RNA, a molecule capable of generating RNA interference, or combinations thereof.

In some embodiments, the polynucleotide antagonists of the disclosure are aptamers. Aptamers are nucleic acid molecules, including double-stranded DNA and single-stranded RNA molecules, which bind to and form tertiary structures that specifically bind to a target molecule, such as a GDF11, GDF8, activin A, activin B, activin C, activin E, BMP6, BMP7, Nodal, ActRIIA, and ActRIIB polypeptide. The generation and therapeutic use of aptamers are well established in the art. See, e.g., U.S. Pat. No. 5,475,096. Additional information on aptamers can be found in U.S. Patent Application Publication No. 20060148748. Nucleic acid aptamers are selected using methods known in the art, for example via the Systematic Evolution of Ligands by Exponential Enrichment (SELEX) process. SELEX is a method for the in vitro evolution of nucleic acid molecules with highly specific binding to target molecules as described in, e.g., U.S. Pat. Nos. 5,475,096, 5,580,737, 5,567,588, 5,707,796, 5,763,177, 6,011,577, and 6,699,843. Another screening method to identify aptamers is described in U.S. Pat. No. 5,270,163. The SELEX process is based on the capacity of nucleic acids for forming a variety of two- and three-dimensional structures, as well as the chemical versatility available within the nucleotide monomers to act as ligands (form specific binding pairs) with virtually any chemical compound, whether monomeric or polymeric, including other nucleic acid molecules and polypeptides. Molecules of any size or composition can serve as targets. The SELEX method involves selection from a mixture of candidate oligonucleotides and step-wise iterations of binding, partitioning and amplification, using the same general selection scheme, to achieve desired binding affinity and selectivity. Starting from a mixture of nucleic acids, which can comprise a segment of randomized sequence, the SELEX method includes steps of contacting the mixture with the target under conditions favorable for binding; partitioning unbound nucleic acids from those nucleic acids which have bound specifically to target molecules; dissociating the nucleic acid-target complexes; amplifying the nucleic acids dissociated from the nucleic acid-target complexes to yield a ligand enriched mixture of nucleic acids. The steps of binding, partitioning, dissociating and amplifying are repeated through as many cycles as desired to yield highly specific high affinity nucleic acid ligands to the target molecule.

Typically, such binding molecules are separately administered to the animal [see, e.g., O'Connor (1991) J. Neurochem. 56:560], but such binding molecules can also be expressed in vivo from polynucleotides taken up by a host cell and expressed in vivo [see, e.g., Oligodeoxynucleotides as Antisense Inhibitors of Gene Expression, CRC Press, Boca Raton, Fla. (1988)].

Any of the polynucleotide ActRII antagonists disclosed herein (e.g., a polynucleotide antagonist of one or more of GDF11, GDF8, GDF3, activin A, activin B, activin AB, activin C, activin E, BMP6, BMP10, ActRIIA, and/or ActRIIB) can be combined with one or more additional ActRII antagonists to achieve the desired effect [e.g., treat or prevent a vascular disorder of the eye in a patient in need thereof; increase vision (e.g., increase visual acuity and/or field) in patient in need thereof that has a vascular disorder of the eye, and/or treat or prevent one or more complications of a vascular disorder of the eye]. For example, a polynucleotide ActRII antagonist disclosed herein can be used in combination with i) one or more additional polynucleotide ActRII antagonists, ii) one or more ActRII polypeptides; iii) one or more ActRII antagonist antibodies; iv) one or more small molecule ActRII antagonists; v) one or more follistatin polypeptides; and/or vi) one or more FLRG polypeptides.

F. Follistatin and FLRG Antagonists

In other aspects, an ActRII antagonist (inhibitor) for use in accordance with the methods disclosed herein is a follistatin or FLRG polypeptide, which may be used alone or in combination with one or more additional supportive therapies to treat or prevent a vascular disorder of the eye (e.g., macular degeneration (e.g., age-related macular degeneration, juvenile macular degeneration, wet macular degeneration, dry macular degeneration, Stargardt's disease, and Best's disease), retinal vein occlusion (e.g, central retinal vein occlusion, hemi-retinal vein occlusion, branch retinal vein occlusion, macular edema following retinal vein occlusion, and ischemic retinal vein occlusion), retinal artery occlusion (e.g, central retinal artery occlusion, hemi-retinal artery occlusion, branch retinal artery occlusion, and ischemic retinal artery occlusion), diabetic retinopathy, diabetic macular edema, ischemic optic neuropathy [e.g., anterior ischemic optic neuropathy (arteritic and non-arteritic) and posterior ischemic optic neuropathy], macular telangiectasia (type I or type II), retinal ischemia (e.g., acute retinal ischemia or chronic retinal ischemia), ocular ischemic syndrome, retinal vasculitis, and retinopathy of prematurity) in a patient in need thereof; increase vision (e.g., increase visual acuity and/or visual field) in patient in need thereof that has a vascular disorder of the eye, and/or treat or prevent one or more complications of vascular disorder of the eye.

The term "follistatin polypeptide" includes polypeptides comprising any naturally occurring polypeptide of follistatin as well as any variants thereof (including mutants, fragments, fusions, and peptidomimetic forms) that retain a useful activity, and further includes any functional monomer or multimer of follistatin. In certain preferred embodiments, follistatin polypeptides of the disclosure bind to and/or inhibit activin activity, particularly activin A. Variants of follistatin polypeptides that retain activin binding properties can be identified based on previous studies involving follistatin and activin interactions. For example, WO2008/030367 discloses specific follistatin domains ("FSDs") that are shown to be important for activin binding. As shown below in SEQ ID NOs: 28-30, the follistatin N-terminal domain ("FSND" SEQ ID NO: 28), FSD2 (SEQ ID NO: 30), and to a lesser extent FSD1 (SEQ ID NO: 29) represent exemplary domains within follistatin that are important for activin binding. In addition, methods for making and testing libraries of polypeptides are described above in the context of ActRII polypeptides, and such methods also pertain to making and testing variants of follistatin. Follistatin polypeptides include polypeptides derived from the sequence of any known follistatin having a sequence at least about 80% identical to the sequence of a follistatin polypeptide, and optionally at least 85%, 90%, 95%, 96%, 97%, 98%, 99% or greater identity. Examples of follistatin polypeptides include the mature follistatin polypeptide or shorter isoforms or other variants of the human follistatin precursor polypeptide (SEQ ID NO: 26) as described, for example, in WO2005/025601.

```
                                      (SEQ ID NO: 26; NCBI Reference No. NP_037541.1)
  1 MVRARHQPGG LCLLLLLLCQ FMEDRSAQAG NCWLRQAKNG RCQVLYKTEL

51 SKEECCSTGR LSTSWTEEDV NDNTLFKWMI FNGGAPNCIP CKETCENVDC

101 GPGKKCRMNK KNKPRCVCAP DCSNITWKGP VCGLDGKTYR NECALLKARC

151 KEQPELEVQY QGRCKKTCRD VFCPGSSTCV VDQTNNAYCV TCNRICPEPA

201 SSEQYLCGND GVTYSSACHL RKATCLLGRS IGLAYEGKCI KAKSCEDIQC

251 TGGKKCLWDF KVGRGRCSLC DELCPDSKSD EPVCASDNAT YASECAMKEA

301 ACSSGVLLEV KHSGSCNSIS EDTEEEEEDE DQDYSFPISS ILEW
```

The signal peptide is underlined; also underlined above are the last 27 residues which represent the C-terminal extension distinguishing this follistatin isoform from the shorter follistatin isoform FST317 shown below.

The human follistatin precursor polypeptide isoform FST317 is as follows:

```
                                      (SEQ ID NO: 27; NCBI Reference No. NP_006341.1)
  1 MVRARHQPGG LCLLLLLLCQ FMEDRSAQAG NCWLRQAKNG RCQVLYKTEL

51 SKEECCSTGR LSTSWIEEDV NDNTLFKWMI FNGGAPNCIP CKETCENVDC

101 GPGKKCRMNK KNKPRCVCAP DCSNITWKGP VCGLDGKTYR NECALLKARC

151 KEQPELEVQY QGRCKKTCRD VFCPGSSTCV VDQTNNAYCV TCNR1CPEPA

201 SSEQYLCGND GVTYSSACHL RKATCLLGRS IGLAYEGKCI KAKSCEDIQC

251 TGGKKCLWDF KVGRGRCSLC DELCPDSKSD EPVCASDNAT YASECAMKEA

301 ACSSGVLLEV KHSGSCN
```

The signal peptide is underlined.

The follistatin N-terminal domain (FSND) sequence is as follows:

```
                                      (SEQ ID NO: 28; FSND)
GNCWLRQAKNGRCQVLYKIELSKEECCSTGRLSTSWIEEDVNDNTLF

KWMIFNGGAPNCIPCK
```

The FSD1 and FSD2 sequences are as follows:

```
                                      (SEQ ID NO: 29; FSD1)
            ETCENVDCGPGKKCRNINKKNKPRCV (SEQ ID NO: 30; FSD2)
            KTCRDVFCPGSSTCVVDQTNNAYCVT
```

In other aspects, an agent for use in accordance with the methods disclosed herein is a follistatin-like related gene (FLRG), also known as follistatin-related protein 3 (FSTL3). The term "FLRG polypeptide" includes polypeptides comprising any naturally occurring polypeptide of FLRG as well as any variants thereof (including mutants, fragments, fusions, and peptidomimetic forms) that retain a useful activity. In certain preferred embodiments, FLRG polypeptides of the disclosure bind to and/or inhibit activin activity, particularly activin A. Variants of FLRG polypeptides that retain activin binding properties can be identified using routine methods to assay FLRG and activin interactions (see, e.g., U.S. Pat. No. 6,537,966). In addition, methods for making and testing libraries of polypeptides are described above in the context of ActRII polypeptides and such methods also pertain to making and testing variants of FLRG. FLRG polypeptides include polypeptides derived from the sequence of any known FLRG having a sequence at least about 80% identical to the sequence of an FLRG polypeptide, and optionally at least 85%, 90%, 95%, 97%, 99% or greater identity.

The human FLRG precursor (follistatin-related protein 3 precursor) polypeptide is as follows:

```
                 (SEQ ID NO: 31; NCBI Reference No. NP_005851.1)
  1 MRPGAPGPLW PLPWGALAWA VGFVSSMGSG NPAPGGVCWL QQGQEATCSL

51 VLQTDVTRAE CCASGNIDTA WSNLTHPGNK INLLGFLGLV HCLPCKDSCD

101 GVECGPGKAC RMLGGRPRCE CAPDCSGLPA RLQVCGSDGA TYRDECELRA

151 ARCRGHPDLS VMYRGRCRKS CEHVVCPRPQ SCVVDQTGSA HCVVCRAAPC

201 PVPSSPGQEL CGNNNVTYIS SCHMRQATCF LGRSIGVRHA GSCAGTPEEP

251 PGGESAEEEE NFV
```

The signal peptide is underlined.

In certain embodiments, functional variants or modified forms of the follistatin polypeptides and FLRG polypeptides include fusion proteins having at least a portion of the follistatin polypeptide or FLRG polypeptide and one or more fusion domains, such as, for example, domains that facilitate isolation, detection, stabilization or multimerization of the polypeptide. Suitable fusion domains are discussed in detail above with reference to the ActRII polypeptides. In some embodiment, an antagonist agent of the disclosure is a fusion protein comprising an activin-binding portion of a follistatin polypeptide fused to an Fc domain. In another embodiment, an antagonist agent of the disclosure is a fusion protein comprising an activin binding portion of an FLRG polypeptide fused to an Fc domain.

Any of the follistatin polypeptides disclosed herein may be combined with one or more additional ActRII antagonists agents of the disclosure to achieve the desired effect (e.g., treat or prevent a vascular disorder of the eye in a patient in need thereof, increase vision in patient in need thereof that has a vascular disorder of the eye, and/or treat or prevent one or more complications of a vascular disorder of the eye). For example, a follistatin polypeptide can be used in combination with i) one or more additional follistatin polypeptides, ii) one or more ActRII polypeptides disclosed herein, iii) one or more ActRII antagonist antibodies; iv) one or more small molecule ActRII antagonists; v) one or more polynucleotide ActRII antagonists; and/or vi) one or more FLRG polypeptides.

Similarly, any of the FLRG polypeptides disclosed herein may be combined with one or more additional ActRII antagonists agents of the disclosure to achieve the desired effect (e.g., treat or prevent a vascular disorder of the eye in a patient in need thereof, increase vision in patient in need thereof that has a vascular disorder of the eye, and/or treat or prevent one or more complications of a vascular disorder of the eye). For example, a FLRG polypeptide can be used in combination with i) one or more additional FLRG polypeptides, ii) one or more ActRII polypeptides disclosed herein, iii) one or more ActRII antagonist antibodies; iv) one or more small molecule ActRII antagonists; v) one or more polynucleotide ActRII antagonists; and/or vi) one or more follistatin polypeptides.

3. Screening Assays

In certain aspects, the present disclosure relates to the use of the subject ActRII polypeptides (e.g., ActRIIA and ActRIIB polypeptides and variants thereof) to identify compounds (agents) which are agonist or antagonists of ActRII polypeptides. Compounds identified through this screening can be tested to assess their ability to improve visual acuity, for example, in animal models.

There are numerous approaches to screening for therapeutic agents for improving vision (e.g., increasing visual acuity and/or visual field) by targeting ActRII signaling (e.g., ActRII signaling via Smad 1, 2, 3, 5, and 8). In certain embodiments, high-throughput screening of compounds can be carried out to identify agents that perturb ActRII-mediated effects on a selected cell line. In certain embodiments, the assay is carried out to screen and identify compounds that specifically inhibit or reduce binding of an ActRII polypeptide to its binding partner, such as an ActRII ligand (e.g., activin A, activin B, activin AB, activin C, GDF8, GDF11 or BMP10). Alternatively, the assay can be used to identify compounds that enhance binding of an ActRII polypeptide to its binding partner such as an ActRII ligand. In a further embodiment, the compounds can be identified by their ability to interact with an ActRII polypeptide.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In certain embodiments, the test agent is a small organic molecule having a molecular weight of less than about 2,000 Daltons.

The test compounds of the disclosure can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S-transferase (GST), photoactivatible crosslinkers or any combinations thereof.

In many drug-screening programs which test libraries of compounds and natural extracts, high-throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between an ActRII polypeptide and its binding partner (e.g., an ActRII ligand).

Merely to illustrate, in an exemplary screening assay of the present disclosure, the compound of interest is contacted with an isolated and purified ActRIIB polypeptide which is ordinarily capable of binding to an ActRIIB ligand, as appropriate for the intention of the assay. To the mixture of the compound and ActRIIB polypeptide is then added to a composition containing an ActRIIB ligand (e.g., GDF11). Detection and quantification of ActRIIB/ActRIIB-ligand complexes provides a means for determining the compound's efficacy at inhibiting (or potentiating) complex formation between the ActRIIB polypeptide and its binding protein. The efficacy of the compound can be assessed by generating dose-response curves from data obtained using various concentrations of the test compound. Moreover, a control assay can also be performed to provide a baseline for comparison. For example, in a control assay, isolated and purified ActRIIB ligand is added to a composition containing the ActRIIB polypeptide, and the formation of ActRIIB/ActRIIB ligand complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between an ActRII polypeptide and its binding protein may be detected by a variety of techniques. For instance, modulation of the formation of complexes can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled ActRII polypeptide and/or its binding protein, by immunoassay, or by chromatographic detection.

In certain embodiments, the present disclosure contemplates the use of fluorescence polarization assays and fluorescence resonance energy transfer (FRET) assays in measuring, either directly or indirectly, the degree of interaction between an ActRII polypeptide and its binding protein. Further, other modes of detection, such as those based on optical waveguides (see, e.g., PCT Publication WO 96/26432 and U.S. Pat. No. 5,677,196), surface plasmon resonance (SPR), surface charge sensors, and surface force sensors, are compatible with many embodiments of the disclosure.

Moreover, the present disclosure contemplates the use of an interaction trap assay, also known as the "two-hybrid assay," for identifying agents that disrupt or potentiate interaction between an ActRII polypeptide and its binding partner. See, e.g., U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). In a specific embodiment, the present disclosure contemplates the use of reverse two-hybrid systems to identify compounds (e.g., small molecules or peptides) that dissociate interactions between an ActRII polypeptide or GDF trap and its binding protein [see, e.g., Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368].

In certain embodiments, the subject compounds are identified by their ability to interact with an ActRII polypeptide. The interaction between the compound and the ActRII polypeptide may be covalent or non-covalent. For example, such interaction can be identified at the protein level using in vitro biochemical methods, including photo-crosslinking, radiolabeled ligand binding, and affinity chromatography [see, e.g., Jakoby W B et al. (1974) Methods in Enzymology 46:1]. In certain cases, the compounds may be screened in a mechanism-based assay, such as an assay to detect compounds which bind to an ActRII polypeptide. This may include a solid-phase or fluid-phase binding event. Alternatively, the gene encoding an ActRII polypeptide can be transfected with a reporter system (e.g., β-galactosidase, luciferase, or green fluorescent protein) into a cell and screened against the library preferably by high-throughput screening or with individual members of the library. Other mechanism-based binding assays may be used; for example, binding assays which detect changes in free energy. Binding assays can be performed with the target fixed to a well, bead or chip or captured by an immobilized antibody or resolved by capillary electrophoresis. The bound compounds may be detected usually using colorimetric endpoints or fluorescence or surface plasmon resonance.

4. Exemplary Therapeutic Uses

As described herein, applicants have discovered that an ActRII antagonist (inhibitor) has a surprising effect on improving vision in an MDS patient. Moreover, in view of the reported mechanism for MDS-associated vision loss [Han et al. (2015) J Glaucoma (Epub ahead of print); Brouzas et al. (2009) Clinical Ophthalmology 3:133-137], the data of the present disclosure suggests that ActRII inhibitors also may have positive effects in treating or preventing other types of eye (ocular) disorders, particularly vascular ocular disorders including, for example, those associated with ischemia and/or vascular insufficiency.

The structural and functional integrity of the eye depends on a regular oxygen and nutrient supply. Being one of the most metabolically active tissues, the retina consumes oxygen more rapidly than other tissues in the body [Cohen et al. (1965) Biochemistry of the Retina. Orlando, Fla.: Academic Press Inc; pp. 36-50; Anderson et al. (1964) Arch Ophthalmol 72:792-795; and Ames A. (1992) Can J Physiol Pharmacol. 70(Suppl):S158-64]. The presence of a dual circulation system makes retinal oxygenation unique [Osborne et al. (2004) Prog Retin Eye Res. 23:91-147]. The photoreceptors and the greater portion of the outer plexiform layer receive nourishment from the choriocapillaris indirectly whereas the inner retinal layers are supplied by the superficial and deep capillary plexuses formed by branches of the central artery of the retina. Inner layers of the retina are known to show highest sensitivity to hypoxic challenges [Janáky et al. (2007) Doc Ophthalmol. 114:45-51], whereas the outer retina is more resistant to a hypoxic stress [Tinjust et al. (2002) Aviat Space Environ Med. 73:1189-94].

A number of systemic and cellular responses such as glycolysis, angiogenesis, vasodilation, and erythropoiesis enable an organism to respond to hypoxia [Harris et al. (2002) Nat Rev Cancer. 2:38-47]. Many tissues are capable of inducing protective mechanisms under hypoxic-ischemic conditions, which are typically induced within minutes of onset, and are of critical importance for limiting damage [Kitagawa et al. (1990) Brain Res. 528:21-4]. However, during prolonged hypoxic conditions, these protective mechanisms are generally diminished/lost within hours of the hypoxic-ischemic insult, leading to cell death and tissue damage [Prass et al. (2003) Stroke. 34:1981-6]. Transcriptional activator hypoxia-inducible factor-1a (HIF-1α) is a master regulator of cellular $O_2$ homeostasis [Iyer et al. (1998) Genes Dev. 12:149-62]. Hypoxia is known to induce HIF-1α and its target genes such as vascular endothelial growth factor (VEGF) and nitric oxide synthase (NOS) in many tissues. Interestingly, overproduction of these factors, such as during prolonged hypoxia, has been implicated in cellular death in hypoxic-ischemic conditions. In addition, enhanced extracellular accumulation of glutamate and inflammatory cytokines, which occurs during prolonged hypoxia, can damage cells and tissues. Increased expression of HIF-1α, VEGF, and various isoforms of NOS has been reported in the retina following hypoxic injury [Kaur et al. (2006) Invest Ophthalmol Vis Sci. 47:1126-41; and Tezel et al. (2004) Curr Opin Ophthalmol. 15:80-4].

Retinal ganglion cells (RGCs) are particularly sensitive to acute, transient, and mild systemic hypoxic stress [Kergoat et al. (2006) Invest Ophthalmol Vis Sci. 47:5423-7]. Loss of RGCs occurs in many ophthalmic conditions such as glaucoma and diabetes (Sucher et al. (1997) Vision Res. 37:3483-93; Abu-El-Asrar et al. (2004) Invest Ophthalmol Vis Sci. 45:2760-6], hypoxia being implicated in such loss [Wax et al. (2002) Mol Neurobiol. 26:45-55; Tezel et al. (2004). Curr Opin Ophthalmol. 15:80-4; and Chen et al. (2007) Stem Cells. 25:2291-301]. Neuronal degeneration resulting from retinal hypoxia-ischemia, caused by oxygen and substrate deprivation, is partially mediated by accumulation of free oxygen radicals [Block et al. (1997) Exp Eye Res. 64:559-64; Muller et al. (1997) Exp Eye Res. 64:637-43; and Szabo et al. (1997) Clin Neurosci. 4:240-5], glutamate excitotoxicity [Kuroiwa T et al. (1985) Acta Neuropathol (Berl) 68:122-9; Osborne et al. (2004) Prog Retin Eye Res. 23:91-147; and Kaur et al. (2006) Invest Ophthalmol Vis Sci. 47:1126-41], inflammation, and disruption of the blood retinal barrier [Kuroiwa et al. (1985) Acta Neuropathol (Berl) 68:122-9; and Kaur et al. (2007) J Pathol. 212:429-39].

Hypoxia-ischemia also results in retinal vascular damage which is associated with fluid accumulation in the extracellular spaces (vasogenic edema) or intracellulary spaces (cytotoxic edema) [Marmor et al. (1999) Doc Ophthalmol. 97:239-49]. The extracellular spaces in the inner retina consist of the narrow clefts between the tightly packed cellular elements. Fluid leaking out from damaged capillaries in the inner retina accumulates in the extracellular spaces displacing the retinal cellular elements and disrupting the normal anatomy of the neuronal connections, resulting in macular edema [Hamann et al. (2005) Acta Ophthalmol Scand. 83:523-5]. Macular edema can further exacerbate retinal ischemia and well as promote increased oxidative stress and inflammation (Guex-Crosier Y. (1999) Doc Ophthalmol. 97:297-309; van Dam P S. (2002) Diabetes Metab Res Rev. 18:176-84; and Miyake et al. (2002) Surv Ophthalmol. 47:S203-8.). Increased permeability of blood-retinal barrier (BRB) resulting in fluid accumulation has been reported to contribute to retinal neuronal degeneration by compression [Antcliff et al. (1999) Semin Ophthalmol. 14:223-32; Marumo T et al. (1999) J Vasc Res. 36:510-15; and Reichenbach et al. (2007) Graefes Arch Clin Exp Ophthalmol. 245:627-36). While initially protective, excess and/or chronic production of VEGF, nitric oxide (NO), and aquaporin-4 during hypoxic-ischemic insults can cause neovascularization and dysfunction of the BRB in the inner retina, resulting in serum leakage into the retinal tissues and retinal edema. In addition to an increase in vascular permeability, ocular hypoxia has also been correlated with endothelial cell death, leukocyte plugging of vessels, and microaneurysms [Linsenmeier et al. (1998) Invest Ophthalmol Vis Sci. 39:1647-57].

Hypoxia-ischemia occurs in various ocular conditions including, for example, retinal artery/vein occlusion or thrombosis, ocular ischemic syndrome, ischemic optic neuropathy, and retinal ischemia. Hypoxia-ischemia also has been implicated in the development of glaucoma [Flammer J. (1994) 'Surv Ophthalmol. 38(Suppl):S3-6; Chung et al. (1999) Surv Ophthalmol. 43(Suppl 1):S43-50; and Tezel et al. (2004) Curr Opin Ophthalmol. 15:80-4], is thought to underlie many of the sight-threatening complications of diabetic eye disease including retinal and optic nerve head neovascularization [Linsenmeier et al. (1998) Invest Ophthalmol Vis Sci. 39:1647-57], and may play a role in age-related macular degeneration [Tso et al. (1982) Ophthalmology. 89:902-15; Yanoff et al. (1984) Surv Ophthalmol. 28 (Suppl):505-11; and Bressler et al. (2001) In: Schachat A P, editor. Retina. St. Louis, Mo.: Mosby]. Systemic causes of ocular hypoxia include the cardiovascular effects, chronic obstructive airways disease, arterial/venous obstructive conditions, [Brown et al. (1988) Int Ophthalmol. 11:239-51] Takayasu's arteritis [Shelhamer et al. (1985) Ann Intern Med. 103:121-6], hyperviscosity syndromes [Ashton et al. (1963) J Pathol Bacteriol. 86:453-61] as well as trauma (e.g., surgery or accidental damage) [Purtscher's retinopathy; Buckley et al. (1996) Postgrad Med J. 72:409-12]. Hypoxia associated with the above conditions is a common cause of visual impairment and blindness [Osborne, et al. (2004) Prog Retin Eye Res. 23:91-147].

Therefore, in certain aspects, the present disclosure provides methods, as well as compositions, for treating or preventing an vascular disorder (disease) of the eye in a patient (subject) in need thereof (particularly mammals such as rodents, cats, dogs, primates, and humans) by administering to the patient a therapeutically effective amount of an ActRII antagonist (inhibitor), or combination of ActRII antagonists. In some embodiments, the disclosure provides methods for using an ActRII antagonist, or combination of ActRII antagonists, to treat or prevent vascular disorders of the eye associated with ischemia. In some embodiments, the disclosure provides methods for using an ActRII antagonist, or combination of ActRII antagonists, to treat or prevent an ischemic eye disease. In some embodiments, the disclosure provides methods for using an ActRII antagonist, or combination of ActRII antagonists, to treat or prevent vascular disorders of the eye associated with microvasculature insufficiency. In some embodiments, the disclosure provides methods for using an ActRII antagonist, or combination of ActRII antagonists, to treat or prevent an ocular microvasculature insufficiency disease. In some embodiments, the disclosure provides methods for using an ActRII antagonist, or combination of ActRII antagonists, to treat or prevent vascular disorders of the eye associated with retinopathy. In some embodiments, the disclosure provides methods for using an ActRII antagonist, or combination of ActRII antagonists, to treat or prevent vascular disorders of the eye associated with optic neuropathy. In some embodiments, the disclosure provides methods for using an ActRII antagonist, or combination of ActRII antagonists, to treat or prevent ischemic retinopathy. In some embodiments, the disclosure provides methods for using an ActRII antagonist, or combination of ActRII antagonists, to treat or prevent ischemic optic neuropathy. In some embodiments, the disclosure provides methods for using an ActRII antagonist, or combination of ActRII antagonists, to treat or prevent retinopathy associated with microvasculature insufficiency. In some embodiments, the disclosure provides methods for using an ActRII antagonist, or combination of ActRII antagonists, to treat or prevent optic neuropathy associated with microvasculature insufficiency. In particular, the disclosure provides methods for using an ActRII antagonist, or combination of ActRII antagonists, to treat or prevent one or more diseases selected from: macular degeneration (e.g., age-related macular degeneration, juvenile macular degeneration, wet macular degeneration, dry macular degeneration, Stargardt's disease, and Best's disease), retinal vein occlusion (e.g, central retinal vein occlusion, hemi-retinal vein occlusion, branch retinal vein occlusion, and ischemic retinal vein occlusion), retinal artery occlusion (e.g, central retinal artery occlusion, hemi-retinal artery occlusion, branch retinal artery occlusion, and ischemic retinal artery occlusion), diabetic retinopathy, ischemic optic neuropathy [e.g., anterior ischemic optic neuropathy (arteritic and non-arteritic) and posterior ischemic optic neuropathy], macular telangiectasia (type I or type II), retinal ischemia (e.g., acute retinal ischemia or chronic retinal ischemia), ocular ischemic syndrome, retinal vasculitis, and retinopathy of prematurity. In some embodiments, methods and compositions disclosed herein for treating an ocular disease result in improving vision in an eye of the patient. In some embodiments, methods and compositions disclosed herein for treating an ocular disease result in increasing visual acuity in an eye of the patient. In some embodiments, methods and compositions disclosed herein for treating an ocular disease result in increasing visual field in an eye of the patient. Optionally, methods of the disclosure for treating or preventing an vascular disorder of the eye may further comprise administration of one or more supportive therapies for treating or preventing the disorder in addition to administration of an ActRII antagonist, or combination of ActRII antagonists [e.g., surgery, laser therapy (e.g., photocoagulation), anti-angiogenic therapy [e.g., VEGF inhibitors such as bevacizumab (Avastin®), ranibizumab (Lucentis®), and Aflibercept (Eylea®)], $Ca^{2+}$ inhibitors (e.g., flunarizine and nifedipine), cryotherapy, hyperbaric oxygenation, $Na^+$ channel blockers (e.g., topiramate), iGluR antagonists (e.g., MK-801, dextromethorphan, eliprodil, and flupirtine), antioxidants (e.g., dimethylthiourea, vitamin E, alph-lipoic acid, superoxide dismutase, catalase, desferrioxamine, mannitol, allopurinol, calcium dobesilate, flupirtine, trimetazidine, and EGB-761), anti-inflammatory agents, cyclodiathermy, cyclocryotherapy, ocular filtering procedures, implantation of drainage valves, antiplatelet therapy (e.g., aspirin, ticlopidine, and clopidogrel), anticoagulant therapy (e.g., warfarin and heparin), steroids, systemic or local corticosteroids (e.g., prednisone triamcinolone (Triesence®), and dexamethasone (Ozurdex®), steroid-sparing immunosuppressants (e.g., cyclosporine, azathioprine, cyclophosphamide, mycophenolate, mofetil, infliximab and etanercept), dietary supplements (e.g., vitamin C, vitamin E, lutein, zeaxanthin, zinc, folic acid, vitamins B6, vitamin B12, and zeaxanthin), vitrectomy, scleral buckle surgery, and pneumatic retinopexy].

In certain aspects, the present disclosure provides methods, as well as compositions, for treating or preventing a vascular disorder of the eye in a patient that has one or more of: anemia, myelodysplastic syndrome, sideroblastic anemia, a hemoglobinopathy, thalassemia, and sickle-cell disease by administering to the patient a therapeutically effective amount of an ActRII antagonist, or combination of ActRII antagonists. In some embodiments, the disclosure provides methods for using an ActRII antagonist, or combination of ActRII antagonists, to treat or prevent vascular disorders of the eye associated with ocular ischemia in a patient that has one or more of: anemia, myelodysplastic syndrome, sideroblastic anemia, a hemoglobinopathy, thalassemia, and sickle-cell disease. In some embodiments, the disclosure provides methods for using an ActRII antagonist, or combination of ActRII antagonists, to treat or prevent an ischemic ocular disease in a patient that has one or more of: anemia, myelodysplastic syndrome, sideroblastic anemia, a hemoglobinopathy, thalassemia, and sickle-cell disease. In some embodiments, the disclosure provides methods for using an ActRII antagonist, or combination of ActRII antagonists, to treat or prevent vascular disorders of the eye associated with microvasculature insufficiency in a patient that has one or more of: anemia, myelodysplastic syndrome, sideroblastic anemia, a hemoglobinopathy, thalassemia, and sickle-cell disease. In some embodiments, the disclosure provides methods for using an ActRII antagonist, or combination of ActRII antagonists, to treat or prevent an ocular microvasculature insufficiency disease in a patient that has one or more of: anemia, myelodysplastic syndrome, sideroblastic anemia, a hemoglobinopathy, thalassemia, and sickle-cell disease. In some embodiments, the disclosure provides methods for using an ActRII antagonist, or combination of ActRII antagonists, to treat or prevent vascular disorders of the eye associated with retinopathy in a patient that has one or more of: anemia, myelodysplastic syndrome, sideroblastic anemia, a hemoglobinopathy, thalassemia, and sickle-cell disease. In some embodiments, the disclosure provides methods for using an ActRII antagonist, or combination of ActRII antagonists, to treat or prevent vascular disorders of the eye associated with optic neuropathy in a patient that has one or more of: anemia, myelodysplastic syndrome, sideroblastic anemia, a hemoglobinopathy, thalassemia, and sickle-cell disease. In some embodiments, the disclosure provides methods for using an ActRII antagonist, or combination of ActRII antagonists, to treat or prevent ischemic retinopathy in a patient that has one or more of: anemia, myelodysplastic syndrome, sideroblastic anemia, a hemoglobinopathy, thalassemia, and sickle-cell disease. In some embodiments, the disclosure provides methods for using an ActRII antagonist, or combination of ActRII antagonists, to treat or prevent ischemic optic neuropathy in a patient that has one or more of: anemia, myelodysplastic syndrome, sideroblastic anemia, a hemoglobinopathy, thalassemia, and sickle-cell disease. In some embodiments, the disclosure provides methods for using an ActRII antagonist, or combination of ActRII antagonists, to treat or prevent retinopathy associated with microvasculature insufficiency in a patient that has one or more of: anemia, myelodysplastic syndrome, sideroblastic anemia, a hemoglobinopathy, thalassemia, and sickle-cell disease. In some embodiments, the disclosure provides methods for using an ActRII antagonist, or combination of ActRII antagonists, to treat or prevent optic neuropathy associated with microvasculature insufficiency in a patient that has one or more of: anemia, myelodysplastic syndrome, sideroblastic anemia, a hemoglobinopathy, thalassemia, and sickle-cell disease. In some embodiments, methods and compositions disclosed herein for treating an ocular disease in a patient that has one or more of: anemia, myelodysplastic syndrome, sideroblastic anemia, a hemoglobinopathy, thalassemia, and sickle-cell disease result in improving vision in an eye of the patient. In some embodiments, methods and compositions disclosed herein for treating a vascular disorder of the eye in a patient that has one or more of: anemia, myelodysplastic syndrome, sideroblastic anemia, a hemoglobinopathy, thalassemia, and sickle-cell disease result in increasing visual acuity in an eye of the patient. In some embodiments, methods and compositions disclosed herein for treating an vascular disorder of the eye in a patient that has one or more of: anemia, myelodysplastic syndrome, sideroblastic anemia, a hemoglobinopathy, thalassemia, and sickle-cell disease result in increasing visual field in an eye of the patient. Optionally, methods of the disclosure for treating or preventing an ocular disease in a patient that has one or more of: anemia, myelodysplastic syndrome, sideroblastic anemia, a hemoglobinopathy, thalassemia, and sickle-cell disease may further comprise administration of one or more supportive therapies for treating or preventing the vascular disorder of the eye in addition to administration of an ActRII antagonist, or combination of ActRII antagonists.

In certain aspects, the present disclosure provides methods and compositions for treating or preventing a vascular disorder of the eye in a patient (subject) having myelodysplastic syndrome (particularly mammals such as rodents, cats, dogs, primates, and humans) by administering to the patient a therapeutically effective amount of an ActRII antagonist, or combination of ActRII antagonists. In some embodiments, the disclosure provides methods for using an ActRII antagonist, or combination of ActRII antagonists, to treat or prevent a vascular disorder of the eye associated with ocular ischemia in a patient having myelodysplastic syndrome. In some embodiments, the disclosure provides methods for using an ActRII antagonist, or combination of ActRII antagonists, to treat or prevent an ischemic ocular disease in a patient having myelodysplastic syndrome. In some embodiments, the disclosure provides methods for using an ActRII antagonist, or combination of ActRII antagonists, to treat or prevent a vascular disorder of the eye associated with microvasculature insufficiency in a patient having myelodysplastic syndrome. In some embodiments, the disclosure provides methods for using an ActRII antagonist, or combination of ActRII antagonists, to treat or prevent an ocular microvasculature insufficiency disease in a patient having myelodysplastic syndrome. In some embodiments, the disclosure provides methods for using an ActRII antagonist, or combination of ActRII antagonists, to treat or prevent a vascular disorder of the eye associated with retinopathy in a patient having myelodysplastic syndrome. In some embodiments, the disclosure provides methods for using an ActRII antagonist, or combination of ActRII antagonists, to treat or prevent a vascular disorder of the eye associated with optic neuropathy in a patient having myelodysplastic syndrome. In some embodiments, the disclosure provides methods for using an ActRII antagonist, or combination of ActRII antagonists, to treat or prevent ischemic retinopathy in a patient having myelodysplastic syndrome. In some embodiments, the disclosure provides methods for using an ActRII antagonist, or combination of ActRII antagonists, to treat or prevent ischemic optic neuropathy in a patient having myelodysplastic syndrome. In some embodiments, the disclosure provides methods for using an ActRII antagonist, or combination of ActRII antagonists, to treat or prevent retinopathy associated with microvasculature insufficiency in a patient having myelodysplastic syndrome. In some embodiments, the disclosure provides methods for using an ActRII antagonist, or combination of ActRII antagonists, to treat or prevent optic neuropathy associated with microvasculature insufficiency in a patient having myelodysplastic syndrome. In some embodiments, methods and compositions disclosed herein for treating a vascular disorder of the eye in a patient having myelodysplastic syndrome result in improving vision in an eye of the patient. In some embodiments, methods and compositions disclosed herein for treating a vascular disorder of the eye in a patient having myelodysplastic syndrome result in increasing visual acuity in an eye of the patient. In some embodiments, methods and compositions disclosed herein for treating a vascular disorder of the eye in a patient having myelodysplastic syndrome result in increasing visual field in an eye of the patient. Optionally, methods of the disclosure for treating or preventing a vascular disorder of the eye in a patient with myelodysplastic syndrome may further comprise administration of one or more supportive therapies for treating or preventing the ocular disease in addition to administration of an ActRII antagonist, or combination of ActRII antagonists.

In certain aspects, the present disclosure provides methods and compositions for improving vision (e.g., increasing visual acuity and or visual field) in a patient in need thereof by administering to the patient a therapeutically effective amount of an ActRII antagonist, or combination of ActRII antagonists. In some embodiments, the disclosure provides methods for using an ActRII antagonist, or combination of ActRII antagonists, to improve vision (e.g., increase visual acuity and or visual field) in a patient with a vascular disorder of the eye. In some embodiments, the disclosure provides methods for using an ActRII antagonist, or combination of ActRII antagonists, to improve vision (e.g., increase visual acuity and or visual field) in a patient with a vascular disorder of the eye associated with ischemic ocular disease. In some embodiments, the disclosure provides methods for using an ActRII antagonist, or combination of ActRII antagonists, to improve vision (e.g., increase visual acuity and or visual field) in a patient with a vascular disorder of the eye associated with microvasculature insufficiency. In some embodiments, the disclosure provides methods for using an ActRII antagonist, or combination of ActRII antagonists, to improve vision (e.g., increase visual acuity and or visual field) in a patient with ocular microvasculature insufficiency disease. In some embodiments, the disclosure provides methods for using an ActRII antagonist, or combination of ActRII antagonists, to improve vision (e.g., increase visual acuity and or visual field) in a patient with a vascular disorder of the eye associated with retinopathy. In some embodiments, the disclosure provides methods for using an ActRII antagonist, or combination of ActRII antagonists, to improve vision (e.g., increase visual acuity and or visual field) in a patient with a vascular disorder of the eye associated with optic neuropathy. In some embodiments, the disclosure provides methods for using an ActRII antagonist, or combination of ActRII antagonists, to improve vision (e.g., increase visual acuity and or visual field) in a patient with ischemic retinopathy. In some embodiments, the disclosure provides methods for using an ActRII antagonist, or combination of ActRII antagonists, to improve vision (e.g., increase visual acuity and or visual field) in a patient with ischemic optic neuropathy. In some embodiments, the disclosure provides methods for using an ActRII antagonist, or combination of ActRII antagonists, to improve vision (e.g., increase visual acuity and or visual field) in a patient with retinopathy associated with microvasculature insufficiency. In some embodiments, the disclosure provides methods for using an ActRII antagonist, or combination of ActRII antagonists, to improve vision (e.g., increase visual acuity and or visual field) in a patient with optic neuropathy associated with microvasculature insufficiency. In particular, the disclosure provides methods for using an ActRII antagonist, or combination of ActRII antagonists, to improve vision (e.g., increase visual acuity and or visual field) in a patient with one or more diseases selected from: macular degeneration (e.g., age-related macular degeneration, juvenile macular degeneration, wet macular degeneration, dry macular degeneration, Stargardt's disease, and Best's disease), retinal vein occlusion (e.g, central retinal vein occlusion, hemi-retinal vein occlusion, branch retinal vein occlusion, and ischemic retinal vein occlusion), retinal artery occlusion (e.g, central retinal artery occlusion, hemi-retinal artery occlusion, branch retinal artery occlusion, and ischemic retinal artery occlusion), diabetic retinopathy, ischemic optic neuropathy [e.g., anterior ischemic optic neuropathy (arteritic and non-arteritic) and posterior ischemic optic neuropathy], macular telangiectasia (type I or type II), retinal ischemia (e.g., acute retinal ischemia or chronic retinal ischemia), ocular ischemic syndrome, retinal vasculitis, and retinopathy of prematurity. In some embodiments, the disclosure provides methods for using an ActRII antagonist, or combination of ActRII antagonists, to improve vision (e.g., increase visual acuity and or visual field) in a patient with anemia. In some embodiments, the disclosure provides methods for using an ActRII antagonist, or combination of ActRII antagonists, to improve vision (e.g., increase visual acuity and or visual field) in a patient with myelodysplastic syndrome. In some embodiments, the disclosure provides methods for using an ActRII antagonist, or combination of ActRII antagonists, to improve vision (e.g., increase visual acuity and or visual field) in a patient with sideroblastic anemia. In some embodiments, the disclosure provides methods for using an ActRII antagonist, or combination of ActRII antagonists, to improve vision (e.g., increase visual acuity and or visual field) in a patient with a hemoglobinopathy. In some embodiments, the disclosure provides methods for using an ActRII antagonist, or combination of ActRII antagonists, to improve vision (e.g., increase visual acuity and or visual field) in a patient with thalassemia. In some embodiments, the disclosure provides methods for using an ActRII antagonist, or combination of ActRII antagonists, to improve vision (e.g., increase visual acuity and or visual field) in a patient with sickle-cell disease. Optionally, methods of the disclosure for improving vision (e.g., increasing visual acuity and or visual field) in a patient with an ocular disease may further comprise administration of one or more supportive therapies for treating or preventing the ocular disease in addition to administration of an ActRII antagonist, or combination of ActRII antagonists.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" as used herein includes amelioration or elimination of the condition once it has been established. In either case, prevention or treatment may be discerned in the diagnosis provided by a physician or other health care provider and the intended result of administration of the therapeutic agent.

In general, treatment or prevention of a disease or condition as described in the present disclosure is achieved by administering one or more of ActRII antagonists (e.g., an ActRIIA and/or ActRIIB antagonist) in an effective amount. An effective amount of an agent refers to an amount effective, at dosages and for periods of time necessary, to achieve the desired therapeutic or prophylactic result. A therapeutically effective amount of an agent of the present disclosure may vary according to factors such as the disease state, age, sex, and weight of the individual, and the ability of the agent to elicit a desired response in the individual. A prophylactically effective amount refers to an amount effective, at dosages and for periods of time necessary, to achieve the desired prophylactic result.

Ocular damage is a complication/manifestation of myelodysplastic syndrome [Han et al. (2015) J Glaucoma (Epub ahead of print); [Brouzas et al. (2009) Clinical Ophthalmology 3:133-137]. Applicants have discovered that treatment with an ActRII inhibitor has a surprising effect on improving vision in an MDS patient. Insight into the mechanism for vision loss in MDS patients suggests that ActRII inhibitor therapy may also be useful in the treatment of other vascular disorders of the eye, particularly those associated with ischemia and/or microvasculature insufficiency. For example, in addition to MDS, other hematological disorders have been associated with ocular damage including, for example, hemoglobinopathy diseases (e.g., sickle cell disease and thalassemia) [de Melo M. B. (2014) Rev Hematol Hemoter 36(5):319-321; and Aksoy et al. (2013) Seminars in Ophthalmology 28(1): 22-26].

Therefore, in certain aspects, the present disclosure provides methods and compositions for improving vision (e.g., visual acuity and/or visual field) in a patient with a hematological disorder by administering one or more ActRII antagonist (e.g., a GDF-ActRII antagonist, an ActRIIA polypeptide, an ActRIIB polypeptide, a GDF trap, etc.). In some embodiments, an ActRII antagonist, or combination of ActRII antagonists, can be used to improve vision (e.g., improve visual acuity and/or visual field) in a patient with anemia. In some embodiments, an ActRII antagonist, or combination of ActRII antagonists, can be used to improve vision (e.g., improve visual acuity and/or visual field) in a patient with MDS. In some embodiments, an ActRII antagonist, or combination of ActRII antagonists, can be used to improve vision (e.g., improve visual acuity and/or visual field) in a patient with a hemoglobinopathy. In some embodiments, an ActRII antagonist, or combination of ActRII antagonists, can be used to improve vision (e.g., improve visual acuity and/or visual field) in a patient with thalassemia. In some embodiments, an ActRII antagonist, or combination of ActRII antagonists, can be used to improve vision (e.g., improve visual acuity and/or visual field) in a patient with sickle cell disease. In some embodiments, an ActRII antagonist, or combination of ActRII antagonists, can be used to improve vision (e.g., improve visual acuity and/or visual field) in a patient with sideroblastic anemia. Optionally, patients having a hematological disorder (e.g., myelodysplastic syndrome, sideroblastic anemia, thalassemia, sickle cell disease, anemia, a hemoglobinopathy, or sideroblastic anemia) and in need of improved vision (improved visual acuity and/or visual field) may be treated with one or more supportive therapies for treating the hematological disorder in addition to an ActRII antagonist, or combination of ActRII antagonists.

Retinal ischemia is a common disease and, due to relatively ineffective treatment, remains a common cause of visual impairment and blindness in the industrialized world [Osborne et al. (2004) Progress in Retinal and Eye Research 23:91-147]. Ischemia refers to a pathological situation involving an inadequacy (not necessarily a complete lack of) blood flow to a tissue, with failure to meet cellular energy demands. In general, ischemia deprives a tissue of three requirements: oxygen, metabolic substrates, and removal of waste products. The loss of these requirements will initially lower homeostatic responses and with time will induce injury to the tissue. If withheld for a sufficiently long time, the tissue will die (an infarct). At a cellular level, ischemic retinal injury consists of a self-reinforcing destructive cascade involving neuronal depolarization, calcium influx, and oxidative stress initiated by energy failure and increased glutamatergic stimulation. Ultimately ischemic damage can lead to loss of cells in the retina including, for example, photoreceptors, ganglion cells and amacrine cells.

Retinal ischemia can be caused by a variety of conditions including, for example, stroke, ocular injury, and diabetes. It is also commonly caused when the central retinal vein becomes occluded or detached from the eye. When the retina loses its oxygen supply, the body tries to compensate by producing various vascular modifying agents including, for example, Vascular Endothelial Growth Factor (VEGF). Unfortunately, this can lead to the growth of abnormal blood vessels on the surface of the retina, leading to blindness. In fact, it has been suggested ischemia is responsible for retinal neovascularization in patients with retinal vein occlusion, diabetes, sickle-cell retinopathy, and retinopathy of prematurity, all of which can ultimately result in retinal vessel hemorrhage and/or retinal detachment [Osborne et al. (2004) Progress in Retinal and Eye Research 23:91-147].

Retinal ischemia can manifest as a chronic or acute disease. Generally, retinal ischemia is first localized to one eye, but it often progresses to affect both eyes over time. In most cases, a patient with retinal ischemia presents with a painless loss of visual acuity and visual field associated with optic disc swelling. The age range of patients with this condition is extensive, and depends in part on the cause of the ischemia. Some patients, however, simply experience sudden visual loss. The degree of visual loss may be severe or the patient may notice only a vague sensation of blurred vision, often described as a shade or veil over a portion of the visual field. Vision loss varies and may cause severe impairment in the visual field and visual acuity. Once occurred, the loss of vision is usually permanent although some recovery is possible in the early stages with appropriate treatment.

There are various ocular and systemic treatments available for treating retinal ischemia, many with limited efficacy and/or potential adverse side effects. These treatments include, for example: surgery, laser therapy (e.g., photocoagulation), anticoagulants (e.g., aspirin and PAF inhibitors), anti-angiogenic therapy (e.g., VEGF inhibitors), $Ca^{2+}$ inhibitors (e.g., flunarizine and nifedipine), cryotherapy, hyperbaric oxygenation, $Na^+$ channel blockers (e.g., topiramate), iGluR antagonists (e.g., MK-801, dextromethorphan, eliprodil, and flupirtine), antioxidants (e.g., dimethylthiourea, vitamin E, alph-lipoic acid, superoxide dismutase, catalase, desferrioxamine, mannitol, allopurinol, calcium dobesilate, flupirtine, trimetazidine, and EGB-761), and anti-inflammatory agents.

In certain aspects, the present disclosure provides methods, as well as compositions, for treating or preventing retinal ischemia in a patient in need thereof by administering one or more ActRII antagonists [e.g., an ActRII polypeptide or variant thereof (e.g., a GDF trap)]. In some embodiments, an ActRII antagonist, or combination of ActRII antagonists, can be used to treat or prevent one or more of: acute retinal ischemia and chronic retinal ischemia. In some embodiments, an ActRII antagonist, or combination of ActRII antagonists, can be used to treat or prevent one or more complication of retinal ischemia selected from: cataracts, corneal edema, ocular hypotony, increased ocular pressure, anterior chamber inflammation, neovascular glaucoma, and iris neovascularization, narrowed retinal arteries, dilated retinal veins, retinal hemorrhages, cotton-wool spots, cherry-red spot, optic nerve neovascularization, retinal neovascularization, ischemic ocular pain, and amaurosis *fugax*. In some embodiments, an ActRII antagonist, or combination of ActRII antagonists, can be used to improve vision (e.g., improve visual acuity and/or visual field) in a patient with retinal ischemia. Optionally, patients afflicted with retinal ischemia may be treated with one or more supportive therapies [e.g., surgery, laser therapy (e.g., photocoagulation), topical medication to lower intraocular pressure, cyclodiathermy, cyclocryotherapy, intravitreal steroids, ocular filtering procedures, implantation of glaucoma drainage valves to treat neovascular glaucoma, antiplatelet therapy (e.g., aspirin, ticlopidine, and clopidogrel), anticoagulant therapy (e.g., warfarin and heparin), and systemic steroid therapy, anti-angiogenic therapy (e.g., VEGF inhibitors), $Ca^{2+}$ inhibitors (e.g., flunarizine and nifedipine), cryotherapy, hyperbaric oxygenation, $Na^+$ channel blockers (e.g., topiramate), iGluR antagonists (e.g., MK-801, dextromethorphan, eliprodil, and flupirtine), antioxidants (e.g., dimethylthiourea, vitamin E, alpha-lipoic acid, superoxide dismutase, catalase, desferrioxamine, mannitol, allopurinol, calcium dobesilate, flupirtine, trimetazidine, and EGB-761), and anti-inflammatory agents] for treating retinal ischemia in addition to an ActRII antagonist, or combination of ActRII antagonists.

Ocular ischemic syndrome (OIS) is a rare disease in which gradual or sudden loss of vision results from chronic vascular insufficiency [Brown et al (1994) Ocular ischemic syndrome. In: Retina. 2nd ed. Mosby. 1515-27; and Chen et al. (2007) *Compr Ophthalmol Update.* 8(1):17-28]. The most common etiology of OIS is sever unilateral or bilateral atherosclerotic disease of the internal carotid artery or marked stenosis at the bifurcation of the common carotid artery. OIS may also be caused by giant cell arteritis. It is postulated that the decrease in vascular perfusion results in tissue hypoxia and increased ocular ischemic, which typically results in neovascularization. The disease is found most often in patients with other risk factors for cardiovascular disease, such as diabetes mellitus, hyperlipidemia, and hypertension. Common anterior pathology includes cataracts, corneal edema, ocular hypotony, increased ocular pressure, anterior chamber inflammation, neovascular glaucoma, and iris neovascularization. Posterior segment signs include narrowed retinal arteries, dilated but nontortuour retinal veins, retinal hemorrhages, cotton-wool spots, cherry-red spot, and optic nerve/retinal neovascularization.

Principal symptoms of OIS include visual loss, light-induced transient visual loss, amaurosis *fugax*, and ischemic ocular pain [Mizener et al. (1997) Ophthalmology. 104(5): 859-64; and Chen et al. (2007) Compr Ophthalmol Update. 8(1):17-28]. Loss of visual acuity is the most frequently encountered symptom, present in 70-90% of patients. While visual loss typically occurs gradually over a period of weeks to months, it can also occur abruptly. About 40% of patients with OIS will present with symptoms of ischemic pain. In general, the pain is characteristically described as a dull ache over the brow, which beings gradually over a prior of hours to days. Amaurosis *fugax* is a transient episode of complete or partial monocular blindness lasting for a period of less than about 10 minutes. A history of amaurosis *fugax* is found in about 9-15% of patients with OIS.

There are various ocular and systemic treatments available for treating OIS, many with limited efficacy and/or potential adverse side effects. Ocular treatments include, for example: surgery or laser therapy (e.g., panretinal photocoagulation) to treat neovascularization of the iris, optic nerve, or retina; topical medication to lower intraocular pressure, cyclodiathermy and cyclocryotherapy to lower intraocular pressure; intravitreal steroids; and ocular filtering procedures and implantation of glaucoma drainage valves to treat neovascular glaucoma. System treatments include, for example: antiplatelet therapy (e.g., aspirin, ticlopidine, and clopidogrel), anticoagulant therapy (e.g., warfarin and heparin), and steroids.

In certain aspects, the present disclosure provides methods, as well as compositions, for treating or preventing ocular ischemic syndrome in a patient in need thereof by administering one or more ActRII antagonists [e.g., an ActRII polypeptide or variant thereof (e.g., a GDF trap)]. In some embodiments, an ActRII antagonist, or combination of ActRII antagonists, can be used to treat or prevent one or more complication of ocular ischemic syndrome selected from: cataracts, corneal edema, ocular hypotony, increased ocular pressure, anterior chamber inflammation, neovascular glaucoma, and iris neovascularization, narrowed retinal arteries, dilated retinal veins, retinal hemorrhages, cotton-wool spots, cherry-red spot, optic nerve neovascularization, retinal neovascularization, ischemic ocular pain, and amaurosis *fugax*. In some embodiments, an ActRII antagonist, or combination of ActRII antagonists, can be used to improve vision (e.g., improve visual acuity and/or visual field) in a patient with ocular ischemic syndrome. Optionally, patients afflicted with ocular ischemic syndrome may be treated with one or more supportive therapies [e.g., panretinal photocoagulation, topical medication to lower intraocular pressure, cyclodiathermy, cyclocryotherapy, intravitreal steroids, ocular filtering procedures, implantation of glaucoma drainage valves to treat neovascular glaucoma, antiplatelet therapy (e.g., aspirin, ticlopidine, and clopidogrel), anticoagulant therapy (e.g., warfarin and heparin), and systemic steroid therapy] for treating ocular ischemic syndrome in addition to an ActRII antagonist, or combination of ActRII antagonists.

Ischemic optic neuropathy (ION) is a sudden loss of central vision, side vision, or both due to a decreased or interrupted blood flow to the eye's optic nerve. There are two major categories of of ION: posterior ischemic optic neuropathy (PION) and anterior ischemic optic neuropathy (AION). AION is generally categorized as either arteritic AION (AAION) or non-arteritic AION (NAION).

PION is generally characterized by damage to the retrobulbar portion of the optic nerve due to ischemia. Despite the term posterior, this pathophysiology may be applied to cases wherein the ischemic damage is anterior, as the condition describes a particular mechanism of visual loss as much as the location of damage in the optic nerve. AION is distinguished by the fact that it occurs spontaneously and unilaterally in patients with predisposing conditions and/or cardiovascular risk factors. PION typically occurs in two categories of patients: i) patients who have undergone a non-ocular surgery that is particularly prolonged or is associated with significant blood loss, and ii) patients who have experienced significant hemorrhaging from an accident or ruptured blood vessel. Patients with a history of high blood pressure, diabetes, and smoking are most susceptible to PION as they generally have a compromised blood vessel autoregulation.

AAION results from temporal arteritis (also called giant cell arteritis), which is an inflammatory disease of medium-sized blood vessels generally occurring in older adults. Most cases of AAION result in near complete vision loss in one eye. If left untreated, the second eye will likely suffer vision loss as well within 1-2 weeks. In contrast, NAION is more frequently observed in slightly younger groups and results from the coincidence of cardiovascular risk factors (e.g., diabetes, hypertension, and high cholesterol levels) in patients with a type of optic disk shape often referred to as "crowded disc" or "disk at risk".

It was once believed that ION damage could not be reversed. However, recent studies have shown improvement of visual acuity in patients who are treated with large doses of corticosteroids (e.g., prednisone) during the early stages of ION [Hayreh et al. (2008) Graefe's Archive for Clinical Experimental Opthalmology 246(7): 1029-1046].

In certain aspects, the present disclosure provides methods and compositions for treating or preventing ischemic optic neuropathy in a patient in need thereof by administering one or more ActRII antagonists [e.g., an ActRII polypeptide or variant thereof (e.g., a GDF trap)]. In some embodiments, an ActRII antagonist, or combination of ActRII antagonists, can be used to treat or prevent one or more of: posterior ischemic optic neuropathy, anterior ischemic optic neuropathy, arteritic anterior ischemic optic neuropathy, and non-arteritic anterior ischemic optic neuropathy. In some embodiments, an ActRII antagonist, or combination of ActRII antagonists, can be used to improve vision (e.g., increase visual acuity and/or visual field) in a patient with one or more of: posterior ischemic optic neuropathy, anterior ischemic optic neuropathy, arteritic anterior ischemic optic neuropathy, and non-arteritic anterior ischemic optic neuropathy. Optionally, patients afflicted with ischemic optic neuropathy may be treated with one or more supportive therapies [e.g., a corticosteroid (prednisone)] for treating ischemic optic neuropathy in addition to an ActRII antagonist, or combination of ActRII antagonists.

Retinal vasculitis can be an isolated condition or a complication of local or systemic disorders characterized by inflammation of the retinal vessels [Walton et al. (2003) Current opinion in ophthalmology. 14(6):413-419; and Ali et al. (2014) The British journal of ophthalmology. 98(6):785-789]. Retinal vasculitis is generally classified based on location: large vessel vasculitis, medium vessel vasculitis, small vessel vasculitis, variable vessel vasculitis, and single-organ vasculitis. The classic feature of retinal vasculitis is presence of sheathing around the vessel wall. The perivascular sheathing is a collection of exudation consisting of inflammatory cells around the affected vessels. This results in appearance of a white cuff around the blood vessels. Patches of retinitis may accompany retinal vasculitis. These are seen in individuals with Adamantiades-Behçet's disease and infectious uveitis. Retinitis may be transient or may be accompanied by retinal necrosis. Intraretinal infiltrates can be sight-threatening and can lead to retinal atrophy, breaks, and detachment. Retinal vasculitis may result in microinfarcts of the retinal nerve fiber layer that manifests as diffuse, fluffy, cotton-wool like spots in the superficial retinal surface. Infectious forms of uveitis associated with retinal vasculitis can be associated with necrosis of retinal layers. Frosted branch angiitis is a descriptive term for retinal vasculitis characterized by severe infiltration of perivascular space with lymphoplasmacytic infiltrates. This gives an appearance of frosted branches of a tree. Occlusion of retinal vasculature secondary to inflammation may result in ischemia of the retina and development of capillary non-perfusion areas. These patients may be more predisposed to develop complications arising out of retinal non-perfusion, such as neovascularization and intraocular hemorrhage. This may result in development of a significant area of retinal non-perfusion. Various other complications that can result include rubeosis, tractional retinal detachment, neovascular glaucoma, and recurrent vitreous hemorrhage.

Non-infectious retinal vasculitis is managed by systemic or local corticosteroids (e.g., prednisone and triamcinolone) and steroid-sparing immunosuppressants (e.g., cyclosporine, azathioprine, cyclophosphamide, mycophenolate, mofetil, infliximab and etanercept). The local delivery of therapeutic agents may be done via intravitreal injections or periocular therapy, although the latter may not be sufficiently adequate for cases of severe retinal vasculitis. The choice of immunosuppressive agents must be tailored based on ocular manifestations, etiology and systemic co-morbidities. Apart from immunosuppression, various therapeutic options such as surgery, cryotherapy, and laser therapy (e.g., pan-retinal photocoagulation) may be used to control retinal vasculitis.

In certain aspects, the present disclosure provides methods and compositions for treating or preventing retinal vasculitis in a patient in need thereof by administering one or more ActRII antagonists [e.g., an ActRII polypeptide or variant thereof (e.g., a GDF trap)]. In some embodiments, an ActRII antagonist, or combination of ActRII antagonists, can be used to treat or prevent one or more of: large vessel vasculitis, medium vessel vasculitis, small vessel vasculitis, variable vessel vasculitis, and single-organ vasculitis. In some embodiments, an ActRII antagonist, or combination of ActRII antagonists, can be used to treat or prevent one or more complication of retinal vasculitis selected from: perivascular sheathing, retinitis, retinal necrosis, intraretinal infiltrates frosted branch capillary non-perfusion, neovascularization, intraocular hemorrhage, rubeosis, retinal detachment, neovascular glaucoma, and recurrent vitreous hemorrhage. In some embodiments, an ActRII antagonist, or combination of ActRII antagonists, can be used to improve vision (e.g., increase visual acuity and/or increase visual field) in a patient with retinal vasculitis (e.g., large vessel vasculitis, medium vessel vasculitis, small vessel vasculitis, variable vessel vasculitis, and single-organ vasculitis). Optionally, patients afflicted with retinal vasculitis may be treated with one or more supportive therapies [e.g., corticosteroids (e.g., prednisone and triamcinolone) and steroid-sparing immunosuppressants (e.g., cyclosporine, azathioprine, cyclophosphamide, mycophenolate, mofetil, infliximab and etanercept)] for treating retinal vasculitis in addition to an ActRII antagonist, or combination of ActRII antagonists.

Macular degeneration results in loss of vision in the center of the visual field (the macula) and generally is caused by damage to the retina [de Jong P T (2006) *N Engl J Med* 255(14): 1474-1485]. It is a major cause of blindness and visual impairment and usually occurs in older adults, afflicting around 20-50 million people globally. As it predominantly manifests in older adults, macular degeneration is often referred to as age-related macular degeneration. In younger patients, macular degeneration is often referred to as juvenile macular degeneration, which is generally the result of an underlying genetic disorder (e.g., Stargardt's disease or Best's disease) [Dryja et al. (1998) *Science* 279(5354): 1107]. In general, macular degeneration manifest as either "dry" (non-exudative) or "wet" (exudative) disease. In dry macular degeneration, yellow deposits (drusen) accumulate in the macular, between the retinal pigment epithelium and the underlying choroid. Large and/or numerous drusen depositions disrupt the pigmented cell layer under the macula, which may cause vision loss due to damaged photoreceptors (cones and rods). In general, wet macular degeneration results from abnormal blood vessel growth (choroidal neovascularization) from the choriocapillaris through the Bruch's membrane. These new vessels are fragile, leading to blood and protein leakage below the macula. Bleeding and scarring from these blood vessels can damage the photoreceptors and thus promote vision loss.

Unfortunately, there are limited treatments for dry macular degeneration. However, a large scientific study (The Age-Related Eye Disease Study 2) showed that, among people at high risk for developing late-stage macular degeneration, taking dietary supplements of vitamin C, vitamin E, lutein, and zeaxanthin in combination with zinc lowered progression to advance stages of the disease by at least 25% [Chew et al. (2013) *Ophthalmology* 120(8): 1604-1611]. Another large study in women showed benefits from taking folic acid and vitamins B6 and B12 [Christen et al. (2009) *Arch Intern Med* 169(4): 335-341]. Other studies have shown that lutein and zeaxanthin may reduce risk of developing dry macular degeneration [Chew et al. (2013) *Ophthalmology* 131(7): 843-850].

The most common therapy for wet macular degeneration is administration of one or more vascular endothelial growth factor (VEGF) antagonists (inhibitors) including, for example, bevacizumab, ranibizumab, and aflibercept. Bevacizumab (Avastin®) is humanized, monoclonal VEGF-A antibody. Similarly, ranibizumab (Lucentis®) is a monoclonal VEGF-A antibody fragment (Fab). Aflibercept (Eylea®) is an immunoglobulin Fc fusion protein comprising portions from the extracellular domains of human VEGF receptors 1 and 2. Although most cases are treated with medication, surgery or laser therapy may also be used to treat wet macular degeneration. In laser therapy, a focused beam of light is used to destroy abnormal blood vessels in the retina, preventing further aberrant vascular growth and leakage. In some cases, wet macular degeneration may be treated with photodynamic therapy, which uses a combination of a light-activated drug (photosensitizer) and a low-power laser. The photosensitive drug is injected into the patient and travels throughout the body, including in the abnormal vessels behind the eye. The low-powered laser is targeted directly on the abnormal vessels to activate the drug and thereby specifically damage the unwanted blood vessels.

In certain aspects, the present disclosure provides methods and compositions for treating or preventing macular degeneration in a patient in need thereof by administering one or more ActRII antagonists [e.g., an ActRII polypeptide or variant thereof (e.g., a GDF trap)]. In some embodiments, an ActRII antagonist, or combination of ActRII antagonists, can be used to treat or prevent one or more of: age-related macular degeneration, juvenile macular degeneration, Stargardt's disease, Best's disease, dry macular degeneration, and wet macular degeneration. In some embodiments, an ActRII antagonist, or combination of ActRII antagonists, can be used to treat or prevent one or more complication of macular degeneration including, for example, druse deposition/accumulation, macular edema, and neovacuolization. In some embodiments, an ActRII antagonist, or combination of ActRII antagonists, can be used to improve vision (e.g., increase visual acuity and/or increase visual field) in a patient with macular degeneration. Optionally, patients afflicted with macular degeneration may be treated with one or more supportive therapies [e.g., a VEGF antagonist (e.g., bevacizumab, ranibizumab, and aflibercept), surgery, laser therapy, photodynamic therapy, and/or dietary supplements (e.g., vitamin C, vitamin E, lutein, zeaxanthin, zinc, folic acid, vitamins B6, vitamin B12, and zeaxanthin)] for treating macular degeneration in addition to an ActRII antagonist, or combination of ActRII antagonists.

Diabetic retinopathy is an ocular manifestation of diabetes and is classified into two types: non-proliferative diabetic retinopathy (NPDR) and proliferative diabetic retinopathy (PDR) [Semeraro et al. (2015) Journal of Diabetes Research 2015(582060) 1-16; Arden et al. (2011) Current Diabetes Reviews 7:291-304; and Eshaq et al. (2014) Redox Biology 2: 661-666]. NPDR is the early stage of the disease with generally mild, or non-existent, symptoms. In NPDR, the blood vessels in the retina are weakened causing microaneurysms. These microanuerysms can leak fluid into the retina, which may lead to macular edema. Accordingly, NPDR complications often manifest as microaneurysms, retinal hemorrhages, macular edema, and macular ischemia. PDR is the more advanced form of the disease. At this stage, circulation problems cause the retina to become oxygen deprived, which promotes formation of new, fragile blood vessels in the retina that can extend into the vitreous. This neovascularization may result in vitreous hemorrhage, which can cloud vision. Other complications of PDR include detachment of the retina due to scar tissue formation and the development of glaucoma. In some cases, increased fluid pressure inside the eye results in optic nerve damage. If left untreated, diabetic retinopathy can cause severe vision loss and even blindness.

Treatment of diabetic retinopathy is generally directed at maintaining visual acuity by monitoring the patient for and treating complications such as macular edema and neovascularization. Such complications of diabetic retinopathy may be treated, for example, by administering VEGF antagonists (e.g., bevacizumab, ranibizumab, and aflibercept) and/or corticosteroids (e.g., triamcinolone and dexamethasone). In some cases, diabetic retinopathy is treated with surgery, laser therapy (e.g., laser photocoagulation, modified grid laser photocoagulation, panretinal photocoagulation, and photodynamic therapy) and/or vitrectomy.

In certain aspects, the present disclosure provides methods and compositions for treating or preventing diabetic retinopathy in a patient in need thereof by administering one or more ActRII antagonists [e.g., an ActRII polypeptide or variant thereof (e.g., a GDF trap)]. In some embodiments, an ActRII antagonist, or combination of ActRII antagonists, can be used to treat or prevent one or more of: non-proliferative diabetic retinopathy and proliferative diabetic retinopathy. In some embodiments, an ActRII antagonist, or combination of ActRII antagonists, can be used to treat or prevent one or more complications of diabetic retinopathy including, for example, microaneurysms, retinal hemorrhages, macular edema, macular ischemia, neovascularization, glaucoma, vitreous hemorrhage, optical nerve damage, and retinal detachment. In some embodiments, an ActRII antagonist, or combination of ActRII antagonists, can be used to improve vision (e.g., increase visual acuity and/or increase visual field) in a patient with diabetic retinopathy. Optionally, patients afflicted with diabetic retinopathy may be treated with one or more supportive therapies [e.g., a VEGF antagonist (e.g., bevacizumab, ranibizumab, and aflibercept), a corticosteroid (triamcinolone and dexamethasone), surgery, laser therapy (e.g., laser photocoagulation, modified grid laser photocoagulation, panretinal photocoagulation, and photodynamic therapy), and/or vitrectomy] for treating diabetic retinopathy in addition to an ActRII antagonist, or combination of ActRII antagonists.

Retinal occlusion is a common vascular disorder of the retina and one of the most common causes of vision loss worldwide [Klein et al. (2000) Tran Am Opthalmol Soc. 98: 133-141]. Retinal occlusion may manifest as retinal arterial occlusion (RAC) or as retinal vein occlusion (RVO). Retinal occlusion is classified according to where the occlusion is located. Occlusion of the central vein at the level of the optic nerve is referenced to as central arterial/retinal vein occlusion (CRAO and CRVO). Occlusion at the primary superior branch or primary inferior branch involving approximately half of the retina is referred to as hemi-retinal arterial/retinal occlusion (HRAO and HRVO). Obstruction at any more distal branches of the retinal is referred to as branch retinal arterial/retinal occlusion (BRAO and BRVO). The location of the occlusion influences the pathogenesis, clinical presentation, and management of retinal occlusion. Retinal occlusion is further subdivided into non-ischemic and ischemic types, according to the amount of retinal capillary ischemia observed.

In general, retinal occlusion is a blockage of a portion of the circulation that supplies blood (RAC) or drains blood (RVO) from the retina. With blockage, pressure builds up in the capillaries, leading to hemorrhage and leakage of fluid and blood. This can cause edema in the macula. Macular ischemia can also develop within these capillaries, which supply oxygen to the retina. Reduced oxygen and nutrient availability promotes neovascularization, which can lead to neovascular glaucoma, vitreous hemorrhage, retinal detachment. Visual morbidity and blindness generally results from a combination of these factors.

Treatment of retinal occlusion is generally directed at maintaining visual acuity by monitoring the patient for and treating complications such as macular edema and neovascularization. Such complications may be treated with VEGF antagonists (e.g., bevacizumab, ranibizumab, and aflibercept) and/or corticosteroids including, for example, triamcinolone (Triesence®) and dexamethasone (Ozurdex®). In some cases, retinal occlusion treated with surgery or laser therapy, including certain types of photodynamic therapy techniques. In refractory cases, vitrectomy may be required, which involves removing the vitreous and replacing it with a saline solution.

In certain aspects, the present disclosure provides methods and compositions for treating or preventing retinal occlusion in a patient in need thereof by administering one or more ActRII antagonists [e.g., an ActRII polypeptide or variant thereof (e.g., a GDF trap)]. In some embodiments, an ActRII antagonist, or combination of ActRII antagonists, can be used to treat or prevent one or more of: central retinal vein occlusion, hemi-retinal vein occlusion, branch retinal vein occlusion, ischemic retinal vein occlusion, non-ischemic retinal vein occlusion, central retinal artery occlusion, hemi-retinal artery occlusion, branch retinal artery occlusion, ischemic retinal artery occlusion, and non-ischemic retinal artery occlusion. In some embodiments, an ActRII antagonist, or combination of ActRII antagonists, can be used to treat or prevent one or more complication of retinal occlusion including, for example, macular edema, macular ischemia, neovascularization, glaucocma, and retinal detachment. In some embodiments, an ActRII antagonist, or combination of ActRII antagonists, can be used to improve vision (e.g., increase visual acuity and/or increase visual field) in a patient with retinal occlusion. Optionally, patients afflicted with retinal occlusion may be treated with one or more supportive therapies [e.g., a VEGF antagonist (e.g., bevacizumab, ranibizumab, and aflibercept), a corticosteroid (triamcinolone and dexamethasone), surgery, laser therapy, photodynamic therapy, and vitrectomy] for treating retinal occlusion in addition to an ActRII antagonist, or combination of ActRII antagonists.

Macular telangiectasia is characterized by damage around the fovea, which is the center of the macula, and manifests in two forms. Type 2 macular telangiectasia is the most common form of the disease and manifests as leakage of the blood vessels around the fovea. This leakage can lead to macular edema and neovascularization, affecting central vision due, in part, to vitreous hemorrhage. Also, scar tissue can form over the macular and the fovea, causing loss of detailed vision. Type 2 macular telangiectasia affects both eyes but not necessarily with the same severity. In Type 1 macular telangiectasia, the blood vessels around the fovea become dilated forming tiny aneurysms, which can promote macular edema and neovascularization. Type 1 macular telangiectasia almost always occurs in one eye, which differentiates it from the Type 2 form of the disease Treatment of macular telangiectasia is generally directed at maintaining visual acuity by monitoring the patient for and treating complications such as macular edema and neovascularization. Such complications of macular telangiectasia may be treated by administering VEGF antagonists (e.g., bevacizumab, ranibizumab, and aflibercept). In some cases, macular telangiectasia treated with surgery, laser therapy (e.g., laser photocoagulation, modified grid laser photocoagulation, panretinal photocoagulation, and photodynamic therapy) and/or vitrectomy.

In certain aspects, the present disclosure provides methods and compositions for treating or preventing macular telangiectasia in a patient in need thereof by administering one or more ActRII antagonists [e.g., an ActRII polypeptide or variant thereof (e.g., a GDF trap)]. In some embodiments, an ActRII antagonist, or combination of ActRII antagonists, can be used to treat or prevent one or more of: Type 2 macular telangiectasia and Type 1 macular telangiectasia. In some embodiments, an ActRII antagonist, or combination of ActRII antagonists, can be used to treat or prevent one or more complication of macular telangiectasia including, for example, microaneurysms, macular edema, neovascularization, and vitreous hemorrhage. In some embodiments, an ActRII antagonist, or combination of ActRII antagonists, can be used to improve vision (e.g., increase visual acuity and/or increase visual field) in a patient with macular telangiectasia. Optionally, patients afflicted with macular telangiectasia may be treated with one or more supportive therapies [e.g., a VEGF antagonist (e.g., bevacizumab, ranibizumab, and aflibercept), surgery, laser therapy (e.g., laser photocoagulation, modified grid laser photocoagulation, panretinal photocoagulation, and photodynamic therapy), and vitrectomy] for treating retinal macular telangiectasia in addition to an ActRII antagonist, or combination of ActRII antagonists.

Retinopathy of prematurity (ROP), also referred to as Terry syndrome or retrolental fibroplasia, is an ocular disease that occurs in premature babies having abnormal blood vessel growth around the retina [Phelps D. L. (2001) *Neo-Review* 2(7):153-166]. Neovascularization around the retina can result in macular edema and vitreous hemorrhage, impairing vision. In some cases, neovascularization leads to scar tissue formation around the retina, which can promote retinal detachment. Patients with ROP, particularly those who developed severe disease, are a greater risk for myopia (near-sightedness), amblyopia (lazy eye), strabismus (misaligned eyes), cataracts, and glaucoma later in life.

Treatment of ROP is generally directed at maintaining visual acuity by monitoring the patient for and treating complications such as macular edema, retinal hemorrhages, neovascularization, vitreous hemorrhage, and retinal detachment. Such complications of ROP may be treated by administering VEGF antagonists (e.g., bevacizumab, ranibizumab, and aflibercept). In some cases, ROP is treated with surgery, laser therapy (e.g., laser photocoagulation, modified grid laser photocoagulation, panretinal photocoagulation, and photodynamic therapy) and/or vitrectomy. Scleral buckle surgery and pneumatic retinopexy are common ophthalmologic procedures for repair retinal detachment. Recently, beta-blockers (e.g., propranolol) were demonstrated slow the progression of ROP, particularly by inhibiting retinal angiogenesis and thus ameliorating blood-retinal barrier dysfunction [Ristori C. (2001) *Invest Ophthalmol Vis Sci* 52(1): 155-170].

In certain aspects, the present disclosure provides methods and compositions for treating or preventing retinopathy of prematurity in a patient in need thereof by administering one or more ActRII antagonists [e.g., an ActRII polypeptide or variant thereof (e.g., a GDF trap)]. In some embodiments, an ActRII antagonist, or combination of ActRII antagonists, can be used to treat or prevent one or more complication of retinopathy of prematurity including, for example, retinal hemorrhages, macular edema, neovascularization, vitreous hemorrhage, and retinal detachment. In some embodiments, an ActRII antagonist, or combination of ActRII antagonists, can be used to improve vision (e.g., increase visual acuity and/or increase visual field) in a patient with retinopathy of prematurity. Optionally, patients afflicted with retinopathy of prematurity may be treated with one or more supportive therapies [e.g., a VEGF antagonist (e.g., bevacizumab, ranibizumab, and aflibercept), a beta blocker (propranolol), surgery, laser therapy (e.g., laser photocoagulation, modified grid laser photocoagulation, panretinal photocoagulation, and photodynamic therapy), vitrectomy, scleral buckle surgery, and/or pneumatic retinopexy] for treating retinopathy of prematurity in addition to an ActRII antagonist, or combination of ActRII antagonists.

As used herein, "in combination with" or "conjoint administration" refers to any form of administration such that additional therapies (e.g., second, third, fourth, etc.) are still effective in the body (e.g., multiple compounds are simultaneously effective in the patient, which may include synergistic effects of those compounds). Effectiveness may not correlate to measurable concentration of the agent in blood, serum, or plasma. For example, the different therapeutic compounds can be administered either in the same formulation or in separate formulations, either concomitantly or sequentially, and on different schedules. Thus, an individual who receives such treatment can benefit from a combined effect of different therapies. One or more ActRII antagonists (e.g., a GDF-ActRII antagonist, an ActRIIA polypeptide, an ActRIIB polypeptide, a GDF trap, antibody etc.) of the disclosure can be administered concurrently with, prior to, or subsequent to, one or more other additional agents or supportive therapies. In general, each therapeutic agent will be administered at a dose and/or on a time schedule determined for that particular agent. The particular combination to employ in a regimen will take into account compatibility of the antagonist of the present disclosure with the therapy and/or the desired.

Visual acuity (VA) is acuteness or clearness of vision, which is dependent, in part, on the sharpness of the retinal focus within the eye and the sensitivity of the interpretative faculty of the brain. Visual acuity is a measure of the spatial resolution of the visual processing system. In some embodiments, VA is tested by requiring the person whose vision is being tested to identify characters, typically numbers or letters, on a chart from a set distance. In general, chart characters are represented as black symbols against a white background. The distance between the person's eyes and the testing chart is set at a sufficient distance to approximate infinity in the way the lens attempts to focus. In some embodiments, twenty feet, or six meters, essentially infinity from an optical perspective.

One non-limiting means for measuring VA is the use of the ESV-3000 ETDRS testing device (see, U.S. Pat. No. 5,078,486), a self-calibrated test lighting. The ESV-3000 device incorporates LED light source technology. The auto-calibration circuitry constantly monitors the LED light source and calibrates the test luminance to 85 cd/m2 or 3 cd/m2. Although designed for clinical trials where large-format ETDRS testing (up to 20/200) is performed at 4 meters, the device can be used in a non-research setting, for example, a hospital or clinic where ocular disease monitoring is conducted. In some embodiments, the test is conducted under standardized lighting conditions, for example, photopic test level of 85 cd/m2. This light level has been recommended by the National Academy of Sciences and by the American National Standards Institute for ETDRS and contrast sensitivity vision testing. Scoring of visual acuity may be accomplished in any manner chosen by the monitor. After providing a baseline evaluation, the increase or decrease in the number of letters that can be identified by the test subject provides a measure of sight increase or decrease during treatment. Other methods of measure VA include, for example, the Snellen test, the E chart test, and the Near test.

In one aspect, the disclosure provides a method and compositions for increasing visual acuity in a subject having a vascular disorder of the eye as described herein. In general, these methods comprise administering to a patient in need thereof an effective amount of one or more ActRII antagonists. In some embodiments, the method provides a means for increasing the number of letters recognizable by a treated eye from about 1 to about 30 letters. In another embodiment, the number of letters recognizable is increased from about 5 to about 25 letters. In a further embodiment, the number of letters recognizable is increased from about 5 to about 20 letters. In another further embodiment, the number of letters recognizable is increased from about 5 to about 15 letters. In a still further embodiment, the number of letters recognizable is increased from about 5 to about 10 letters. In a yet another embodiment, the number of letters recognizable is increased from about 10 to about 25 letters. In a yet still further embodiment, the number of letters recognizable is increased from about 15 to about 25 letters. In yet still another embodiment, the number of letters recognizable is increased from about 20 to about 25 letters.

In general, visual field may be determined through visual field testing the full horizontal and vertical range of what a patient is able to see peripherally. This type of testing is usually performed with an automated perimetry test in which the patient stares at a source of light straight ahead and random lights of different densities are flashed in their peripheral field of vision. The patient presses a button or other means to indicate that they can see the light. Visual field tests that may be used in accordance with the methods described herein include for example, the Amsler grid test, the confrontation test, the perimetry test, and the tangent screen test.

In one aspect, the disclosure provides a method and compositions for increasing visual filed in a subject having a vascular disorder of the eye as described herein. In general, these methods comprise administering to a patient in need thereof an effective amount of one or more ActRII antagonists. In some embodiments, the method provides a means for increasing the visual field of a patient by at least 10% (e.g., at least 15%, at least 20%, at least 25%, at least 30%, at least 40%, at least 50%, at least 60%, at least 70%, at least 80%, at least 90%).

The most common causes of ineffective erythropoiesis are the thalassemia syndromes, hereditary hemoglobinopathies in which imbalances in the production of intact alpha- and beta-hemoglobin chains lead to increased apoptosis during erythroblast maturation (Schrier, 2002, Curr Opin Hematol 9:123-126). Thalassemias are collectively among the most frequent genetic disorders worldwide, with changing epidemiologic patterns predicted to contribute to a growing public health problem in both the U.S. and globally (Vichinsky, 2005, Ann NY Acad Sci 1054:18-24). Thalassemia syndromes are named according to their severity. Thus, α-thalassemias include α-thalassemia minor (also known as α-thalassemia trait; two affected α-globin genes), hemoglobin H disease (three affected α-globin genes), and α-thalassemia major (also known as hydrops fetalis; four affected α-globin genes). β-Thalassemias include β-thalassemia minor (also known as β-thalassemia trait; one affected β-globin gene), β-thalassemia intermedia (two affected β-globin genes), hemoglobin E thalassemia (two affected β-globin genes), and β-thalassemia major (also known as Cooley's anemia; two affected β-globin genes resulting in a complete absence of β-globin protein). β-Thalassemia impacts multiple organs, is associated with considerable morbidity and mortality, and currently requires life-long care. Although life expectancy in patients with β-thalassemia has increased in recent years due to use of regular blood transfusions in combination with iron chelation, iron overload resulting both from transfusions and from excessive gastrointestinal absorption of iron can cause serious complications such as heart disease, thrombosis, hypogonadism, hypothyroidism, diabetes, osteoporosis, and osteopenia (Rund et al, 2005, N Engl J Med 353:1135-1146).

ActRII antagonists, optionally in combination with one or more additional supportive therapies, can be used for treating a thalassemia syndromes.

ActRII antagonists, optionally in combination with one or more additional supportive therapies, can be used for treating disorders of ineffective erythropoiesis besides thalassemia syndromes. Such disorders include sideroblastic anemia (inherited or acquired); dyserythropoietic anemia (Types I and II); sickle cell anemia; hereditary spherocytosis; pyruvate kinase deficiency; megaloblastic anemias, potentially caused by conditions such as folate deficiency (due to congenital diseases, decreased intake, or increased requirements), cobalamin deficiency (due to congenital diseases, pernicious anemia, impaired absorption, pancreatic insufficiency, or decreased intake), certain drugs, or unexplained causes (congenital dyserythropoietic anema, refractory megaloblastic anemia, or erythroleukemia); myelophthisic anemias, including myelofibrosis (myeloid metaplasia) and myelophthisis; congenital erythropoietic porphyria; and lead poisoning.

Myelodysplastic syndromes (MDS) are a diverse collection of hematological disorders characterized by ineffective production of myeloid blood cells and risk of transformation to acute myeloid leukemia. In MDS patients, hematopoietic stem cells do not mature into healthy red blood cells, white blood cells, or platelets. MDS disorders include, for example, refractory anemia, refractory cytopenia with unilineage dysplasia (RCUD), refractory anemia with ringed sideroblasts (RARS), refractory anemia with ringed sideroblasts associated with marked thrombocytosis (RARS-T), refractory anemia with excess blasts (RAEB-1), refractory anemia with excess blasts in transformation (RAEB-2), refractory cytopenia with multilineage dysplasia (RCMD), MDS unclassified (MDS-U), and myelodysplastic syndrome associated with an isolated 5q chromosome abnormality [MDS with del(5q)].

MDS patients eventually require blood transfusions and/or treatment with erythropoietic growth factors (e.g., ESAs such as EPO) alone or in combination with a colony-stimulating factor [e.g., an analog of granulocyte colony-stimulating factor (G-CSF) such as filgrastim or an analog of granulocyte macrophage colony-stimulating factor (GM-GSF) such as sargramostim] to increase red blood cell levels. The frequency of transfusions depends on the extent of the disease and on the presence of comorbidities. Chronic transfusions are known to increase hemoglobin levels, which in turn improve brain and peripheral tissue oxygenation, thereby improving physical activity and mental alertness. However, many MDS patients develop side-effects from the use of such therapies. For example, patients who receive frequent red blood cell transfusions can develop tissue and organ damage from iron accumulation and generation of toxic reactive oxygen species. Accordingly, one or more ActRII antagonist agents of the disclosure (e.g., a GDF-ActRII antagonist, an ActRIIA polypeptide, an ActRIIB polypeptide, a GDF trap, etc.), optionally combined with an EPO receptor activator, may be used to treat patients with MDS or sideroblastic anemias. In certain embodiments, patients suffering from MDS or a siderblastic anemia may be treated using one or more ActRII antagonist agents of the disclosure (e.g., a GDF-ActRII antagonist, an ActRIIA polypeptide, an ActRIIB polypeptide, a GDF trap, etc.), optionally in combination with an EPO receptor activator. In other embodiments, patients suffering from MDS or a sideroblastic anemia may be treated using a combination of one or more ActRII antagonist agents of the disclosure (e.g., a GDF-ActRII antagonist, an ActRIIA polypeptide, an ActRIIB polypeptide, a GDF Trap, etc.) and one or more additional therapeutic agents for treating MDS including, for example, ESAs; G-CSF analogs, including filgrastim; GM-CSF analogs, including sargramostim; lenalidomide; thalidomide; pomalidomide, hypomethylating agents, including azacitidine and decitabine; iron-chelating agents, including deferoxamine and deferasirox; thrombopoietin mimetics, including romiplostim and eltrombopag; chemotherapeutic agents, including cytarabine (ara-C) alone or in combination with idarubicin, topotecan, or fludarabine; immunosuppressants, including antithymocyte globulin, alemtuzumab, and cyclosporine; histone deacetylase inhibitors (HDAC inhibitors), including vorinostat, valproic acid, phenylbutyrate, entinostat, MGCD0103, and other class I nuclear HDAC inhibitors, class II non-nuclear HDAC inhibitors, pan HDAC inhibitors, and isoform-specific HDAC inhibitors; farnesyltransferase inhibitors, including as tipifarnib and lonafarnib; tumor necrosis factor-alpha (TNF-α) inhibitors, including etanercept or infliximab; inhibitors of glutathione-S-transferase (GST) P1-1, including ezatiostat; and inhitors of CD33, including gemtuzumab ozogamicin.

As described herein, patients that exhibit ring sideroblasts may be particularly suited to treatment with ActRII antagonists. Sideroblastic anemias can be classified broadly into congenital (inherited) and acquired forms, which can be further subdivided as shown in Table 1.

TABLE 1

Classification of Sideroblastic Anemias*

| Class | Gene | Anemia Severity | Iron Homeostasis |
|---|---|---|---|
| Congenital | | | |
| Nonsyndromic | | | |
| X-linked | ALAS2 | Mild to severe | Iron overload |
| SLC25A38 deficiency | SLC25A38 | Severe | Iron overload |
| Glutaredoxin 5 deficiency | GLRX5 | Mild to severe | Iron overload |
| Erythropoietic protoporphyria | FECH | Mild | — |
| Syndromic | | | |
| X-linked with ataxia | ABCB7 | Mild to moderate | — |
| SIFD | Unknown | Severe | Iron overload |
| Pearson marrow-pancreas Syndrome | mtDNA | Severe | — |
| Myopathy, lactic acidosis, and sideroblastic anemia (MLASA) | PUS1/YARS2 | Mild to severe | — |
| Thiamine-responsive megaloblastic anemia (TRMA) | SLC19A2 | Severe | — |
| Syndromic/nonsyndromic of unknown cause | Unknown | Variable | — |
| Acquired | | | |
| Clonal/Neoplastic | | | |
| MDS** | Variable | Mild to severe | Iron overload |
| Metabolic | | | |
| Alcoholism | — | Variable | — |
| Drug-induced | — | Variable | — |
| Copper deficiency (zinc toxicity) | — | Variable | — |
| Hypothermia | — | Variable | — |

*See Bottomley et al., 2014, Hematol Oncol Clin N Am 28:653-670.
**See table below for MDS subclassifications according to the World Health Organization.

Novel sequencing techniques have led in the past few years to identification of dozens of genes that are recurrently mutated in MDS. A 2013 list of such genes classified by type is shown in Table 3. One or more such mutations can be found in almost all patients with MDS, and knowing the nature of the genes involved has improved understanding of how MDS develops and evolves, although it has not yet had an impact on treatment. Whole-genome sequencing applied to MDS patient samples has identified an entirely novel class of cancer-associated genes encoding mRNA splicing (spliceosome) factors. The first such gene identified in MDS was SF3B1, which is mutated particularly frequently in patients with RARS [Papaemmanuil et al. (2011) N Engl J Med 365:1384-1395]. Other major categories of mutated genes are epigenetic (DNA methylation) regulators, transcription factors, and signaling molecules [Cazzola et al. (2013) Blood 122:4021-4034; Bejar et al. (2014) Blood 124:2793-2803]. The extent to which these mutations co-occur in MDS patients seems to vary with gene type. For example, approximately 50% of MDS patients possess one of ten genes identified to date encoding mutant splicing factors, but these mutant genes rarely co-occur in the same patient [Bejar et al. (2014) Blood 124:2793-2803]. Thus, these mutant genes are seldom redundant markers for the same individuals. Genes encoding mutant epigenetic regulators co-occur more frequently with each other and with mutant splicing factor genes in the same patient. As disclosed herein, the differential occurrence of mutant genes such as those listed in Table 3 provides a genetic signature that can assist in predicting which patients with MDS or sideroblastic anemia are likely to be either responsive or nonresponsive therapeutically to an ActRII antagonist.

TABLE 3

MDS-Associated Somatic Mutations*

| Gene | Frequency in MDS (% cases) |
|---|---|
| RNA Splicing | |
| SF3B1 | 14-28 |
| SRSF2 | 15 |
| U2AF1 | 8 |
| ZRSR2 | 6 |
| PRPF40B | 1 |
| SF3A1 | 1 |
| SF1 | 1 |
| U2AF65 | <1 |
| LUC7L2 | Rare |
| PRPF8 | Rare |
| Epigenetic Regulators | |
| TET2 | 19-26 |
| ASXL1 | 10-20 |
| DNMT3A | 10 |
| IDH1/IDH2 | 4-12 |
| EZH2 | 6 |
| UTX | 1 |
| ATRX | <1 |
| Transcription Factors | |
| RUNX1 | 10-20 |
| TP53 | 4-14 |
| ETV6 | 1-3 |
| PHF6 | Rare |
| WT1 | Rare |
| Signaling | |
| NRAS | 10 |
| CBL | 3 |
| JAK2 | 3 |
| FLT3 | 2-3 |
| KRAS | 1-2 |
| c-KIT | 1 |
| BRAF | <1 |
| CDKN2A | <1 |
| GNAS | <1 |
| PTEN | <1 |
| PTPN11 | <1 |
| CBLB | Rare |
| MPL, CSF1R | Rare |
| Others | |
| NPM1 | 2-3 |

*From Tothova et al. (2013) Clin Cancer Res 19:1637-1643.

Among the genes listed in Table 3, the gene encoding splicing factor 3B1 (SF3B1) has been implicated recently as critical in MDS, particularly in the RARS, RARS-T, and RCMD-RS subtypes [Malcovati et al. (2011) Blood 118: 6239-6246; Dolatshad et al. (2014) Leukemia doi: 10.1038/leu.2014.331 epub ahead of print]. Somatic mutations in SF3B1 also occur in hematologic cancers including chronic lymphocytic leukemia (CLL), and acute myeloid leukemia (AML) as well as in breast cancer, pancreatic cancer, gastric cancer, prostate cancer, and uveal melanoma [Malcovati et al. (2011) Blood 118:6239-6246; Wang et al. (2011) N Engl J Med 365:2497-2506; The Cancer Genome Atlas Network (2012) Nature 490:61-70; Biankin et al. (2012) Nature 491:399-405; Chesnais et al. (2012) Oncotarget 3:1284-1293; Furney et al. (2013) Cancer Discov 3:1122-1129; Je et al. (2013) Int J Cancer 133:260-266]. A spectrum of SF3B1 mutations, many clustered at a few locations in the protein, have been identified in clinical samples or in cell lines exposed to high concentrations of pladienolide [Webb et al. (2013) Drug Discov Today 18:43-49]. SF3B1 mutations identified in MDS include, for example, K182E, E491G, R590K, E592K, R625C, R625G, N626D, N626S, H662Y, T663A, K666M, K666Q, K666R, Q670E, G676D, V701I, I704N, I704V, G740R, A744P, D781G, and A1188V. SF3B1 mutations identified in cancer include, for example, N619K, N626H, N626Y, R630S, I704T, G740E, K741N, G742D, D894G, Q903R, R1041H, and I1241T. Finally, SF3B1 mutations found in both MDS and cancer include, for example, G347V, E622D, Y623C, R625H, R625L, H662D, H662Q, T663I, K666E, K666N, K666T, K700E, and V701F.

In one embodiment of the disclosure, ActRII antagonists are useful for treating a vascular disorder of the eye in patients, including MDS patients or patients with sideroblastic anemia, in whom more than 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, or 95% of erythroid precursors are ring sideroblasts, e.g., in refractory anemia with ring sideroblasts (RARS), RARS associated with marked thrombocytosis (RARS-T), or refractory cytopenia with multilineage dysplasia (RCMD, also known as RCMD-RS in patients where ring sideroblasts are prominent).

Numerous genes contribute to classical sickle-cell disease (SCD; drepanocytosis). Primarily, sickle-cell disease is an inherited disorder caused by a mutation in the β-globin gene (a mutation of a glutamate to a valine at codon 6). See, e.g., Kassim et al. (2013) Annu Rev Med, 64: 451-466. Sickle-cell anemia refers to the most common form of sickle-cell disease, with a homozygous mutation in the $\beta^S$ allele (HbSS), affecting 60 to 70% of people with sickle-cell disease. Because of the mutation in the β-globin gene, abnormal hemoglobin molecules are produced with a hydrophobic motif that is exposed when it is in a deoxygenated state [see, e.g., Eaton et al. (1990) Adv Protein Chem, 40: 63-279; Steinberg, M H (1999) N Engl J Med 340(13): 1021-1030; and Ballas et al. (1992) Blood, 79(8): 2154-63]. Once exposed, the chains of the separate hemoglobin molecules polymerize, which results in damage to the red blood cell membrane and cellular dehydration. The membrane damage is manifested, in part, by a redistribution of membrane lipids leading to the expression of phosphatidylserine on the outer leaflet of the erythrocyte membrane [see, e.g., (2002) Blood 99(5): 1564-1571]. Externalized phosphatidylserine promotes adhesion to both macrophages and activated endothelial cells, which contributes to vascular (vaso) occlusion. Thus, at low oxygen states, the red cell's hemoglobin precipitates into long crystals that cause it to elongate, morphologically switching into a "sickled" red blood cell. Both genotype and the extent and degree of deoxygenation contribute to the severity of hemoglobin polymerization. It has been demonstrated that the presence of fetal hemoglobin proportionally reduces the amount of pathological hemoglobin polymers and is protective from vaso-occlusive crises.

The mainstay of treatment for the majority of patients with sickle-cell disease is supportive. Current treatment options for patients with sickle-cell disease include antibiotics, pain management [e.g., treatment with one or more narcotics, non-steroid anti-inflammatory drugs, and/or corticosteroids), intravenous fluids, blood transfusion, surgery, iron chelation therapy (e.g., deferroxamine) and hydroxyurea (e.g. Droxia®)]. In some embodiments, one or more ActRII antagonist agents of the disclosure (e.g., a GDF-ActRII antagonist, an ActRIIA polypeptide, an ActRIIB polypeptide, a GDF trap, etc.), may be used to treat sickle-cell disease in a patient in need thereof in combination with one or more additional agents and/or supportive therapies for treating sickle-cell disease (e.g., treatment with one or more narcotics, non-steroid anti-inflammatory drugs, and/or corticosteroids), intravenous fluids, blood transfusion, surgery, iron chelation therapy (e.g., deferroxamine) and hydroxyurea).

In certain embodiments, the present disclosure provides methods for managing a patient that has been treated with, or is a candidate to be treated with, one or more one or more ActRII antagonists of the disclosure [e.g., an ActRIIA polypeptide as well as variants thereof (e.g. a GDF trap)] by measuring one or more hematologic parameters in the patient. The hematologic parameters may be used to evaluate appropriate dosing for a patient who is a candidate to be treated with the antagonist of the present disclosure, to monitor the hematologic parameters during treatment, to evaluate whether to adjust the dosage during treatment with one or more antagonist of the disclosure, and/or to evaluate an appropriate maintenance dose of one or more antagonists of the disclosure. If one or more of the hematologic parameters are outside the normal level, dosing with one or more ActRII antagonists may be reduced, delayed, or terminated.

Hematologic parameters that may be measured in accordance with the methods provided herein include, for example, red blood cell levels, blood pressure, iron stores, and other agents found in bodily fluids that correlate with increased red blood cell levels, using art recognized methods. Such parameters may be determined using a blood sample from a patient. Increases in red blood cell levels, hemoglobin levels, and/or hematocrit levels may cause increases in blood pressure.

In one embodiment, if one or more hematologic parameters are outside the normal range or on the high side of normal in a patient who is a candidate to be treated with one or more ActRII antagonists, then onset of administration of the one or more antagonists may be delayed until the hematologic parameters have returned to a normal or acceptable level either naturally or via therapeutic intervention. For example, if a candidate patient is hypertensive or pre-hypertensive, then the patient may be treated with a blood pressure lowering agent in order to reduce the patient's blood pressure. Any blood pressure lowering agent appropriate for the individual patient's condition may be used including, for example, diuretics, adrenergic inhibitors (including alpha blockers and beta blockers), vasodilators, calcium channel blockers, angiotensin-converting enzyme (ACE) inhibitors, or angiotensin II receptor blockers. Blood pressure may alternatively be treated using a diet and exercise regimen. Similarly, if a candidate patient has iron stores that are lower than normal, or on the low side of normal, then the patient may be treated with an appropriate regimen of diet and/or iron supplements until the patient's iron stores have returned to a normal or acceptable level. For patients having higher than normal red blood cell levels and/or hemoglobin levels, then administration of the one or more antagonists of the disclosure may be delayed until the levels have returned to a normal or acceptable level.

In certain embodiments, if one or more hematologic parameters are outside the normal range or on the high side of normal in a patient who is a candidate to be treated with one or more ActRII antagonists agents, then the onset of administration may not be delayed. However, the dosage amount or frequency of dosing of the one or more antagonists may be set at an amount that would reduce the risk of an unacceptable increase in the hematologic parameters arising upon administration of the one or more antagonists of the disclosure. Alternatively, a therapeutic regimen may be developed for the patient that combines one or more ActRII antagonist agents (e.g., a GDF-ActRII antagonist, an ActRIIA polypeptide, an ActRIIB polypeptide, a GDF trap, etc.) with a therapeutic agent that addresses the undesirable level of the hematologic parameter. For example, if the patient has elevated blood pressure, then a therapeutic regimen may be designed involving administration of one or more ActRII antagonists and a blood pressure lowering agent. For a patient having lower than desired iron stores, a therapeutic regimen may be developed involving one or more ActRII antagonists and iron supplementation.

In one embodiment, baseline parameter(s) for one or more hematologic parameters may be established for a patient who is a candidate to be treated with one or more ActRII antagonists agents and an appropriate dosing regimen established for that patient based on the baseline value(s). Alternatively, established baseline parameters based on a patient's medical history could be used to inform an appropriate antagonist dosing regimen for a patient. For example, if a healthy patient has an established baseline blood pressure reading that is above the defined normal range it may not be necessary to bring the patient's blood pressure into the range that is considered normal for the general population prior to treatment with the one or more antagonist of the disclosure. A patient's baseline values for one or more hematologic parameters prior to treatment with one or more ActRII antagonists may also be used as the relevant comparative values for monitoring any changes to the hematologic parameters during treatment with the one or more antagonists described herein.

In certain embodiments, one or more hematologic parameters are measured in patients who are being treated with a one or more ActRII antagonists. The hematologic parameters may be used to monitor the patient during treatment and permit adjustment or termination of the dosing with the one or more antagonists of the disclosure or additional dosing with another therapeutic agent. For example, if administration of one or more ActRII antagonists results in an increase in blood pressure, red blood cell level, or hemoglobin level, or a reduction in iron stores, then the dose of the one or more antagonists of the disclosure may be reduced in amount or frequency in order to decrease the effects of the one or more antagonists of the disclosure on the one or more hematologic parameters. If administration of one or more ActRII antagonists results in a change in one or more hematologic parameters that is adverse to the patient, then the dosing of the one or more antagonists described herein may be terminated either temporarily, until the hematologic parameter(s) return to an acceptable level, or permanently. Similarly, if one or more hematologic parameters are not brought within an acceptable range after reducing the dose or frequency of administration of the one or more antagonists described herein, then the dosing may be terminated. As an alternative, or in addition to, reducing or terminating the dosing with the one or more antagonists described herein, the patient may be dosed with an additional therapeutic agent that addresses the undesirable level in the hematologic parameter(s), such as, for example, a blood pressure lowering agent or an iron supplement. For example, if a patient being treated with one or more ActRII antagonists has elevated blood pressure, then dosing with the one or more antagonists of the disclosure may continue at the same level and a blood-pressure-lowering agent is added to the treatment regimen, dosing with the one or more antagonist (e.g., in amount and/or frequency) and a blood-pressure-lowering agent is added to the treatment regimen, or dosing with the one or more antagonist may be terminated and the patient may be treated with a blood-pressure-lowering agent.

6. Pharmaceutical Compositions

In certain aspects, one or more ActRII antagonists of the disclosure can be administered alone or as a component of a pharmaceutical formulation (also referred to as a therapeutic composition or pharmaceutical composition). A pharmaceutical formulation refers to a preparation which is in such form as to permit the biological activity of an active ingredient (e.g., an agent of the present disclosure) contained therein to be effective and which contains no additional components which are unacceptably toxic to a subject to which the formulation would be administered. The subject compounds may be formulated for administration in any convenient way for use in human or veterinary medicine. For example, one or more agents of the present disclosure may be formulated with a pharmaceutically acceptable carrier. A pharmaceutically acceptable carrier refers to an ingredient in a pharmaceutical formulation, other than an active ingredient, which is generally nontoxic to a subject. A pharmaceutically acceptable carrier includes, but is not limited to, a buffer, excipient, stabilizer, and/or preservative. In general, pharmaceutical formulations for use in the present disclosure are in a pyrogen-free, physiologically-acceptable form when administered to a subject. Therapeutically useful agents other than those described herein, which may optionally be included in the formulation as described above, may be administered in combination with the subject agents in the methods of the present disclosure.

Typically, compounds will be administered to the eye including, e.g., by topical administration, intraocular (e.g., intravitreal) injection, or by implant or device. An intravitreal injection can be injected, for example, through the pars plana, 3 mm to 4 mm posterior to the limbus. Pharmaceutical compositions for administration to the eye may formulated in a variety of ways including, for example, eye drops, ophthalmic solutions, ophthalmic suspensions, ophthalmic emulsions, intravitreal injections, sub-Tenon injections, ophthalmic biodrodible implant, and non-bioeordible ophthalmic inserts or depots.

In some embodiments compounds will be administered parenterally [e.g., by intravenous (I. V.) injection, intraarterial injection, intraosseous injection, intramuscular injection, intrathecal injection, subcutaneous injection, or intradermal injection].

Pharmaceutical compositions suitable for ocular or parenteral administration may comprise one or more agents of the disclosure in combination with one or more pharmaceutically acceptable sterile isotonic aqueous or nonaqueous solutions, dispersions, suspensions or emulsions, or sterile powders which may be reconstituted into sterile solutions or dispersions just prior to use. Solutions or dispersions may contain antioxidants, buffers, bacteriostats, suspending agents, thickening agents, or solutes which render the formulation isotonic with the blood of the intended recipient. Examples of suitable aqueous and nonaqueous carriers which may be employed in the pharmaceutical formulations of the present disclosure include water, ethanol, polyols (e.g., glycerol, propylene glycol, polyethylene glycol, etc.), vegetable oils (e.g., olive oil), injectable organic esters (e.g., ethyl oleate), and suitable mixtures thereof. Proper fluidity can be maintained, for example, by the use of coating materials (e.g., lecithin), by the maintenance of the required particle size in the case of dispersions, and by the use of surfactants.

In some embodiments, a therapeutic method of the present disclosure includes administering the pharmaceutical composition systemically, or locally, from an implant or device. Further, the pharmaceutical composition may be encapsulated or injected in a form for delivery to a target tissue site (e.g., bone marrow or muscle). In certain embodiments, compositions of the present disclosure may include a matrix capable of delivering one or more of the agents of the present disclosure to a target tissue site (e.g., bone marrow or muscle), providing a structure for the developing tissue and optimally capable of being resorbed into the body. For example, the matrix may provide slow release of one or more agents of the present disclosure. Such matrices may be formed of materials presently in use for other implanted medical applications.

The choice of matrix material may be based on one or more of: biocompatibility, biodegradability, mechanical properties, cosmetic appearance, and interface properties. The particular application of the subject compositions will define the appropriate formulation. Potential matrices for the compositions may be biodegradable and chemically defined calcium sulfate, tricalciumphosphate, hydroxyapatite, polylactic acid, and polyanhydrides. Other potential materials are biodegradable and biologically well-defined, including, for example, bone or dermal collagen. Further matrices are comprised of pure proteins or extracellular matrix components. Other potential matrices are non-biodegradable and chemically defined, including, for example, sintered hydroxyapatite, bioglass, aluminates, or other ceramics.

Matrices may be comprised of combinations of any of the above mentioned types of material including, for example, polylactic acid and hydroxyapatite or collagen and tricalciumphosphate. The bioceramics may be altered in composition (e.g., calcium-aluminate-phosphate) and processing to alter one or more of pore size, particle size, particle shape, and biodegradability.

In certain embodiments, pharmaceutical compositions of the present disclosure can be administered orally, for example, in the form of capsules, cachets, pills, tablets, lozenges (using a flavored basis such as sucrose and acacia or tragacanth), powders, granules, a solution or a suspension in an aqueous or non-aqueous liquid, an oil-in-water or water-in-oil liquid emulsion, or an elixir or syrup, or pastille (using an inert base, such as gelatin and glycerin, or sucrose and acacia), and/or a mouth wash, each containing a predetermined amount of a compound of the present disclosure and optionally one or more other active ingredients. A compound of the present disclosure and optionally one or more other active ingredients may also be administered as a bolus, electuary, or paste.

In solid dosage forms for oral administration (e.g., capsules, tablets, pills, dragees, powders, and granules), one or more compounds of the present disclosure may be mixed with one or more pharmaceutically acceptable carriers including, for example, sodium citrate, dicalcium phosphate, a filler or extender (e.g., a starch, lactose, sucrose, glucose, mannitol, and silicic acid), a binder (e.g. carboxymethylcellulose, an alginate, gelatin, polyvinyl pyrrolidone, sucrose, and acacia), a humectant (e.g., glycerol), a disintegrating agent (e.g., agar-agar, calcium carbonate, potato or tapioca starch, alginic acid, a silicate, and sodium carbonate), a solution retarding agent (e.g. paraffin), an absorption accelerator (e.g. a quaternary ammonium compound), a wetting agent (e.g., cetyl alcohol and glycerol monostearate), an absorbent (e.g., kaolin and bentonite clay), a lubricant (e.g., a talc, calcium stearate, magnesium stearate, solid polyethylene glycols, sodium lauryl sulfate), a coloring agent, and mixtures thereof. In the case of capsules, tablets, and pills, the pharmaceutical formulation (composition) may also comprise a buffering agent. Solid compositions of a similar type may also be employed as fillers in soft and hard-filled gelatin capsules using one or more excipients including, e.g., lactose or a milk sugar as well as a high molecular-weight polyethylene glycol.

Liquid dosage forms for oral administration of the pharmaceutical composition may include pharmaceutically acceptable emulsions, microemulsions, solutions, suspensions, syrups, and elixirs. In addition to the active ingredient(s), the liquid dosage form may contain an inert diluent commonly used in the art including, for example, water or other solvent, a solubilizing agent and/or emulsifier [e.g., ethyl alcohol, isopropyl alcohol, ethyl carbonate, ethyl acetate, benzyl alcohol, benzyl benzoate, propylene glycol, or 1,3-butylene glycol, an oil (e.g., cottonseed, groundnut, corn, germ, olive, castor, and sesame oil), glycerol, tetrahydrofuryl alcohol, a polyethylene glycol, a fatty acid ester of sorbitan, and mixtures thereof]. Besides inert diluents, the oral formulation can also include an adjuvant including, for example, a wetting agent, an emulsifying and suspending agent, a sweetening agent, a flavoring agent, a coloring agent, a perfuming agent, a preservative agent, and combinations thereof.

Suspensions, in addition to the active compounds, may contain suspending agents including, for example, an ethoxylated isostearyl alcohol, polyoxyethylene sorbitol, a sorbitan ester, microcrystalline cellulose, aluminum metahydroxide, bentonite, agar-agar, tragacanth, and combinations thereof.

Prevention of the action and/or growth of microorganisms may be ensured by the inclusion of various antibacterial and antifungal agents including, for example, paraben, chlorobutanol, and phenol sorbic acid.

In certain embodiments, it may be desirable to include an isotonic agent including, for example, a sugar or sodium chloride into the compositions. In addition, prolonged absorption of an injectable pharmaceutical form may be brought about by the inclusion of an agent that delays absorption, including, for example, aluminum monostearate and gelatin.

It is understood that the dosage regimen will be determined by the attending physician considering various factors which modify the action of the one or more of the agents of the present disclosure. The various factors include, but are not limited to, the patient's red blood cell count, hemoglobin level, the desired target red blood cell count, the patient's age, the patient's sex, the patient's diet, the severity of any disease that may be contributing to a depressed red blood cell level, the time of administration, and other clinical factors. The addition of other known active agents to the final composition may also affect the dosage. Progress can be monitored by periodic assessment of one or more of red blood cell levels, hemoglobin levels, reticulocyte levels, and other indicators of the hematopoietic process.

In certain embodiments, the present disclosure also provides gene therapy for the in vivo production of one or more of the agents of the present disclosure. Such therapy would achieve its therapeutic effect by introduction of the agent sequences into cells or tissues having one or more of the disorders as listed above. Delivery of the agent sequences can be achieved, for example, by using a recombinant expression vector such as a chimeric virus or a colloidal dispersion system. Preferred therapeutic delivery of one or more of agent sequences of the disclosure is the use of targeted liposomes.

Various viral vectors which can be utilized for gene therapy as taught herein include adenovirus, herpes virus, vaccinia, or an RNA virus (e.g., a retrovirus). The retroviral vector may be a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous sarcoma virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing one or more of the agents of the present disclosure.

Alternatively, tissue culture cells can be directly transfected with plasmids encoding the retroviral structural genes (gag, pol, and env), by conventional calcium phosphate transfection. These cells are then transfected with the vector plasmid containing the genes of interest. The resulting cells release the retroviral vector into the culture medium.

Another targeted delivery system for one or more of the agents of the present disclosure is a colloidal dispersion system. Colloidal dispersion systems include, for example, macromolecule complexes, nanocapsules, microspheres, beads, and lipid-based systems including oil-in-water emulsions, micelles, mixed micelles, and liposomes. In certain embodiments, the preferred colloidal system of this disclosure is a liposome. Liposomes are artificial membrane vesicles which are useful as delivery vehicles in vitro and in vivo. RNA, DNA, and intact virions can be encapsulated within the aqueous interior and be delivered to cells in a biologically active form [see, e.g., Fraley, et al. (1981) Trends Biochem. Sci., 6:77]. Methods for efficient gene transfer using a liposome vehicle are known in the art [see, e.g., Mannino, et al. (1988) Biotechniques, 6:682, 1988].

The composition of the liposome is usually a combination of phospholipids, which may include a steroid (e.g. cholesterol). The physical characteristics of liposomes depend on pH, ionic strength, and the presence of divalent cations. Other phospholipids or other lipids may also be used, including, for example a phosphatidyl compound (e.g., phosphatidylglycerol, phosphatidylcholine, phosphatidylserine, phosphatidylethanolamine, sphingolipid, cerebroside, or a ganglioside), egg phosphatidylcholine, dipalmitoylphosphatidylcholine, and distearoylphosphatidylcholine. The targeting of liposomes is also possible based on, for example, organ specificity, cell specificity, and organelle specificity and is known in the art.

EXEMPLIFICATION

The invention now being generally described, it will be more readily understood by reference to the following examples, which are included merely for purposes of illustration of certain embodiments and embodiments of the present invention, and are not intended to limit the invention.

Example 1: ActRIIa-Fc Fusion Proteins

Applicants constructed a soluble ActRIIA fusion protein that has the extracellular domain of human ActRIIa fused to a human or mouse Fc domain with a minimal linker in between. The constructs are referred to as ActRIIA-hFc and ActRIIA-mFc, respectively.

ActRIIA-hFc is shown below as purified from CHO cell lines (SEQ ID NO: 32):

ILGRSETQECLFFNANVVEKDRTNQTGVEPCYGDKDKRRHCFATWKNISG

SIEIVKQGCWLDDINCYDRTDCVEKKDSPEVYFCCCEGNMCNEKESYFPE

MEVTQPTSNPVTPKPPTGGGTHTCPPCPAPELLGGPSVFLEPPKPKDTLM

ISRTPEVTCVVVDVSHEDPEVKFNWYVDGVEVHNAKTKPREEQYNSTYRV

VSVLTVLHQDWLNGKEYKCKVSNKALPVPIEKTISKAKGQPREPQVYTLP

PSREEMTKNQVSLTCLVKGFYPSDIAVEWESNGQPENNYKTTPPVLDSDG

SFELYSKLTVDKSRWQQGNVESCSVMHEALHNHYTQKSLSLSPGK

The ActRIIA-hFc and ActRIIA-mFc proteins were expressed in CHO cell lines. Three different leader sequences were considered:

(i) Honey bee mellitin (HBML):
(SEQ ID NO: 33)
MKFLVNVALVFMVVYISYIYA (ii) Tissue plasminogen activator (TPA):
(SEQ ID NO: 34)
MDAMKRGLCCVLLLCGAVFVSP (iii) Native:
(SEQ ID NO: 35)
MGAAAKLAFAVFLISCSSGA.

The selected form employs the TPA leader and has the following unprocessed amino acid sequence:

(SEQ ID NO: 36)
MDAMKRGLCCVLLLCGAVFVSPGAAILGRSETQECLFFNANVVEKDRTNQ

TGVEPCYGDKDKRRHCFATWKNISGSIEIVKQGCWLDDINCYDRTDCVEK

KDSPEVYFCCCEGNMCNEKFSYFPEMEVTQPTSNPVTPKPPTGGGTHTCP

PCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKA

LPVPIEKTISKAKGQPREPQVYTLPPSREEMTKNQVSLTCLVKGFYPSDI

AVEWESNGQPENNYKTTPPVLDSDGSFFLYSKLTVDKSRWQQGNVFSCSV

MHEALHNHYTQKSLSLSPGK

This polypeptide is encoded by the following nucleic acid sequence:

(SEQ ID NO: 37)
ATGGATGCAATGAAGAGAGGGCTCTGCTGTGTGCTGCTGCTGTGTGGAGC

AGTCTTCGTTTCGCCCGGCGCCGCTATACTTGGTAGATCAGAAACTCAGG

AGTGTCTTTTTTTAATGCTAATTGGGAAAAAGACAGAACCAATCAAACTG

GTGTTGAACCGTGTTATGGTGACAAAGATAAACGGCGGCATTGTTTTGCT

ACCTGGAAGAATATTTCTGGTTCCATTGAATAGTGAAACAAGGTTGTTGG

CTGGATGATATCAACTGCTATGACAGGACTGATTGTGTAGAAAAAAAAGA

CAGCCCTGAAGTATATTTCTGTTGCTGTGAGGGCAATATGTGTAATGAAA

AGTTTTCTTATTTTCCGGAGATGGAAGTCACACAGCCCACTTCAAATCCA

GTTACACCTAAGCCACCCACCGGTGGTGGAACTCACACATGCCCACCGTG

CCCAGCACCTGAACTCCTGGGGGGACCGTCAGTCTTCCTCTTCCCCCCAA

AACCCAAGGACACCCTCATGATCTCCCGGACCCCTGAGGTCACATGCGTG

GTGGTGGACGTGAGCCACGAAGACCCTGAGGTCAAGTTCAACTGGTACGT

GGACGGCGTGGAGGTGCATAATGCCAAGACAAAGCCGCGGGAGGAGCAGT

ACAACAGCACGTACCGTGTGGTCAGCGTCCTCACCGTCCTGCACCAGGAC

TGGCTGAATGGCAAGGAGTACAAGTGCAAGGTCTCCAACAAAGCCCTCCC

AGTCCCCATCGAGAAACCATCTCCAAAGCCAAAGGGCAGCCCCGAGAAC

CACAGGTGTACACCCTGCCCCCATCCCGGGAGGAGATGACCAAGAACCAG

GTCAGCCTGACCTGCCTGGTCAAAGGCTTCTATCCCAGCGACATCGCCGT

GGAGTGGGAGAGCAATGGGCAGCCGGAGAACAACTACAAGACCACGCCTC

-continued

```
CCGTGCTGGACTCCGACGGCTCCTTCTTCCTCTATAGCAAGCTCACCGTG

GACAAGAGCAGGTGGCAGCAGGGGAACGTCTTCTCATGCTCCGTGATGCA

TGAGGCTCTGCACAACCACTACACGCAGAAGAGCCTCTCCCTGTCTCCGG

GTAAATGAGAATTC
```

Both ActRIIA-hFc and ActRIIA-mFc were remarkably amenable to recombinant expression. As shown in FIG. 3, the protein was purified as a single, well-defined peak of protein. N-terminal sequencing revealed a single sequence of -ILGRSETQE (SEQ ID NO: 38). Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. The ActRIIA-hFc protein was purified to a purity of >98% as determined by size exclusion chromatography and >95% as determined by SDS PAGE.

ActRIIA-hFc and ActRIIA-mFc showed a high affinity for ligands. GDF-11 or activin A were immobilized on a Biacore™ CM5 chip using standard amine-coupling procedure. ActRIIA-hFc and ActRIIA-mFc proteins were loaded onto the system, and binding was measured. ActRIIA-hFc bound to activin with a dissociation constant ($K_D$) of $5 \times 10^{-12}$ and bound to GDF11 with a $K_D$ of $9.96 \times 10^{-9}$. See FIG. 4. ActRIIA-mFc behaved similarly.

The ActRIIA-hFc was very stable in pharmacokinetic studies. Rats were dosed with 1 mg/kg, 3 mg/kg, or 10 mg/kg of ActRIIA-hFc protein, and plasma levels of the protein were measured at 24, 48, 72, 144 and 168 hours. In a separate study, rats were dosed at 1 mg/kg, 10 mg/kg, or 30 mg/kg. In rats, ActRIIA-hFc had an 11-14 day serum half-life, and circulating levels of the drug were quite high after two weeks (11 µg/ml, 110 µg/ml, or 304 µg/ml for initial administrations of 1 mg/kg, 10 mg/kg, or 30 mg/kg, respectively.) In cynomolgus monkeys, the plasma half-life was substantially greater than 14 days, and circulating levels of the drug were 25 µg/ml, 304 µg/ml, or 1440 µg/ml for initial administrations of 1 mg/kg, 10 mg/kg, or 30 mg/kg, respectively.

Example 2: Characterization of an ActRIIA-hFc Protein

ActRIIA-hFc fusion protein was expressed in stably transfected CHO-DUKX B11 cells from a pAID4 vector (SV40 ori/enhancer, CMV promoter), using a tissue plasminogen leader sequence of SEQ ID NO: 34. The protein, purified as described above in Example 1, had a sequence of SEQ ID NO: 32. The Fc portion is a human IgG1 Fc sequence, as shown in SEQ ID NO: 32. Protein analysis reveals that the ActRIIA-hFc fusion protein is formed as a homodimer with disulfide bonding.

The CHO-cell-expressed material has a higher affinity for activin B ligand than that reported for an ActRIIa-hFc fusion protein expressed in human 293 cells [see, del Re et al. (2004) J Biol Chem. 279(50:53126-53135]. Additionally, the use of the TPA leader sequence provided greater production than other leader sequences and, unlike ActRIIA-Fc expressed with a native leader, provided a highly pure N-terminal sequence. Use of the native leader sequence resulted in two major species of ActRIIA-Fc, each having a different N-terminal sequence.

Example 3: Alternative ActRIIA-Fc Proteins

A variety of ActRIIA variants that may be used according to the methods described herein are described in the International Patent Application published as WO2006/012627 (see e.g., pp. 55-58), incorporated herein by reference in its entirety. An alternative construct may have a deletion of the C-terminal tail (the final 15 amino acids of the extracellular domain of ActRIIA. The sequence for such a construct is presented below (Fc portion underlined) (SEQ ID NO: 39):

```
ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM

TGGGTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPVPIEKTISKAKGQPREPQVYTLPPSREEMTKNQVSLTCL

VKGFYPSDIAVEWESNGQPENNYKTTPPVLDSDGSFFLYSKLTVDKSRWQ

QGNVFSCSVMHEALHNHYTQKSLSLSPGK
```

Example 4: Generation of ActRIIB-Fc Fusion Proteins

Applicants constructed a soluble ActRIIB fusion protein that has the extracellular domain of human ActRIIB fused to a human or mouse Fc domain with a minimal linker (three glycine amino acids) in between. The constructs are referred to as ActRIIB-hFc and ActRIIB-mFc, respectively.

ActRIIB-hFc is shown below as purified from CHO cell lines (SEQ ID NO: 40):

```
GRGEAETRECIYYNANVVELERTNQSGLERCEGEQDKRLHCYASWRNSSG

TIELVKKGCWLDDFNCYDRQECVATEENPQVYFCCCEGNFCNERFTHLPE

AGGPEVTYEPPPTAPTGGGTHTCPPCPAPELLGGPSVFLFPPKPKDTLMI

SRTPEVTCVVVDVSHEDPEVKFNWYVDGVEVHNAKTKPREEQYNSTYRVV

SVLTVLHQDWLNGKEYKCKVSNKALPVPIEKTISKAKGQPREPQVYTLPP

SREEMTKNQVSLTCLVKGFYPSDIAVEWESNGQPENNYKTTPPVLDSDGS

FFLYSKLTVDKSRWQQGNVFSCSVMHEALHNHYTQKSLSLSPGK
```

The ActRIIB-hFc and ActRIIB-mFc proteins were expressed in CHO cell lines. Three different leader sequences were considered: (i) Honey bee mellitin (HBML), ii) Tissue plasminogen activator (TPA), and (iii) Native: MGAAAKLAFAVFLISCSSGA (SEQ ID NO: 77).

The selected form employs the TPA leader and has the following unprocessed amino acid sequence (SEQ ID NO: 41):

```
MDAMKRGLCCVLLLCGAVFVSPGASGRGEAETRECIYYNANVVELERTNQ

SGLERCEGEQDKRLHCYASWRNSSGTIELVKKGCWLDDFNCYDRQECVAI

EENPQVYFCCCEGNFCNERFTHLPEAGGPEVTYEPPPTAPTGGGTHTCPP

CPAPELLGGPSVFLFPPKPKDTLMISRTPEVTCVVVDVSHEDPEVKFNVV

YVDGVEVHNAKTKPREEQYNSTYRVVSVLTVLHQDWLNGKEYKCKVSNKA

LPVPIEKTISKAKGQPREPQVYTLPPSREEMTKNQVSLTCLVKGFYPSDI

AVEWESNGQPENNYKTTPPVLDSDGSFFLYSKLTVDKSRWQQGNVFSCSV

MITEALHNHYTQKSLSLSPGK
```

This polypeptide is encoded by the following nucleic acid sequence (SEQ ID NO: 42):

```
A TGGATGCAAT GAAGAGAGGG CTCTGCTGTG TGCTGCTGCT GTGTGGAGCA

GTCTTCGTTT CGCCCGGCGC CTCTGGGCGT GGGGAGGCTG AGACACGGGA

GTGCATCTAC TACAACGCCA ACTGGGAGCT GGAGCGCACC AACCAGAGCG

GCCTGGAGCG CTGCGAAGGC GAGCAGGACA AGCGGCTGCA CTGCTACGCC

TCCTGGCGCA ACAGCTCTGG CACCATCGAG CTCGTGAAGA AGGGCTGCTG

GCTAGATGAC TTCAACTGCT ACGATAGGCA GGAGTGTGTG GCCACTGAGG

AGAACCCCCA GGTGTACTTC TGCTGCTGTG AAGGCAACTT CTGCAACGAG

CGCTTCACTC ATTTGCCAGA GGCTGGGGGC CCGGAAGTCA CGTACGAGCC

ACCCCCGACA GCCCCCACCG GTGGTGGAAC TCACACATGC CCACCGTGCC

CAGCACCTGA ACTCCTGGGG GGACCGTCAG TCTTCCTCTT CCCCCCAAAA

CCCAAGGACA CCCTCATGAT CTCCCGGACC CCTGAGGTCA CATGCGTGGT

GGTGGACGTG AGCCACGAAG ACCCTGAGGT CAAGTTCAAC TGGTACGTGG

ACGGCGTGGA GGTGCATAAT GCCAAGACAA AGCCGCGGGA GGAGCAGTAC

AACAGCACGT ACCGTGTGGT CAGCGTCCTC ACCGTCCTGC ACCAGGACTG

GCTGAATGGC AAGGAGTACA AGTGCAAGGT CTCCAACAAA GCCCTCCCAG

TCCCCATCGA GAAAACCATC TCCAAAGCCA AAGGGCAGCC CCGAGAACCA

CAGGTGTACA CCCTGCCCCC ATCCCGGGAG GAGATGACCA AGAACCAGGT

CAGCCTGACC TGCCTGGTCA AAGGCTTCTA TCCCAGCGAC ATCGCCGTGG

AGTGGGAGAG CAATGGGCAG CCGGAGAACA ACTACAAGAC CACGCCTCCC

GTGCTGGACT CCGACGGCTC CTTCTTCCTC TATAGCAAGC TCACCGTGGA

CAAGAGCAGG TGGCAGCAGG GGAACGTCTT CTCATGCTCC GTGATGCATG

AGGCTCTGCA CAACCACTAC ACGCAGAAGA GCCTCTCCCT GTCTCCGGGT

AAATGA
```

N-terminal sequencing of the CHO-cell-produced material revealed a major sequence of -GRGEAE (SEQ ID NO: 43). Notably, other constructs reported in the literature begin with an -SGR . . . sequence.

Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

ActRIIB-Fc fusion proteins were also expressed in HEK293 cells and COS cells. Although material from all cell lines and reasonable culture conditions provided protein with muscle-building activity in vivo, variability in potency was observed perhaps relating to cell line selection and/or culture conditions.

Applicants generated a series of mutations in the extracellular domain of ActRIIB and produced these mutant proteins as soluble fusion proteins between extracellular ActRIIB and an Fc domain. The background ActRIIB-Fc fusion has the sequence of SEQ ID NO: 40.

Various mutations, including N- and C-terminal truncations, were introduced into the background ActRIIB-Fc protein. Based on the data presented herein, it is expected that these constructs, if expressed with a TPA leader, will lack the N-terminal serine. Mutations were generated in ActRIIB extracellular domain by PCR mutagenesis. After PCR, fragments were purified through a Qiagen column, digested with SfoI and AgeI and gel purified. These fragments were ligated into expression vector pAID4 (see WO2006/012627) such that upon ligation it created fusion chimera with human IgG1. Upon transformation into E. coli DH5 alpha, colonies were picked and DNAs were isolated. For murine constructs (mFc), a murine IgG2a was substituted for the human IgG1. Sequences of all mutants were verified.

All of the mutants were produced in HEK293T cells by transient transfection. In summary, in a 500 ml spinner, HEK293T cells were set up at $6 \times 10^5$ cells/ml in Freestyle (Invitrogen) media in 250 ml volume and grown overnight. Next day, these cells were treated with DNA:PEI (1:1) complex at 0.5 ug/ml final DNA concentration. After 4 hrs, 250 ml media was added and cells were grown for 7 days. Conditioned media was harvested by spinning down the cells and concentrated.

Mutants were purified using a variety of techniques, including, for example, a protein A column, and eluted with low pH (3.0) glycine buffer. After neutralization, these were dialyzed against PBS.

Mutants were also produced in CHO cells by similar methodology. Mutants were tested in binding assays and/or bioassays described in WO 2008/097541 and WO 2006/012627 incorporated by reference herein. In some instances, assays were performed with conditioned medium rather than purified proteins. Additional variations of ActRIIB are described in U.S. Pat. No. 7,842,663.

Applicant generated an ActRIIB(25-131)-hFc fusion protein, which comprises the human ActRIIB extracellular domain with N-terminal and C-terminal truncations (residues 25-131 of the native protein SEQ ID NO: 1) fused N-terminally with a TPA leader sequence substituted for the native ActRIIB leader and C-terminally with a human Fc domain via a minimal linker (three glycine residues) (FIG. 16). A nucleotide sequence encoding this fusion protein is shown in FIGS. 17A and 17B. Applicants modified the codons and found a variant nucleic acid encoding the ActRIIB(25-131)-hFc protein that provided substantial improvement in the expression levels of initial transformants (FIGS. 18A and 18B).

The mature protein has an amino acid sequence as follows (N-terminus confirmed by N-terminal sequencing)(SEQ ID NO: 78):

```
ETRECIYYNA NWELERTNQS GLERCEGEQD KRLHCYASWR NSSGTIELVK

KGCWLDDFNC YDRQECVATE ENPQVYFCCC EGNFCNERFT HLPEAGGPEV

TYEPPPTGGG THTCPPCPAP ELLGGPSVFL FPPKPKDTLM ISRTPEVTCV

VVDVSHEDPE VKFNWYVDGV EVHNAKTKPR EEQYNSTYRV VSVLTVLHQD

WLNGKEYKCK VSNKALPAPI EKTISKAKGQ PREPQVYTLP PSREEMTKNQ

VSLTCLVKGF YPSDIAVEWE SNGQPENNYK TTPPVLDSDG SFFLYSKLTV

DKSRWQQGNV FSCSVMHEAL HNHYTQKSLS LSPGK
```

Amino acids 1-107 are derived from ActRIIB

The expressed molecule was purified using a series of column chromatography steps, including for example, three or more of the following, in any order: Protein A chromatography, Q sepharose chromatography, phenylsepharose chromatography, size exclusion chromatography and cation exchange chromatography. The purification could be completed with viral filtration and buffer exchange.

Affinities of several ligands for ActRIIB(25-131)-hFc and its full-length counterpart ActRIIB(20-134)-hFc were evaluated in vitro with a Biacore™ instrument, and the results are summarized in the table below. Kd values were obtained by steady-state affinity fit due to very rapid association and dissociation of the complex, which prevented accurate determination of $k_{on}$ and $k_{off}$. ActRIIB(25-131)-hFc bound activin A, activin B, and GDF11 with high affinity.

Ligand Affinities of ActRIIB-hFc Forms:

| Fusion Construct | Activin A (e-11) | Activin B (e-11) | GDF11 (e-11) |
| --- | --- | --- | --- |
| ActRIIB(20-134)-hFc | 1.6 | 1.2 | 3.6 |
| ActRIIB(25-131)-hFc | 1.8 | 1.2 | 3.1 |

Example 5: Generation of a GDF Trap

Applicants constructed a GDF trap as follows. A polypeptide having a modified extracellular domain of ActRIIB (amino acids 20-134 of SEQ ID NO: 1 with an L79D substitution) with greatly reduced activin A binding relative to GDF11 and/or myostatin (as a consequence of a leucine-to-aspartate substitution at position 79 in SEQ ID NO:1) was fused to a human or mouse Fc domain with a minimal linker (three glycine amino acids) in between. The constructs are referred to as ActRIIB(L79D 20-134)-hFc and ActRIIB (L79D 20-134)-mFc, respectively. Alternative forms with a glutamate rather than an aspartate at position 79 performed similarly (L79E). Alternative forms with an alanine rather than a valine at position 226 with respect to SEQ ID NO: 44, below were also generated and performed equivalently in all respects tested. The aspartate at position 79 (relative to SEQ ID NO: 1, or position 60 relative to SEQ ID NO: 44) is indicated with double underlining below. The valine at position 226 relative to SEQ ID NO: 44 is also indicated by double underlining below.

The GDF trap ActRIIB(L79D 20-134)-hFc is shown below as purified from CHO cell lines (SEQ ID NO: 44).

```
GRGEAETRECIYYNANVVELERTNQSGLERCEGEQDKRLHCYASWRNSSG

TIELVKKGCWDDDFNCYDRQECVAIEENPQVYFCCCEGNFCNERFTHLPE

AGGPEVTYEPPPTAPTGGGTHTCPPCPAPELLGGPSVFLFPPKPKDTLMI
```

-continued
```
SRTPEVTCVVVDVSHEDPEVKFNWYVDGVEVHNAKTKPREEQYNSTYRVV

SVLTVLHQDWLNGKEYKCKVSNKALPVPIEKTISKAKGQPREPQVYTLPP

SREEMTKNQVSLTCLVKGFYPSDIAVEWESNGQPENNYKTTPPVLDSDGS

FFLYSKLTVDKSRWQQGNVFSCSVMHEALHNHYTQKSLSLSPGK
```

The ActRIIB-derived portion of the GDF trap has an amino acid sequence set forth below (SEQ ID NO: 45), and that portion could be used as a monomer or as a non-Fc fusion protein as a monomer, dimer, or greater-order complex. GRGEAETRECIYYNANWELERTNQSGLER-CEGEQDKRLHCYASWRNSSGTIELVKKGC WDDDFNCYDRQECVATEENPQVYFCCCEGNFCNER-FTHLPEAGGPEVTYEPPPTAPT (SEQ ID NO: 45)

The GDF trap protein was expressed in CHO cell lines. Three different leader sequences were considered:
(i) Honey bee melittin (HBML), (ii) Tissue plasminogen activator (TPA), and (iii) Native.

The selected form employs the TPA leader and has the following unprocessed amino acid sequence:

```
                                         (SEQ ID NO: 46)
MDAMKRGLCCVLLLCGAVFVSPGASGRGEAETRECIYYNANVVELERTNQ

SGLERCEGEQDKRLHCYASWRNSSGTIELVKKGCWDDDFNCYDRQECVAI

EENPQVYFCCCEGNFCNERFTHLPEAGGPEVTYEPPPTAPTGGGTHTCPP

CPAPELLGGPSVFLFPPKPKDTLMISRTPEVTCVVVDVSHEDPEVKFNVV
```

-continued

YVDGVEVHNAKTKPREEQYNSTYRVVSVLTVLHQDWLNGKEYKCKVSNKA

LPAPIEKTISKAKGQPREPQVYTLPPSREEMTKNQVSLTCLVKGFYPSDI

AVEWESNGQPENNYKTTPPVLDSDGSFFLYSKLTVDKSRWQQGNVFSCSV

MHEALHNHYTQKSLSLSPGK

This polypeptide is encoded by the following nucleic acid sequence (SEQ ID NO: 47):

A TGGATGCAAT GAAGAGAGGG CTCTGCTGTG TGCTGCTGCT GTGTGGAGCA

GTCTTCGTTT CGCCCGGCGC CTCTGGGCGT GGGGAGGCTG AGACACGGGA

GTGCATCTAC TACAACGCCA ACTGGGAGCT GGAGCGCACC AACCAGAGCG

GCCTGGAGCG CTGCGAAGGC GAGCAGGACA AGCGGCTGCA CTGCTACGCC

TCCTGGCGCA ACAGCTCTGG CACCATCGAG CTCGTGAAGA AGGGCTGCTG

GGACGATGAC TTCAACTGCT ACGATAGGCA GGAGTGTGTG GCCACTGAGG

AGAACCCCCA GGTGTACTTC TGCTGCTGTG AAGGCAACTT CTGCAACGAG

CGCTTCACTC ATTTGCCAGA GGCTGGGGGC CCGGAAGTCA CGTACGAGCC

ACCCCCGACA GCCCCCACCG GTGGTGGAAC TCACACATGC CCACCGTGCC

CAGCACCTGA ACTCCTGGGG GGACCGTCAG TCTTCCTCTT CCCCCCAAAA

CCCAAGGACA CCCTCATGAT CTCCCGGACC CCTGAGGTCA CATGCGTGGT

GGTGGACGTG AGCCACGAAG ACCCTGAGGT CAAGTTCAAC TGGTACGTGG

ACGGCGTGGA GGTGCATAAT GCCAAGACAA AGCCGCGGGA GGAGCAGTAC

AACAGCACGT ACCGTGTGGT CAGCGTCCTC ACCGTCCTGC ACCAGGACTG

GCTGAATGGC AAGGAGTACA AGTGCAAGGT CTCCAACAAA GCCCTCCCAG

TCCCCATCGA GAAAACCATC TCCAAAGCCA AAGGGCAGCC CCGAGAACCA

CAGGTGTACA CCCTGCCCCC ATCCCGGGAG GAGATGACCA AGAACCAGGT

CAGCCTGACC TGCCTGGTCA AAGGCTTCTA TCCCAGCGAC ATCGCCGTGG

AGTGGGAGAG CAATGGGCAG CCGGAGAACA ACTACAAGAC CACGCCTCCC

GTGCTGGACT CCGACGGCTC CTTCTTCCTC TATAGCAAGC TCACCGTGGA

CAAGAGCAGG TGGCAGCAGG GGAACGTCTT CTCATGCTCC GTGATGCATG

AGGCTCTGCA CAACCACTAC ACGCAGAAGA GCCTCTCCCT GTCTCCGGGT

AAATGA

Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. In an example of a purification scheme, the cell culture medium is passed over a protein A column, washed in 150 mM Tris/NaCl (pH 8.0), then washed in 50 mM Tris/NaCl (pH 8.0) and eluted with 0.1 M glycine, pH 3.0. The low pH eluate is kept at room temperature for 30 minutes as a viral clearance step. The eluate is then neutralized and passed over a Q-sepharose ion-exchange column and washed in 50 mM Tris pH 8.0, 50 mM NaCl, and eluted in 50 mM Tris pH 8.0, with an NaCl concentration between 150 mM and 300 mM. The eluate is then changed into 50 mM Tris pH 8.0, 1.1 M ammonium sulfate and passed over a phenyl sepharose column, washed, and eluted in 50 mM Tris pH 8.0 with ammonium sulfate between 150 and 300 mM. The eluate is dialyzed and filtered for use.

Additional GDF traps (ActRIIB-Fc fusion proteins modified so as to reduce the ratio of activin A binding relative to myostatin or GDF11 binding) are described in WO 2008/097541 and WO 2006/012627, incorporated by reference herein.

Example 6: Bioassay for GDF-11- and Activin-Mediated Signaling

An A-204 reporter gene assay was used to evaluate the effects of ActRIIB-Fc proteins and GDF traps on signaling by GDF-11 and activin A. Cell line: human rhabdomyosarcoma (derived from muscle). Reporter vector: pGL3 (CAGA)12 (described in Dennler et al, 1998, EMBO 17: 3091-3100). The CAGA12 motif is present in TGF-beta responsive genes (e.g., PAI-1 gene), so this vector is of general use for factors signaling through SMAD2 and 3.

Day 1: Split A-204 cells into 48-well plate.

Day 2: A-204 cells transfected with 10 ug pGL3(CAGA) 12 or pGL3(CAGA)12(10 ug)+ pRLCMV (1 μg) and Fugene.

Day 3: Add factors (diluted into medium+0.1% BSA). Inhibitors need to be preincubated with factors for 1 hr before adding to cells. Six hrs later, cells were rinsed with PBS and lysed.

This is followed by a luciferase assay. In the absence of any inhibitors, activin A showed 10-fold stimulation of reporter gene expression and an ED50~2 ng/ml. GDF-11: 16 fold stimulation, ED50:~1.5 ng/ml.

ActRIIB(20-134) is a potent inhibitor of activin A, GDF-8, and GDF-11 activity in this assay. As described below, ActRIIB variants were also tested in this assay.

Example 7: ActRIIB-Fc Variants, Cell-Based Activity

Activity of ActRIIB-Fc proteins and GDF traps was tested in a cell-based assay as described above. Results are summarized in the table below. Some variants were tested in different C-terminal truncation constructs. As discussed above, truncations of five or fifteen amino acids caused reduction in activity. The GDF traps (L79D and L79E variants) showed substantial loss of activin A inhibition while retaining almost wild-type inhibition of GDF-11. Soluble ActRIIB-Fc Binding to GDF11 and Activin A:

| ActRIIB-Fc Variations | Portion of ActRIIB (corresponds to amino acids of SEQ ID NO: 1) | GDF11 Inhibition Activity | Activin Inhibition Activity |
|---|---|---|---|
| R64 | 20-134 | +++ (approx. $10^{-8}$M $K_I$) | +++ (approx. $10^{-8}$M $K_I$) |
| A64 | 20-134 | + (approx. $10^{-6}$M $K_I$) | + (approx. $10^{-6}$M $K_I$) |
| R64 | 20-129 | +++ | +++ |
| R64 K74A | 20-134 | ++++ | ++++ |
| R64 A24N | 20-134 | +++ | +++ |
| R64 A24N | 20-119 | ++ | ++ |
| R64 A24N K74A | 20-119 | + | + |
| R64 L79P | 20-134 | + | + |
| R64 L79P K74A | 20-134 | + | + |
| R64 L79D | 20-134 | +++ | + |
| R64 L79E | 20-134 | +++ | + |
| R64K | 20-134 | +++ | +++ |
| R64K | 20-129 | +++ | +++ |
| R64 P129S P130A | 20-134 | +++ | +++ |
| R64N | 20-134 | + | + |

\+ Poor activity (roughly $1 \times 10^{-6}$ $K_I$)
++ Moderate activity (roughly $1 \times 10^{-7}$ $K_I$)
+++ Good (wild-type) activity (roughly $1 \times 10^{-8}$ $K_I$)
++++ Greater than wild-type activity Several variants have been assessed for serum half-life in rats. ActRIIB(20-134)-Fc has a serum half-life of approximately 70 hours. ActRIIB(A24N 20-134)-Fc has a serum half-life of approximately 100-150 hours. The A24N variant has activity in the cell-based assay (above) and that is equivalent to the wild-type molecule. Coupled with the longer half-life, this means that over time an A24N variant will give greater effect per unit of protein than the wild-type molecule. The A24N variant, and any of the other variants tested above, may be combined with the GDF trap molecules, such as the L79D or L79E variants.

Example 8: GDF-11 and Activin A Binding

Binding of certain ActRIIB-Fc proteins and GDF traps to ligands was tested in a Biacore™ assay.

The ActRIIB-Fc variants or wild-type protein were captured onto the system using an anti-hFc antibody. Ligands were injected and flowed over the captured receptor proteins. Results are summarized in the tables below.

Ligand-Binding Specificity IIB Variants.

| | GDF11 | | |
|---|---|---|---|
| Protein | Kon (1/Ms) | Koff (1/s) | KD (M) |
| ActRIIB(20-134)-hFc | 1.34e−6 | 1.13e−4 | 8.42e−11 |
| ActRIIB(A24N 20-134)-hFc | 1.21e−6 | 6.35e−5 | 5.19e−11 |
| ActRIIB(L79D 20-134)-hFc | 6.7e−5 | 4.39e−4 | 6.55e−10 |
| ActRIIB(L79E 20-134)-hFc | 3.8e−5 | 2.74e−4 | 7.16e−10 |
| ActRIIB(R64K 20-134)-hFc | 6.77e−5 | 2.41e−5 | 3.56e−11 |

| | GDF8 | | |
|---|---|---|---|
| Protein | Kon (1/Ms) | Koff (1/s) | KD (M) |
| ActRIIB(20-134)-hFc | 3.69e−5 | 3.45e−5 | 9.35e−11 |
| ActRIIB(A24N 20-134)-hFc | | | |
| ActRIIB(L79D 20-134)-hFc | 3.85e−5 | 8.3e−4 | 2.15e−9 |
| ActRIIB(L79E 20-134)-hFc | 3.74e−5 | 9e−4 | 2.41e−9 |
| ActRIIB(R64K 20-134)-hFc | 2.25e−5 | 4.71e−5 | 2.1e−10 |
| ActRIIB(R64K 20-129)-hFc | 9.74e−4 | 2.09e−4 | 2.15e−9 |
| ActRIIB(P129S, P130R 20-134)-hFc | 1.08e−5 | 1.8e−4 | 1.67e−9 |
| ActRIIB(K74A 20-134)-hFc | 2.8e−5 | 2.03e−5 | 7.18e−11 |

| | Activin A | | |
|---|---|---|---|
| Protein | Kon (1/Ms) | Koff (1/s) | KD (M) |
| ActRIIB(20-134)-hFc | 5.94e6 | 1.59e−4 | 2.68e−11 |
| ActRIIB(A24N 20-134)-hFc | 3.34e6 | 3.46e−4 | 1.04e−10 |
| ActRIIB(L79D 20-134)-hFc | | | Low binding |
| ActRIIB(L79E 20-134)-hFc | | | Low binding |

-continued

| ActRIIB | | | |
|---|---|---|---|
| ActRIIB(R64K 20-134)-hFc | 6.82e6 | 3.25e−4 | 4.76e−11 |
| ActRIIB(R64K 20-129)-hFc | 7.46e6 | 6.28e−4 | 8.41e−11 |
| ActRIIB(P129S, P130R 20-134)-hFc | 5.02e6 | 4.17e−4 | 8.31e−11 |

These data obtained in a cell-free assay confirm the cell-based assay data, demonstrating that the A24N variant retains ligand-binding activity that is similar to that of the ActRIIB(20-134)-hFc molecule and that the L79D or L79E molecule retains myostatin and GDF11 binding but shows markedly decreased (non-quantifiable) binding to activin A.

Other variants have been generated and tested, as reported in WO2006/012627 (incorporated herein by reference in its entirety). See, e.g., pp. 59-60, using ligands coupled to the device and flowing receptor over the coupled ligands. Notably, K74Y, K74F, K74I (and presumably other hydrophobic substitutions at K74, such as K74L), and D80I, cause a decrease in the ratio of activin A (ActA) binding to GDF11 binding, relative to the wild-type K74 molecule. A table of data with respect to these variants is reproduced below:
Soluble ActRIIB-Fc Variants Binding to GDF11 and Activin A (Biacore™ Assay)

| ActRIIB | ActA | GDF11 |
|---|---|---|
| WT (64A) | KD = 1.8e−7M (+) | KD = 2.6e−7M (+) |
| WT (64R) | na | KD = 8.6e−8M (+++) |
| +15tail | KD ~2.6e−8M (+++) | KD = 1.9e−8M (++++) |
| E37A | * | * |
| R40A | − | − |
| D54A | − | * |
| K55A | ++ | * |
| R56A | * | * |
| K74A | KD = 4.35e−9 M (+++++) | KD = 5.3e−9M (+++++) |
| K74Y | * | −− |
| K74F | * | −− |
| K74I | * | −− |
| W78A | * | * |
| L79A | + | * |
| D80K | * | * |
| D80R | * | * |
| D80A | * | * |
| D80F | * | * |
| D80G | * | * |
| D80M | * | * |
| D80N | * | * |
| D80I | * | −− |
| F82A | ++ | − |

\* No observed binding
−− <1/5 WT binding
− ~1/2 WT binding
+ WT
++ <2x increased binding
+++ ~5x increased binding
++++ ~10x increased binding
+++++ ~40x increased binding Example 9: Generation of a GDF Trap with Truncated ActRIIB Extracellular Domain A a GDF trap referred to as ActRIIB(L79D 20-134)-hFc was generated by N-terminal fusion of TPA leader to the ActRIIB extracellular domain (residues 20-134 in SEQ ID NO:1) containing a leucine-to-aspartate substitution (at residue 79 in SEQ ID NO:1) and C-terminal fusion of human Fc domain with minimal linker (three glycine residues) (FIG. 5). A nucleotide sequence corresponding to this fusion protein is shown in FIGS. 6A and 6B.

A GDF trap with truncated ActRIIB extracellular domain, referred to as ActRIIB(L79D 25-131)-hFc, was generated by N-terminal fusion of TPA leader to truncated extracellular domain (residues 25-131 in SEQ ID NO:1) containing a leucine-to-aspartate substitution (at residue 79 in SEQ ID NO:1) and C-terminal fusion of human Fc domain with minimal linker (three glycine residues) (FIG. 7, SEQ ID NO: 61). The processed form of ActRIIB(L79D 25-131)-hFc (SEQ ID NO: 64) is shown in FIG. 9. One nucleotide sequence encoding this fusion protein is shown in FIGS. 8A and 8B (SEQ ID NO: 62), and an alternative nucleotide sequence encoding exactly the same fusion protein is shown in FIGS. 11A and 11B (SEQ ID NO: 66).

Example 10: Selective Ligand Binding by GDF Trap with Double-Truncated ActRIIB Extracelluar Domain The affinity of GDF traps and other ActRIIB-hFc proteins for several ligands was evaluated in vitro with a Biacore™ instrument. Results are summarized in the table below. Kd values were obtained by steady-state affinity fit due to the very rapid association and dissociation of the complex, which prevented accurate determination of $k_{on}$ and $k_{off}$.

Ligand Selectivity of ActRIIB-hFc Variants:

| Fusion Construct | Activin A (Kd e-11) | Activin B (Kd e-11) | GDF11 (Kd e-11) |
|---|---|---|---|
| ActRIIB(L79 20-134)-hFc | 1.6 | 1.2 | 3.6 |
| ActRIIB(L79D 20-134)-hFc | 1350.0 | 78.8 | 12.3 |
| ActRIIB(L79 25-131)-hFc | 1.8 | 1.2 | 3.1 |
| ActRIIB(L79D 25-131)-hFc | 2290.0 | 62.1 | 7.4 |

The GDF trap with a truncated extracellular domain, ActRIIB(L79D 25-131)-hFc, equaled or surpassed the ligand selectivity displayed by the longer variant, ActRIIB (L79D 20-134)-hFc, with pronounced loss of activin A binding, partial loss of activin B binding, and nearly full retention of GDF11 binding compared to ActRIIB-hFc counterparts lacking the L79D substitution. Note that truncation alone (without L79D substitution) did not alter selectivity among the ligands displayed here [compare ActRIIB (L79 25-131)-hFc with ActRIIB(L79 20-134)-hFc]. ActRIIB(L79D 25-131)-hFc also retains strong to intermediate binding to the Smad 2/3 signaling ligand GDF8 and the Smad 1/5/8 ligands BMP6 and BMP10.

Example 11: GDF Trap Derived from ActRIIB5

Others have reported an alternate, soluble form of ActRIIB (designated ActRIIB5), in which exon 4, including the ActRIIB transmembrane domain, has been replaced by a different C-terminal sequence (see, e.g., WO 2007/053775).

The sequence of native human ActRIIB5 without its leader is as follows:

(SEQ ID NO: 48)
GRGEAETRECIYYNANWELERTNQSGLERCEGEQDKRLHCYASWRNSSGT

IELVKKGCWLDDFNCYDRQECVATEENPQVYFCCCEGNFCNERFTHLPEA

GGPEGPWASTTIPSGGPEATAAAGDQGSGALWLCLEGPAHE

An leucine-to-aspartate substitution, or other acidic substitutions, may be performed at native position 79 (underlined) as described to construct the variant ActRIIB5(L79D), which has the following sequence:

(SEQ ID NO: 49)
GRGEAETRECIYYNANWELERTNQSGLERCEGEQDKRLHCYASWRNSSGT

IELVKKGCWDDDFNCYDRQECVATEENPQVYFCCCEGNFCNERFTHLPEA

GGPEGPWASTTIPSGGPEATAAAGDQGSGALWLCLEGPAHE

This variant may be connected to human Fc (double underline) with a TGGG linker (SEQ ID NO: 23) (single underline) to generate a human ActRIIB5(L79D)-hFc fusion protein with the following sequence:

(SEQ ID NO: 50)
GRGEAETRECIYYNANWELERTNQSGLERCEGEQDKRLHCYASWRNSSG

TIELVKKGCWDDDFNCYDRQECVAIEENPQVYFCCCEGNFCNERFTHLP

EAGGPEGPWASTTIPSGGPEATAAAGDQGSGALWLCLEGPAHE<u>TGGGTH

TCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCK

VSNKALPAPIEKTISKAKGQPREPQVYTLPPSREEMTKNQVSLTCLVKG

FYPSDIAVEWESNGQPENNYKTTPPVLDSDGSFFLYSKLTVDKSRWQQG

NVFSCSVMHEALHNHYTQKSLSLSPGK</u>.

This construct may be expressed in CHO cells.

Figure 13A:
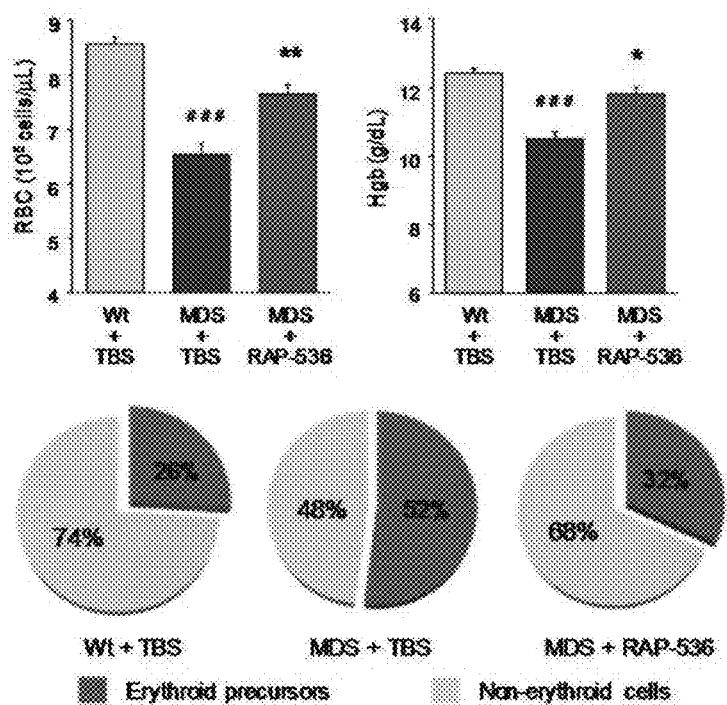
FIGS. 13A and 13B show that a GDF trap can mitigate ineffective erythropoiesis and ameliorate anemia at multiple stages of disease severity in a mouse model of MDS.

Example 12: Effect of a GDF Trap on Ineffective Erythropoiesis and Anemia in a Mouse Model of MDS Applicants investigated effects of the GDF trap ActRIIB (L79D 25-131)-mFc in the NUP98-HOXD13 mouse model of MDS, which is characterized by abortive precursor maturation and ineffective hematopoiesis. In this model, disease severity increases with age, eventually progressing to acute myeloid leukemia in the majority of mice, and they have a mean life span of approximately 14 months. Starting at approximately 4 months of age, these mice exhibit anemia, leukopenia, ineffective erythropoiesis, and bone marrow that is normocellular to hypercellular [Lin et al. (2005) Blood 106:287-295]. To monitor the effects of chronic administration, MDS mice were treated with ActRIIB(L79D 25-131)-mFc (10 mg/kg, s.c.) or vehicle twice weekly beginning at 4 months of age and continuing for 7 months, while blood samples (50 µL) were collected at baseline and monthly thereafter for complete blood count analysis. As expected, 6-month-old MDS mice developed severe anemia compared to wild-type mice (FIG. 13A), and bone marrow analyses revealed increased numbers of erythroid precursors (FIG. 13A) and a lower myeloid/erythroid (M/E) ratio [Suragani et al. (2014) Nat Med 20:408-414] in MDS mice compared to age-matched FVB wild-type mice, indicative of ineffective erythropoiesis. In 6-month-old MDS mice, treatment with ActRIIB(L79D 25-131)-mFc significantly increased RBC count (by 16.9%) and hemoglobin concentration (by 12.5%) (FIG. 13A), reduced erythroid precursor cell count in bone marrow (FIG. 13A), and normalized the M/E ratio to that of wild-type mice [Suragani et al. (2014) Nat Med 20:408-414].

Figure 13B:
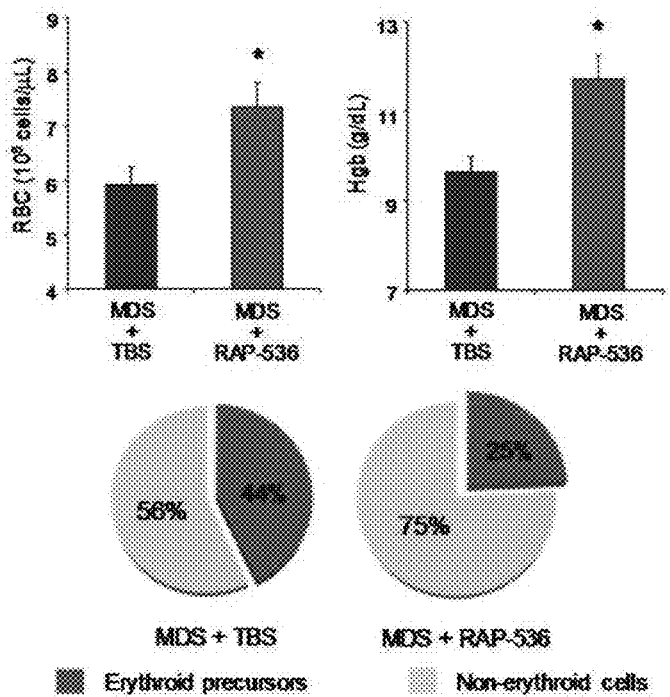

In MDS mice at 12 months of age, ActRIIB(L79D 25-131)-mFc treatment significantly increased RBC count (by 18.3%) and hemoglobin level (by 13.0%) (FIG. 13B), reduced erythroid precursor cell count (FIG. 13B), and improved the M:E ratio [Suragani et al. (2014) Nat Med 20:408-414], as compared to vehicle. ActRIIB(L79D 25-131)-mFc treatment did not affect the absolute number of myeloid precursors. Flow cytometry confirmed that ActRIIB (L79D 25-131)-mFc treatment reduced erythroid hyperplasia in MDS mice at both ages. A time-course analysis in MDS mice treated with ActRIIB(L79D 25-131)-mFc for 7 months showed a sustained elevation in RBC numbers for the duration of the study [Suragani et al. (2014) Nat Med 20:408-414]. Together, these results indicate that treatment with a GDF trap ameliorates anemia, erythroid hyperplasia and ineffective erythropoiesis in MDS mice regardless of disease severity.

Example 13: Cytologic and Genetic Signatures in MDS Patients Therapeutically Responsive to a GDF Trap A recombinant fusion protein containing modified activin receptor type IIB and IgG Fc [ActRIIB(L79D 25-131)-hFc, also known as luspatercept or ACE-536] is being developed for the treatment of anemias due to ineffective erythropoiesis such as myelodysplastic syndromes (MDS). Patients with MDS often have elevated levels of EPO and may be non-responsive or refractory to erythropoiesis-stimulating agents (ESAs). MDS patients have also been shown to have increased serum levels of GDF11 [Suragani et al. (2014) Nat Med 20:408-414] and increased Smad 2/3 signaling in the bone marrow [Zhou et al. (2008) Blood 112:3434-3443]. ActRIIB(L79D 25-131)-hFc binds to ligands in the TGFβ superfamily, including GDF11, inhibits Smad 2/3 signaling, and promotes late-stage erythroid differentiation via a mechanism distinct from ESAs. A murine version, ActRIIB (L79D 25-131)-mFc, reduced Smad2 signaling, increased hemoglobin (Hb) levels, and decreased bone marrow erythroid hyperplasia in a mouse model of MDS [Suragani et al. (2014) Nat Med 20:408-414]. In a healthy-volunteer study, ActRIIB(L79D 25-131)-hFc was well-tolerated and increased Hb levels [Attie et al. (2014) Am J Hematol 89:766-770].

Applicants are conducting an ongoing, phase 2, multi-center, open-label, dose-finding study to evaluate the effects of ActRIIB(L79D 25-131)-hFc on anemia in patients with Low or Int-1 risk MDS who have either high transfusion burden (HTB, defined as ≥4 units RBC per 8 weeks prior to baseline) or low transfusion burden (LTB, defined as <4 units RBC per 8 weeks prior to baseline). Study outcomes include erythroid response (either Hb increase in LTB patients or reduced transfusion burden in HTB patients), safety, tolerability, pharmacokinetics, and pharmacodynamic biomarkers. Inclusion criteria include: Low or Int-1 risk MDS, age ≥18 yr, anemia (defined as either being HTB patient or having baseline Hb<10.0 g/dL in LTB patient), EPO>500 U/L or nonresponsive/refractory to ESAs, no prior azacitidine or decitabine, and no current treatment with ESA, granulocyte colony-stimulating factor (G-CSF), granulocyte-macrophage colony-stimulating factor (GM-CSF), or lenalidomide, thalidomide or pomalidomide. In the dose-escalation phase, ActRIIB(L79D 25-131)-hFc was administered by subcutaneous injection once every 3 weeks in seven sequential cohorts (n=3-6) at dose levels of 0.125, 0.25, 0.5, 0.75, 1.0, 1.33 and 1.75 mg/kg for up to 5 doses with a 3-month follow-up.

Data were available for 26 patients (seven LTB/19 HTB). Median age was 71 yr (range: 27-88 yr), 50% were female, 54% had prior EPO therapy, and 15% had prior lenalidomide. Patient classification by WHO subtype was as follows: 15% RARS, 46% RCMD-RS, 15% RCMD, 15% RAEB-1 (including two patients with ≥15% ring sideroblasts) and 8% del (5q). Mean (SD) baseline Hgb for the LTB patients (n=7) was 9.1 (0.4) g/dL. Mean (SD) units RBC transfused in the 8 weeks prior to treatment was 0.9 (1.1) units for the LTB patients and 6.3 (2.4) units for the HTB patients. Two of the seven LTB patients had an increase in mean Hb≥1.5 g/dL over 8 weeks compared to baseline. Mean maximum Hb increase in the LTB patients was 0.8, 1.0, 2.2, and 3.5 g/dL in the 0.125 (n=1), 0.25 (n=1), 0.75 (n=3), and 1.75 (n=2) mg/kg dose groups, respectively. Six of the seven LTB patients achieved RBC transfusion independence (RBC-TI) for ≥8 weeks during the study. The dose levels ranging from 0.75 mg/kg to 1.75 mg/kg were deemed to be active doses. Among the five patients in the active dose groups, four (80%) achieved the pre-specified endpoint of Hgb increase of ≥1.5 g/dl for ≥2 weeks. Two patients (40%) achieved a HI-E response [International Working Group; Cheson et al. (2000) Blood 96:3671-3674; Cheson et al. (2006) Blood 108:419-425], defined as an Hgb increase of ≥1.5 g/dl for ≥8 weeks in LTB patients. In HTB patients, the HI-E response is defined as a reduction in transfusion burden of at least four units of red blood cells transfused over an 8 week period as compared to the 8 weeks prior to study start. In the active dose groups, five of 12 (42%) HTB patients met the pre-specified endpoint of a reduction of ≥4 RBC units or ≥50% reduction in RBC units transfused over an 8-week interval during the treatment period compared to the 8 weeks prior to treatment, and the same patients (five of 12, 42%) achieved a HI-E response; three of 12 (25%) of HTB patients in the active dose groups achieved RBC-TI≥8 weeks during the study. Increases in neutrophil count following study drug administration were observed in some patients. Finally, ActRIIB(L79D 25-131)-hFc was generally well tolerated. No related serious adverse events have been reported to date. The most frequent adverse events regardless of causality were: diarrhea (n=4, grade ½), bone pain, fatigue, muscle spasms, myalgia, and nasopharyngitis (n=3 each, grade ½).

Assessment of bone marrow aspirates demonstrated an association between the presence of ring sideroblasts (considered positive if ≥15% of erythroid precursors exhibited ring sideroblast morphology) and responsiveness to ActRIIB (L79D 25-131)-hFc in the active dose groups (0.75-1.75 mg/kg). The overall response rate (using HI-E criteria, described above) across both LTB and HTB patients was seven of 17 (41%). Among patients positive for ring sideroblasts at baseline, seven of 13 (54%) patients achieved a HI-E response, and notably none of the four patients negative for ring sideroblasts at baseline achieved a HI-E response.

Bone marrow aspirates from patients were also evaluated for the presence of mutations in 21 different genes that are known to harbor mutations (primarily somatic mutations) associated with MDS. Genomic DNA was isolated from bone marrow aspirates, selected coding regions of the 21 genes were amplified by polymerase chain reaction, and the DNA sequences of these regions were determined using next-generation sequencing (Myeloid Molecular Profile 21-gene panel, Genoptix, Inc., Carlsbad, Calif.). This analysis examined activated signaling genes (KIT, JAK2, NRAS, CBL, and MPL), transcription factors (RUNX1, ETV6), epigenetic genes (IDH1, IDH2, TET2, DNMT3A, EZH2, ASXL1, and SETBP1), RNA splicing genes (SF3B1, U2AF1, ZRSF2, and SRSF2), and tumor suppressors/others (TP53, NPM1, PHF6). Analysis of SF3B1 specifically targeted exons 13-16. Of these 21 MDS-associated genes evaluated, mutations in SF3B1 were more frequently detected in bone marrow cells in the responsive patients than in the nonresponsive patients. Individual SF3B1 mutations detected in these patients are shown in the following table. The same mutation sometimes occurred in multiple patients.

| Nucleotide | Nucleotide Substitution | Amino Acid Substitution | Exon |
| --- | --- | --- | --- |
| 1873 | C → T | R625C | 14 |
| 1874 | G → T | R625L | 14 |
| 1986 | C → G | H662Q | 14 |
| 2098 | A → G | K700E | 15 |
| 2342 | A → G | D781G | 16 |

In patients with SF3B1 mutations in the active dose groups, six of nine (67%) achieved HI-E responses, including all three patients that achieved transfusion independence for greater than 8 weeks. In patients not having an SF3B1 mutation, only one of eight (13%) achieved a HI-E response. Mutations in SF3B1 are frequently observed in MDS patients with ring sideroblasts and are associated with ineffective erythropoiesis.

These results indicate that patients with MDS exhibiting ≥15% ring sideroblasts (and patients with other forms of sideroblastic anemia), and/or at least one mutation in SF3B1 are more likely to respond therapeutically to ActRIIB(L79D 25-131)-hFc than MDS patients with <15% ring sideroblasts and/or no mutation in SF3B1. Based on these data, selective treatment of any of these patient subgroups is expected to greatly increase the benefit/risk ratio of treatment with ActRII inhibitors.

Example 14: Improvement in Visual Acuity in a MDS Patient Therapeutically Responsive to a GDF Trap ActRIIB(L79D 25-131)-hFc treatment was also observed to have a surprising effect on vision. In the above-described phase 2 MDS study, a male patient with poor vision (e.g., requiring corrective lens to perform certain activities) was shown to be responsive to ActRIIB(L79D 25-131)-hFc therapy. Prior to treatment the patient was afflicted with chronic anemia, requiring regular blood transfusions. ActRIIB(L79D 25-131)-hFc resulted in significant and sustained increases in hemoglobin levels the patient. Indeed, the patient achieved transfusion independence for ≥8 months during the study. In addition, significant improvement in vision was observed in the patient. In fact, the patient no longer required corrective lens to perform certain activities. These data therefore indicate that, in addition to positive effects on treating anemia, ActRII inhibitors may be used to improve vision in MDS patients. Moreover, in view of the reported mechanism for MDS-associated vision loss, as discussed below, the data suggest that ActRII inhibitors also may have positive effects on treating other types of ocular disorders.

It has been reported that retinal nerve fiber layer thickness is decreased in patients with various hematologic disorders, particularly those associated with anemia [Han et al. (2015) J Glaucoma (Epub ahead of print)]. Such changes in the retinal nerve fiber are associated with reduced visual acuity and other pathological changes in the eye. Studies indicate that retinal damage in these patients may be due to ischemic optic neuropathy. For example, loss of vision in MDS patients has been associated with the manifestation of NAION [Brouzas et al. (2009) Clinical Ophthalmology 3:133-137]. In such MDS patients, it is believed that the initiation of NAION is through a mechanism of ischemia and/or microvascular insufficiency. Indeed, it has been demonstrated that therapy for treating ischemia-hypoxia improves visual acuity in MDS patients. Accordingly, the data of the instant application suggests that ActRII antagonists may be used to treat other related ocular disorders, particularly those associated with ischemia and microvascular insufficiency.

Example 15: Effects of ActRII Polypeptides on Lesion Size and Leakage after Laser-Induced Choroidal Neovascularization The effects of ActRIIA-Fc (see Example 1), ActRIIB-Fc (see Example 4), and ActRIIB(L79D 25-131)-Fc (see Example 9) on lesion size and leakage in a rat model of laser-induced choroidal neovascularization are to be evaluated.

At day 1 of the study, 20 Brown Norway rats (6-8 weeks of age) receive bilateral laser treatment to produce 3 lesions per eye. Animals are dilated with 1% Cyclogyl solution and protected from light. Following observable dilation, the animals are sedated. The fundus of sedated animals is observed and recorded using a Micron IV small animal funduscope (Phoenix Research). Laser treatments are performed using a thermal laser which is connected through the Micron IV custom laser attachment. A total of 3 lesions per eye are placed in the right eye using a wavelength of 532 nm. The resultant fundus images are recorded and evaluated to confirm the laser has successfully produced a bubble through the Bruch's membrane.

Following laser treatment, the rats are separated into one of 4 treatment groups: a) s.c. administration of vehicle (PBS) on days 1, 8, and 15; b) s.c. administration of ActRIIA-Fc (10 mg/kg) on days 1, 8, and 15; c) s.c. administration of ActRIIB-Fc (10 mg/kg) on days 1, 8, and 15; and d) s.c. administration of ActRIIB(L79D 25-131)-Fc (10 mg/kg) on days 1, 8, and 15.

At day 22, the rats are evaluated for reduction of lesion size and leakage by in vivo fluorescein angiographs. Animals are anesthetized and then receive an IP injection of 10% fluorescein sodium at 1 μl/gram of body weight. Fundus images are then captured as 8-bit TIFF files using the Micron III and exciter/barrier filters for a target wavelength of 488 nm. Standard color fundus photos are also captured for each eye. All TIFF images are quantified using computerized image-analysis software (e.g., ImageJ, NIH, USA). The boundary of lesions are then individually traced freehand, and the resultant image is subjected to multi-Otsu thresholding to eliminate background signal and quantify the area in pixels. Areas of hemorrhage or where two lesions are overlapping are excluded from analysis.

Example 16: Effects of ActRII Polypeptides on Lesion Size and Leakage in a Rat Model of Streptozotocin-Induced Diabetes Model The effects of ActRIIA-Fc (see Example 1), ActRIIB-Fc (see Example 4), and ActRIIB(L79D 25-131)-Fc (see Example 9) on lesion size and leakage in a rat model of streptozotocin (STZ) induced diabetes are to be evaluated.

STZ is a small molecule that causes depletion of the pancreatic islet cells following systemic administration. The islet cell death causes a loss of insulin production and subsequent dysregulation of blood glucose levels leading to hyperglycemia within days. This model has been used to study inflammation, vascular pathology, and signaling pathways in the pathogenesis of diabetic retinopathy and diabetic macular edema. At eight weeks following induction of diabetes with STZ, there is a significant and progressive loss of visual acuity and contrast sensitivity. Since the primary endpoints accepted by regulatory agencies for human clinical trials are focused on quantitative measurements of visual acuity and contrast sensitivity, this is an excellent model for testing the activity of therapeutic agents to prevent diabetic vision loss.

At day 1 of the study, 20 Brown Norway rats (8-12 weeks of age) are given a single intraperitoneal injection of STZ (50 mg/kg of body weight in 10 mmol/L of citrate buffer, pH 4.5). Serum glucose levels will be examined two days after the STZ injection and weekly thereafter. Only animals with blood glucose levels higher than 350 mg/dl will be used as diabetic rats.

Six to eight weeks following STZ treatment, the rats are separated into one of 4 treatment groups: a) s.c. administration of vehicle (PBS) on days 1, 8, and 15; b) s.c. administration of ActRIIA-Fc (10 mg/kg) on days 1, 8, and 15; c) s.c. administration of ActRIIB-Fc (10 mg/kg) on days 1, 8, and 15; and d) s.c. administration of ActRIIB(L79D 25-131)-Fc (10 mg/kg) on days 1, 8, and 15.

At day 22 following the start of therapy, the rats are evaluated for reduction of lesion size and leakage by in vivo fluorescein angiographs as described above in Example 15.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

We claim:

1. A method for treating a vascular disorder of the eye in a patient, comprising administering to a patient in need thereof an effective amount of an activin type II receptor (ActRII) antagonist, wherein the patient has chronic anemia and myelodysplastic syndrome, wherein the ActRII antagonist comprises a polypeptide comprising an amino acid sequence that is at least 90% identical to the sequence of amino acids 29-109 of SEQ ID NO: 1, wherein the polypeptide comprises an acidic amino acid at the amino acid position corresponding to position 79 of SEQ ID NO: 1, and wherein the polypeptide is capable of binding to GDF8 and/or GDF11.

2. The method of claim 1, wherein the vascular disorder of the eye is associated with ischemia.

3. The method of claim 1, wherein the vascular disorder of the eye is associated with microvascular insufficiency.

4. The method of claim 1, wherein the ActRII antagonist is an ActRII polypeptide comprising an amino acid sequence that is at least 95% identical to the sequence of amino acids 29-109 of SEQ ID NO: 1.

5. The method of claim 1, wherein the polypeptide comprises a D at position 79 with respect to SEQ ID NO: 1.

6. The method of claim 1, wherein the polypeptide is a fusion protein comprising, in addition to an ActRII polypeptide domain an immunoglobulin Fc domain.

7. The method of claim 6, wherein the fusion protein further comprises a linker domain positioned between the ActRII domain and the immunoglobulin Fc domain.

8. The method of claim 6, wherein the polypeptide is an ActRII-Fc fusion protein comprising a polypeptide selected from the group consisting of:

a) a polypeptide comprising the amino acid sequence of SEQ ID NO: 40 or comprising an amino acid sequence that is at least 90% identical to the amino acid sequence of SEQ ID NO: 40;

b) a polypeptide comprising the amino acid sequence of SEQ ID NO: 41 or comprising an amino acid sequence that is at least 90% identical to the amino acid sequence of SEQ ID NO: 41;

c) a polypeptide comprising the amino acid sequence of SEQ ID NO: 44 or comprising an amino acid sequence that is at least 90% identical to the amino acid sequence of SEQ ID NO: 44;

d) a polypeptide comprising the amino acid sequence of SEQ ID NO: 46 or comprising an amino acid sequence that is at least 90% identical to the amino acid sequence of SEQ ID NO: 46;

e) a polypeptide comprising the amino acid sequence of SEQ ID NO: 50 or comprising an amino acid sequence that is at least 90% identical to the amino acid sequence of SEQ ID NO: 50;

f) a polypeptide comprising the amino acid sequence of SEQ ID NO: 61 or comprising an amino acid sequence that is at least 90% identical to the amino acid sequence of SEQ ID NO: 61;

g) a polypeptide comprising the amino acid sequence of SEQ ID NO: 64 or comprising an amino acid sequence that is at least 90% identical to the amino acid sequence of SEQ ID NO: 64;

h) a polypeptide comprising the amino acid sequence of SEQ ID NO: 78 or comprising an amino acid sequence that is at least 90% identical to the amino acid sequence of SEQ ID NO: 78; and i) a polypeptide comprising the amino acid sequence of SEQ ID NO: 79 or comprising an amino acid sequence that is at least 90% identical to the amino acid sequence of SEQ ID NO: 79.

9. The method of claim 6, wherein the polypeptide is an ActRII-Fc fusion protein comprising a polypeptide selected from the group consisting of:

a) a polypeptide comprising the amino acid sequence of SEQ ID NO: 40 or comprising an amino acid sequence that is at least 95% identical to the amino acid sequence of SEQ ID NO: 40;
b) a polypeptide comprising the amino acid sequence of SEQ ID NO: 41 or comprising an amino acid sequence that is at least 95% identical to the amino acid sequence of SEQ ID NO: 41;
c) a polypeptide comprising the amino acid sequence of SEQ ID NO: 44 or comprising an amino acid sequence that is at least 95% identical to the amino acid sequence of SEQ ID NO: 44;
d) a polypeptide comprising the amino acid sequence of SEQ ID NO: 46 or comprising an amino acid sequence that is at least 95% identical to the amino acid sequence of SEQ ID NO: 46;
e) a polypeptide comprising the amino acid sequence of SEQ ID NO: 50 or comprising an amino acid sequence that is at least 95% identical to the amino acid sequence of SEQ ID NO: 50;
f) a polypeptide comprising the amino acid sequence of SEQ ID NO: 61 or comprising an amino acid sequence that is at least 95% identical to the amino acid sequence of SEQ ID NO: 61;
g) a polypeptide comprising the amino acid sequence of SEQ ID NO: 64 or comprising an amino acid sequence that is at least 95% identical to the amino acid sequence of SEQ ID NO: 64;
h) a polypeptide comprising the amino acid sequence of SEQ ID NO: 78 or comprising an amino acid sequence that is at least 95% identical to the amino acid sequence of SEQ ID NO: 78; and
i) a polypeptide comprising the amino acid sequence of SEQ ID NO: 79 or comprising an amino acid sequence that is at least 95% identical to the amino acid sequence of SEQ ID NO: 79.

10. The method of claim 6, wherein the polypeptide is an ActRII-Fc fusion protein comprising a polypeptide selected from the group consisting of:
a) a polypeptide comprising the amino acid sequence of SEQ ID NO: 40 or comprising an amino acid sequence that is at least 98% identical to the amino acid sequence of SEQ ID NO: 40;
b) a polypeptide comprising the amino acid sequence of SEQ ID NO: 41 or comprising an amino acid sequence that is at least 98% identical to the amino acid sequence of SEQ ID NO: 41;
c) a polypeptide comprising the amino acid sequence of SEQ ID NO: 44 or comprising an amino acid sequence that is at least 98% identical to the amino acid sequence of SEQ ID NO: 44;
d) a polypeptide comprising the amino acid sequence of SEQ ID NO: 46 or comprising an amino acid sequence that is at least 98% identical to the amino acid sequence of SEQ ID NO: 46;
e) a polypeptide comprising the amino acid sequence of SEQ ID NO: 50 or comprising an amino acid sequence that is at least 98% identical to the amino acid sequence of SEQ ID NO: 50;
f) a polypeptide comprising the amino acid sequence of SEQ ID NO: 61 or comprising an amino acid sequence that is at least 98% identical to the amino acid sequence of SEQ ID NO: 61;
g) a polypeptide comprising the amino acid sequence of SEQ ID NO: 64 or comprising an amino acid sequence that is at least 98% identical to the amino acid sequence of SEQ ID NO: 64;
h) a polypeptide comprising the amino acid sequence of SEQ ID NO: 78 or comprising an amino acid sequence that is at least 98% identical to the amino acid sequence of SEQ ID NO: 78; and
i) a polypeptide comprising the amino acid sequence of SEQ ID NO: 79 or comprising an amino acid sequence that is at least 98% identical to the amino acid sequence of SEQ ID NO: 79.

11. The method of claim 8, wherein the polypeptide comprises a D at position 79 with respect to SEQ ID NO: 1.

12. The method of claim 8, wherein the polypeptide comprises a E at position 79 with respect to SEQ ID NO: 1.

13. The method of claim 4, wherein the polypeptide comprises one or more amino acid modifications selected from: a glycosylated amino acid, a PEGylated amino acid, a farnesylated amino acid, an acetylated amino acid, a biotinylated amino acid, and an amino acid conjugated to a lipid moiety.

14. The method of claim 13, wherein the polypeptide is glycosylated and has a mammalian glycosylation pattern.

15. The method of claim 14, wherein the polypeptide is glycosylated and has a glycosylation pattern obtainable from a Chinese hamster ovary cell line.

16. The method of claim 4, wherein the polypeptide binds to GDF11.

17. The method of claim 4, wherein the polypeptide binds to GDF8.

18. The method of claim 4, wherein the polypeptide binds to activin B.

19. The method of claim 1, wherein the method further comprises administering to the patient one or more additional active agents or supportive therapies for treating or reducing the severity of an eye disorder.

20. The method of claim 19, wherein the one or more additional active agents or supportive therapies is selected from the group consisting of: surgery, laser therapy, photocoagulation, anti-angiogenic therapy, VEGF inhibitors, bevacizumab, ranibizumab, aflibercept, $Ca^{2+}$ inhibitors, flunarizine, nifedipine, cryotherapy, hyperbaric oxygenation, $Na^+$ channel blockers, topiramate, iGluR antagonists, MK-801, dextromethorphan, eliprodil, flupirtine, antioxidants, dimethylthiourea, alpha-lipoic acid, superoxide dismutase, catalase, desferrioxamine, mannitol, allopurinol, calcium dobesilate, flupirtine, trimetazidine, EGB-761, anti-inflammatory agents, cyclodiathermy, cyclocryotherapy, ocular filtering procedures, implantation of drainage valves, antiplatelet therapy, aspirin, ticlopidine, clopidogrel, anticoagulant therapy, warfarin, heparin, steroids, systemic or local corticosteroids, prednisone triamcinolone, fluocinolone acetonide, dexamethasone, steroid-sparing immunosuppressants, cyclosporine, azathioprine, cyclophosphamide, mycophenolate, mofetil, infliximab, etanercept, dietary supplements, vitamin C, vitamin E, lutein, zinc, folic acid, vitamin B6, vitamin B12, zeaxanthin, vitrectomy, scleral buckle surgery, and pneumatic retinopexy.

21. The method of claim 19, wherein the one or more additional active agents is selected from the group consisting of: a vascular endothelial growth factor (VEGF) inhibitor, a VEGF-A inhibitor, a placental growth factor (PLGF) inhibitor, a VEGF and PLGF inhibitor, aflibercept, ranibizumab, and bevacizumab.

22. The method of claim 1, wherein the ActRII antagonist is administered by ocular or intravitreal administration.

23. The method of claim 4, wherein the polypeptide is an ActRII-Fc fusion protein comprising a polypeptide comprising an amino acid sequence that is at least 95% identical to the amino acid sequence of SEQ ID NO: 64.

24. The method of claim 4, wherein the polypeptide is an ActRII-Fc fusion protein comprising a polypeptide comprising the amino acid sequence of SEQ ID NO: 64.

25. The method of claim 1, wherein the ActRII antagonist is an ActRII polypeptide comprising the sequence of amino acids 29-109 of SEQ ID NO: 1; but wherein the polypeptide comprises an acidic amino acid at the amino acid position corresponding to position 79 of SEQ ID NO: 1.

26. The method of claim 1, wherein the ActRII antagonist is an ActRII polypeptide comprising an amino acid sequence that is at least 90% identical to the sequence of amino acids 25-131 of SEQ ID NO: 1.

27. The method of claim 1, wherein the ActRII antagonist is an ActRII polypeptide comprising an amino acid sequence that is at least 95% identical to the sequence of amino acids 25-131 of SEQ ID NO: 1.

28. The method of claim 1, wherein the ActRII antagonist is an ActRII polypeptide comprising the sequence of amino acids 25-131 of SEQ ID NO: 1; but wherein the polypeptide comprises an acidic amino acid at the amino acid position corresponding to position 79 of SEQ ID NO: 1.

29. The method of claim 4, wherein the polypeptide comprises a D at position 79 with respect to SEQ ID NO: 1.

30. The method of claim 4, wherein the polypeptide comprises an E at position 79 with respect to SEQ ID NO: 1.

31. A method for improving vision in a patient that has a vascular disorder of the eye, comprising administering to a patient in need thereof an effective amount of an activin type II receptor (ActRII) antagonist, wherein the patient has chronic anemia and myelodysplastic syndrome, wherein the ActRII antagonist comprises a polypeptide comprising an amino acid sequence that is at least 90% identical to the sequence of amino acids 29-109 of SEQ ID NO: 1, wherein the polypeptide comprises an acidic amino acid at the amino acid position corresponding to position 79 of SEQ ID NO: 1, and wherein the polypeptide is capable of binding to GDF8 and/or GDF11.

32. The method of claim 31, wherein the method increases visual acuity.

33. The method of claim 31, wherein the ActRII antagonist comprises a polypeptide comprising an amino acid sequence that is at least 95% identical to the sequence of amino acids 29-109 of SEQ ID NO: 1.

34. The method of claim 31, wherein the ActRII antagonist comprises a polypeptide comprising the amino acid sequence of amino acids 29-109 of SEQ ID NO: 1, but wherein the polypeptide comprises an acidic amino acid at the amino acid position corresponding to position 79 of SEQ ID NO: 1.

35. The method of claim 31, wherein the ActRII antagonist comprises a polypeptide comprising an amino acid sequence that is at least 90% identical to the sequence of amino acids 25-132 of SEQ ID NO: 1.

36. The method of claim 31, wherein the ActRII antagonist comprises a polypeptide comprising an amino acid sequence that is at least 95% identical to the sequence of amino acids 25-132 of SEQ ID NO: 1.

37. The method of claim 31, wherein the ActRII antagonist comprises a polypeptide comprising the amino acid sequence of amino acids 25-132 of SEQ ID NO: 1, but wherein the polypeptide comprises an acidic amino acid at the amino acid position corresponding to position 79 of SEQ ID NO: 1.

38. A method of treating or reducing the severity of an eye disorder in a patient, comprising administering to a patient in need thereof an effective amount of an activin type II receptor (ActRII) antagonist, wherein the patient has chronic anemia and myelodysplastic syndrome, wherein the ActRII antagonist comprises a polypeptide comprising an amino acid sequence that is at least 90% identical to the sequence of amino acids 29-109 of SEQ ID NO: 1, wherein the polypeptide comprises an acidic amino acid at the amino acid position corresponding to position 79 of SEQ ID NO: 1, and wherein the polypeptide is capable of binding to GDF8 and/or GDF11.

39. The method of claim 38, wherein the ActRII antagonist comprises a polypeptide comprising an amino acid sequence that is at least 95% identical to the sequence of amino acids 29-109 of SEQ ID NO: 1.

40. The method of claim 38, wherein the ActRII antagonist comprises a polypeptide comprising the amino acid sequence of amino acids 29-109 of SEQ ID NO: 1, but wherein the polypeptide comprises an acidic amino acid at the amino acid position corresponding to position 79 of SEQ ID NO: 1.

41. The method of claim 38, wherein the ActRII antagonist comprises a polypeptide comprising an amino acid sequence that is at least 90% identical to the sequence of amino acids 25-131 of SEQ ID NO: 1.

42. The method of claim 38, wherein the ActRII antagonist comprises a polypeptide comprising an amino acid sequence that is at least 95% identical to the sequence of amino acids 25-131 of SEQ ID NO: 1.

43. The method of claim 38, wherein the ActRII antagonist comprises a polypeptide comprising the amino acid sequence of amino acids 25-131 of SEQ ID NO: 1, but wherein the polypeptide comprises an acidic amino acid at the amino acid position corresponding to position 79 of SEQ ID NO: 1.

* * * * *

SEQUENCE LISTING

```
<160> NUMBER OF SEQ ID NOS: 86

<210> SEQ ID NO 1
<211> LENGTH: 512
<212> TYPE: PRT
<213> ORGANISM: Homo sapiens
```

<400> SEQUENCE: 1

```
Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
        195                 200                 205

Leu Met Asn Asp Phe Val Ala Val Lys Ile Phe Pro Leu Gln Asp Lys
    210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
    290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
        355                 360                 365

Val Leu Glu Gly Ala Ile Asn Phe Gln Arg Asp Ala Phe Leu Arg Ile
    370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
```

```
                    405                 410                 415
Glu Ile Gly Gln His Pro Ser Leu Glu Glu Leu Gln Glu Val Val Val
                420                 425                 430

His Lys Lys Met Arg Pro Thr Ile Lys Asp His Trp Leu Lys His Pro
            435                 440                 445

Gly Leu Ala Gln Leu Cys Val Thr Ile Glu Glu Cys Trp Asp His Asp
        450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
            500                 505                 510

<210> SEQ ID NO 2
<211> LENGTH: 115
<212> TYPE: PRT
<213> ORGANISM: Homo sapiens

<400> SEQUENCE: 2

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 3
<211> LENGTH: 100
<212> TYPE: PRT
<213> ORGANISM: Homo sapiens

<400> SEQUENCE: 3

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala
```

-continued

100

<210> SEQ ID NO 4
<211> LENGTH: 512
<212> TYPE: PRT
<213> ORGANISM: Homo sapiens

<400> SEQUENCE: 4

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Ala
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
        195                 200                 205

Leu Met Asn Asp Phe Val Ala Val Lys Ile Phe Pro Leu Gln Asp Lys
    210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
    290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
        355                 360                 365

```
Val Leu Glu Gly Ala Ile Asn Phe Gln Arg Asp Ala Phe Leu Arg Ile
370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
                420                 425                 430

His Lys Lys Met Arg Pro Thr Ile Lys Asp His Trp Leu Lys His Pro
            435                 440                 445

Gly Leu Ala Gln Leu Cys Val Thr Ile Glu Glu Cys Trp Asp His Asp
450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
                500                 505                 510

<210> SEQ ID NO 5
<211> LENGTH: 115
<212> TYPE: PRT
<213> ORGANISM: Homo sapiens

<400> SEQUENCE: 5

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
                20                  25                  30

Glu Gln Asp Lys Arg Leu His Cys Tyr Ala Ser Trp Ala Asn Ser Ser
            35                  40                  45

Gly Thr Ile Glu Leu Val Lys Lys Gly Cys Trp Leu Asp Asp Phe Asn
50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Pro Glu Val Thr Tyr Glu Pro Pro Pro Thr
                100                 105                 110

Ala Pro Thr
        115

<210> SEQ ID NO 6
<211> LENGTH: 100
<212> TYPE: PRT
<213> ORGANISM: Homo sapiens

<400> SEQUENCE: 6

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
                20                  25                  30

Glu Gln Asp Lys Arg Leu His Cys Tyr Ala Ser Trp Ala Asn Ser Ser
            35                  40                  45

Gly Thr Ile Glu Leu Val Lys Lys Gly Cys Trp Leu Asp Asp Phe Asn
50                  55                  60
```

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala
            100

<210> SEQ ID NO 7
<211> LENGTH: 1536
<212> TYPE: DNA
<213> ORGANISM: Homo sapiens

<400> SEQUENCE: 7

| | |
|---|---:|
| atgacggcgc cctgggtggc cctcgccctc tctctgggat cgctgtgcgc cggctctggg | 60 |
| cgtggggagg ctgagacacg ggagtgcatc tactacaacg ccaactggga gctggagcgc | 120 |
| accaaccaga gcggcctgga gcgctgcgaa ggcgagcagg acaagcggct gcactgctac | 180 |
| gcctcctggc gcaacagctc tggcaccatc gagctcgtga agaagggctg ctggctagat | 240 |
| gacttcaact gctacgatag caggagtgt gtggccactg aggagaaccc ccaggtgtac | 300 |
| ttctgctgct gtgaaggcaa cttctgcaac gaacgcttca ctcatttgcc agaggctggg | 360 |
| ggcccggaag tcacgtacga gccacccccg acagccccca ccctgctcac ggtgctggcc | 420 |
| tactcactgc tgcccatcgg ggccttttcc ctcatcgtcc tgctggcctt ttggatgtac | 480 |
| cggcatcgca agccccccta cggtcatgtg acatccatg aggaccctgg gcctccacca | 540 |
| ccatcccctc tggtgggcct gaagccactg cagctgctgg agatcaaggc tcggggcgc | 600 |
| tttggctgtg tctggaaggc ccagctcatg aatgactttg tagctgtcaa gatcttccca | 660 |
| ctccaggaca gcagtcgtg gcagagtgaa cgggagatct tcagcacacc tggcatgaag | 720 |
| cacgagaacc tgctacagtt cattgctgcc gagaagcgag gctccaacct cgaagtagag | 780 |
| ctgtggctca tcacggcctt ccatgacaag ggctcccctca cggattacct caaggggaac | 840 |
| atcatcacat ggaacgaact gtgtcatgta gcagagacga tgtcacgagg cctctcatac | 900 |
| ctgcatgagg atgtgcctg gtgccgtggc gagggccaca agccgtctat tgcccacagg | 960 |
| gactttaaaa gtaagaatgt attgctgaag agcgacctca cagccgtgct ggctgacttt | 1020 |
| ggcttggctg ttcgatttga gccagggaaa cctccagggg acacccacgg acaggtaggc | 1080 |
| acgagacggt acatggctcc tgaggtgctc gagggagcca tcaacttcca gagagatgcc | 1140 |
| ttcctgcgca ttgacatgta tgccatgggg ttggtgctgt gggagcttgt gtctcgctgc | 1200 |
| aaggctgcag acgacccgt ggatgagtac atgctgccct ttgaggaaga gattggccag | 1260 |
| caccctttcgt tggaggagct gcaggaggtg gtggtgcaca agaagatgag gcccaccatt | 1320 |
| aaagatcact ggttgaaaca cccgggcctg gcccagcttt gtgtgaccat cgaggagtgc | 1380 |
| tgggaccatg atgcagaggc tcgcttgtcc gcgggctgtg tggaggagcg ggtgtccctg | 1440 |
| attcggaggt cggtcaacgg cactacctcg gactgtctcg tttccctggt gacctctgtc | 1500 |
| accaatgtgg acctgccccc taaagagtca agcatc | 1536 |

<210> SEQ ID NO 8
<211> LENGTH: 345
<212> TYPE: DNA
<213> ORGANISM: Homo sapiens

<400> SEQUENCE: 8

| | |
|---|---:|
| gggcgtgggg aggctgagac acgggagtgc atctactaca acgccaactg ggagctggag | 60 |

-continued

```
cgcaccaacc agagcggcct ggagcgctgc gaaggcgagc aggacaagcg gctgcactgc       120
tacgcctcct ggcgcaacag ctctggcacc atcgagctcg tgaagaaggg ctgctggcta       180
gatgacttca actgctacga taggcaggag tgtgtggcca ctgaggagaa ccccccaggtg      240 tacttctgct gctgtgaagg caacttctgc aacgaacgct tcactcattt gccagaggct       300
gggggcccgg aagtcacgta cgagccaccc ccgacagccc ccacc                      345
```

<210> SEQ ID NO 9
<211> LENGTH: 513
<212> TYPE: PRT
<213> ORGANISM: Homo sapiens

<400> SEQUENCE: 9

```
Met Gly Ala Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
        35                  40                  45

Pro Cys Tyr Gly Asp Lys Asp Lys Arg Arg His Cys Phe Ala Thr Trp
    50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125

Pro Val Thr Pro Lys Pro Pro Tyr Tyr Asn Ile Leu Leu Tyr Ser Leu
    130                 135                 140

Val Pro Leu Met Leu Ile Ala Gly Ile Val Ile Cys Ala Phe Trp Val
145                 150                 155                 160

Tyr Arg His His Lys Met Ala Tyr Pro Pro Val Leu Val Pro Thr Gln
                165                 170                 175

Asp Pro Gly Pro Pro Pro Ser Pro Leu Leu Gly Leu Lys Pro Leu
            180                 185                 190

Gln Leu Leu Glu Val Lys Ala Arg Gly Arg Phe Gly Cys Val Trp Lys
        195                 200                 205

Ala Gln Leu Leu Asn Glu Tyr Val Ala Val Lys Ile Phe Pro Ile Gln
    210                 215                 220

Asp Lys Gln Ser Trp Gln Asn Glu Tyr Glu Val Tyr Ser Leu Pro Gly
225                 230                 235                 240

Met Lys His Glu Asn Ile Leu Gln Phe Ile Gly Ala Glu Lys Arg Gly
                245                 250                 255

Thr Ser Val Asp Val Asp Leu Trp Leu Ile Thr Ala Phe His Glu Lys
            260                 265                 270

Gly Ser Leu Ser Asp Phe Leu Lys Ala Asn Val Val Ser Trp Asn Glu
        275                 280                 285

Leu Cys His Ile Ala Glu Thr Met Ala Arg Gly Leu Ala Tyr Leu His
    290                 295                 300

Glu Asp Ile Pro Gly Leu Lys Asp Gly His Lys Pro Ala Ile Ser His
305                 310                 315                 320

Arg Asp Ile Lys Ser Lys Asn Val Leu Leu Lys Asn Asn Leu Thr Ala
```

```
            325                 330                 335
Cys Ile Ala Asp Phe Gly Leu Ala Leu Lys Phe Glu Ala Gly Lys Ser
        340                 345                 350

Ala Gly Asp Thr His Gly Gln Val Gly Thr Arg Arg Tyr Met Ala Pro
        355                 360                 365

Glu Val Leu Glu Gly Ala Ile Asn Phe Gln Arg Asp Ala Phe Leu Arg
    370                 375                 380

Ile Asp Met Tyr Ala Met Gly Leu Val Leu Trp Glu Leu Ala Ser Arg
385                 390                 395                 400

Cys Thr Ala Ala Asp Gly Pro Val Asp Glu Tyr Met Leu Pro Phe Glu
                405                 410                 415

Glu Glu Ile Gly Gln His Pro Ser Leu Glu Asp Met Gln Glu Val Val
            420                 425                 430

Val His Lys Lys Lys Arg Pro Val Leu Arg Asp Tyr Trp Gln Lys His
        435                 440                 445

Ala Gly Met Ala Met Leu Cys Glu Thr Ile Glu Glu Cys Trp Asp His
    450                 455                 460

Asp Ala Glu Ala Arg Leu Ser Ala Gly Cys Val Gly Glu Arg Ile Thr
465                 470                 475                 480

Gln Met Gln Arg Leu Thr Asn Ile Ile Thr Thr Glu Asp Ile Val Thr
                485                 490                 495

Val Val Thr Met Val Thr Asn Val Asp Phe Pro Pro Lys Glu Ser Ser
            500                 505                 510

Leu

<210> SEQ ID NO 10
<211> LENGTH: 115
<212> TYPE: PRT
<213> ORGANISM: Homo sapiens

<400> SEQUENCE: 10

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro
        115

<210> SEQ ID NO 11
<211> LENGTH: 100
<212> TYPE: PRT
<213> ORGANISM: Homo sapiens

<400> SEQUENCE: 11

Ile Leu Gly Arg Ser Glu Thr Gln Glu Cys Leu Phe Phe Asn Ala Asn
1               5                   10                  15
```

```
Trp Glu Lys Asp Arg Thr Asn Gln Thr Gly Val Glu Pro Cys Tyr Gly
         20                  25                  30

Asp Lys Asp Lys Arg Arg His Cys Phe Ala Thr Trp Lys Asn Ile Ser
         35                  40              45

Gly Ser Ile Glu Ile Val Lys Gln Gly Cys Trp Leu Asp Asp Ile Asn
     50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                 85                  90                  95

Phe Pro Glu Met
            100

<210> SEQ ID NO 12
<211> LENGTH: 1539
<212> TYPE: DNA
<213> ORGANISM: Homo sapiens

<400> SEQUENCE: 12
```

| | | | | | |
|---|---|---|---|---|---|
| atgggagctg | ctgcaaagtt | ggcgtttgcc | gtctttctta | tctcctgttc | ttcaggtgct | 60 |
| atacttggta | gatcagaaac | tcaggagtgt | cttttcttta | atgctaattg | ggaaaaagac | 120 |
| agaaccaatc | aaactggtgt | tgaaccgtgt | tatggtgaca | agataaacg | gcggcattgt | 180 |
| tttgctacct | ggaagaatat | ttctggttcc | attgaaatag | tgaaacaagg | ttgttggctg | 240 |
| gatgatatca | actgctatga | caggactgat | tgtgtagaaa | aaaagacag | ccctgaagta | 300 |
| tattttgtt | gctgtgaggg | caatatgtgt | aatgaaaagt | tttcttattt | tccggagatg | 360 |
| gaagtcacac | agcccacttc | aaatccagtt | acacctaagc | caccctatta | caacatcctg | 420 |
| ctctattcct | tggtgccact | tatgttaatt | gcggggattg | tcatttgtgc | attttgggtg | 480 |
| tacaggcatc | acaagatggc | ctaccctcct | gtacttgttc | caactcaaga | cccaggacca | 540 |
| ccccccacctt | ctccattact | aggtttgaaa | ccactgcagt | tattagaagt | gaaagcaagg | 600 |
| ggaagatttg | ttgtgtctg | gaaagcccag | ttgcttaacg | aatatgtggc | tgtcaaaata | 660 |
| tttccaatac | aggacaaaca | gtcatggcaa | atgaatacg | aagtctacag | tttgcctgga | 720 |
| atgaagcatg | agaacatatt | acagttcatt | ggtgcagaaa | aacgaggcac | cagtgttgat | 780 |
| gtggatcttt | ggctgatcac | agcatttcat | gaaaagggtt | cactatcaga | ctttcttaag | 840 |
| gctaatgtgg | tctcttggaa | tgaactgtgt | catattgcag | aaaccatggc | tagaggattg | 900 |
| gcatatttac | atgaggatat | acctggccta | aagatggcc | acaaacctgc | catatctcac | 960 |
| agggacatca | aaagtaaaaa | tgtgctgttg | aaaaacaacc | tgacagcttg | cattgctgac | 1020 |
| tttgggttgg | ccttaaaatt | tgaggctggc | aagtctgcag | cgatacccca | tggacaggtt | 1080 |
| ggtacccgga | ggtacatggc | tccagaggta | ttagagggtg | ctataaactt | ccaaagggat | 1140 |
| gcattttga | ggatagatat | gtatgccatg | ggattagtcc | tatgggaact | gcttctcgc | 1200 |
| tgtactgctg | cagatggacc | tgtagatgaa | tacatgttgc | catttgagga | ggaaattggc | 1260 |
| cagcatccat | ctcttgaaga | catgcaggaa | gttgttgtgc | ataaaaaaaa | gaggcctgtt | 1320 |
| ttaagagatt | attggcagaa | acatgctgga | atggcaatgc | tctgtgaaac | cattgaagaa | 1380 |
| tgttgggatc | acgacgcaga | agccaggtta | tcagctggat | gtgtaggtga | agaattacc | 1440 |
| cagatgcaga | gactaacaaa | tattattacc | acagaggaca | ttgtaacagt | ggtcacaatg | 1500 |
| gtgacaaatg | ttgactttcc | tcccaaagaa | tctagtcta | | | 1539 |

<210> SEQ ID NO 13
<211> LENGTH: 345
<212> TYPE: DNA
<213> ORGANISM: Homo sapiens

<400> SEQUENCE: 13

```
atacttggta gatcagaaac tcaggagtgt cttttcttta atgctaattg ggaaaaagac      60
agaaccaatc aaactggtgt tgaaccgtgt tatggtgaca agataaacg gcggcattgt     120
tttgctacct ggaagaatat ttctggttcc attgaaatag tgaaacaagg ttgttggctg     180
gatgatatca actgctatga caggactgat tgtgtagaaa aaaagacag ccctgaagta     240
tattttttgtt gctgtgaggg caatatgtgt aatgaaaagt tttcttattt tccggagatg     300
gaagtcacac agcccacttc aaatccagtt acacctaagc caccc                     345
```

<210> SEQ ID NO 14
<211> LENGTH: 225
<212> TYPE: PRT
<213> ORGANISM: Homo sapiens

<400> SEQUENCE: 14

```
Thr His Thr Cys Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225
```

<210> SEQ ID NO 15
<211> LENGTH: 223
<212> TYPE: PRT
<213> ORGANISM: Homo sapiens -continued

```
<400> SEQUENCE: 15

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 16
<211> LENGTH: 232
<212> TYPE: PRT
<213> ORGANISM: Homo sapiens

<400> SEQUENCE: 16

Glu Pro Lys Ser Cys Asp Thr Pro Pro Cys Pro Arg Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Gln Phe Lys Trp Tyr Val
    50                  55                  60

Asp Gly Val Glu Val His Asn Ala Lys Thr Lys Pro Arg Glu Glu Gln
65                  70                  75                  80

Tyr Asn Ser Thr Phe Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Thr Lys Gly Gln Pro
        115                 120                 125

Arg Glu Pro Gln Val Tyr Thr Leu Pro Pro Ser Arg Glu Glu Met Thr
    130                 135                 140
```

```
Lys Asn Gln Val Ser Leu Thr Cys Leu Val Lys Gly Phe Tyr Pro Ser
145                 150                 155                 160

Asp Ile Ala Val Glu Trp Glu Ser Ser Gly Gln Pro Glu Asn Asn Tyr
                165                 170                 175

Asn Thr Thr Pro Pro Met Leu Asp Ser Asp Gly Ser Phe Phe Leu Tyr
            180                 185                 190

Ser Lys Leu Thr Val Asp Lys Ser Arg Trp Gln Gln Gly Asn Ile Phe
        195                 200                 205

Ser Cys Ser Val Met His Glu Ala Leu His Asn Arg Phe Thr Gln Lys
    210                 215                 220

Ser Leu Ser Leu Ser Pro Gly Lys
225                 230

<210> SEQ ID NO 17
<211> LENGTH: 279
<212> TYPE: PRT
<213> ORGANISM: Homo sapiens

<400> SEQUENCE: 17

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro Ala Pro
    50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
            100                 105                 110

Gly Val Glu Val His Asn Ala Lys Thr Lys Pro Arg Glu Glu Gln Tyr
        115                 120                 125

Asn Ser Thr Phe Arg Val Val Ser Val Leu Thr Val Leu His Gln Asp
    130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
        195                 200                 205

Ile Ala Val Glu Trp Glu Ser Ser Gly Gln Pro Glu Asn Asn Tyr Asn
    210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270

Leu Ser Leu Ser Pro Gly Lys
        275
```

```
<210> SEQ ID NO 18
<211> LENGTH: 229
<212> TYPE: PRT
<213> ORGANISM: Homo sapiens

<400> SEQUENCE: 18

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 19
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gly Gly
1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20
```

```
Gly Gly Gly Gly
1

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Thr Gly Gly Gly Gly
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Gly Gly Gly Gly
1               5

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Gly Gly Gly
1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Gly Gly Gly
1

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Gly Gly Gly Ser
1               5

<210> SEQ ID NO 26
<211> LENGTH: 344
<212> TYPE: PRT
<213> ORGANISM: Homo sapiens
```

<400> SEQUENCE: 26

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Gly Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
    210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
    290                 295                 300

Gly Val Leu Leu Glu Val Lys His Ser Gly Ser Cys Asn Ser Ile Ser
305                 310                 315                 320

Glu Asp Thr Glu Glu Glu Glu Asp Glu Asp Gln Tyr Ser Phe
                325                 330                 335

Pro Ile Ser Ser Ile Leu Glu Trp
            340

<210> SEQ ID NO 27
<211> LENGTH: 317
<212> TYPE: PRT
<213> ORGANISM: Homo sapiens

<400> SEQUENCE: 27

Met Val Arg Ala Arg His Gln Pro Gly Gly Leu Cys Leu Leu Leu Leu
1               5                   10                  15

```
Leu Leu Cys Gln Phe Met Glu Asp Arg Ser Ala Gln Ala Gly Asn Cys
             20                  25                  30

Trp Leu Arg Gln Ala Lys Asn Gly Arg Cys Gln Val Leu Tyr Lys Thr
         35                  40                  45

Glu Leu Ser Lys Glu Glu Cys Cys Ser Thr Gly Arg Leu Ser Thr Ser
 50                  55                  60

Trp Thr Glu Glu Asp Val Asn Asp Asn Thr Leu Phe Lys Trp Met Ile
 65                  70                  75                  80

Phe Asn Gly Gly Ala Pro Asn Cys Ile Pro Cys Lys Glu Thr Cys Glu
                 85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
290                 295                 300

Gly Val Leu Leu Glu Val Lys His Ser Gly Ser Cys Asn
305                 310                 315

<210> SEQ ID NO 28
<211> LENGTH: 63
<212> TYPE: PRT
<213> ORGANISM: Homo sapiens

<400> SEQUENCE: 28

Gly Asn Cys Trp Leu Arg Gln Ala Lys Asn Gly Arg Cys Gln Val Leu
1               5                  10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys
    50                  55                  60

<210> SEQ ID NO 29
```

```
<211> LENGTH: 25
<212> TYPE: PRT
<213> ORGANISM: Homo sapiens

<400> SEQUENCE: 29

Glu Thr Cys Glu Asn Val Asp Cys Gly Pro Gly Lys Lys Cys Arg Met
1               5                   10                  15

Asn Lys Lys Asn Lys Pro Arg Cys Val
            20                  25

<210> SEQ ID NO 30
<211> LENGTH: 26
<212> TYPE: PRT
<213> ORGANISM: Homo sapiens

<400> SEQUENCE: 30

Lys Thr Cys Arg Asp Val Phe Cys Pro Gly Ser Ser Thr Cys Val Val
1               5                   10                  15

Asp Gln Thr Asn Asn Ala Tyr Cys Val Thr
            20                  25

<210> SEQ ID NO 31
<211> LENGTH: 263
<212> TYPE: PRT
<213> ORGANISM: Homo sapiens

<400> SEQUENCE: 31

Met Arg Pro Gly Ala Pro Gly Pro Leu Trp Pro Leu Pro Trp Gly Ala
1               5                   10                  15

Leu Ala Trp Ala Val Gly Phe Val Ser Ser Met Gly Ser Gly Asn Pro
            20                  25                  30

Ala Pro Gly Gly Val Cys Trp Leu Gln Gln Gly Gln Glu Ala Thr Cys
        35                  40                  45

Ser Leu Val Leu Gln Thr Asp Val Thr Arg Ala Glu Cys Cys Ala Ser
    50                  55                  60

Gly Asn Ile Asp Thr Ala Trp Ser Asn Leu Thr His Pro Gly Asn Lys
65                  70                  75                  80

Ile Asn Leu Leu Gly Phe Leu Gly Leu Val His Cys Leu Pro Cys Lys
                85                  90                  95

Asp Ser Cys Asp Gly Val Glu Cys Gly Pro Gly Lys Ala Cys Arg Met
            100                 105                 110

Leu Gly Gly Arg Pro Arg Cys Glu Cys Ala Pro Asp Cys Ser Gly Leu
        115                 120                 125

Pro Ala Arg Leu Gln Val Cys Gly Ser Asp Gly Ala Thr Tyr Arg Asp
    130                 135                 140

Glu Cys Glu Leu Arg Ala Ala Arg Cys Arg Gly His Pro Asp Leu Ser
145                 150                 155                 160

Val Met Tyr Arg Gly Arg Cys Arg Lys Ser Cys Glu His Val Val Cys
                165                 170                 175

Pro Arg Pro Gln Ser Cys Val Val Asp Gln Thr Gly Ser Ala His Cys
            180                 185                 190

Val Val Cys Arg Ala Ala Pro Cys Pro Val Pro Ser Ser Pro Gly Gln
        195                 200                 205

Glu Leu Cys Gly Asn Asn Asn Val Thr Tyr Ile Ser Ser Cys His Met
    210                 215                 220

Arg Gln Ala Thr Cys Phe Leu Gly Arg Ser Ile Gly Val Arg His Ala
225                 230                 235                 240
```

```
Gly Ser Cys Ala Gly Thr Pro Glu Glu Pro Pro Gly Gly Glu Ser Ala
                245                 250                 255

Glu Glu Glu Glu Asn Phe Val
            260
```

<210> SEQ ID NO 32
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
                20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
                100                 105                 110

Lys Pro Pro Thr Gly Gly Gly Thr His Thr Cys Pro Pro Cys Pro Ala
            115                 120                 125

Pro Glu Leu Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
                180                 185                 190

Tyr Asn Ser Thr Tyr Arg Val Val Ser Val Leu Thr Val Leu His Gln
            195                 200                 205

Asp Trp Leu Asn Gly Lys Glu Tyr Lys Cys Lys Val Ser Asn Lys Ala
    210                 215                 220

Leu Pro Val Pro Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
                245                 250                 255

Lys Asn Gln Val Ser Leu Thr Cys Leu Val Lys Gly Phe Tyr Pro Ser
                260                 265                 270

Asp Ile Ala Val Glu Trp Glu Ser Asn Gly Gln Pro Glu Asn Asn Tyr
            275                 280                 285

Lys Thr Thr Pro Pro Val Leu Asp Ser Asp Gly Ser Phe Phe Leu Tyr
    290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335
```

```
Ser Leu Ser Leu Ser Pro Gly Lys
            340

<210> SEQ ID NO 33
<211> LENGTH: 21
<212> TYPE: PRT
<213> ORGANISM: Apis sp.

<400> SEQUENCE: 33

Met Lys Phe Leu Val Asn Val Ala Leu Val Phe Met Val Val Tyr Ile
1               5                   10                  15

Ser Tyr Ile Tyr Ala
            20

<210> SEQ ID NO 34
<211> LENGTH: 22
<212> TYPE: PRT
<213> ORGANISM: Unknown
<220> FEATURE:
<223> OTHER INFORMATION: Description of Unknown:
      Tissue plasminogen activator peptide

<400> SEQUENCE: 34

Met Asp Ala Met Lys Arg Gly Leu Cys Cys Val Leu Leu Leu Cys Gly
1               5                   10                  15

Ala Val Phe Val Ser Pro
            20

<210> SEQ ID NO 35
<211> LENGTH: 20
<212> TYPE: PRT
<213> ORGANISM: Unknown
<220> FEATURE:
<223> OTHER INFORMATION: Description of Unknown:
      Native peptide

<400> SEQUENCE: 35

Met Gly Ala Ala Ala Lys Leu Ala Phe Ala Val Phe Leu Ile Ser Cys
1               5                   10                  15

Ser Ser Gly Ala
            20

<210> SEQ ID NO 36
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Asp Ala Met Lys Arg Gly Leu Cys Cys Val Leu Leu Leu Cys Gly
1               5                   10                  15

Ala Val Phe Val Ser Pro Gly Ala Ala Ile Leu Gly Arg Ser Glu Thr
            20                  25                  30

Gln Glu Cys Leu Phe Phe Asn Ala Asn Trp Glu Lys Asp Arg Thr Asn
        35                  40                  45

Gln Thr Gly Val Glu Pro Cys Tyr Gly Asp Lys Asp Lys Arg Arg His
    50                  55                  60

Cys Phe Ala Thr Trp Lys Asn Ile Ser Gly Ser Ile Glu Ile Val Lys
65                  70                  75                  80

Gln Gly Cys Trp Leu Asp Asp Ile Asn Cys Tyr Asp Arg Thr Asp Cys
```

```
                85                  90                  95
Val Glu Lys Lys Asp Ser Pro Glu Val Tyr Phe Cys Cys Cys Glu Gly
            100                 105                 110
Asn Met Cys Asn Glu Lys Phe Ser Tyr Phe Pro Glu Met Glu Val Thr
        115                 120                 125
Gln Pro Thr Ser Asn Pro Val Thr Pro Lys Pro Pro Thr Gly Gly Gly
    130                 135                 140
Thr His Thr Cys Pro Pro Cys Pro Ala Pro Glu Leu Leu Gly Gly Pro
145                 150                 155                 160
Ser Val Phe Leu Phe Pro Pro Lys Pro Lys Asp Thr Leu Met Ile Ser
                165                 170                 175
Arg Thr Pro Glu Val Thr Cys Val Val Val Asp Val Ser His Glu Asp
            180                 185                 190
Pro Glu Val Lys Phe Asn Trp Tyr Val Asp Gly Val Glu Val His Asn
        195                 200                 205
Ala Lys Thr Lys Pro Arg Glu Glu Gln Tyr Asn Ser Thr Tyr Arg Val
    210                 215                 220
Val Ser Val Leu Thr Val Leu His Gln Asp Trp Leu Asn Gly Lys Glu
225                 230                 235                 240
Tyr Lys Cys Lys Val Ser Asn Lys Ala Leu Pro Val Pro Ile Glu Lys
                245                 250                 255
Thr Ile Ser Lys Ala Lys Gly Gln Pro Arg Glu Pro Gln Val Tyr Thr
            260                 265                 270
Leu Pro Pro Ser Arg Glu Glu Met Thr Lys Asn Gln Val Ser Leu Thr
        275                 280                 285
Cys Leu Val Lys Gly Phe Tyr Pro Ser Asp Ile Ala Val Glu Trp Glu
    290                 295                 300
Ser Asn Gly Gln Pro Glu Asn Asn Tyr Lys Thr Thr Pro Pro Val Leu
305                 310                 315                 320
Asp Ser Asp Gly Ser Phe Phe Leu Tyr Ser Lys Leu Thr Val Asp Lys
                325                 330                 335
Ser Arg Trp Gln Gln Gly Asn Val Phe Ser Cys Ser Val Met His Glu
            340                 345                 350
Ala Leu His Asn His Tyr Thr Gln Lys Ser Leu Ser Leu Ser Pro Gly
        355                 360                 365
Lys

<210> SEQ ID NO 37
<211> LENGTH: 1114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
atggatgcaa tgaagagagg gctctgctgt gtgctgctgc tgtgtggagc agtcttcgtt      60
tcgcccggcg ccgctatact tggtagatca gaaactcagg agtgtctttt tttaatgcta     120
attgggaaaa agacagaacc aatcaaactg gtgttgaacc gttattggt gacaaagata      180 aacggcggca ttgttttgct acctggaaga atatttctgg ttccattgaa tagtgaaaca     240
aggttgttgg ctggatgata tcaactgcta tgacaggact gattgtgtag aaaaaaaaga     300
cagccctgaa gtatatttct gttgctgtga gggcaatatg tgtaatgaaa agttttctta     360
ttttccggag atggaagtca cacagcccac ttcaaatcca gttacaccta agccacccac     420
```

```
cggtggtgga actcacacat gcccaccgtg cccagcacct gaactcctgg ggggaccgtc      480
agtcttcctc ttccccccaa aacccaagga caccctcatg atctcccgga cccctgaggt      540
cacatgcgtg gtggtggacg tgagccacga agaccctgag gtcaagttca actggtacgt      600
ggacggcgtg gaggtgcata atgccaagac aaagccgcgg gaggagcagt acaacagcac      660
gtaccgtgtg gtcagcgtcc tcaccgtcct gcaccaggac tggctgaatg caaggagta      720 caagtgcaag gtctccaaca aagccctccc agtccccatc gagaaaacca tctccaaagc      780
caaagggcag ccccgagaac acaggtgta caccctgccc ccatcccggg aggagatgac      840
caagaaccag gtcagcctga cctgcctggt caaaggcttc tatcccagcg acatcgccgt      900
ggagtgggag agcaatgggc agccggagaa caactacaag accacgcctc ccgtgctgga      960
ctccgacggc tccttcttcc tctatagcaa gctcaccgtg gacaagagca ggtggcagca     1020
ggggaacgtc ttctcatgct ccgtgatgca tgaggctctg cacaaccact acacgcagaa     1080
gagcctctcc ctgtctccgg gtaaatgaga attc                                 1114
```

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ile Leu Gly Arg Ser Glu Thr Gln Glu
1               5

<210> SEQ ID NO 39
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Thr Gly Gly Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

```
Val Asp Gly Val Glu Val His Asn Ala Lys Thr Lys Pro Arg Glu Glu
            165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
            195                 200                 205

Ala Leu Pro Val Pro Ile Glu Lys Thr Ile Ser Lys Ala Lys Gly Gln
            210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
            245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
            275                 280                 285

Tyr Ser Lys Leu Thr Val Asp Lys Ser Arg Trp Gln Gln Gly Asn Val
            290                 295                 300

Phe Ser Cys Ser Val Met His Glu Ala Leu His Asn His Tyr Thr Gln
305                 310                 315                 320

Lys Ser Leu Ser Leu Ser Pro Gly Lys
            325

<210> SEQ ID NO 40
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
            35                  40                  45

Gly Thr Ile Glu Leu Val Lys Lys Gly Cys Trp Leu Asp Asp Phe Asn
        50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
            85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
            115                 120                 125

Glu Leu Leu Gly Gly Pro Ser Val Phe Leu Phe Pro Pro Lys Pro Lys
            130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
            165                 170                 175

Gly Val Glu Val His Asn Ala Lys Thr Lys Pro Arg Glu Glu Gln Tyr
```

```
                180                 185                 190
Asn Ser Thr Tyr Arg Val Val Ser Val Leu Thr Val Leu His Gln Asp
            195                 200                 205

Trp Leu Asn Gly Lys Glu Tyr Lys Cys Lys Val Ser Asn Lys Ala Leu
    210                 215                 220

Pro Val Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
            275                 280                 285

Thr Thr Pro Pro Val Leu Asp Ser Asp Gly Ser Phe Phe Leu Tyr Ser
        290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 41
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Asp Val Ser His Glu Asp Pro
            180                 185                 190
```

```
Glu Val Lys Phe Asn Trp Tyr Val Asp Gly Val Glu Val His Asn Ala
            195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Val Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
    275                 280                 285

Leu Val Lys Gly Phe Tyr Pro Ser Asp Ile Ala Val Glu Trp Glu Ser
290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
    355                 360                 365

<210> SEQ ID NO 42
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
atggatgcaa tgaagagagg gctctgctgt gtgctgctgc tgtgtggagc agtcttcgtt      60
tcgcccggcg cctctgggcg tgggaggct  gagacacggg agtgcatcta ctacaacgcc     120
aactgggagc tggagcgcac caaccagagc ggcctggagc gctgcgaagg cgagcaggac     180
aagcggctgc actgctacgc ctcctggcgc aacagctctg gcaccatcga gctcgtgaag     240
aagggctgct ggctagatga cttcaactgc tacgataggc aggagtgtgt ggccactgag     300
gagaaccccc aggtgtactt ctgctgctgt gaaggcaact tctgcaacga gcgcttcact     360
catttgccag aggctggggg cccggaagtc acgtacgagc accccccgac agcccccacc     420
ggtggtggaa ctcacacatg cccaccgtgc ccagcacctg aactcctggg gggaccgtca     480
gtcttcctct tccccccaaa acccaaggac accctcatga tctcccggac ccctgaggtc     540
acatgcgtgg tggtggacgt gagccacgaa gaccctgagg tcaagttcaa ctggtacgtg     600
gacggcgtgg aggtgcataa tgccaagaca aagccgcggg aggagcagta caacagcacg     660
taccgtgtgg tcagcgtcct caccgtcctg caccaggact ggctgaatgg caaggagtac     720
aagtgcaagg tctccaacaa agccctccca gtccccatcg agaaaaccat ctccaaagcc     780
aaagggcagc ccgagaaacc acaggtgtac accctgcccc catcccggga ggagatgacc     840
aagaaccagg tcagcctgac ctgcctggtc aaaggcttct atcccagcga catcgccgtg     900
gagtgggaga gcaatgggca gccggagaac aactacaaga ccacgcctcc cgtgctggac     960
tccgacggct ccttcttcct ctatagcaag ctcaccgtgg acaagagcag gtggcagcag    1020
gggaacgtct tctcatgctc cgtgatgcat gaggctctgc acaaccacta cacgcagaag    1080
```
agcctctccc tgtctccggg taaatga                                              1107

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Arg Gly Glu Ala Glu
1               5

<210> SEQ ID NO 44
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Val Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
            260                 265                 270

```
Ile Ala Val Glu Trp Glu Ser Asn Gly Gln Pro Glu Asn Asn Tyr Lys
            275                 280                 285

Thr Thr Pro Pro Val Leu Asp Ser Asp Gly Ser Phe Phe Leu Tyr Ser
            290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 45
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 46
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Asp Asp Asp Phe Asn Cys Tyr Asp Arg Gln Glu Cys
                85                  90                  95
```

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365

<210> SEQ ID NO 47
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
atggatgcaa tgaagagagg gctctgctgt gtgctgctgc tgtgtggagc agtcttcgtt      60
tcgcccggcg cctctgggcg tggggaggct gagacacggg agtgcatcta ctacaacgcc     120
aactgggagc tggagcgcac caaccagagc ggcctggagc gctgcgaagg cgagcaggac     180
aagcggctgc actgctacgc ctcctggcgc aacagctctg gcaccatcga gctcgtgaag     240
aagggctgct gggacgatga cttcaactgc tacgataggc aggagtgtgt ggccactgag     300
gagaaccccc aggtgtactt ctgctgctgt gaaggcaact tctgcaacga gcgcttcact     360
catttgccag aggctggggg cccggaagtc acgtacgagc cccccgac agccccacc       420 ggtggtggaa ctcacacatg cccaccgtgc ccagcacctg aactcctggg gggaccgtca     480
gtcttcctct tccccccaaa acccaaggac accctcatga tctcccggac ccctgaggtc     540

```
acatgcgtgg tggtggacgt gagccacgaa gaccctgagg tcaagttcaa ctggtacgtg    600
gacggcgtgg aggtgcataa tgccaagaca aagccgcggg aggagcagta caacagcacg    660
taccgtgtgg tcagcgtcct caccgtcctg caccaggact ggctgaatgg caaggagtac    720
aagtgcaagg tctccaacaa agccctccca gtccccatcg agaaaaccat ctccaaagcc    780
aaagggcagc cccgagaacc acaggtgtac accctgcccc catcccggga ggagatgacc    840
aagaaccagg tcagcctgac ctgcctggtc aaaggcttct atcccagcga catcgccgtg    900
gagtgggaga gcaatgggca gccggagaac aactacaaga ccacgcctcc cgtgctggac    960
tccgacggct ccttcttcct ctatagcaag ctcaccgtgg acaagagcag gtggcagcag   1020
gggaacgtct tctcatgctc cgtgatgcat gaggctctgc acaaccacta cacgcagaag   1080
agcctctccc tgtctccggg taaatga                                       1107
```

<210> SEQ ID NO 48
<211> LENGTH: 141
<212> TYPE: PRT
<213> ORGANISM: Homo sapiens

<400> SEQUENCE: 48

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Gly Pro Trp Ala Ser Thr Thr Ile
            100                 105                 110

Pro Ser Gly Gly Pro Glu Ala Thr Ala Ala Gly Asp Gln Gly Ser
        115                 120                 125

Gly Ala Leu Trp Leu Cys Leu Glu Gly Pro Ala His Glu
    130                 135                 140
```

<210> SEQ ID NO 49
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Asp Phe Asn
    50                  55                  60
```

```
Cys Tyr Asp Arg Gln Glu Cys Val Ala Thr Glu Asn Pro Gln Val
 65                  70                  75                  80

Tyr Phe Cys Cys Cys Glu Gly Asn Phe Cys Asn Glu Arg Phe Thr His
                 85                  90                  95

Leu Pro Glu Ala Gly Gly Pro Glu Gly Pro Trp Ala Ser Thr Thr Ile
            100                 105                 110

Pro Ser Gly Gly Pro Glu Ala Thr Ala Ala Gly Asp Gln Gly Ser
        115                 120                 125

Gly Ala Leu Trp Leu Cys Leu Glu Gly Pro Ala His Glu
    130                 135                 140
```

<210> SEQ ID NO 50
<211> LENGTH: 370
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Gly Arg Gly Glu Ala Glu Thr Arg Glu Cys Ile Tyr Tyr Asn Ala Asn
 1               5                  10                  15

Trp Glu Leu Glu Arg Thr Asn Gln Ser Gly Leu Glu Arg Cys Glu Gly
             20                  25                  30

Glu Gln Asp Lys Arg Leu His Cys Tyr Ala Ser Trp Arg Asn Ser Ser
         35                  40                  45

Gly Thr Ile Glu Leu Val Lys Lys Gly Cys Trp Asp Asp Asp Phe Asn
 50                  55                  60

Cys Tyr Asp Arg Gln Glu Cys Val Ala Thr Glu Asn Pro Gln Val
 65                  70                  75                  80

Tyr Phe Cys Cys Cys Glu Gly Asn Phe Cys Asn Glu Arg Phe Thr His
                 85                  90                  95

Leu Pro Glu Ala Gly Gly Pro Glu Gly Pro Trp Ala Ser Thr Thr Ile
            100                 105                 110

Pro Ser Gly Gly Pro Glu Ala Thr Ala Ala Gly Asp Gln Gly Ser
        115                 120                 125

Gly Ala Leu Trp Leu Cys Leu Glu Gly Pro Ala His Glu Thr Gly Gly
    130                 135                 140

Gly Thr His Thr Cys Pro Pro Cys Pro Ala Pro Glu Leu Leu Gly Gly
145                 150                 155                 160

Pro Ser Val Phe Leu Phe Pro Pro Lys Pro Lys Asp Thr Leu Met Ile
                165                 170                 175

Ser Arg Thr Pro Glu Val Thr Cys Val Val Val Asp Val Ser His Glu
            180                 185                 190

Asp Pro Glu Val Lys Phe Asn Trp Tyr Val Asp Gly Val Glu Val His
        195                 200                 205

Asn Ala Lys Thr Lys Pro Arg Glu Glu Gln Tyr Asn Ser Thr Tyr Arg
    210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Ala Leu Pro Ala Pro Ile Glu
                245                 250                 255

Lys Thr Ile Ser Lys Ala Lys Gly Gln Pro Arg Glu Pro Gln Val Tyr
            260                 265                 270

Thr Leu Pro Pro Ser Arg Glu Glu Met Thr Lys Asn Gln Val Ser Leu
        275                 280                 285
```

```
Thr Cys Leu Val Lys Gly Phe Tyr Pro Ser Asp Ile Ala Val Glu Trp
    290                 295                 300

Glu Ser Asn Gly Gln Pro Glu Asn Asn Tyr Lys Thr Thr Pro Pro Val
305                 310                 315                 320

Leu Asp Ser Asp Gly Ser Phe Phe Leu Tyr Ser Lys Leu Thr Val Asp
                325                 330                 335

Lys Ser Arg Trp Gln Gln Gly Asn Val Phe Ser Cys Ser Val Met His
                340                 345                 350

Glu Ala Leu His Asn His Tyr Thr Gln Lys Ser Leu Ser Leu Ser Pro
            355                 360                 365

Gly Lys
    370

<210> SEQ ID NO 51
<211> LENGTH: 116
<212> TYPE: PRT
<213> ORGANISM: Homo sapiens

<400> SEQUENCE: 51

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
                20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
                100                 105                 110

Lys Pro Pro Thr
            115

<210> SEQ ID NO 52
<211> LENGTH: 150
<212> TYPE: PRT
<213> ORGANISM: Rattus sp.

<400> SEQUENCE: 52

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
                20                  25                  30

Asn Ala Asn Trp Glu Leu Glu Arg Thr Asn Gln Ser Gly Leu Glu Arg
            35                  40                  45

Cys Glu Gly Glu Gln Asp Lys Arg Leu His Cys Tyr Ala Ser Trp Pro
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
                100                 105                 110
```

Phe Thr His Leu Pro Glu Pro Gly Pro Glu Val Thr Tyr Glu Pro
            115                 120                 125

Pro Pro Thr Ala Pro Thr Leu Leu Thr Val Leu Ala Tyr Ser Leu Leu
130                 135                 140

Pro Ile Gly Gly Leu Ser
145                 150

<210> SEQ ID NO 53
<211> LENGTH: 150
<212> TYPE: PRT
<213> ORGANISM: Sus scrofa

<400> SEQUENCE: 53

Met Thr Ala Pro Trp Ala Ala Leu Ala Leu Leu Trp Gly Ser Leu Cys
1               5                   10                  15

Val Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
            115                 120                 125

Pro Pro Thr Ala Pro Thr Leu Leu Thr Val Leu Ala Tyr Ser Leu Leu
130                 135                 140

Pro Ile Gly Gly Leu Ser
145                 150

<210> SEQ ID NO 54
<211> LENGTH: 150
<212> TYPE: PRT
<213> ORGANISM: Mus musculus

<400> SEQUENCE: 54

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Pro Gly Gly Pro Glu Val Thr Tyr Glu Pro
            115                 120                 125

Pro Pro Thr Ala Pro Thr Leu Leu Thr Val Leu Ala Tyr Ser Leu Leu
            130                 135                 140

Pro Ile Gly Gly Leu Ser
145                 150

<210> SEQ ID NO 55
<211> LENGTH: 150
<212> TYPE: PRT
<213> ORGANISM: Homo sapiens

<400> SEQUENCE: 55

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
            130                 135                 140

Pro Ile Gly Gly Leu Ser
145                 150

<210> SEQ ID NO 56
<211> LENGTH: 150
<212> TYPE: PRT
<213> ORGANISM: Bos taurus

<400> SEQUENCE: 56

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Arg Asp Lys Arg Leu His Cys Tyr Ala Ser Trp Arg
50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
            130                 135                 140

```
Pro Val Gly Gly Leu Ser
145                 150

<210> SEQ ID NO 57
<211> LENGTH: 150
<212> TYPE: PRT
<213> ORGANISM: Xenopus sp.

<400> SEQUENCE: 57

Met Gly Ala Ser Val Ala Leu Thr Phe Leu Leu Leu Ala Thr Phe
1               5                   10                  15

Arg Ala Gly Ser Gly His Asp Glu Val Glu Thr Arg Glu Cys Ile Tyr
                20                  25                  30

Tyr Asn Ala Asn Trp Glu Leu Glu Lys Thr Asn Gln Ser Gly Val Glu
            35                  40                  45

Arg Leu Val Glu Gly Lys Lys Asp Lys Arg Leu His Cys Tyr Ala Ser
        50                  55                  60

Trp Arg Asn Asn Ser Gly Phe Ile Glu Leu Val Lys Lys Gly Cys Trp
65                  70                  75                  80

Leu Asp Asp Phe Asn Cys Tyr Asp Arg Gln Glu Cys Ile Ala Lys Glu
                85                  90                  95

Glu Asn Pro Gln Val Phe Phe Cys Cys Cys Glu Gly Asn Tyr Cys Asn
                100                 105                 110

Lys Lys Phe Thr His Leu Pro Glu Val Glu Thr Phe Asp Pro Lys Pro
            115                 120                 125

Gln Pro Ser Ala Ser Val Leu Asn Ile Leu Ile Tyr Ser Leu Leu Pro
        130                 135                 140

Ile Val Gly Leu Ser Met
145                 150

<210> SEQ ID NO 58
<211> LENGTH: 150
<212> TYPE: PRT
<213> ORGANISM: Homo sapiens

<400> SEQUENCE: 58

Met Gly Ala Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
                20                  25                  30

Phe Asn Ala Asn Trp Glu Lys Asp Arg Thr Asn Gln Thr Gly Val Glu
            35                  40                  45

Pro Cys Tyr Gly Asp Lys Asp Lys Arg Arg His Cys Phe Ala Thr Trp
        50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
                100                 105                 110

Lys Phe Ser Tyr Phe Pro Glu Met Glu Val Thr Gln Pro Thr Ser Asn
            115                 120                 125

Pro Val Thr Pro Lys Pro Pro Tyr Tyr Asn Ile Leu Leu Tyr Ser Leu
        130                 135                 140

Val Pro Leu Met Leu Ile
145                 150
```

<210> SEQ ID NO 59
<211> LENGTH: 154
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (8)..(8)
<223> OTHER INFORMATION: Thr, Ala or not present
<220> FEATURE:
<221> NAME/KEY: MOD_RES
<222> LOCATION: (121)..(121)
<223> OTHER INFORMATION: Pro, Ala, Val or Met

<400> SEQUENCE: 59

Met Thr Ala Pro Trp Ala Ala Xaa Leu Ala Leu Leu Trp Gly Ser Leu
1               5                   10                  15

Cys Ala Gly Ser Gly Arg Gly Glu Ala Glu Thr Arg Glu Cys Ile Tyr
            20                  25                  30

Tyr Asn Ala Asn Trp Glu Leu Glu Arg Thr Asn Gln Ser Gly Leu Glu
        35                  40                  45

Arg Leu Cys Glu Gly Glu Gln Asp Lys Arg Leu His Cys Tyr Ala Ser
    50                  55                  60

Trp Arg Asn Ser Ser Gly Thr Ile Glu Leu Val Lys Lys Gly Cys Trp
65                  70                  75                  80

Leu Asp Asp Phe Asn Cys Tyr Asp Arg Gln Glu Cys Val Ala Thr Glu
                85                  90                  95

Glu Asn Pro Gln Val Tyr Phe Cys Cys Cys Glu Gly Asn Phe Cys Asn
            100                 105                 110

Glu Arg Phe Thr His Leu Pro Glu Xaa Gly Gly Pro Glu Val Thr Tyr
        115                 120                 125

Glu Pro Lys Pro Pro Thr Ala Pro Thr Leu Leu Thr Val Leu Ala Tyr
    130                 135                 140

Ser Leu Leu Pro Ile Gly Gly Leu Ser Met
145                 150

<210> SEQ ID NO 60
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
tcatttaccc ggggacaggg agaggctctt ctgcgtgtag tggttgtgca gagcctcatg      60
catcacggag catgagaaga cgttccctg ctgccacctg ctcttgtcca cggtgagctt     120
gctatagagg aagaaggagc cgtcggagtc cagcacggga ggcgtggtct tgtagttgtt    180
ctccggctgc ccattgctct cccactccac ggcgatgtcg ctgggataga agcctttgac    240
caggcaggtc aggctgacct ggttcttggt catctcctcc cgggatgggg gcagggtgta    300
cacctgtggt tctcggggct gccctttggc tttggagatg gttttctcga tggggctgg    360 gagggctttg ttggagacct tgcacttgta ctccttgcca ttcagccagt cctggtgcag    420
gacggtgagg acgctgacca cacgtacgt gctgttgtac tgctcctccc gcggctttgt     480
cttggcatta tgcacctcca cgccgtccac gtaccagttg aacttgacct cagggtcttc    540

```
gtggctcacg tccaccacca cgcatgtgac ctcaggggtc cgggagatca tgagggtgtc    600
cttgggtttt gggggaaga ggaagactga cggtccccc aggagttcag gtgctgggca      660
cggtgggcat gtgtgagttc caccaccggt gggggctgtc gggggtggct cgtacgtgac    720
ttccgggccc ccagcctctg gcaaatgagt gaagcgctcg ttgcagaagt tgccttcaca    780
gcagcagaag tacacctggg ggttctcctc agtggccaca cactcctgcc tatcgtagca    840
gttgaagtca tcatcccagc agccttcttc acgagctcg atggtgccag agctgttgcg    900
ccaggaggcg tagcagtgca gccgcttgtc ctgctcgcct cgcagcgct ccaggccgct    960 ctggttggtg cgctccagct cccagttggc gttgtagtag atgcactccc gtgtctcagc    1020
ctccccacgc cagaggcgc cgggcgaaac gaagactgct ccacacagca gcagcacaca    1080
gcagagccct ctcttcattg catccat                                       1107
```

<210> SEQ ID NO 61
<211> LENGTH: 360
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 61

Met Asp Ala Met Lys Arg Gly Leu Cys Cys Val Leu Leu Cys Gly
1               5                   10                  15

Ala Val Phe Val Ser Pro Gly Ala Ala Glu Thr Arg Glu Cys Ile Tyr
            20                  25                  30

Tyr Asn Ala Asn Trp Glu Leu Glu Arg Thr Asn Gln Ser Gly Leu Glu
        35                  40                  45

Arg Cys Glu Gly Glu Gln Asp Lys Arg Leu His Cys Tyr Ala Ser Trp
    50                  55                  60

Arg Asn Ser Ser Gly Thr Ile Glu Leu Val Lys Lys Gly Cys Trp Asp
65                  70                  75                  80

Asp Asp Phe Asn Cys Tyr Asp Arg Gln Glu Cys Val Ala Thr Glu Glu
                85                  90                  95

Asn Pro Gln Val Tyr Phe Cys Cys Cys Glu Gly Asn Phe Cys Asn Glu
            100                 105                 110

Arg Phe Thr His Leu Pro Glu Ala Gly Gly Pro Glu Val Thr Tyr Glu
        115                 120                 125

Pro Pro Pro Thr Gly Gly Gly Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

```
Arg Glu Pro Gln Val Tyr Thr Leu Pro Pro Ser Arg Glu Glu Met Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 62
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (76)..(396)

<400> SEQUENCE: 62
atggatgcaa tgaagagagg gctctgctgt gtgctgctgc tgtgtggagc agtcttcgtt    60
tcgcccggcg ccgct gag aca cgg gag tgc atc tac tac aac gcc aac tgg   111
                Glu Thr Arg Glu Cys Ile Tyr Tyr Asn Ala Asn Trp
                  1               5                  10 gag ctg gag cgc acc aac cag agc ggc ctg gag cgc tgc gaa ggc gag   159
Glu Leu Glu Arg Thr Asn Gln Ser Gly Leu Glu Arg Cys Glu Gly Glu
         15                  20                  25 cag gac aag cgg ctg cac tgc tac gcc tcc tgg cgc aac agc tct ggc   207
Gln Asp Lys Arg Leu His Cys Tyr Ala Ser Trp Arg Asn Ser Ser Gly
 30                  35                  40 acc atc gag ctc gtg aag aag ggc tgc tgg gac gat gac ttc aac tgc   255
Thr Ile Glu Leu Val Lys Lys Gly Cys Trp Asp Asp Asp Phe Asn Cys
 45                  50                  55                  60 tac gat agg cag gag tgt gtg gcc act gag gag aac ccc cag gtg tac   303
Tyr Asp Arg Gln Glu Cys Val Ala Thr Glu Glu Asn Pro Gln Val Tyr
                 65                  70                  75 ttc tgc tgc tgt gaa ggc aac ttc tgc aac gag cgc ttc act cat ttg   351
Phe Cys Cys Cys Glu Gly Asn Phe Cys Asn Glu Arg Phe Thr His Leu
             80                  85                  90 cca gag gct ggg ggc ccg gaa gtc acg tac gag cca ccc ccg aca        396
Pro Glu Ala Gly Gly Pro Glu Val Thr Tyr Glu Pro Pro Pro Thr
         95                 100                 105 ggtggtggaa ctcacacatg cccaccgtgc ccagcacctg aactcctggg ggaccgtca    456 gtcttcctct tccccccaaa acccaaggac accctcatga tctcccggac ccctgaggtc   516
acatgcgtgg tggtggacgt gagccacgaa gaccctgagg tcaagttcaa ctggtacgtg   576
gacggcgtgg aggtgcataa tgccaagaca aagccgcggg aggagcagta caacagcacg   636
taccgtgtgg tcagcgtcct caccgtcctg caccaggact ggctgaatgg caaggagtac   696
aagtgcaagg tctccaacaa agccctccca gcccccatcg agaaaccat ctccaaagcc    756 aaagggcagc cccgagaacc acaggtgtac accctgcccc catcccggga ggagatgacc   816
```

```
aagaaccagg tcagcctgac ctgcctggtc aaaggcttct atcccagcga catcgccgtg    876
gagtgggaga gcaatgggca gccggagaac aactacaaga ccacgcctcc cgtgctggac    936
tccgacggct ccttcttcct ctatagcaag ctcaccgtgg acaagagcag gtggcagcag    996
gggaacgtct tctcatgctc cgtgatgcat gaggctctgc acaaccacta cacgcagaag   1056
agcctctccc tgtccccggg taaatga                                       1083
```

<210> SEQ ID NO 63
<211> LENGTH: 1083
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 63

```
tcatttaccc ggggacaggg agaggctctt ctgcgtgtag tggttgtgca gagcctcatg     60
catcacggag catgagaaga cgttcccctg ctgccacctg ctcttgtcca cggtgagctt    120
gctatagagg aagaaggagc cgtcggagtc cagcacggga ggcgtggtct tgtagttgtt    180
ctccggctgc ccattgctct cccactccac ggcgatgtcg ctgggataga agcctttgac    240
caggcaggtc aggctgacct ggttcttggt catctcctcc cgggatgggg gcagggtgta    300
cacctgtggt tctcggggct gccctttggc tttggagatg gttttctcga tgggggctgg    360
gagggctttg ttggagacct tgcacttgta ctccttgcca ttcagccagt cctggtgcag    420
gacggtgagg acgctgacca cacggtacgt gctgttgtac tgctcctccc gcggctttgt    480
cttggcatta tgcacctcca cgccgtccac gtaccagttg aacttgacct cagggtcttc    540
gtggctcacg tccaccacca cgcatgtgac ctcaggggtc cgggagatca tgagggtgtc    600
cttgggtttt gggggaaga ggaagactga cggtcccccc aggagttcag gtgctgggca    660
cggtgggcat gtgtgagttc caccacctgt cgggggtggc tcgtacgtga cttccgggcc    720
cccagcctct ggcaaatgag tgaagcgctc gttgcagaag ttgccttcac agcagcagaa    780
gtacacctgg gggttctcct cagtggccac acactcctgc ctatcgtagc agttgaagtc    840
atcgtcccag cagcccttct tcacgagctc gatggtgcca gagctgttgc gccaggaggc    900
gtagcagtgc agccgcttgt cctgctcgcc ttcgcagcgc tccaggccgc tctggttggt    960
gcgctccagc tcccagttgg cgttgtagta gatgcactcc cgtgtctcag cggcgccggg   1020
cgaaacgaag actgctccac acagcagcag cacacagcag agccctctct tcattgcatc   1080
cat                                                                1083
```

<210> SEQ ID NO 64
<211> LENGTH: 335
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 64

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45
```

Val Lys Lys Gly Cys Trp Asp Asp Phe Asn Cys Tyr Asp Arg Gln
 50                  55                  60

Glu Cys Val Ala Thr Glu Asn Pro Gln Val Tyr Phe Cys Cys
 65                  70                  75                  80

Glu Gly Asn Phe Cys Asn Glu Arg Phe Thr His Leu Pro Ala Gly
                 85                  90                  95

Gly Pro Glu Val Thr Tyr Glu Pro Pro Thr Gly Gly Thr His
            100                 105                 110

Thr Cys Pro Pro Cys Pro Ala Pro Glu Leu Leu Gly Pro Ser Val
            115                 120                 125

Phe Leu Phe Pro Pro Lys Pro Lys Asp Thr Leu Met Ile Ser Arg Thr
130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
            195                 200                 205

Cys Lys Val Ser Asn Lys Ala Leu Pro Ala Pro Ile Glu Lys Thr Ile
            210                 215                 220

Ser Lys Ala Lys Gly Gln Pro Arg Glu Pro Gln Val Tyr Thr Leu Pro
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
            275                 280                 285

Asp Gly Ser Phe Phe Leu Tyr Ser Lys Leu Thr Val Asp Lys Ser Arg
            290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 65
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Asp Asp Phe Asn Cys Tyr Asp Arg Gln
 50                  55                  60

Glu Cys Val Ala Thr Glu Glu Asn Pro Gln Val Tyr Phe Cys Cys
 65                  70                  75                  80

```
Glu Gly Asn Phe Cys Asn Glu Arg Phe Thr His Leu Pro Glu Ala Gly
            85                  90                  95

Gly Pro Glu Val Thr Tyr Glu Pro Pro Thr
        100                 105

<210> SEQ ID NO 66
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (76)..(396)

<400> SEQUENCE: 66
atggatgcaa tgaagagagg gctctgctgt gtgctgctgc tgtgtggagc agtcttcgtt    60
tcgcccggcg ccgcc gaa acc cgc gaa tgt att tat tac aat gct aat tgg    111
              Glu Thr Arg Glu Cys Ile Tyr Tyr Asn Ala Asn Trp
                1               5                   10 gaa ctc gaa cgg acg aac caa tcc ggg ctc gaa cgg tgt gag ggg gaa    159
Glu Leu Glu Arg Thr Asn Gln Ser Gly Leu Glu Arg Cys Glu Gly Glu
     15                  20                  25 cag gat aaa cgc ctc cat tgc tat gcg tcg tgg agg aac tcc tcc ggg    207
Gln Asp Lys Arg Leu His Cys Tyr Ala Ser Trp Arg Asn Ser Ser Gly
 30                  35                  40 acg att gaa ctg gtc aag aaa ggg tgc tgg gac gac gat ttc aat tgt    255
Thr Ile Glu Leu Val Lys Lys Gly Cys Trp Asp Asp Asp Phe Asn Cys
45                  50                  55                  60 tat gac cgc cag gaa tgt gtc gcg acc gaa gag aat ccg cag gtc tat    303
Tyr Asp Arg Gln Glu Cys Val Ala Thr Glu Glu Asn Pro Gln Val Tyr
                 65                  70                  75 ttc tgt tgt tgc gag ggg aat ttc tgt aat gaa cgg ttt acc cac ctc    351
Phe Cys Cys Cys Glu Gly Asn Phe Cys Asn Glu Arg Phe Thr His Leu
                 80                  85                  90 ccc gaa gcc ggc ggg ccc gag gtg acc tat gaa ccc ccg ccc acc        396
Pro Glu Ala Gly Gly Pro Glu Val Thr Tyr Glu Pro Pro Thr
             95                 100                 105 ggtggtggaa ctcacacatg cccaccgtgc ccagcacctg aactcctggg gggaccgtca    456
gtcttcctct tccccccaaa acccaaggac accctcatga tctcccggac ccctgaggtc    516
acatgcgtgg tggtggacgt gagccacgaa gaccctgagg tcaagttcaa ctggtacgtg    576
gacggcgtgg aggtgcataa tgccaagaca aagccgcggg aggagcagta caacagcacg    636
taccgtgtgg tcagcgtcct caccgtcctg caccaggact ggctgaatgg caaggagtac    696
aagtgcaagg tctccaacaa agccctccca gcccccatcg agaaaaccat ctccaaagcc    756
aaagggcagc ccgagaacc acaggtgtac accctgcccc catcccggga ggagatgacc    816
aagaaccagg tcagcctgac ctgcctggtc aaaggcttct atcccagcga catcgccgtg    876
gagtgggaga gcaatgggca gccggagaac aactacaaga ccacgcctcc cgtgctggac    936
tccgacggct ccttcttcct ctatagcaag ctcaccgtgg acaagagcag gtggcagcag    996
gggaacgtct tctcatgctc cgtgatgcat gaggctctgc acaaccacta cacgcagaag    1056
agcctctccc tgtccccggg taaatga                                        1083

<210> SEQ ID NO 67
<211> LENGTH: 1083
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 67

```
tcatttaccc ggggacaggg agaggctctt ctgcgtgtag tggttgtgca gagcctcatg    60
catcacggag catgagaaga cgttcccctg ctgccacctg ctcttgtcca cggtgagctt   120
gctatagagg aagaaggagc cgtcggagtc cagcacggga ggcgtggtct tgtagttgtt   180
ctccggctgc ccattgctct cccactccac ggcgatgtcg ctgggataga agcctttgac   240
caggcaggtc aggctgacct ggttcttggt catctcctcc cggatggggg cagggtgta   300
cacctgtggt tctcggggct gccctttggc tttggagatg gttttctcga tgggggctgg   360
gagggctttg ttggagacct tgcacttgta ctccttgcca ttcagccagt cctggtgcag   420
gacggtgagg acgctgacca cacggtacgt gctgttgtac tgctcctccc gcggctttgt   480
cttggcatta tgcacctcca cgccgtccac gtaccagttg aacttgacct cagggtcttc   540
gtggctcacg tccaccacca cgcatgtgac ctcagggtc cgggagatca tgagggtgtc   600
cttgggtttt ggggggaaga ggaagactga cggtcccccc aggagttcag gtgctgggca   660
cggtgggcat gtgtgagttc caccaccggt gggcgggggt tcataggtca cctcgggccc   720
gccggcttcg gggaggtggg taaaccgttc attacagaaa ttcccctcgc aacaacagaa   780
atagacctgc ggattctctt cggtcgcgac acattcctgg cggtcataac aattgaaatc   840
gtcgtcccag caccctttct tgaccagttc aatcgtcccg gaggagttcc tccacgacgc   900
atagcaatgg aggcgtttat cctgttcccc ctcacaccgt tcgagcccgg attggttcgt   960
ccgttcgagt tcccaattag cattgtaata aatacattcg cgggtttcgg cggcgccggg  1020
cgaaacgaag actgctccac acagcagcag cacacagcag agccctctct tcattgcatc  1080
cat                                                                1083
```

<210> SEQ ID NO 68
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 68

```
gaaacccgcg aatgtattta ttacaatgct aattgggaac tcgaacggac gaaccaatcc    60
gggctcgaac ggtgtgaggg ggaacaggat aaacgcctcc attgctatgc gtcgtggagg   120
aactcctccg ggacgattga actggtcaag aaagggtgct gggacgacga tttcaattgt   180
tatgaccgcc aggaatgtgt cgcgaccgaa gagaatccgc aggtctattt ctgttgttgc   240
gaggggaatt tctgtaatga acggtttacc cacctccccg aagccggcgg gcccgaggtg   300
acctatgaac ccccgcccac c                                             321
```

<210> SEQ ID NO 69
<211> LENGTH: 115
<212> TYPE: PRT
<213> ORGANISM: Homo sapiens

<400> SEQUENCE: 69

```
Ile Leu Gly Arg Ser Glu Thr Gln Glu Cys Leu Phe Phe Asn Ala Asn
1               5                   10                  15
```

Trp Glu Lys Asp Arg Thr Asn Gln Thr Gly Val Glu Pro Cys Tyr Gly
                20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
        50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
               100                 105                 110

Lys Pro Pro
       115

<210> SEQ ID NO 70
<211> LENGTH: 115
<212> TYPE: PRT
<213> ORGANISM: Ovis aries

<400> SEQUENCE: 70

Ile Leu Gly Arg Ser Glu Thr Gln Glu Cys Ile Phe Tyr Asn Ala Asn
1               5                   10                  15

Trp Glu Arg Asp Arg Thr Asn Arg Thr Gly Val Glu Ser Cys Tyr Gly
                20                  25                  30

Asp Lys Asp Lys Arg Arg His Cys Phe Ala Thr Trp Lys Asn Ile Ser
            35                  40                  45

Gly Ser Ile Asp Ile Val Lys Gln Gly Cys Trp Leu Asp Asp Ile Asn
        50                  55                  60

Cys Tyr Asp Arg Thr Asp Cys Ile Glu Lys Lys Asp Ser Pro Glu Val
65                  70                  75                  80

Tyr Phe Cys Cys Cys Glu Gly Asn Met Cys Asn Glu Arg Phe Ser Tyr
                85                  90                  95

Phe Pro Glu Met Glu Val Thr Gln Pro Thr Ser Asn Pro Val Thr Pro
               100                 105                 110

Lys Pro Pro
       115

<210> SEQ ID NO 71
<211> LENGTH: 115
<212> TYPE: PRT
<213> ORGANISM: Condylura cristata

<400> SEQUENCE: 71

Ile Leu Gly Arg Ser Glu Thr Gln Glu Cys Leu Phe Phe Asn Ala Asn
1               5                   10                  15

Trp Glu Arg Asp Arg Thr Asn Gln Thr Gly Val Glu Pro Cys Tyr Gly
                20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
        50                  55                  60

Cys Tyr Asp Arg Thr Asp Cys Ile Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Ala Pro
        115

<210> SEQ ID NO 72
<211> LENGTH: 115
<212> TYPE: PRT
<213> ORGANISM: Mus musculus

<400> SEQUENCE: 72

Ile Leu Gly Arg Ser Glu Thr Gln Glu Cys Leu Phe Phe Asn Ala Asn
1               5                   10                  15

Trp Glu Arg Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
50                  55                  60

Cys Tyr Asp Arg Thr Asp Cys Ile Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro
        115

<210> SEQ ID NO 73
<211> LENGTH: 115
<212> TYPE: PRT
<213> ORGANISM: Gallus gallus

<400> SEQUENCE: 73

Ile Leu Gly Arg Ser Glu Thr Gln Glu Cys Ile Tyr Tyr Asn Ala Asn
1               5                   10                  15

Trp Glu Lys Asp Lys Thr Asn Arg Ser Gly Ile Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
50                  55                  60

Cys Tyr Asp Arg Asn Asp Cys Ile Glu Lys Lys Asp Ser Pro Glu Val
65                  70                  75                  80

Phe Phe Cys Cys Cys Glu Gly Asn Met Cys Asn Glu Arg Phe Phe Tyr
                85                  90                  95

Phe Pro Glu Met Glu Val Thr Gln Pro Thr Ser Asn Pro Val Thr Pro
            100                 105                 110

Lys Pro Pro
        115

<210> SEQ ID NO 74
<211> LENGTH: 115
<212> TYPE: PRT
<213> ORGANISM: Bos taurus

<400> SEQUENCE: 74

Ile Leu Gly Arg Ser Glu Thr Gln Glu Cys Ile Phe Tyr Asn Ala Asn

```
            1               5                   10                  15
Trp Glu Arg Asp Arg Thr Asn Arg Thr Gly Val Glu Ser Cys Tyr Gly
                20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
        50                  55                  60

Cys Tyr Asp Arg Thr Asp Cys Ile Glu Lys Lys Asp Ser Pro Glu Val
65                  70                  75                  80

Tyr Phe Cys Cys Cys Glu Gly Asn Met Cys Asn Glu Arg Phe Ser Tyr
                85                  90                  95

Phe Pro Glu Met Glu Val Thr Gln Pro Thr Ser Asn Pro Val Thr Pro
                100                 105                 110

Lys Pro Pro
        115

<210> SEQ ID NO 75
<211> LENGTH: 115
<212> TYPE: PRT
<213> ORGANISM: Tyto alba

<400> SEQUENCE: 75

Ile Leu Gly Arg Ser Glu Thr Gln Glu Cys Ile Tyr Tyr Asn Ala Asn
1               5                   10                  15

Trp Glu Lys Asp Lys Thr Asn Arg Ser Gly Ile Glu Pro Cys Tyr Gly
                20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
        50                  55                  60

Cys Tyr Asp Arg Asn Asp Cys Ile Glu Lys Lys Asp Ser Pro Glu Val
65                  70                  75                  80

Phe Phe Cys Cys Cys Glu Gly Asn Met Cys Asn Glu Arg Phe Phe Tyr
                85                  90                  95

Phe Pro Glu Met Glu Val Thr Gln Pro Thr Ser Asn Pro Val Thr Pro
                100                 105                 110

Lys Pro Pro
        115

<210> SEQ ID NO 76
<211> LENGTH: 115
<212> TYPE: PRT
<213> ORGANISM: Myotis davidii

<400> SEQUENCE: 76

Ile Leu Gly Arg Ser Glu Thr Gln Glu Cys Ile Phe Tyr Asn Ala Asn
1               5                   10                  15

Trp Glu Arg Asp Lys Thr Asn Arg Thr Gly Val Glu Leu Cys Tyr Gly
                20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
        50                  55                  60

Cys Tyr Asp Arg Thr Asp Cys Ile Glu Lys Lys Asp Ser Pro Glu Val
65                  70                  75                  80

Tyr Phe Cys Cys Cys Glu Gly Asn Met Cys Asn Glu Arg Phe Ser Tyr
```

```
                    85                  90                  95

Phe Pro Glu Met Glu Val Thr Gln Pro Thr Ser Asn Pro Val Thr Pro
            100                 105                 110

Lys Pro Pro
        115

<210> SEQ ID NO 77
<211> LENGTH: 20
<212> TYPE: PRT
<213> ORGANISM: Unknown
<220> FEATURE:
<223> OTHER INFORMATION: Description of Unknown:
      Native peptide

<400> SEQUENCE: 77

Met Gly Ala Ala Ala Lys Leu Ala Phe Ala Val Phe Leu Ile Ser Cys
1               5                   10                  15

Ser Ser Gly Ala
            20

<210> SEQ ID NO 78
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Gly Gly Thr His
            100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
    130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
    210                 215                 220

Ser Lys Ala Lys Gly Gln Pro Arg Glu Pro Gln Val Tyr Thr Leu Pro
```

```
            225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
                260                 265                 270

Gly Gln Pro Glu Asn Asn Tyr Lys Thr Thr Pro Pro Val Leu Asp Ser
                275                 280                 285

Asp Gly Ser Phe Phe Leu Tyr Ser Lys Leu Thr Val Asp Lys Ser Arg
                290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 79
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Met Asp Ala Met Lys Arg Gly Leu Cys Cys Val Leu Leu Leu Cys Gly
1               5                   10                  15

Ala Val Phe Val Ser Pro Gly Ala Ala Glu Thr Arg Glu Cys Ile Tyr
                20                  25                  30

Tyr Asn Ala Asn Trp Glu Leu Glu Arg Thr Asn Gln Ser Gly Leu Glu
                35                  40                  45

Arg Cys Glu Gly Glu Gln Asp Lys Arg Leu His Cys Tyr Ala Ser Trp
    50                  55                  60

Arg Asn Ser Ser Gly Thr Ile Glu Leu Val Lys Lys Gly Cys Trp Leu
65                  70                  75                  80

Asp Asp Phe Asn Cys Tyr Asp Arg Gln Glu Cys Val Ala Thr Glu Glu
                85                  90                  95

Asn Pro Gln Val Tyr Phe Cys Cys Cys Glu Gly Asn Phe Cys Asn Glu
                100                 105                 110

Arg Phe Thr His Leu Pro Glu Ala Gly Gly Pro Glu Val Thr Tyr Glu
                115                 120                 125

Pro Pro Pro Thr Gly Gly Gly Thr His Thr Cys Pro Pro Cys Pro Ala
                130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
                180                 185                 190

Asp Gly Val Glu Val His Asn Ala Lys Thr Lys Pro Arg Glu Glu Gln
                195                 200                 205

Tyr Asn Ser Thr Tyr Arg Val Val Ser Val Leu Thr Val Leu His Gln
                210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255
```

```
Arg Glu Pro Gln Val Tyr Thr Leu Pro Pro Ser Arg Glu Glu Met Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 80
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (73)..(396)

<400> SEQUENCE: 80
atggatgcaa tgaagagagg gctctgctgt gtgctgctgc tgtgtggagc agtcttcgtt      60
tcgcccggcg cc gct gag aca cgg gag tgc atc tac tac aac gcc aac tgg    111
              Ala Glu Thr Arg Glu Cys Ile Tyr Tyr Asn Ala Asn Trp
              1               5                   10 gag ctg gag cgc acc aac cag agc ggc ctg gag cgc tgc gaa ggc gag      159
Glu Leu Glu Arg Thr Asn Gln Ser Gly Leu Glu Arg Cys Glu Gly Glu
    15                  20                  25 cag gac aag cgg ctg cac tgc tac gcc tcc tgg cgc aac agc tct ggc      207
Gln Asp Lys Arg Leu His Cys Tyr Ala Ser Trp Arg Asn Ser Ser Gly
30                  35                  40                  45 acc atc gag ctc gtg aag aag ggc tgc tgg cta gat gac ttc aac tgc      255
Thr Ile Glu Leu Val Lys Lys Gly Cys Trp Leu Asp Asp Phe Asn Cys
                50                  55                  60 tac gat agg cag gag tgt gtg gcc act gag gag aac ccc cag gtg tac      303
Tyr Asp Arg Gln Glu Cys Val Ala Thr Glu Glu Asn Pro Gln Val Tyr
            65                  70                  75 ttc tgc tgc tgt gaa ggc aac ttc tgc aac gag cgc ttc act cat ttg      351
Phe Cys Cys Cys Glu Gly Asn Phe Cys Asn Glu Arg Phe Thr His Leu
        80                  85                  90 cca gag gct ggg ggc ccg gaa gtc acg tac gag cca ccc ccg aca           396
Pro Glu Ala Gly Gly Pro Glu Val Thr Tyr Glu Pro Pro Pro Thr
    95                  100                 105 ggtggtggaa ctcacacatg cccaccgtgc ccagcacctg aactcctggg ggaccgtca      456 gtcttcctct tccccccaaa acccaaggac accctcatga tctcccggac ccctgaggtc      516
acatgcgtgg tggtggacgt gagccacgaa gaccctgagg tcaagttcaa ctggtacgtg      576
gacggcgtgg aggtgcataa tgccaagaca aagccgcggg aggagcagta caacagcacg      636
taccgtgtgg tcagcgtcct caccgtcctg caccaggact ggctgaatgg caaggagtac      696
aagtgcaagg tctccaacaa agccctccca gcccccatcg agaaaaccat ctccaaagcc      756
aaagggcagc ccgagaacc acaggtgtac accctgcccc catcccggga ggagatgacc      816
```

| | |
|---|---|
| aagaaccagg tcagcctgac ctgcctggtc aaaggcttct atcccagcga catcgccgtg | 876 |
| gagtgggaga gcaatgggca gccggagaac aactacaaga ccacgcctcc cgtgctggac | 936 |
| tccgacggct ccttcttcct ctatagcaag ctcaccgtgg acaagagcag gtggcagcag | 996 |
| gggaacgtct tctcatgctc cgtgatgcat gaggctctgc acaaccacta cacgcagaag | 1056 |
| agcctctccc tgtccccggg taaatga | 1083 |

<210> SEQ ID NO 81
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

| | |
|---|---|
| tcatttaccc ggggacaggg agaggctctt ctgcgtgtag tggttgtgca gagcctcatg | 60 |
| catcacggag catgagaaga cgttcccctg ctgccacctg ctcttgtcca cggtgagctt | 120 |
| gctatagagg aagaaggagc cgtcggagtc cagcacggga ggcgtggtct tgtagttgtt | 180 |
| ctccggctgc ccattgctct cccactccac ggcgatgtcg ctgggataga agcctttgac | 240 |
| caggcaggtc aggctgacct ggttcttggt catctcctcc cgggatgggg gcagggtgta | 300 |
| cacctgtggt tctcggggct gccctttggc tttggagatg gttttctcga tggggctgg | 360 |
| gagggctttg ttggagacct tgcacttgta ctccttgcca ttcagccagt cctggtgcag | 420 |
| gacggtgagg acgctgacca cacgtacgt gctgttgtac tgctcctccc gcggctttgt | 480 |
| cttggcatta tgcacctcca cgccgtccac gtaccagttg aacttgacct cagggtcttc | 540 |
| gtggctcacg tccaccacca cgcatgtgac ctcaggggtc cggagatca tgagggtgtc | 600 |
| cttgggtttt gggggaaga ggaagactga cggtccccc aggagttcag gtgctgggca | 660 |
| cggtgggcat gtgtgagttc caccacctgt cggggtggc tcgtacgtga cttccgggcc | 720 |
| cccagcctct ggcaaatgag tgaagcgctc gttgcagaag ttgccttcac agcagcagaa | 780 |
| gtacacctgg gggttctcct cagtggccac acactcctgc ctatcgtagc agttgaagtc | 840 |
| atctagccag cagcccttct tcacgagctc gatggtgcca gagctgttgc gccaggaggc | 900 |
| gtagcagtgc agccgcttgt cctgctcgcc ttcgcagcgc tccaggccgc tctggttggt | 960 |
| gcgctccagc tccagttgg cgttgtagta gatgcactcc cgtgtctcag cggcgccggg | 1020 |
| cgaaacgaag actgctccac acagcagcag cacacagcag agccctctct tcattgcatc | 1080 |
| cat | 1083 |

<210> SEQ ID NO 82
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (73)..(396)

<400> SEQUENCE: 82

| | |
|---|---|
| atggatgcaa tgaagagagg gctctgctgt gtgctgctgc tgtgtggagc agtcttcgtt | 60 |
| tcgcccggcg cc gcc gaa acc cgc gaa tgt att tat tac aat gct aat tgg | 111 |
|                         Ala Glu Thr Arg Glu Cys Ile Tyr Tyr Asn Ala Asn Trp | |
|                          1           5                10 | |

| gaa ctc gaa cgg acg aac caa tcc ggg ctc gaa cgg tgt gag ggg gaa | 159 |
| Glu Leu Glu Arg Thr Asn Gln Ser Gly Leu Glu Arg Cys Glu Gly Glu | |
|  15                  20                  25                     | |
| cag gat aaa cgc ctc cat tgc tat gcg tcg tgg agg aac tcc tcc ggg | 207 |
| Gln Asp Lys Arg Leu His Cys Tyr Ala Ser Trp Arg Asn Ser Ser Gly | |
|  30              35                  40                  45     | |
| acg att gaa ctg gtc aag aaa ggg tgc tgg ctg gac gat ttc aat tgt | 255 |
| Thr Ile Glu Leu Val Lys Lys Gly Cys Trp Leu Asp Asp Phe Asn Cys | |
|          50                  55                  60             | |
| tat gac cgc cag gaa tgt gtc gcg acc gaa gag aat ccg cag gtc tat | 303 |
| Tyr Asp Arg Gln Glu Cys Val Ala Thr Glu Glu Asn Pro Gln Val Tyr | |
|              65                  70                  75         | |
| ttc tgt tgt tgc gag ggg aat ttc tgt aat gaa cgg ttt acc cac ctc | 351 |
| Phe Cys Cys Cys Glu Gly Asn Phe Cys Asn Glu Arg Phe Thr His Leu | |
|                  80                  85                  90     | |
| ccc gaa gcc ggc ggg ccc gag gtg acc tat gaa ccc ccg ccc acc     | 396 |
| Pro Glu Ala Gly Gly Pro Glu Val Thr Tyr Glu Pro Pro Pro Thr     | |
|  95                 100                 105                     | | ggtggtggaa ctcacacatg cccaccgtgc ccagcacctg aactcctggg gggaccgtca  456 gtcttcctct tccccccaaa acccaaggac accctcatga tctcccggac ccctgaggtc  516 acatgcgtgt tggtggacgt gagccacgaa gaccctgagg tcaagttcaa ctggtacgtg  576 gacggcgtgg aggtgcataa tgccaagaca aagccgcggg aggagcagta caacagcacg  636 taccgtgtgt cagcgtcctc accgtcctg caccaggact ggctgaatgg caaggagtac  696 aagtgcaagg tctccaacaa agccctccca gcccccatcg agaaaaccat ctccaaagcc  756 aaagggcagc cccgagaacc acaggtgtac accctgcccc catcccggga ggagatgacc  816 aagaaccagg tcagcctgac ctgcctggtc aaaggcttct atcccagcga catcgccgtg  876 gagtgggaga gcaatgggca gccggagaac aactacaaga ccacgcctcc cgtgctggac  936 tccgacggct ccttcttcct ctatagcaag ctcaccgtgg acaagagcag gtggcagcag  996 gggaacgtct tctcatgctc cgtgatgcat gaggctctgc acaaccacta cacgcagaag  1056 agcctctccc tgtccccggg taaatga  1083

<210> SEQ ID NO 83
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
tcatttaccc ggggacaggg agaggctctt ctgcgtgtag tggttgtgca gagcctcatg   60
catcacggag catgagaaga cgttcccctg ctgccacctg ctcttgtcca cggtgagctt  120
gctatagagg aagaaggagc cgtcggagtc cagcacggga ggcgtggtct tgtagttgtt  180
ctccggctgc ccattgctct cccactccac ggcgatgtcg ctgggataga agcctttgac  240
caggcaggtc aggctgacct ggttcttggt catctcctcc cgggatgggg gcagggtgta  300
cacctgtggt tctcggggct gcccttggc tttggagatg gttttctcga tgggggctgg  360
gagggctttg ttggagacct tgcacttgta ctccttgcca ttcagccagt cctggtgcag  420
gacggtgagg acgctgacca cacggtacgt gctgttgtac tgctcctccc gcggctttgt  480
cttggcatta tgcacctcca cgccgtccac gtaccagttg aacttgacct cagggtcttc  540
gtggctcacg tccaccacca cgcatgtgac ctcagggtc cgggagatca tgagggtgtc  600

```
cttgggtttt ggggggaaga ggaagactga cggtccccc aggagttcag gtgctgggca        660
cggtgggcat gtgtgagttc caccaccggt gggcggggt tcataggtca cctcgggccc        720
gccggcttcg gggaggtggg taaaccgttc attacagaaa ttcccctcgc aacaacagaa       780
atagacctgc ggattctctt cggtcgcgac acattcctgg cggtcataac aattgaaatc       840
gtccagccag caccctttct tgaccagttc aatcgtcccg gaggagttcc tccacgacgc       900
atagcaatgg aggcgtttat cctgttcccc ctcacaccgt tcgagcccgg attggttcgt       960
ccgttcgagt tcccaattag cattgtaata aatacattcg cgggtttcgg cggcgccggg      1020
cgaaacgaag actgctccac acagcagcag cacacagcag agccctctct tcattgcatc      1080
cat                                                                    1083
```

<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Synthetic
    6xHis tag

<400> SEQUENCE: 84

His His His His His His
1               5

<210> SEQ ID NO 85
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 85

Ala Glu Thr Arg Glu Cys Ile Tyr Tyr Asn Ala Asn Trp Glu Leu Glu
1               5                   10                  15

Arg Thr Asn Gln Ser Gly Leu Glu Arg Cys Glu Gly Glu Gln Asp Lys
            20                  25                  30

Arg Leu His Cys Tyr Ala Ser Trp Arg Asn Ser Ser Gly Thr Ile Glu
        35                  40                  45

Leu Val Lys Lys Gly Cys Trp Leu Asp Asp Phe Asn Cys Tyr Asp Arg
    50                  55                  60

Gln Glu Cys Val Ala Thr Glu Glu Asn Pro Gln Val Tyr Phe Cys Cys
65                  70                  75                  80

Cys Glu Gly Asn Phe Cys Asn Glu Arg Phe Thr His Leu Pro Glu Ala
                85                  90                  95

Gly Gly Pro Glu Val Thr Tyr Glu Pro Pro Pro Thr
            100                 105

<210> SEQ ID NO 86
<211> LENGTH: 1107
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 86

```
atggatgcaa tgaagagagg gctctgctgt gtgctgctgc tgtgtggagc agtcttcgtt         60
tcgcccggcg cctctgggcg tgggaggct gagacacggg agtgcatcta ctacaacgcc         120
```

```
aactgggagc tggagcgcac caaccagagc ggcctggagc gctgcgaagg cgagcaggac    180
aagcggctgc actgctacgc ctcctggcgc aacagctctg gcaccatcga gctcgtgaag    240
aagggctgct gggatgatga cttcaactgc tacgataggc aggagtgtgt ggccactgag    300
gagaaccccc aggtgtactt ctgctgctgt gaaggcaact tctgcaacga gcgcttcact    360
catttgccag aggctggggg cccggaagtc acgtacgagc cacccccgac agcccccacc    420
ggtggtggaa ctcacacatg cccaccgtgc ccagcacctg aactcctggg gggaccgtca    480
gtcttcctct tccccccaaa acccaaggac accctcatga tctcccggac ccctgaggtc    540
acatgcgtgg tggtggacgt gagccacgaa gaccctgagg tcaagttcaa ctggtacgtg    600
gacggcgtgg aggtgcataa tgccaagaca aagccgcggg aggagcagta caacagcacg    660
taccgtgtgg tcagcgtcct caccgtcctg caccaggact ggctgaatgg caaggagtac    720
aagtgcaagg tctccaacaa agccctccca gcccccatcg agaaaaccat ctccaaagcc    780
aaagggcagc cccgagaacc acaggtgtac accctgcccc catcccggga ggagatgacc    840
aagaaccagg tcagcctgac ctgcctggtc aaaggcttct atcccagcga catcgccgtg    900
gagtgggaga gcaatgggca gccggagaac aactacaaga ccacgcctcc cgtgctggac    960
tccgacggct ccttcttcct ctatagcaag ctcaccgtgg acaagagcag gtggcagcag   1020
gggaacgtct tctcatgctc cgtgatgcat gaggctctgc acaaccacta cacgcagaag   1080
agcctctccc tgtccccggg taaatga                                       1107
```